US008652043B2

(12) United States Patent
Drucker et al.

(10) Patent No.: US 8,652,043 B2
(45) **Date of Patent: *Feb. 18, 2014**

(54) ANALYTE MONITORING DEVICE AND METHODS OF USE

(75) Inventors: Steven H. Drucker, Oakland, CA (US); Robert Y. Jin, Castro Valley, CA (US); Jeffery V. Funderburk, Fremont, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/555,057

(22) Filed: Jul. 20, 2012

(65) Prior Publication Data

US 2012/0316412 A1 Dec. 13, 2012

Related U.S. Application Data

(63) Continuation of application No. 10/336,195, filed on Jan. 3, 2003, which is a continuation of application No. 09/753,746, filed on Jan. 2, 2001, now Pat. No. 6,560,471.

(51) Int. Cl.
*A61B 5/00* (2006.01)
*A61B 5/05* (2006.01)

(52) U.S. Cl.
USPC ............ 600/365; 600/345; 600/347; 600/309

(58) Field of Classification Search
USPC .......................................... 600/309, 345–366
See application file for complete search history.

(56) References Cited

U.S. PATENT DOCUMENTS 2,402,306 A 6/1946 Turkel
2,719,797 A 10/1955 Rosenblatt et al.
3,132,123 A 5/1964 Harris, Jr. et al.

(Continued)

FOREIGN PATENT DOCUMENTS

AU 2002246889 12/2005
CA 2433144 8/2002

(Continued)

OTHER PUBLICATIONS

"Poretics Polycarbonate Membrane", *Osmonics Filtration and Separation Group*, 2002.

(Continued)

*Primary Examiner* — Navin Natnithithadha
(74) *Attorney, Agent, or Firm* — Jackson & Co., LLP

(57) ABSTRACT

An analyte monitor includes a sensor, a sensor control unit, and a display unit. The sensor has, for example, a substrate, a recessed channel formed in the substrate, and conductive material disposed in the recessed channel to form a working electrode. The sensor control unit typically has a housing adapted for placement on skin and is adapted to receive a portion of an electrochemical sensor. The sensor control unit also includes two or more conductive contacts disposed on the housing and configured for coupling to two or more contact pads on the sensor. A transmitter is disposed in the housing and coupled to the plurality of conductive contacts for transmitting data obtained using the sensor. The display unit has a receiver for receiving data transmitted by the transmitter of the sensor control unit and a display coupled to the receiver for displaying an indication of a level of an analyte. The analyte monitor may also be part of a drug delivery system to alter the level of the analyte based on the data obtained using the sensor.

20 Claims, 31 Drawing Sheets

(56) References Cited

U.S. PATENT DOCUMENTS 3,210,578 A 10/1965 Sherer
3,219,533 A 11/1965 Mullins
3,260,656 A 7/1966 Ross, Jr.
3,282,875 A 11/1966 Connolly et al.
3,304,413 A 2/1967 Lehmann et al.
3,310,606 A 3/1967 Fritz
3,381,371 A 5/1968 Russell
3,397,191 A 8/1968 Beckerbauer
3,635,926 A 1/1972 Gresham et al.
3,651,318 A 3/1972 Czekajewski
3,652,475 A 3/1972 Wada et al.
3,653,841 A 4/1972 Klein
3,698,386 A 10/1972 Fried
3,719,564 A 3/1973 Lilly, Jr. et al.
3,768,014 A 10/1973 Smith et al.
3,775,182 A 11/1973 Patton et al.
3,776,832 A 12/1973 Oswin et al.
3,785,939 A 1/1974 Hsu
3,791,871 A 2/1974 Rowley
3,826,244 A 7/1974 Salcman et al.
3,837,339 A 9/1974 Aisenberg et al.
3,838,033 A 9/1974 Mindt et al.
3,851,018 A 11/1974 Kelly
3,898,984 A 8/1975 Mandel et al.
3,919,051 A 11/1975 Koch et al.
3,926,760 A 12/1975 Allen et al.
3,929,971 A 12/1975 Roy
3,930,889 A 1/1976 Ruggiero et al.
3,933,593 A 1/1976 Sternberg
3,943,918 A 3/1976 Lewis
3,957,613 A 5/1976 Macur
3,964,974 A 6/1976 Banauch et al.
3,966,580 A 6/1976 Janata et al.
3,972,320 A 8/1976 Kalman
3,979,274 A 9/1976 Newman
3,982,530 A 9/1976 Storch
4,008,717 A 2/1977 Kowarski
4,016,866 A 4/1977 Lawton
4,024,312 A 5/1977 Korpman
4,032,729 A 6/1977 Koistinen
4,036,749 A 7/1977 Anderson
4,037,563 A 7/1977 Pflueger et al.
4,040,908 A 8/1977 Clark, Jr.
4,052,754 A 10/1977 Homsy
4,055,175 A 10/1977 Clemens et al.
4,059,406 A 11/1977 Fleet
4,059,708 A 11/1977 Heiss, Jr. et al.
4,067,322 A 1/1978 Johnson
4,073,713 A 2/1978 Newman
4,076,596 A 2/1978 Connery et al.
4,076,656 A 2/1978 White et al.
4,098,574 A 7/1978 Dappen
4,100,048 A 7/1978 Pompei et al.
4,120,292 A 10/1978 LeBlanc, Jr. et al.
4,129,128 A 12/1978 McFarlane
4,146,029 A 3/1979 Ellinwood, Jr.
4,151,845 A 5/1979 Clemens
4,154,231 A 5/1979 Russell
4,168,205 A 9/1979 Danninger et al.
4,172,770 A 10/1979 Semersky et al.
4,178,916 A 12/1979 McNamara
4,184,429 A 1/1980 Widmer
4,193,982 A 3/1980 Avrameas et al.
4,197,840 A 4/1980 Beck et al.
4,206,755 A 6/1980 Klein
4,215,703 A 8/1980 Willson
4,224,125 A 9/1980 Nakamura et al.
4,240,438 A 12/1980 Updike et al.
4,240,889 A 12/1980 Yoda et al.
4,241,438 A 12/1980 Kern
4,245,634 A 1/1981 Albisser et al.
4,247,297 A 1/1981 Berti et al.
4,253,469 A 3/1981 Aslan
4,255,500 A 3/1981 Hooke
4,259,540 A 3/1981 Sabia
4,271,449 A 6/1981 Grogan
4,275,225 A 6/1981 Krespan
4,282,872 A 8/1981 Franetzki et al.
4,294,258 A 10/1981 Bernard
4,318,784 A 3/1982 Higgins et al.
4,324,257 A 4/1982 Albarda et al.
4,327,725 A 5/1982 Cortese et al.
4,331,869 A 5/1982 Rollo
4,335,255 A 6/1982 Krespan
4,340,458 A 7/1982 Lerner et al.
4,344,438 A 8/1982 Schultz
4,345,603 A 8/1982 Schulman
4,352,960 A 10/1982 Dormer et al.
4,353,888 A 10/1982 Sefton
4,356,074 A 10/1982 Johnson
4,357,282 A 11/1982 Anderson et al.
4,360,019 A 11/1982 Portner et al.
4,365,637 A 12/1982 Johnson
4,366,033 A 12/1982 Richter et al.
4,374,013 A 2/1983 Enfors
4,375,399 A 3/1983 Havas et al.
4,384,586 A 5/1983 Christiansen
4,388,166 A 6/1983 Suzuki et al.
4,390,621 A 6/1983 Bauer
4,392,933 A 7/1983 Nakamura et al.
4,401,122 A 8/1983 Clark, Jr.
4,403,847 A 9/1983 Chrestensen
4,403,984 A 9/1983 Ash et al.
4,404,066 A 9/1983 Johnson
4,407,288 A 10/1983 Langer et al.
4,407,959 A 10/1983 Tsuji et al.
4,415,666 A 11/1983 D'Orazio et al.
4,417,588 A 11/1983 Houghton et al.
4,418,148 A 11/1983 Oberhardt
4,419,535 A 12/1983 O'Hara
4,420,564 A 12/1983 Tsuji et al.
4,425,920 A 1/1984 Bourland et al.
4,427,004 A 1/1984 Miller et al.
4,427,770 A 1/1984 Chen et al.
4,431,004 A 2/1984 Bessman et al.
4,431,507 A 2/1984 Nankai et al.
4,436,094 A 3/1984 Cerami
4,440,175 A 4/1984 Wilkins
4,442,841 A 4/1984 Uehara et al.
4,443,218 A 4/1984 DeCant, Jr. et al.
4,444,892 A 4/1984 Malmros
4,450,842 A 5/1984 Zick et al.
4,458,686 A 7/1984 Clark, Jr.
4,461,691 A 7/1984 Frank
4,467,811 A 8/1984 Clark, Jr.
4,469,110 A 9/1984 Slama
4,476,003 A 10/1984 Frank et al.
4,477,314 A 10/1984 Richter et al.
4,478,976 A 10/1984 Goertz et al.
4,483,924 A 11/1984 Tsuji et al.
4,484,987 A 11/1984 Gough
4,494,950 A 1/1985 Fischell
4,498,843 A 2/1985 Schneider et al.
4,499,249 A 2/1985 Nakagawa et al.
4,506,680 A 3/1985 Stokes
4,512,348 A 4/1985 Uchigaki et al.
RE31,916 E 6/1985 Oswin et al.
4,522,690 A 6/1985 Venkatasetty
4,524,114 A 6/1985 Samuels et al.
4,526,661 A 7/1985 Steckhan et al.
4,526,948 A 7/1985 Resnick
4,527,240 A 7/1985 Kvitash
4,530,696 A 7/1985 Bisera et al.
4,534,356 A 8/1985 Papadakis
4,534,825 A 8/1985 Koning et al.
4,538,616 A 9/1985 Rogoff
4,543,955 A 10/1985 Schroeppel
4,544,869 A 10/1985 Pittaway
4,545,382 A 10/1985 Higgins et al.
4,552,840 A 11/1985 Riffer
4,554,927 A 11/1985 Fussell
4,560,534 A 12/1985 Kung et al.
4,561,443 A 12/1985 Hogrefe et al.
4,569,589 A 2/1986 Neufeld

(56) References Cited

U.S. PATENT DOCUMENTS 4,571,292 A 2/1986 Liu et al.
4,573,994 A 3/1986 Fischell et al.
4,577,642 A 3/1986 Stokes
4,578,215 A 3/1986 Bradley
4,581,336 A 4/1986 Malloy et al.
4,583,976 A 4/1986 Ferguson
4,595,011 A 6/1986 Phillips
4,595,479 A 6/1986 Kimura et al.
4,614,760 A 9/1986 Homan et al.
4,619,754 A 10/1986 Niki et al.
4,619,793 A 10/1986 Lee
4,627,445 A 12/1986 Garcia et al.
4,627,908 A 12/1986 Miller
4,633,878 A 1/1987 Bombardieri
4,633,881 A 1/1987 Moore et al.
4,637,403 A 1/1987 Garcia et al.
RE32,361 E 2/1987 Duggan
4,648,408 A 3/1987 Hutcheson et al.
4,650,547 A 3/1987 Gough
4,653,513 A 3/1987 Dombrowski
4,654,197 A 3/1987 Lilja et al.
4,655,880 A 4/1987 Liu
4,655,885 A 4/1987 Hill et al.
4,658,463 A 4/1987 Sugita et al.
4,663,824 A 5/1987 Kenmochi
4,671,288 A 6/1987 Gough
4,672,970 A 6/1987 Uchida et al.
4,674,652 A 6/1987 Aten et al.
4,679,562 A 7/1987 Luksha
4,680,268 A 7/1987 Clark, Jr.
4,681,111 A 7/1987 Silvian
4,682,602 A 7/1987 Prohaska
4,684,537 A 8/1987 Graetzel et al.
4,685,463 A 8/1987 Williams
4,686,624 A 8/1987 Blum et al.
4,698,582 A 10/1987 Braun et al.
4,699,157 A 10/1987 Shonk
4,703,756 A 11/1987 Gough et al.
4,711,245 A 12/1987 Higgins et al.
4,711,251 A 12/1987 Stokes
4,714,462 A 12/1987 DiDomenico
4,714,874 A 12/1987 Morris et al.
4,717,673 A 1/1988 Wrighton et al.
4,718,893 A 1/1988 Dorman
4,721,601 A 1/1988 Wrighton et al.
4,721,677 A 1/1988 Clark, Jr.
4,726,378 A 2/1988 Kaplan
4,726,716 A 2/1988 McGuire
4,731,051 A 3/1988 Fischell
4,731,726 A 3/1988 Allen, III
4,747,828 A 5/1988 Tseo
4,749,985 A 6/1988 Corsberg
4,750,496 A 6/1988 Reinhart
4,753,652 A 6/1988 Langer et al.
4,755,173 A 7/1988 Konopka
4,757,022 A 7/1988 Shults et al.
4,758,323 A 7/1988 Davis et al.
4,759,371 A 7/1988 Franetzki
4,759,828 A 7/1988 Young et al.
4,764,416 A 8/1988 Ueyama et al.
4,776,904 A 10/1988 Charlton et al.
4,776,944 A 10/1988 Janata et al.
4,777,953 A 10/1988 Ash et al.
4,779,618 A 10/1988 Mund et al.
4,781,798 A 11/1988 Gough
4,784,736 A 11/1988 Lonsdale et al.
4,787,398 A 11/1988 Garcia et al.
4,787,837 A 11/1988 Bell
4,795,707 A 1/1989 Niiyama et al.
4,796,634 A 1/1989 Huntsman et al.
4,803,243 A 2/1989 Fujimoto et al.
4,803,625 A 2/1989 Fu et al.
4,803,726 A 2/1989 Levine et al.
4,805,624 A 2/1989 Yao et al.
4,805,625 A 2/1989 Wyler
4,810,470 A 3/1989 Burkhardt et al.
4,813,424 A 3/1989 Wilkins
4,815,469 A 3/1989 Cohen et al.
4,820,399 A 4/1989 Senda et al.
4,821,733 A 4/1989 Peck
4,822,337 A 4/1989 Newhouse et al.
4,826,810 A 5/1989 Aoki
4,830,959 A 5/1989 McNeil et al.
4,832,034 A 5/1989 Pizziconi et al.
4,832,797 A 5/1989 Vadgama et al.
4,835,372 A 5/1989 Gombrich et al.
RE32,947 E 6/1989 Dormer et al.
4,836,904 A 6/1989 Armstrong et al.
4,837,049 A 6/1989 Byers et al.
4,838,887 A 6/1989 Idriss
4,840,893 A 6/1989 Hill et al.
RE32,974 E 7/1989 Porat et al.
4,844,076 A 7/1989 Lesho et al.
4,845,035 A 7/1989 Fanta et al.
4,848,351 A 7/1989 Finch
4,849,458 A 7/1989 Reed et al.
4,852,573 A 8/1989 Kennedy
4,854,322 A 8/1989 Ash et al.
4,856,340 A 8/1989 Garrison
4,857,713 A 8/1989 Brown
4,858,617 A 8/1989 Sanders
4,870,561 A 9/1989 Love et al.
4,871,351 A 10/1989 Feingold
4,871,440 A 10/1989 Nagata et al.
4,874,499 A 10/1989 Smith et al.
4,874,500 A 10/1989 Madou et al.
4,875,486 A 10/1989 Rapoport et al.
4,882,013 A 11/1989 Turner et al.
4,883,057 A 11/1989 Broderick
4,886,740 A 12/1989 Vadgama
4,889,744 A 12/1989 Quaid
4,890,620 A 1/1990 Gough
4,890,621 A 1/1990 Hakky
4,891,104 A 1/1990 Liston et al.
4,894,137 A 1/1990 Takizawa et al.
4,896,142 A 1/1990 Aycox et al.
4,897,162 A 1/1990 Lewandowski et al.
4,897,173 A 1/1990 Nankai et al.
4,897,457 A 1/1990 Nakamura et al.
4,899,839 A 2/1990 Dessertine et al.
4,900,405 A 2/1990 Otagawa et al.
4,902,294 A 2/1990 Gosserez
4,907,857 A 3/1990 Giuliani et al.
4,909,908 A 3/1990 Ross et al.
4,911,794 A 3/1990 Parce et al.
4,917,800 A 4/1990 Lonsdale et al.
4,919,114 A 4/1990 Miyazaki
4,919,141 A 4/1990 Zier et al.
4,919,767 A 4/1990 Vadgama et al.
4,919,770 A 4/1990 Preidel et al.
4,920,969 A 5/1990 Suzuki
4,920,977 A 5/1990 Haynes
4,923,586 A 5/1990 Katayama et al.
4,925,268 A 5/1990 Iyer et al.
4,927,407 A 5/1990 Dorman
4,927,516 A 5/1990 Yamaguchi et al.
4,929,426 A 5/1990 Bodai et al.
4,931,795 A 6/1990 Gord
4,934,369 A 6/1990 Maxwell
4,935,105 A 6/1990 Churchouse
4,935,345 A 6/1990 Guilbeau et al.
4,936,956 A 6/1990 Wrighton
4,938,860 A 7/1990 Wogoman
4,942,127 A 7/1990 Wada et al.
4,944,299 A 7/1990 Silvian
4,945,045 A 7/1990 Forrest et al.
4,950,378 A 8/1990 Nagata
4,953,552 A 9/1990 DeMarzo
4,954,129 A 9/1990 Giuliani et al.
4,955,861 A 9/1990 Enegren et al.
4,957,115 A 9/1990 Selker
4,958,148 A 9/1990 Olson
4,958,632 A 9/1990 Duggan
4,963,245 A 10/1990 Weetall

(56) References Cited

U.S. PATENT DOCUMENTS 4,963,595 A 10/1990 Ward et al.
4,968,400 A 11/1990 Shimomura et al.
4,969,468 A 11/1990 Byers et al.
4,970,145 A 11/1990 Bennetto et al.
4,974,592 A 12/1990 Branco
4,974,929 A 12/1990 Curry
4,975,175 A 12/1990 Karube et al.
4,979,509 A 12/1990 Hakky
4,984,929 A 1/1991 Rock et al.
4,986,271 A 1/1991 Wilkins
4,986,671 A 1/1991 Sun et al.
4,988,341 A 1/1991 Columbus et al.
4,988,758 A 1/1991 Fukuda et al.
4,990,845 A 2/1991 Gord
4,991,582 A 2/1991 Byers et al.
4,992,794 A 2/1991 Brouwers
4,994,068 A 2/1991 Hufnagle
4,994,167 A 2/1991 Shults et al.
4,995,402 A 2/1991 Smith et al.
5,001,054 A 3/1991 Wagner
5,002,054 A 3/1991 Ash et al.
5,002,055 A 3/1991 Merki et al.
5,002,572 A 3/1991 Picha
5,007,427 A 4/1991 Suzuki et al.
5,007,929 A 4/1991 Quaid
5,014,718 A 5/1991 Mitchen
5,016,172 A 5/1991 Dessertine
5,016,201 A 5/1991 Bryan et al.
5,016,631 A 5/1991 Hogrefe et al.
5,019,974 A 5/1991 Beckers
5,027,499 A 7/1991 Prohaska
5,029,583 A 7/1991 Meserol et al.
5,030,333 A 7/1991 Clark, Jr.
5,034,112 A 7/1991 Murase et al.
5,034,192 A 7/1991 Wrighton et al.
5,035,860 A 7/1991 Kleingeld et al.
5,036,860 A 8/1991 Leigh et al.
5,036,861 A 8/1991 Sembrowich et al.
5,037,527 A 8/1991 Hayashi et al.
5,047,044 A 9/1991 Smith et al.
5,049,487 A 9/1991 Phillips et al.
5,050,612 A 9/1991 Matsumura
5,055,171 A 10/1991 Peck
5,058,592 A 10/1991 Whisler
5,059,654 A 10/1991 Hou et al.
5,063,081 A 11/1991 Cozzette et al.
5,067,491 A 11/1991 Taylor et al.
5,068,536 A 11/1991 Rosenthal
5,070,535 A 12/1991 Hochmair et al.
5,072,732 A 12/1991 Rapoport et al.
5,073,500 A 12/1991 Saito et al.
5,074,977 A 12/1991 Cheung et al.
5,076,273 A 12/1991 Schoendorfer et al.
5,077,476 A 12/1991 Rosenthal
5,078,854 A 1/1992 Burgess et al.
5,082,550 A 1/1992 Rishpon et al.
5,082,786 A 1/1992 Nakamoto
5,084,828 A 1/1992 Kaufman et al.
5,088,981 A 2/1992 Howson et al.
5,089,112 A 2/1992 Skotheim et al.
5,094,951 A 3/1992 Rosenberg
5,095,904 A 3/1992 Seligman et al.
5,096,560 A 3/1992 Takai et al.
5,096,836 A 3/1992 Macho et al.
5,097,834 A 3/1992 Skrabal
5,101,814 A 4/1992 Palti
5,106,365 A 4/1992 Hernandez
5,108,564 A 4/1992 Szuminsky et al.
5,108,819 A 4/1992 Heller et al.
5,108,889 A 4/1992 Smith et al.
5,109,850 A 5/1992 Blanco et al.
5,111,539 A 5/1992 Hiruta et al.
5,111,818 A 5/1992 Suzuki et al.
5,114,678 A 5/1992 Crawford et al.
5,120,420 A 6/1992 Nankai et al.
5,120,421 A 6/1992 Glass et al.
5,126,034 A 6/1992 Carter et al.
5,126,247 A 6/1992 Palmer et al.
5,130,009 A 7/1992 Marsoner et al.
5,131,441 A 7/1992 Simpson et al.
5,133,856 A 7/1992 Yamaguchi et al.
5,134,391 A 7/1992 Okada
5,135,003 A 8/1992 Souma
5,137,028 A 8/1992 Nishimura
5,139,023 A 8/1992 Stanley et al.
5,140,393 A 8/1992 Hijikihigawa et al.
5,140,985 A 8/1992 Schroeder et al.
5,141,868 A 8/1992 Shanks et al.
5,147,725 A 9/1992 Pinchuk
5,153,827 A 10/1992 Coutre et al.
5,160,418 A 11/1992 Mullen
5,161,532 A 11/1992 Joseph
5,165,407 A 11/1992 Wilson et al.
5,168,046 A 12/1992 Hamamoto et al.
5,171,689 A 12/1992 Kawaguri et al.
5,174,291 A 12/1992 Schoonen et al.
5,176,632 A 1/1993 Bernardi
5,176,644 A 1/1993 Srisathapat et al.
5,176,662 A 1/1993 Bartholomew et al.
5,182,707 A 1/1993 Cooper et al.
5,184,359 A 2/1993 Tsukamura et al.
5,185,256 A 2/1993 Nankai et al.
5,190,038 A 3/1993 Polson et al.
5,190,041 A 3/1993 Palti
5,192,415 A 3/1993 Yoshioka et al.
5,192,416 A 3/1993 Wang et al.
5,193,539 A 3/1993 Schulman et al.
5,193,540 A 3/1993 Schulman et al.
5,197,322 A 3/1993 Indravudh
5,198,192 A 3/1993 Saito et al.
5,198,367 A 3/1993 Aizawa et al.
5,198,771 A 3/1993 Fidler et al.
5,200,051 A 4/1993 Cozzette et al.
5,202,261 A 4/1993 Musho et al.
5,205,920 A 4/1993 Oyama et al.
5,206,145 A 4/1993 Cattell
5,208,147 A 5/1993 Kagenow et al.
5,208,154 A 5/1993 Weaver et al.
5,209,229 A 5/1993 Gilli
5,215,887 A 6/1993 Saito
5,216,597 A 6/1993 Beckers
5,217,442 A 6/1993 Davis
5,217,595 A 6/1993 Smith et al.
5,226,423 A 7/1993 Tenerz et al.
5,227,042 A 7/1993 Zawodzinski et al.
5,229,282 A 7/1993 Yoshioka et al.
5,231,988 A 8/1993 Wernicke et al.
5,232,668 A 8/1993 Grant et al.
5,234,835 A 8/1993 Nestor et al.
5,235,003 A 8/1993 Ward et al.
5,243,696 A 9/1993 Carr et al.
5,243,983 A 9/1993 Tarr et al.
5,246,867 A 9/1993 Lakowicz et al.
5,249,576 A 10/1993 Goldberger et al.
5,250,439 A 10/1993 Musho et al.
5,251,126 A 10/1993 Kahn et al.
5,257,971 A 11/1993 Lord et al.
5,257,980 A 11/1993 Van Antwerp et al.
5,259,769 A 11/1993 Cruise et al.
5,261,401 A 11/1993 Baker et al.
5,262,035 A 11/1993 Gregg et al.
5,262,305 A 11/1993 Heller et al.
5,264,092 A 11/1993 Skotheim et al.
5,264,103 A 11/1993 Yoshioka et al.
5,264,104 A 11/1993 Gregg et al.
5,264,105 A 11/1993 Gregg et al.
5,264,106 A 11/1993 McAleer et al.
5,265,888 A 11/1993 Yamamoto et al.
5,266,179 A 11/1993 Nankai et al.
5,269,212 A 12/1993 Peters et al.
5,269,891 A 12/1993 Colin
5,271,736 A 12/1993 Picha
5,271,815 A 12/1993 Wong
5,272,060 A 12/1993 Hamamoto et al.

(56) References Cited

U.S. PATENT DOCUMENTS 5,275,159 A 1/1994 Griebel
5,276,610 A 1/1994 Maeda et al.
5,278,079 A 1/1994 Gubinski et al.
5,279,294 A 1/1994 Anderson
5,279,543 A 1/1994 Glikfeld et al.
5,281,319 A 1/1994 Kaneko et al.
5,282,848 A 2/1994 Schmitt
5,282,950 A 2/1994 Dietze et al.
5,284,140 A 2/1994 Allen et al.
5,284,156 A 2/1994 Schramm et al.
5,284,570 A 2/1994 Savage et al.
5,284,748 A 2/1994 Mroczkowski et al.
5,285,513 A 2/1994 Kaufman et al.
5,285,792 A 2/1994 Sjoquist et al.
5,286,362 A 2/1994 Hoenes et al.
5,286,364 A 2/1994 Yacynych et al.
5,288,636 A 2/1994 Pollmann et al.
5,291,887 A 3/1994 Stanley et al.
5,293,546 A 3/1994 Tadros et al.
5,298,144 A 3/1994 Spokane
5,299,571 A 4/1994 Mastrototaro
5,304,127 A 4/1994 Kawahara et al.
5,304,468 A 4/1994 Phillips et al.
5,307,263 A 4/1994 Brown
5,309,919 A 5/1994 Snell et al.
5,310,469 A 5/1994 Cunningham et al.
5,310,885 A 5/1994 Maier et al.
5,312,361 A 5/1994 Zadini et al.
5,312,762 A 5/1994 Guiseppi-Elie
5,314,450 A 5/1994 Thompson
5,314,471 A 5/1994 Brauker et al.
5,316,008 A 5/1994 Suga et al.
5,318,521 A 6/1994 Slettenmark
5,320,098 A 6/1994 Davidson
5,320,725 A 6/1994 Gregg et al.
5,322,063 A 6/1994 Allen et al.
5,324,303 A 6/1994 Strong et al.
5,324,316 A 6/1994 Schulman et al.
5,324,322 A 6/1994 Grill et al.
5,326,356 A 7/1994 Della Valle et al.
5,326,449 A 7/1994 Cunningham
5,328,460 A 7/1994 Lord et al.
5,330,521 A 7/1994 Cohen
5,330,634 A 7/1994 Wong et al.
5,331,555 A 7/1994 Hashimoto et al.
5,331,966 A 7/1994 Bennett et al.
5,332,479 A 7/1994 Uenoyama et al.
5,336,204 A 8/1994 Matyas
5,337,258 A 8/1994 Dennis
5,337,747 A 8/1994 Neftel
5,340,722 A 8/1994 Wolfbeis et al.
5,342,409 A 8/1994 Mullett
5,342,789 A 8/1994 Chick et al.
5,343,869 A 9/1994 Pross et al.
5,344,454 A 9/1994 Clarke et al.
5,348,788 A 9/1994 White
5,350,407 A 9/1994 McClure et al.
5,352,348 A 10/1994 Young et al.
5,352,351 A 10/1994 White
5,354,319 A 10/1994 Wyborny et al.
5,354,447 A 10/1994 Uenoyama et al.
5,354,449 A 10/1994 Band et al.
5,356,348 A 10/1994 Bellio et al.
5,356,786 A 10/1994 Heller et al.
5,358,514 A 10/1994 Schulman et al.
5,362,307 A 11/1994 Guy et al.
5,364,797 A 11/1994 Olson et al.
5,366,609 A 11/1994 White et al.
5,368,028 A 11/1994 Palti
5,368,224 A 11/1994 Richardson et al.
5,368,562 A 11/1994 Blomquist et al.
5,370,622 A 12/1994 Livingston et al.
5,371,687 A 12/1994 Holmes, II et al.
5,371,734 A 12/1994 Fischer
5,372,133 A 12/1994 Hogen Esch
5,372,719 A 12/1994 Afeyan et al.
5,375,604 A 12/1994 Kelly et al.
5,376,070 A 12/1994 Purvis et al.
5,376,251 A 12/1994 Kaneko et al.
5,377,258 A 12/1994 Bro
5,378,628 A 1/1995 Gratzel et al.
5,379,238 A 1/1995 Stark
5,380,422 A 1/1995 Negishi et al.
5,380,536 A 1/1995 Hubbell et al.
5,382,346 A 1/1995 Uenoyama et al.
5,384,028 A 1/1995 Ito
5,387,327 A 2/1995 Khan
5,390,671 A 2/1995 Lord et al.
5,391,250 A 2/1995 Cheney, II et al.
5,393,903 A 2/1995 Gratzel et al.
5,395,504 A 3/1995 Saurer et al.
5,397,848 A 3/1995 Yang et al.
5,399,823 A 3/1995 McCusker
5,400,782 A 3/1995 Beaubiah
5,401,376 A 3/1995 Foos et al.
5,405,510 A 4/1995 Betts et al.
5,407,554 A 4/1995 Saurer
5,408,999 A 4/1995 Singh et al.
5,410,471 A 4/1995 Alyfuku et al.
5,410,474 A 4/1995 Fox
5,411,536 A 5/1995 Armstrong
5,411,647 A 5/1995 Johnson et al.
5,411,866 A 5/1995 Luong
5,413,690 A 5/1995 Kost et al.
5,422,246 A 6/1995 Koopal et al.
5,425,361 A 6/1995 Fenzlein et al.
5,425,717 A 6/1995 Mohiuddin
5,426,032 A 6/1995 Phillips
5,429,129 A 7/1995 Lovejoy et al.
5,429,735 A 7/1995 Johnson et al.
5,431,160 A 7/1995 Wilkins
5,431,691 A 7/1995 Snell et al.
5,431,806 A 7/1995 Suzuki et al.
5,431,921 A 7/1995 Thombre
5,433,710 A 7/1995 Van Antwerp et al.
5,437,973 A 8/1995 Vadgama et al.
5,437,999 A 8/1995 Diebold et al.
5,438,984 A 8/1995 Schoendorfer
5,445,611 A 8/1995 Eppstein et al.
5,445,920 A 8/1995 Saito
5,448,992 A 9/1995 Kupershmidt
5,451,260 A 9/1995 Versteeg et al.
5,452,173 A 9/1995 Brannon et al.
5,453,199 A 9/1995 Afeyan et al.
5,453,278 A 9/1995 Chan et al.
5,456,692 A 10/1995 Smith, Jr. et al.
5,456,940 A 10/1995 Funderburk
5,458,140 A 10/1995 Eppstein et al.
5,460,618 A 10/1995 Harreld
5,462,051 A 10/1995 Oka et al.
5,462,064 A 10/1995 D'Angelo et al.
5,462,525 A 10/1995 Srisathapat et al.
5,462,645 A 10/1995 Albery et al.
5,466,218 A 11/1995 Srisathapat et al.
5,466,356 A 11/1995 Schneider et al.
5,469,846 A 11/1995 Khan
5,472,317 A 12/1995 Field et al.
5,473,990 A 12/1995 Anderson et al.
5,474,552 A 12/1995 Palti
5,476,460 A 12/1995 Montalvo
5,476,488 A 12/1995 Morgan et al.
5,476,776 A 12/1995 Wilkins
5,477,855 A 12/1995 Schindler et al.
5,482,008 A 1/1996 Stafford et al.
5,482,473 A 1/1996 Lord et al.
5,484,404 A 1/1996 Schulman et al.
5,487,751 A 1/1996 Radons et al.
5,491,474 A 2/1996 Suni et al.
5,494,562 A 2/1996 Maley et al.
5,496,453 A 3/1996 Uenoyama et al.
5,497,772 A 3/1996 Schulman et al.
5,501,665 A 3/1996 Jhuboo et al.
5,501,956 A 3/1996 Wada et al.
5,502,396 A 3/1996 Desarzens et al.

(56) References Cited

U.S. PATENT DOCUMENTS 5,505,709 A 4/1996 Funderburk
5,505,713 A 4/1996 Van Antwerp
5,507,288 A 4/1996 Bocker et al.
5,508,171 A 4/1996 Walling et al.
5,508,203 A 4/1996 Fuller et al.
5,509,410 A 4/1996 Hill et al.
5,513,636 A 5/1996 Palti
5,514,103 A 5/1996 Srisathapat et al.
5,514,253 A 5/1996 Davis et al.
5,518,006 A 5/1996 Mawhirt et al.
5,518,601 A 5/1996 Foos et al.
5,520,731 A 5/1996 Esser et al.
5,520,787 A 5/1996 Hanagan et al.
5,522,865 A 6/1996 Schulman et al.
5,525,511 A 6/1996 D'Costa
5,526,120 A 6/1996 Jina et al.
5,527,288 A 6/1996 Gross et al.
5,527,307 A 6/1996 Srisathapat et al.
5,529,676 A 6/1996 Maley et al.
5,531,679 A 7/1996 Schulman et al.
5,531,878 A 7/1996 Vadgama et al.
5,538,007 A 7/1996 Gorman
5,538,511 A 7/1996 Van Antwerp et al.
5,540,828 A 7/1996 Yacynych
5,544,651 A 8/1996 Wilk
5,545,152 A 8/1996 Funderburk et al.
5,545,191 A 8/1996 Mann et al.
5,545,220 A 8/1996 Andrews et al.
5,545,223 A 8/1996 Neuenfeldt et al.
5,549,113 A 8/1996 Halleck et al.
5,549,115 A 8/1996 Morgan et al.
5,549,675 A 8/1996 Neuenfeldt et al.
5,551,427 A 9/1996 Altman
5,551,953 A 9/1996 Lattin et al.
5,552,027 A 9/1996 Birkle et al.
5,553,616 A 9/1996 Ham et al.
5,554,166 A 9/1996 Lange et al.
5,556,524 A 9/1996 Albers
5,558,640 A 9/1996 Pfeiler et al.
5,560,357 A 10/1996 Faupel et al.
5,562,713 A 10/1996 Silvian
5,564,439 A 10/1996 Picha
5,565,085 A 10/1996 Ikeda et al.
5,567,302 A 10/1996 Song et al.
5,568,806 A 10/1996 Cheney, II et al.
5,569,186 A 10/1996 Lord et al.
5,569,212 A 10/1996 Brown
5,569,462 A 10/1996 Martinson et al.
5,571,395 A 11/1996 Park et al.
5,571,682 A 11/1996 Jacobs et al.
5,573,506 A 11/1996 Vasko
5,573,647 A 11/1996 Maley et al.
5,575,895 A 11/1996 Ikeda et al.
5,575,930 A 11/1996 Tietje-Girault et al.
5,580,527 A 12/1996 Bell et al.
5,580,794 A 12/1996 Allen
5,582,184 A 12/1996 Erickson et al.
5,582,593 A 12/1996 Hultman
5,582,697 A 12/1996 Ikeda et al.
5,582,698 A 12/1996 Flaherty et al.
5,584,813 A 12/1996 Livingston et al.
5,584,876 A 12/1996 Bruchman et al.
5,586,553 A 12/1996 Halili et al.
5,587,273 A 12/1996 Yan et al.
5,588,560 A 12/1996 Benedict et al.
5,589,045 A 12/1996 Hyodo
5,589,133 A 12/1996 Suzuki
5,589,326 A 12/1996 Deng et al.
5,589,563 A 12/1996 Ward et al.
5,590,651 A 1/1997 Shaffer et al.
5,593,390 A 1/1997 Castellano et al.
5,593,440 A 1/1997 Brauker et al.
5,593,852 A 1/1997 Heller et al.
5,594,906 A 1/1997 Holmes, II et al.
5,596,150 A 1/1997 Arndt et al.
5,596,994 A 1/1997 Bro
5,601,435 A 2/1997 Quy
5,601,694 A 2/1997 Maley et al.
5,605,152 A 2/1997 Slate et al.
5,607,565 A 3/1997 Azarnia et al.
5,611,900 A 3/1997 Worden et al.
5,615,671 A 4/1997 Schoonen et al.
5,616,222 A 4/1997 Maley et al.
5,617,851 A 4/1997 Lipkovker
5,623,925 A 4/1997 Swenson et al.
5,624,537 A 4/1997 Turner et al.
5,628,309 A 5/1997 Brown
5,628,310 A 5/1997 Rao et al.
5,628,890 A 5/1997 Carter et al.
5,629,981 A 5/1997 Nerlikar
5,637,095 A 6/1997 Nason et al.
5,640,470 A 6/1997 Lyer et al.
5,640,764 A 6/1997 Strojnik
5,640,954 A 6/1997 Pfeiffer et al.
5,642,365 A 6/1997 Murakami et al.
5,643,212 A 7/1997 Coutre et al.
5,647,853 A 7/1997 Feldmann et al.
5,650,062 A 7/1997 Ikeda et al.
5,651,767 A 7/1997 Schulman et al.
5,651,869 A 7/1997 Yoshioka et al.
5,653,735 A 8/1997 Chen et al.
5,653,756 A 8/1997 Clarke et al.
5,653,863 A 8/1997 Genshaw et al.
5,658,250 A 8/1997 Blomquist et al.
5,658,330 A 8/1997 Carlisle et al.
5,660,163 A 8/1997 Schulman et al.
5,662,694 A 9/1997 Lidman et al.
5,665,065 A 9/1997 Colman et al.
5,667,983 A 9/1997 Abel et al.
5,670,031 A 9/1997 Hintsche et al.
5,676,820 A 10/1997 Wang et al.
5,678,571 A 10/1997 Brown
5,679,690 A 10/1997 Andre et al.
5,680,858 A 10/1997 Hansen et al.
5,682,233 A 10/1997 Brinda
5,682,884 A 11/1997 Hill
5,683,562 A 11/1997 Schaffar et al.
5,686,717 A 11/1997 Knowles et al.
5,686,829 A 11/1997 Girault
5,690,893 A 11/1997 Ozawa et al.
5,694,952 A 12/1997 Lidman et al.
5,695,473 A 12/1997 Olsen
5,695,623 A 12/1997 Michel et al.
5,695,947 A 12/1997 Guo et al.
5,695,949 A 12/1997 Galen et al.
5,696,314 A 12/1997 McCaffrey et al.
5,701,894 A 12/1997 Cherry et al.
5,704,354 A 1/1998 Preidel et al.
5,704,922 A 1/1998 Brown
5,706,807 A 1/1998 Picha
5,707,502 A 1/1998 McCaffrey et al.
5,708,247 A 1/1998 McAleer et al.
5,710,011 A 1/1998 Forrow et al.
5,710,630 A 1/1998 Essenpreis et al.
5,711,001 A 1/1998 Bussan et al.
5,711,297 A 1/1998 Iliff et al.
5,711,861 A 1/1998 Ward et al.
5,711,862 A 1/1998 Sakoda et al.
5,711,868 A 1/1998 Maley et al.
5,713,353 A 2/1998 Castano
5,713,888 A 2/1998 Neuenfeldt et al.
5,714,123 A 2/1998 Sohrab
5,718,234 A 2/1998 Warden et al.
5,720,720 A 2/1998 Laske et al.
5,720,733 A 2/1998 Brown
5,720,862 A 2/1998 Hamamoto et al.
5,721,783 A 2/1998 Anderson
5,722,397 A 3/1998 Eppstein
5,727,548 A 3/1998 Hill et al.
5,728,074 A 3/1998 Castellano et al.
5,728,352 A 3/1998 Poto et al.
5,730,124 A 3/1998 Yamauchi
5,730,654 A 3/1998 Brown
5,730,714 A 3/1998 Guy et al.

(56) References Cited

U.S. PATENT DOCUMENTS 5,733,336 A 3/1998 Neuenfeldt et al.
5,735,273 A 4/1998 Kurnik et al.
5,735,285 A 4/1998 Albert et al.
5,739,039 A 4/1998 Girault et al.
5,741,211 A 4/1998 Renirie et al.
5,741,319 A 4/1998 Woloszko et al.
5,741,330 A 4/1998 Brauker et al.
5,741,634 A 4/1998 Nozoe et al.
5,741,688 A 4/1998 Oxenboll et al.
5,743,262 A 4/1998 Lepper, Jr. et al.
5,746,217 A 5/1998 Erickson et al.
5,746,697 A 5/1998 Swedlow et al.
5,747,453 A 5/1998 Holladay et al.
5,747,669 A 5/1998 Suzuki
5,748,103 A 5/1998 Flach et al.
5,749,832 A 5/1998 Vadgama et al.
5,749,907 A 5/1998 Mann
5,750,926 A 5/1998 Schulman et al.
5,756,632 A 5/1998 Ward et al.
5,759,364 A 6/1998 Charlton et al.
5,766,151 A 6/1998 Valley et al.
5,770,028 A 6/1998 Maley et al.
5,771,001 A 6/1998 Cobb
5,771,890 A 6/1998 Tamada
5,771,891 A 6/1998 Gozani
5,772,586 A 6/1998 Heinonen et al.
5,776,106 A 7/1998 Matyas
5,777,060 A 7/1998 Van Antwerp
5,779,665 A 7/1998 Mastrototaro et al.
5,781,455 A 7/1998 Hyodo
5,782,814 A 7/1998 Brown et al.
5,782,912 A 7/1998 Brauker et al.
5,785,681 A 7/1998 Indravudh
5,786,439 A 7/1998 Van Antwerp et al.
5,786,584 A 7/1998 Button et al.
5,787,900 A 8/1998 Butler et al.
5,788,678 A 8/1998 Van Antwerp
5,791,344 A 8/1998 Schulman et al.
5,792,117 A 8/1998 Brown
5,792,668 A 8/1998 Fuller et al.
5,795,543 A 8/1998 Poto et al.
5,795,774 A 8/1998 Matsumoto et al.
5,798,065 A 8/1998 Picha
5,800,387 A 9/1998 Duffy et al.
5,800,420 A 9/1998 Gross et al.
5,800,529 A 9/1998 Brauker et al.
5,804,047 A 9/1998 Karube et al.
5,804,048 A 9/1998 Wong et al.
5,806,517 A 9/1998 Gerhardt et al.
5,807,315 A 9/1998 Van Antwerp et al.
5,807,375 A 9/1998 Gross et al.
5,807,406 A 9/1998 Brauker et al.
5,811,487 A 9/1998 Schulz, Jr. et al.
5,814,599 A 9/1998 Mitragotri et al.
5,820,551 A 10/1998 Hill et al.
5,820,570 A 10/1998 Erickson et al.
5,820,622 A 10/1998 Gross et al.
5,822,715 A 10/1998 Worthington et al.
5,823,802 A 10/1998 Bartley
5,825,488 A 10/1998 Kohl et al.
5,827,179 A 10/1998 Lichter et al.
5,827,183 A 10/1998 Kurnik et al.
5,827,184 A 10/1998 Netherly et al.
5,828,943 A 10/1998 Brown
5,830,132 A 11/1998 Robinson
5,830,341 A 11/1998 Gilmartin
5,832,448 A 11/1998 Brown
5,833,603 A 11/1998 Kovacs et al.
5,834,224 A 11/1998 Ruger et al.
5,836,887 A 11/1998 Oka et al.
5,836,989 A 11/1998 Shelton
5,837,454 A 11/1998 Cozzette et al.
5,837,546 A 11/1998 Allen et al.
5,837,728 A 11/1998 Purcell
5,840,020 A 11/1998 Heinonen et al.
5,840,148 A 11/1998 Campbell et al.
5,840,240 A 11/1998 Stenoien et al.
5,842,983 A 12/1998 Abel et al.
5,843,140 A 12/1998 Strojnik
5,844,862 A 12/1998 Cocatre-Zilgien
5,846,702 A 12/1998 Deng et al.
5,846,744 A 12/1998 Athey et al.
5,848,991 A 12/1998 Gross et al.
5,851,197 A 12/1998 Marano et al.
5,854,078 A 12/1998 Asher et al.
5,854,189 A 12/1998 Kruse et al.
5,857,967 A 1/1999 Frid et al.
5,857,983 A 1/1999 Douglas et al.
5,860,917 A 1/1999 Comanor et al.
5,861,009 A 1/1999 Armstrong et al.
5,861,019 A 1/1999 Sun et al.
5,862,803 A 1/1999 Besson et al.
5,871,465 A 2/1999 Vasko
5,871,499 A 2/1999 Hahn et al.
5,871,514 A 2/1999 Wiklund et al.
5,872,713 A 2/1999 Douglas et al.
5,872,820 A 2/1999 Upadrasta
5,873,990 A 2/1999 Wojciechowski et al.
5,876,484 A 3/1999 Raskin et al.
5,879,163 A 3/1999 Brown et al.
5,879,311 A 3/1999 Duchon et al.
5,879,373 A 3/1999 Roper et al.
5,880,829 A 3/1999 Kauhaniemi et al.
5,882,494 A 3/1999 Van Antwerp
5,885,211 A 3/1999 Eppstein et al.
5,885,245 A 3/1999 Lynch et al.
5,885,429 A 3/1999 Friese et al.
5,887,133 A 3/1999 Brown et al.
5,895,235 A 4/1999 Droz
5,895,371 A 4/1999 Levitas et al.
5,897,493 A 4/1999 Brown
5,897,578 A 4/1999 Wiklund et al.
5,898,025 A 4/1999 Burg et al.
5,899,855 A 5/1999 Brown
5,899,931 A 5/1999 Deschamp et al.
5,904,708 A 5/1999 Goedeke
5,913,310 A 6/1999 Brown
5,913,827 A 6/1999 Gorman
5,913,998 A 6/1999 Butler et al.
5,914,026 A 6/1999 Blubaugh, Jr. et al.
5,916,445 A 6/1999 Hjerten et al.
5,917,346 A 6/1999 Gord
5,918,603 A 7/1999 Brown
5,919,215 A 7/1999 Wiklund et al.
5,924,979 A 7/1999 Swedlow et al.
5,925,021 A 7/1999 Castellano et al.
5,928,130 A 7/1999 Schmidt
5,931,791 A 8/1999 Saltzstein et al.
5,931,814 A 8/1999 Alex et al.
5,933,136 A 8/1999 Brown
5,935,099 A 8/1999 Peterson et al.
5,935,785 A 8/1999 Reber et al.
5,940,801 A 8/1999 Brown
5,942,979 A 8/1999 Luppino
5,944,661 A 8/1999 Swette et al.
5,945,345 A 8/1999 Blatt et al.
5,947,749 A 9/1999 Rathburn
5,947,921 A 9/1999 Johnson et al.
5,948,512 A 9/1999 Kubota et al.
5,949,790 A 9/1999 Pehkonen et al.
5,950,632 A 9/1999 Reber et al.
5,951,300 A 9/1999 Brown
5,951,492 A 9/1999 Douglas et al.
5,951,521 A 9/1999 Mastrototaro et al.
5,951,836 A 9/1999 McAleer et al.
5,954,643 A 9/1999 VanAntwerp
5,954,685 A 9/1999 Tierney
5,954,700 A 9/1999 Kovelman
5,954,954 A 9/1999 Houck et al.
5,956,501 A 9/1999 Brown
5,957,854 A 9/1999 Besson et al.
5,957,890 A 9/1999 Mann et al.
5,957,903 A 9/1999 Mirzaee et al.
5,957,958 A 9/1999 Schulman et al.

(56) References Cited

U.S. PATENT DOCUMENTS 5,959,050 A 9/1999 Mosbach et al.
5,960,403 A 9/1999 Brown
5,961,451 A 10/1999 Reber et al.
5,963,132 A 10/1999 Yoakum
5,964,804 A 10/1999 Brauker et al.
5,964,993 A 10/1999 Blubaugh, Jr. et al.
5,965,380 A 10/1999 Heller et al.
5,968,839 A 10/1999 Blatt et al.
5,971,922 A 10/1999 Arita et al.
5,971,941 A 10/1999 Simons et al.
5,972,199 A 10/1999 Heller et al.
5,974,124 A 10/1999 Schlueter, Jr. et al.
5,976,085 A 11/1999 Kimball et al.
5,977,476 A 11/1999 Guha et al.
5,981,294 A 11/1999 Blatt et al.
5,985,129 A 11/1999 Gough et al.
5,987,352 A 11/1999 Klein et al.
5,987,353 A 11/1999 Khatchatrian et al.
5,989,409 A 11/1999 Kurnik et al.
5,994,476 A 11/1999 Shin et al.
5,995,860 A 11/1999 Sun et al.
5,995,869 A 11/1999 Cormier et al.
5,997,475 A 12/1999 Bortz
5,997,476 A 12/1999 Brown
5,997,501 A 12/1999 Gross et al.
5,998,791 A 12/1999 Matsumora
5,999,848 A 12/1999 Gord et al.
5,999,849 A 12/1999 Gord et al.
6,001,067 A 12/1999 Shults et al.
6,001,471 A 12/1999 Bries et al.
6,002,954 A 12/1999 Van Antwerp et al.
6,002,961 A 12/1999 Mitragotri et al.
6,004,441 A 12/1999 Fujiwara et al.
6,007,845 A 12/1999 Domb
6,011,984 A 1/2000 Van Antwerp et al.
6,013,113 A 1/2000 Mika
6,014,577 A 1/2000 Henning et al.
6,015,390 A 1/2000 Krag
6,016,448 A 1/2000 Busacker et al.
6,017,435 A 1/2000 Hassard et al.
6,018,678 A 1/2000 Mitragotri et al.
6,020,110 A 2/2000 Williams et al.
6,023,629 A 2/2000 Tamada
6,024,699 A 2/2000 Surwit et al.
6,026,320 A 2/2000 Carlson et al.
6,027,445 A 2/2000 Von Bahr
6,027,459 A 2/2000 Shain et al.
6,027,692 A 2/2000 Galen et al.
6,032,059 A 2/2000 Henning et al.
6,032,199 A 2/2000 Lim et al.
6,033,866 A 3/2000 Guo et al.
6,034,622 A 3/2000 Levine
6,035,237 A 3/2000 Schulman et al.
6,036,924 A 3/2000 Simons et al.
6,040,194 A 3/2000 Chick et al.
6,041,253 A 3/2000 Kost et al.
6,043,437 A 3/2000 Schulman et al.
6,046,056 A 4/2000 Parce et al.
6,048,691 A 4/2000 Maracas
6,049,727 A 4/2000 Crothall
6,051,372 A 4/2000 Bayerl et al.
6,051,389 A 4/2000 Ahl et al.
6,056,718 A 5/2000 Funderburk et al.
6,057,377 A 5/2000 Sasaki et al.
6,059,946 A 5/2000 Yukawa et al.
6,063,459 A 5/2000 Velte
6,063,637 A 5/2000 Arnold et al.
6,065,154 A 5/2000 Hulings et al.
6,066,083 A 5/2000 Slater et al.
6,066,243 A 5/2000 Anderson et al.
6,066,448 A 5/2000 Wohlstadter et al.
6,067,474 A 5/2000 Schulman et al.
6,068,615 A 5/2000 Brown et al.
6,071,249 A 6/2000 Cunningham et al.
6,071,251 A 6/2000 Cunningham et al.
6,071,294 A 6/2000 Simons et al.
6,071,391 A 6/2000 Gotoh et al.
6,071,406 A 6/2000 Tsou
6,073,049 A 6/2000 Alt et al.
6,074,725 A 6/2000 Kennedy
6,081,735 A 6/2000 Diab et al.
6,081,736 A 6/2000 Colvin et al.
6,083,523 A 7/2000 Dionne et al.
6,083,710 A 7/2000 Heller et al.
6,088,608 A 7/2000 Schulman et al.
6,091,975 A 7/2000 Daddona et al.
6,091,976 A 7/2000 Pfeiffer et al.
6,093,156 A 7/2000 Cunningham et al.
6,093,167 A 7/2000 Houben et al.
6,093,172 A 7/2000 Funderburk et al.
6,097,831 A 8/2000 Wieck et al.
6,099,484 A 8/2000 Douglas et al.
6,101,478 A 8/2000 Brown
6,103,033 A 8/2000 Say et al.
6,103,533 A 8/2000 Hassard et al.
6,106,780 A 8/2000 Douglas et al.
6,107,083 A 8/2000 Collins et al.
6,110,148 A 8/2000 Brown et al.
6,110,152 A 8/2000 Kovelman
6,113,537 A 9/2000 Castano
6,113,578 A 9/2000 Brown
6,115,634 A 9/2000 Donders et al.
6,117,290 A 9/2000 Say
6,119,028 A 9/2000 Schulman et al.
6,120,676 A 9/2000 Heller et al.
6,121,009 A 9/2000 Heller et al.
6,122,351 A 9/2000 Schlueter, Jr. et al.
6,122,536 A 9/2000 Sun et al.
6,123,827 A 9/2000 Wong et al.
6,123,902 A 9/2000 Koch et al.
6,125,978 A 10/2000 Ando et al.
6,134,461 A 10/2000 Say et al.
6,134,504 A 10/2000 Douglas et al.
6,135,978 A 10/2000 Houben et al.
6,139,718 A 10/2000 Kurnik et al.
6,141,573 A 10/2000 Kurnik et al.
6,142,939 A 11/2000 Eppstein et al.
6,142,972 A 11/2000 Cheikh
6,143,164 A 11/2000 Heller et al.
6,144,837 A 11/2000 Quy
6,144,869 A 11/2000 Berner et al.
6,144,871 A 11/2000 Saito et al.
6,144,922 A 11/2000 Douglas et al.
6,148,094 A 11/2000 Kinsella
6,150,128 A 11/2000 Uretsky
6,151,586 A 11/2000 Brown
6,153,062 A 11/2000 Saito et al.
6,153,069 A 11/2000 Pottgen et al.
6,154,675 A 11/2000 Juran et al.
6,154,676 A 11/2000 Levine
6,159,147 A 12/2000 Lichter et al.
6,161,095 A 12/2000 Brown
6,162,611 A 12/2000 Heller et al.
6,162,639 A 12/2000 Douglas
6,164,284 A 12/2000 Schulman et al.
6,167,362 A 12/2000 Brown et al.
6,167,614 B1 1/2001 Tuttle et al.
6,168,563 B1 1/2001 Brown
6,168,568 B1 1/2001 Gavriely
6,169,155 B1 1/2001 Alvarez et al.
6,170,318 B1 1/2001 Lewis
6,171,294 B1 1/2001 Southam et al.
6,175,752 B1 1/2001 Say et al.
6,180,416 B1 1/2001 Kurnik et al.
6,186,145 B1 2/2001 Brown
6,187,062 B1 2/2001 Oweis et al.
6,189,536 B1 2/2001 Martinez et al.
6,192,891 B1 2/2001 Gravel et al.
6,193,873 B1 2/2001 Ohara et al.
6,196,970 B1 3/2001 Brown
6,198,957 B1 3/2001 Green
6,200,265 B1 3/2001 Walsh et al.
6,200,772 B1 3/2001 Vadgama et al.
6,201,979 B1 3/2001 Kurnik et al.

(56) References Cited

U.S. PATENT DOCUMENTS 6,201,980 B1 3/2001 Darrow et al.
6,201,993 B1 3/2001 Kruse et al.
6,206,841 B1 3/2001 Cunningham et al.
6,206,856 B1 3/2001 Mahurkar
6,207,400 B1 3/2001 Kwon
6,208,894 B1 3/2001 Schulman et al.
6,210,272 B1 4/2001 Brown
6,210,976 B1 4/2001 Sabbadini
6,212,416 B1 4/2001 Ward et al.
6,212,424 B1 4/2001 Robinson
6,214,185 B1 4/2001 Offenbacher et al.
6,216,033 B1 4/2001 Southam et al.
6,219,565 B1 4/2001 Cupp et al.
6,219,574 B1 4/2001 Cormier et al.
6,223,083 B1 4/2001 Rosar
6,223,471 B1 5/2001 Barber
6,224,745 B1 5/2001 Baltruschat
6,230,051 B1 5/2001 Cormier et al.
6,230,059 B1 5/2001 Duffin
6,231,879 B1 5/2001 Li et al.
6,232,130 B1 5/2001 Wolf
6,232,370 B1 5/2001 Kubota et al.
6,232,783 B1 5/2001 Merrill
6,233,080 B1 5/2001 Brenner et al.
6,233,471 B1 5/2001 Berner et al.
6,233,539 B1 5/2001 Brown
6,238,813 B1 5/2001 Maile et al.
6,239,925 B1 5/2001 Ardrey et al.
6,241,704 B1 6/2001 Peterson et al.
6,241,862 B1 6/2001 McAleer et al.
6,241,863 B1 6/2001 Monbouquette
6,246,330 B1 6/2001 Nielsen
6,246,992 B1 6/2001 Brown
6,248,065 B1 6/2001 Brown
6,248,067 B1 6/2001 Causey, III et al.
6,248,093 B1 6/2001 Moberg
6,251,260 B1 6/2001 Heller et al.
6,251,280 B1 6/2001 Dai et al.
6,252,032 B1 6/2001 Van Antwerp et al.
6,253,804 B1 7/2001 Safabash
6,254,586 B1 7/2001 Mann et al.
6,256,522 B1 7/2001 Schultz
6,256,643 B1 7/2001 Cork et al.
6,259,587 B1 7/2001 Sheldon et al.
6,259,937 B1 7/2001 Schulman et al.
6,260,022 B1 7/2001 Brown
6,264,825 B1 7/2001 Blackburn et al.
6,266,645 B1 7/2001 Simpson
6,267,724 B1 7/2001 Taylor
6,268,161 B1 7/2001 Han et al.
6,268,913 B1 7/2001 Rising
6,270,455 B1 8/2001 Brown
6,272,364 B1 8/2001 Kurnik
6,272,480 B1 8/2001 Tresp et al.
6,274,285 B1 8/2001 Gries et al.
6,274,686 B1 8/2001 Mosbach
6,275,717 B1 8/2001 Gross et al.
6,280,416 B1 8/2001 Van Antwerp et al.
6,280,587 B1 8/2001 Matsumoto
6,281,006 B1 8/2001 Heller et al.
6,282,179 B1 8/2001 Sherman
6,283,943 B1 9/2001 Dy et al.
6,284,126 B1 9/2001 Kurnik et al.
6,284,478 B1 9/2001 Heller et al.
6,285,897 B1 9/2001 Kilcoyne et al.
6,289,238 B1 9/2001 Besson et al.
6,293,925 B1 9/2001 Safabash et al.
6,294,281 B1 9/2001 Heller
6,295,463 B1 9/2001 Stenzler
6,295,506 B1 9/2001 Heinonen et al.
6,298,254 B2 10/2001 Tamada
6,299,578 B1 10/2001 Kurnik et al.
6,299,757 B1 10/2001 Feldman et al.
6,300,002 B1 10/2001 Webb et al.
6,301,499 B1 10/2001 Carlson et al.
6,302,855 B1 10/2001 Lav et al.
6,304,766 B1 10/2001 Colvin, Jr. et al.
6,306,104 B1 10/2001 Cunningham et al.
6,309,351 B1 10/2001 Kurnik et al.
6,309,384 B1 10/2001 Harrington et al.
6,309,526 B1 10/2001 Fujiwara et al.
6,309,884 B1 10/2001 Cooper et al.
6,310,110 B1 10/2001 Markowitz et al.
6,312,388 B1 11/2001 Marcovecchio et al.
6,315,721 B2 11/2001 Schulman et al.
6,315,738 B1 11/2001 Nishikawa et al.
6,319,540 B1 11/2001 Van Antwerp et al.
6,319,566 B1 11/2001 Polanyi et al.
6,320,357 B1 11/2001 Peters et al.
6,324,428 B1 11/2001 Weinberg et al.
6,325,978 B1 12/2001 Labuda et al.
6,325,979 B1 12/2001 Hahn et al.
6,326,160 B1 12/2001 Dunn et al.
6,329,161 B1 12/2001 Heller et al.
6,329,929 B1 12/2001 Weijand et al.
6,330,426 B2 12/2001 Brown et al.
6,330,464 B1 12/2001 Colvin, Jr. et al.
6,331,518 B2 12/2001 Hemm et al.
6,333,189 B1 12/2001 Holladay et al.
6,334,778 B1 1/2002 Brown
6,336,900 B1 1/2002 Alleckson et al.
6,338,790 B1 1/2002 Feldman et al.
6,340,421 B1 1/2002 Vachon et al.
6,340,588 B1 1/2002 Nova et al.
6,341,232 B1 1/2002 Conn et al.
6,343,225 B1 1/2002 Clark, Jr.
6,352,505 B1 3/2002 Bortz
6,356,774 B1 3/2002 Bernstein et al.
6,356,776 B1 3/2002 Berner et al.
6,358,237 B1 3/2002 Paukovits et al.
6,360,888 B1 3/2002 McIvor et al.
6,363,282 B1 3/2002 Nichols et al.
6,365,670 B1 4/2002 Fry
6,366,793 B1 4/2002 Bell et al.
6,366,794 B1 4/2002 Moussy et al.
6,368,141 B1 4/2002 VanAntwerp et al.
6,368,272 B1 4/2002 Porumbescu
6,368,274 B1 4/2002 Van Antwerp et al.
6,370,410 B2 4/2002 Kurnik et al.
6,370,941 B2 4/2002 Nakamura
6,377,894 B1 4/2002 Deweese et al.
6,379,301 B1 4/2002 Worthington et al.
6,379,317 B1 4/2002 Kintzig et al.
6,383,767 B1 5/2002 Polak
6,387,048 B1 5/2002 Schulman et al.
6,391,643 B1 5/2002 Chen et al.
6,393,318 B1 5/2002 Conn et al.
6,394,952 B1 5/2002 Anderson et al.
6,398,562 B1 6/2002 Butler et al.
6,398,727 B1 6/2002 Bui et al.
6,402,689 B1 6/2002 Scarantino et al.
6,402,691 B1 6/2002 Peddicord et al.
6,405,066 B1 6/2002 Essenpreis et al.
6,406,066 B1 6/2002 Uegane
6,406,426 B1 6/2002 Reuss et al.
6,409,674 B1 6/2002 Brockway et al.
6,413,393 B1 7/2002 Van Antwerp et al.
6,416,471 B1 7/2002 Kumar et al.
6,416,651 B1 7/2002 Millar
6,418,332 B1 7/2002 Mastrototaro et al.
6,418,346 B1 7/2002 Nelson et al.
6,424,847 B1 7/2002 Mastrototaro et al.
6,424,867 B1 7/2002 Snell et al.
6,427,088 B1 7/2002 Bowman, IV et al.
6,434,409 B1 8/2002 Pfeiffer et al.
6,438,414 B1 8/2002 Conn et al.
6,440,068 B1 8/2002 Brown et al.
6,441,747 B1 8/2002 Khair et al.
6,442,433 B1 8/2002 Linberg
6,442,637 B1 8/2002 Hawkins et al.
6,443,942 B2 9/2002 Van Antwerp et al.
6,447,448 B1 9/2002 Ishikawa et al.
6,447,542 B1 9/2002 Weadock
6,454,710 B1 9/2002 Ballerstadt et al.

(56) References Cited

U.S. PATENT DOCUMENTS 6,459,917 B1 10/2002 Gowda et al.
6,461,496 B1 10/2002 Feldman et al.
6,462,162 B2 10/2002 Van Antwerp et al.
6,464,687 B1 10/2002 Ishikawa et al.
6,464,848 B1 10/2002 Matsumoto
6,464,849 B1 10/2002 Say et al.
6,466,810 B1 10/2002 Ward et al.
6,468,222 B1 10/2002 Mault et al.
6,469,526 B1 10/2002 Franklin
6,471,645 B1 10/2002 Warkentin et al.
6,471,689 B1 10/2002 Joseph et al.
6,472,122 B1 10/2002 Schulman et al.
6,475,180 B2 11/2002 Peterson et al.
6,475,750 B1 11/2002 Han et al.
6,477,392 B1 11/2002 Honigs et al.
6,477,395 B2 11/2002 Schulman et al.
6,478,736 B1 11/2002 Mault
6,480,730 B2 11/2002 Darrow et al.
6,481,440 B2 11/2002 Gielen et al.
6,482,158 B2 11/2002 Mault
6,482,604 B2 11/2002 Kwon
6,484,045 B1 11/2002 Holker et al.
6,484,046 B1 11/2002 Say et al.
6,485,138 B1 11/2002 Kubota et al.
6,485,465 B2 11/2002 Moberg et al.
6,487,429 B2 11/2002 Hockersmith et al.
6,494,830 B1 12/2002 Wessel
6,496,728 B2 12/2002 Li et al.
6,498,043 B1 12/2002 Schulman et al.
6,498,941 B1 12/2002 Jackson
6,505,059 B1 1/2003 Kollias et al.
6,510,329 B2 1/2003 Heckel
6,512,939 B1 1/2003 Colvin et al.
6,513,532 B2 2/2003 Mault et al.
6,514,460 B1 2/2003 Fendrock
6,514,718 B2 2/2003 Heller et al.
6,515,593 B1 2/2003 Stark et al.
6,520,326 B2 2/2003 McIvor et al.
6,520,997 B1 2/2003 Pekkarinen et al.
6,526,298 B1 2/2003 Khalil et al.
6,527,729 B1 3/2003 Turcott
6,528,584 B2 3/2003 Kennedy et al.
6,529,755 B2 3/2003 Kurnik et al.
6,529,772 B2 3/2003 Carlson et al.
6,530,915 B1 3/2003 Eppstein et al.
6,534,322 B1 3/2003 Sabbadini
6,534,323 B1 3/2003 Sabbadini
6,534,711 B1 3/2003 Pollack
6,535,753 B1 3/2003 Raskas
6,537,243 B1 3/2003 Henning et al.
6,537,318 B1 3/2003 Ita et al.
6,540,675 B2 4/2003 Aceti et al.
6,541,107 B1 4/2003 Zhong et al.
6,544,212 B2 4/2003 Galley et al.
6,545,085 B2 4/2003 Kilgour et al.
6,546,268 B1 4/2003 Ishikawa et al.
6,546,269 B1 4/2003 Kurnik
6,547,839 B2 4/2003 Zhang et al.
6,549,796 B2 4/2003 Sohrab
6,551,276 B1 4/2003 Mann et al.
6,551,494 B1 4/2003 Heller et al.
6,551,496 B1 4/2003 Moles et al.
6,553,241 B2 4/2003 Mannheimer et al.
6,553,244 B2 4/2003 Lesho et al.
6,554,798 B1 4/2003 Mann et al.
6,558,320 B1 5/2003 Causey, III et al.
6,558,321 B1 5/2003 Burd et al.
6,558,351 B1 5/2003 Steil et al.
6,560,471 B1 5/2003 Heller et al.
6,561,978 B1 5/2003 Conn et al.
6,562,001 B2 5/2003 Lebel et al.
6,564,105 B2 5/2003 Starkweather et al.
6,565,509 B1 5/2003 Say et al.
6,569,309 B2 5/2003 Otsuka et al.
6,569,521 B1 5/2003 Sheridan et al.
6,571,128 B2 5/2003 Lebel et al.
6,571,200 B1 5/2003 Mault
6,572,545 B2 6/2003 Knobbe et al.
6,574,490 B2 6/2003 Abbink et al.
6,575,905 B2 6/2003 Knobbe et al.
6,576,101 B1 6/2003 Heller et al.
6,576,117 B1 6/2003 Iketaki et al.
6,577,893 B1 6/2003 Besson et al.
6,577,899 B2 6/2003 Lebel et al.
6,579,242 B2 6/2003 Bui et al.
6,579,498 B1 6/2003 Eglise
6,579,690 B1 6/2003 Bonnecaze et al.
6,584,335 B1 6/2003 Haar et al.
6,585,644 B2 7/2003 Lebel et al.
6,585,675 B1 7/2003 O'Mahony et al.
6,585,763 B1 7/2003 Keilman et al.
6,587,705 B1 7/2003 Kim et al.
6,588,644 B2 7/2003 Simon
6,589,205 B1 7/2003 Meadows
6,589,229 B1 7/2003 Connelly et al.
6,591,125 B1 7/2003 Buse et al.
6,591,126 B2 7/2003 Roeper et al.
6,594,514 B2 7/2003 Berner et al.
6,595,919 B2 7/2003 Berner et al.
6,595,929 B2 7/2003 Stivoric et al.
6,599,406 B1 7/2003 Kawanaka et al.
6,602,678 B2 8/2003 Kwon et al.
6,602,909 B1 8/2003 Jarowski
6,605,072 B2 8/2003 Struys et al.
6,605,200 B1 8/2003 Mao et al.
6,605,201 B1 8/2003 Mao et al.
6,607,509 B2 8/2003 Bobroff et al.
6,607,658 B1 8/2003 Heller et al.
6,610,012 B2 8/2003 Mault
6,612,306 B1 9/2003 Mault
6,612,984 B1 9/2003 Kerr
6,613,379 B2 9/2003 Ward et al.
6,615,078 B1 9/2003 Burson et al.
6,616,819 B1 9/2003 Liamos et al.
6,618,603 B2 9/2003 Varalli et al.
6,618,934 B1 9/2003 Feldman et al.
6,620,106 B2 9/2003 Mault
6,627,058 B1 9/2003 Chan
6,629,776 B2 10/2003 Bell et al.
6,629,934 B2 10/2003 Mault et al.
6,633,772 B2 10/2003 Ford et al.
6,635,014 B2 10/2003 Starkweather et al.
6,635,167 B1 10/2003 Richards et al.
6,638,772 B1 10/2003 Douglas et al.
6,641,533 B2 11/2003 Causey, III et al.
6,642,015 B2 11/2003 Vachon et al.
6,644,321 B1 11/2003 Behm
6,645,142 B2 11/2003 Braig et al.
6,645,181 B1 11/2003 Lavi et al.
6,648,821 B2 11/2003 Lebel et al.
6,653,091 B1 11/2003 Dunn et al.
6,654,625 B1 11/2003 Say et al.
6,659,948 B2 12/2003 Lebel et al.
6,668,196 B1 12/2003 Villegas et al.
6,671,554 B2 12/2003 Gibson et al.
6,673,596 B1 1/2004 Sayler et al.
6,673,625 B2 1/2004 Satcher, Jr. et al.
6,682,938 B1 1/2004 Satcher, Jr. et al.
6,683,040 B2 1/2004 Bragulla et al.
6,683,535 B1 1/2004 Utke
6,687,522 B2 2/2004 Tamada
6,687,546 B2 2/2004 Lebel et al.
6,689,056 B1 2/2004 Kilcoyne et al.
6,689,091 B2 2/2004 Bui et al.
6,689,265 B2 2/2004 Heller et al.
6,693,069 B2 2/2004 Korber et al.
6,694,158 B2 2/2004 Polak
6,694,191 B2 2/2004 Starkweather et al.
6,695,860 B1 2/2004 Ward et al.
6,699,218 B2 3/2004 Flaherty et al.
6,699,383 B2 3/2004 Lemire et al.
6,702,857 B2 3/2004 Brauker et al.
6,702,972 B1 3/2004 Markle
6,704,587 B1 3/2004 Kumar et al.

(56) References Cited

U.S. PATENT DOCUMENTS 6,705,833 B2 3/2004 Tam et al.
6,708,049 B1 3/2004 Berson et al.
6,711,423 B2 3/2004 Colvin, Jr.
6,721,587 B2 4/2004 Gough
6,723,046 B2 4/2004 Lichtenstein et al.
6,728,560 B2 4/2004 Kollias et al.
6,730,200 B1 5/2004 Stewart et al.
6,731,976 B2 5/2004 Penn et al.
6,733,446 B2 5/2004 Lebel et al.
6,733,655 B1 5/2004 Davies et al.
6,734,162 B2 5/2004 Van Antwerp et al.
6,736,777 B2 5/2004 Kim et al.
6,737,401 B2 5/2004 Kim et al.
6,738,654 B2 5/2004 Sohrab
6,740,075 B2 5/2004 Lebel et al.
6,741,163 B1 5/2004 Roberts
6,741,876 B1 5/2004 Scecina et al.
6,741,877 B1 5/2004 Shults et al.
6,743,635 B2 6/2004 Neel et al.
6,749,587 B2 6/2004 Flaherty
6,750,311 B1 6/2004 Van Antwerp et al.
6,758,810 B2 7/2004 Lebel et al.
6,764,581 B1 7/2004 Forrow et al.
6,766,183 B2 7/2004 Walsh et al.
6,766,201 B2 7/2004 Von Arx et al.
6,768,425 B2 7/2004 Flaherty et al.
6,770,030 B1 8/2004 Schaupp et al.
6,770,729 B2 8/2004 Van Antwerp et al.
6,771,995 B2 8/2004 Kurnik et al.
6,773,563 B2 8/2004 Matsumoto
6,773,565 B2 8/2004 Kunimoto et al.
6,773,671 B1 8/2004 Lewis et al.
6,780,297 B2 8/2004 Matsumoto et al.
6,780,871 B2 8/2004 Glick et al.
6,784,274 B2 8/2004 Van Antwerp et al.
6,790,178 B1 9/2004 Mault et al.
6,793,802 B2 9/2004 Lee et al.
6,794,195 B2 9/2004 Colvin, Jr.
6,799,149 B2 9/2004 Hartlaub
6,800,451 B2 10/2004 Daniloff et al.
6,800,488 B2 10/2004 Khan et al.
6,801,041 B2 10/2004 Karinka et al.
6,801,420 B2 10/2004 Talbot et al.
6,802,957 B2 10/2004 Jung et al.
6,804,544 B2 10/2004 Van Antwerp et al.
6,809,507 B2 10/2004 Morgan et al.
6,809,653 B1 10/2004 Mann et al.
6,809,807 B1 10/2004 Erickson et al.
6,810,290 B2 10/2004 Lebel et al.
6,811,533 B2 11/2004 Lebel et al.
6,811,534 B2 11/2004 Bowman, IV et al.
6,811,659 B2 11/2004 Vachon
6,812,031 B1 11/2004 Carlsson
6,813,516 B2 11/2004 Ujhelyi et al.
6,813,519 B2 11/2004 Lebel et al.
6,814,843 B1 11/2004 Bhullar et al.
6,815,186 B2 11/2004 Clark, Jr.
6,816,742 B2 11/2004 Kim et al.
6,827,829 B2 12/2004 Kawanaka et al.
6,830,549 B2 12/2004 Bui et al.
6,835,553 B2 12/2004 Han et al.
6,837,858 B2 1/2005 Cunningham et al.
6,840,912 B2 1/2005 Kloepfer et al.
6,844,023 B2 1/2005 Schulman et al.
RE38,698 E 2/2005 Kurnik et al.
6,849,237 B2 2/2005 Housefield et al.
6,850,790 B2 2/2005 Berner et al.
6,852,500 B1 2/2005 Hoss et al.
6,852,694 B2 2/2005 Van Antwerp et al.
6,853,854 B1 2/2005 Proniewicz et al.
6,855,115 B2 2/2005 Fonseca et al.
6,856,928 B2 2/2005 Harmon
6,858,403 B2 2/2005 Han et al.
6,862,465 B2 3/2005 Shults et al.
6,862,466 B2 3/2005 Ackerman
6,867,051 B1 3/2005 Anderson et al.
6,869,413 B2 3/2005 Langley et al.
6,872,200 B2 3/2005 Mann et al.
6,873,268 B2 3/2005 Lebel et al.
6,875,386 B1 4/2005 Ward et al.
6,879,849 B2 4/2005 Begic
6,881,378 B1 4/2005 Zimmer et al.
6,881,551 B2 4/2005 Heller et al.
6,882,940 B2 4/2005 Potts et al.
6,885,883 B2 4/2005 Parris et al.
6,891,317 B2 5/2005 Pei et al.
6,892,085 B2 5/2005 McIvor et al.
6,893,552 B1 5/2005 Wang et al.
6,895,263 B2 5/2005 Shin et al.
6,899,683 B2 5/2005 Mault et al.
6,899,684 B2 5/2005 Mault et al.
6,902,905 B2 6/2005 Burson et al.
6,904,301 B2 6/2005 Raskas
6,907,127 B1 6/2005 Kravitz et al.
6,915,147 B2 7/2005 Lebel et al.
6,918,874 B1 7/2005 Hatch et al.
6,922,578 B2 7/2005 Eppstein et al.
6,922,584 B2 7/2005 Wang et al.
RE38,775 E 8/2005 Kurnik et al.
6,923,764 B2 8/2005 Aceti et al.
6,923,936 B2 8/2005 Swanson et al.
6,925,317 B1 8/2005 Samuels et al.
6,925,393 B1 8/2005 Kalatz et al.
6,927,246 B2 8/2005 Noronha et al.
6,931,327 B2 8/2005 Goode, Jr. et al.
6,932,084 B2 8/2005 Estes et al.
6,932,894 B2 8/2005 Mao et al.
6,936,006 B2 8/2005 Sabra
6,936,029 B2 8/2005 Mann et al.
6,940,590 B2 9/2005 Colvin, Jr. et al.
6,941,163 B2 9/2005 Ford et al.
6,946,299 B2 9/2005 Neel et al.
6,946,996 B2 9/2005 Koyama
6,949,816 B2 9/2005 Brown et al.
6,950,708 B2 9/2005 Bowman IV et al.
6,951,631 B1 10/2005 Catt et al.
6,952,603 B2 10/2005 Gerber et al.
6,952,604 B2 10/2005 DeNuzzio et al.
6,953,693 B2 10/2005 Neel et al.
6,954,673 B2 10/2005 Von Arx et al.
6,955,650 B2 10/2005 Mault et al.
6,957,102 B2 10/2005 Silver et al.
6,957,107 B2 10/2005 Rogers et al.
6,958,691 B1 10/2005 Anderson et al.
6,958,705 B2 10/2005 Lebel et al.
6,959,247 B2 10/2005 Neel et al.
6,964,871 B2 11/2005 Bell et al.
6,965,791 B1 11/2005 Hitchcock et al.
6,968,294 B2 11/2005 Gutta et al.
6,968,375 B1 11/2005 Brown
6,972,080 B1 12/2005 Tomioka et al.
6,973,706 B2 12/2005 Say et al.
6,974,437 B2 12/2005 Lebel et al.
6,978,182 B2 12/2005 Mazar et al.
6,979,326 B2 12/2005 Mann et al.
6,990,366 B2 1/2006 Say et al.
6,991,096 B2 1/2006 Gottlieb et al.
6,997,907 B2 2/2006 Safabash et al.
6,997,920 B2 2/2006 Mann et al.
6,998,247 B2 2/2006 Monfre et al.
6,999,810 B2 2/2006 Berner et al.
7,003,336 B2 2/2006 Holker et al.
7,003,341 B2 2/2006 Say et al.
7,004,901 B2 2/2006 Fish
7,005,048 B1 2/2006 Watanabe et al.
7,005,857 B2 2/2006 Stiene et al.
7,011,630 B2 3/2006 Desai et al.
7,016,721 B2 3/2006 Lee et al.
7,018,366 B2 3/2006 Easter
7,018,568 B2 3/2006 Tierney
7,022,072 B2 4/2006 Fox et al.
7,024,236 B2 4/2006 Ford et al.
7,024,245 B2 4/2006 Lebel et al.
7,025,743 B2 4/2006 Mann et al.

(56) References Cited

U.S. PATENT DOCUMENTS 7,029,444 B2 4/2006 Shin et al.
7,034,677 B2 4/2006 Steinthal et al.
7,039,810 B1 5/2006 Nichols
7,041,057 B1 5/2006 Faupel et al.
7,041,468 B2 5/2006 Drucker et al.
7,045,054 B1 5/2006 Buck et al.
7,049,277 B2 5/2006 Bragulla et al.
7,052,472 B1 5/2006 Miller et al.
7,052,483 B2 5/2006 Wojcik
7,056,302 B2 6/2006 Douglas
7,058,437 B2 6/2006 Buse et al.
7,060,059 B2 6/2006 Keith et al.
7,070,580 B2 7/2006 Nielsen
7,072,718 B2 7/2006 VonArx et al.
7,072,802 B2 7/2006 Hartlaub
7,074,307 B2 7/2006 Simpson et al.
7,077,328 B2 7/2006 Krishnaswamy et al.
7,081,195 B2 7/2006 Simpson et al.
7,082,334 B2 7/2006 Boute et al.
7,098,803 B2 8/2006 Mann et al.
7,108,778 B2 9/2006 Simpson et al.
7,109,878 B2 9/2006 Mann et al.
7,110,803 B2 9/2006 Shults et al.
7,112,265 B1 9/2006 McAleer et al.
7,113,821 B1 9/2006 Sun et al.
7,115,884 B1 10/2006 Walt et al.
7,133,710 B2 11/2006 Acosta et al.
7,134,999 B2 11/2006 Brauker et al.
7,135,100 B1 11/2006 Lau et al.
7,136,689 B2 11/2006 Shults et al.
7,137,964 B2 11/2006 Flaherty
7,150,975 B2 12/2006 Tamada et al.
7,153,265 B2 12/2006 Vachon
7,160,251 B2 1/2007 Neel et al.
7,160,678 B1 1/2007 Kayyem et al.
7,163,511 B2 1/2007 Conn et al.
7,166,074 B2 1/2007 Reghabi et al.
7,169,289 B2 1/2007 Schulein et al.
7,171,274 B2 1/2007 Starkweather et al.
7,177,690 B2 2/2007 Woods et al.
7,183,068 B2 2/2007 Burson et al.
7,183,102 B2 2/2007 Monfre et al.
7,187,528 B2 3/2007 Talbot et al.
7,189,341 B2 3/2007 Li et al.
7,190,988 B2 3/2007 Say et al.
7,192,450 B2 3/2007 Brauker et al.
7,198,606 B2 4/2007 Boecker et al.
7,203,549 B2 4/2007 Schommer et al.
7,207,974 B2 4/2007 Safabash et al.
7,215,991 B2 5/2007 Besson et al.
7,218,890 B1 5/2007 Iseli et al.
7,225,535 B2 6/2007 Feldman et al.
7,226,978 B2 6/2007 Tapsak et al.
7,228,163 B2 6/2007 Ackerman
7,233,817 B2 6/2007 Yen
7,241,265 B2 7/2007 Cummings et al.
7,248,912 B2 7/2007 Gough et al.
7,248,929 B2 7/2007 Meadows et al.
7,261,691 B1 8/2007 Asomani
7,267,665 B2 9/2007 Steil et al.
7,276,029 B2 10/2007 Goode, Jr. et al.
7,278,983 B2 10/2007 Ireland et al.
7,295,867 B2 11/2007 Berner et al.
7,299,082 B2 11/2007 Feldman et al.
7,310,544 B2 12/2007 Brister et al.
7,318,816 B2 1/2008 Bobroff et al.
7,324,012 B2 1/2008 Mann et al.
7,329,239 B2 2/2008 Safabash et al.
7,344,499 B1 3/2008 Prausnitz et al.
7,347,973 B2 3/2008 Douglas et al.
7,354,420 B2 4/2008 Steil et al.
7,364,592 B2 4/2008 Carr-Brendel et al.
7,366,556 B2 4/2008 Brister et al.
7,379,765 B2 5/2008 Petisce et al.
7,384,396 B2 6/2008 Samuels et al.
7,399,277 B2 7/2008 Saidara et al.
7,402,153 B2 7/2008 Steil et al.
7,406,105 B2 7/2008 DelMain et al.
7,417,164 B2 8/2008 Suri
7,424,318 B2 9/2008 Brister et al.
7,426,408 B2 9/2008 DeNuzzio et al.
7,460,898 B2 12/2008 Brister et al.
7,467,003 B2 12/2008 Brister et al.
7,467,065 B2 12/2008 Neel et al.
7,471,972 B2 12/2008 Rhodes et al.
7,494,465 B2 2/2009 Brister et al.
7,497,827 B2 3/2009 Brister et al.
7,519,408 B2 4/2009 Rasdal et al.
7,519,478 B2 4/2009 Bartkowiak et al.
7,523,004 B2 4/2009 Bartkowiak et al.
7,525,298 B2 4/2009 Morgan et al.
7,545,272 B2 6/2009 Goodnow et al.
7,547,281 B2 6/2009 Hayes et al.
7,583,990 B2 9/2009 Goode, Jr. et al.
7,587,287 B2 9/2009 Connolly et al.
7,591,801 B2 9/2009 Brauker et al.
7,599,726 B2 10/2009 Goode, Jr. et al.
7,613,491 B2 11/2009 Boock et al.
7,615,007 B2 11/2009 Shults et al.
7,618,369 B2 11/2009 Hayter et al.
7,624,028 B1 11/2009 Brown
7,632,228 B2 12/2009 Brauker et al.
7,637,868 B2 12/2009 Saint et al.
7,640,048 B2 12/2009 Dobbles et al.
7,651,596 B2 1/2010 Petisce et al.
7,654,956 B2 2/2010 Brister et al.
7,657,297 B2 2/2010 Simpson et al.
7,689,437 B1 3/2010 Teller et al.
7,711,402 B2 5/2010 Shults et al.
7,713,574 B2 5/2010 Brister et al.
7,715,893 B2 5/2010 Kamath et al.
7,761,130 B2 7/2010 Simpson et al.
7,771,352 B2 8/2010 Shults et al.
7,774,145 B2 8/2010 Brauker et al.
7,775,975 B2 8/2010 Brister et al.
7,778,680 B2 8/2010 Goode, Jr. et al.
7,783,333 B2 8/2010 Brister et al.
7,792,562 B2 9/2010 Shults et al.
7,797,028 B2 9/2010 Goode, Jr. et al.
7,819,161 B2 10/2010 Neel et al.
7,826,981 B2 11/2010 Goode, Jr. et al.
7,828,728 B2 11/2010 Boock et al.
7,831,287 B2 11/2010 Brister et al.
7,835,777 B2 11/2010 Shults et al.
7,857,760 B2 12/2010 Brister et al.
7,860,545 B2 12/2010 Shults et al.
7,875,293 B2 1/2011 Shults et al.
7,881,763 B2 2/2011 Brauker et al.
7,883,015 B2 2/2011 Ackermann et al.
7,885,697 B2 2/2011 Brister et al.
7,896,809 B2 3/2011 Simpson et al.
7,899,511 B2 3/2011 Shults et al.
7,901,354 B2 3/2011 Shults et al.
7,901,394 B2 3/2011 Ireland et al.
7,914,450 B2 3/2011 Goode et al.
7,914,460 B2 3/2011 Melker et al.
7,925,321 B2 4/2011 Goode et al.
7,933,639 B2 4/2011 Goode et al.
7,955,261 B2 6/2011 Goode et al.
7,955,856 B2 6/2011 Neel et al.
7,959,569 B2 6/2011 Goode et al.
7,979,104 B2 7/2011 Kamath et al.
7,986,986 B2 7/2011 Goode et al.
8,160,669 B2 4/2012 Brauker et al.
2001/0011224 A1 8/2001 Brown
2001/0016310 A1 8/2001 Brown et al.
2001/0016682 A1 8/2001 Berner et al.
2001/0016683 A1 8/2001 Darrow et al.
2001/0020124 A1 9/2001 Tamada
2001/0029340 A1 10/2001 Mault et al.
2001/0032278 A1 10/2001 Brown et al.
2001/0037060 A1 11/2001 Thompson et al.
2001/0037069 A1 11/2001 Carlson et al.
2001/0039504 A1 11/2001 Linberg et al.

(56) References Cited

U.S. PATENT DOCUMENTS

| | | | |
|---|---|---|---|
| 2001/0041830 | A1 | 11/2001 | Varalli et al. |
| 2001/0044581 | A1 | 11/2001 | Mault |
| 2001/0044588 | A1 | 11/2001 | Mault |
| 2001/0047125 | A1 | 11/2001 | Quy |
| 2001/0049096 | A1 | 12/2001 | Brown |
| 2001/0049470 | A1 | 12/2001 | Mault et al. |
| 2001/0051768 | A1 | 12/2001 | Schulman et al. |
| 2001/0056328 | A1 | 12/2001 | Trippel et al. |
| 2002/0002326 | A1 | 1/2002 | Causey, III et al. |
| 2002/0002328 | A1 | 1/2002 | Tamada |
| 2002/0004640 | A1 | 1/2002 | Conn et al. |
| 2002/0009810 | A1 | 1/2002 | O'Connor et al. |
| 2002/0010414 | A1 | 1/2002 | Coston et al. |
| 2002/0016530 | A1 | 2/2002 | Brown |
| 2002/0016535 | A1 | 2/2002 | Martin et al. |
| 2002/0019022 | A1 | 2/2002 | Dunn et al. |
| 2002/0019330 | A1 | 2/2002 | Murray et al. |
| 2002/0019586 | A1 | 2/2002 | Teller et al. |
| 2002/0019748 | A1 | 2/2002 | Brown |
| 2002/0022883 | A1 | 2/2002 | Burg |
| 2002/0023852 | A1 | 2/2002 | McIvor et al. |
| 2002/0026111 | A1 | 2/2002 | Ackerman |
| 2002/0026937 | A1 | 3/2002 | Mault |
| 2002/0027164 | A1 | 3/2002 | Mault et al. |
| 2002/0028995 | A1 | 3/2002 | Mault |
| 2002/0040208 | A1 | 4/2002 | Flaherty et al. |
| 2002/0042090 | A1 | 4/2002 | Heller et al. |
| 2002/0042561 | A1 | 4/2002 | Schulman et al. |
| 2002/0043471 | A1 | 4/2002 | Ikeda et al. |
| 2002/0045808 | A1 | 4/2002 | Ford et al. |
| 2002/0047867 | A1 | 4/2002 | Mault et al. |
| 2002/0049482 | A1 | 4/2002 | Fabian et al. |
| 2002/0053637 | A1 | 5/2002 | Conn et al. |
| 2002/0055673 | A1 | 5/2002 | Van Antwerp et al. |
| 2002/0062069 | A1 | 5/2002 | Mault |
| 2002/0063060 | A1 | 5/2002 | Gascoyne et al. |
| 2002/0065453 | A1 | 5/2002 | Lesho et al. |
| 2002/0068858 | A1 | 6/2002 | Braig et al. |
| 2002/0068860 | A1 | 6/2002 | Clark, Jr. |
| 2002/0072858 | A1 | 6/2002 | Cheng |
| 2002/0077765 | A1 | 6/2002 | Mault |
| 2002/0077766 | A1 | 6/2002 | Mault |
| 2002/0081559 | A1 | 6/2002 | Brown et al. |
| 2002/0083461 | A1 | 6/2002 | Hutcheson et al. |
| 2002/0084196 | A1 | 7/2002 | Liamos et al. |
| 2002/0087056 | A1 | 7/2002 | Aceti et al. |
| 2002/0091312 | A1 | 7/2002 | Berner et al. |
| 2002/0099282 | A1 | 7/2002 | Knobbe et al. |
| 2002/0099997 | A1 | 7/2002 | Piret |
| 2002/0103425 | A1 | 8/2002 | Mault |
| 2002/0107433 | A1 | 8/2002 | Mault |
| 2002/0107476 | A1 | 8/2002 | Mann et al. |
| 2002/0109600 | A1 | 8/2002 | Mault et al. |
| 2002/0109621 | A1 | 8/2002 | Khair et al. |
| 2002/0111547 | A1 | 8/2002 | Knobbe et al. |
| 2002/0119711 | A1 | 8/2002 | Van Antwerp et al. |
| 2002/0124017 | A1 | 9/2002 | Mault |
| 2002/0128594 | A1 | 9/2002 | Das et al. |
| 2002/0130042 | A1 | 9/2002 | Moerman et al. |
| 2002/0133378 | A1 | 9/2002 | Mault et al. |
| 2002/0151796 | A1 | 10/2002 | Koulik |
| 2002/0151816 | A1 | 10/2002 | Rich et al. |
| 2002/0155615 | A1 | 10/2002 | Novikov et al. |
| 2002/0161286 | A1 | 10/2002 | Gerber et al. |
| 2002/0161288 | A1 | 10/2002 | Shin et al. |
| 2002/0169369 | A1 | 11/2002 | Ward et al. |
| 2002/0177764 | A1 | 11/2002 | Sohrab |
| 2002/0182241 | A1 | 12/2002 | Borenstein et al. |
| 2002/0188185 | A1 | 12/2002 | Sohrab |
| 2002/0188216 | A1 | 12/2002 | Kayyali et al. |
| 2002/0193885 | A1 | 12/2002 | Legeay et al. |
| 2002/0198513 | A1 | 12/2002 | Lebel et al. |
| 2003/0004457 | A1 | 1/2003 | Andersson |
| 2003/0006669 | A1 | 1/2003 | Pei et al. |
| 2003/0023171 | A1 | 1/2003 | Sato et al. |
| 2003/0023182 | A1 | 1/2003 | Mault et al. |
| 2003/0023317 | A1 | 1/2003 | Brauker et al. |
| 2003/0028089 | A1 | 2/2003 | Galley et al. |
| 2003/0028120 | A1 | 2/2003 | Mault et al. |
| 2003/0032077 | A1 | 2/2003 | Itoh et al. |
| 2003/0032867 | A1 | 2/2003 | Crothall et al. |
| 2003/0032868 | A1 | 2/2003 | Graskov et al. |
| 2003/0032874 | A1 | 2/2003 | Rhodes et al. |
| 2003/0036773 | A1 | 2/2003 | Whitehurst et al. |
| 2003/0040683 | A1 | 2/2003 | Rule et al. |
| 2003/0042137 | A1 | 3/2003 | Mao et al. |
| 2003/0050537 | A1 | 3/2003 | Wessel |
| 2003/0050546 | A1 | 3/2003 | Desai et al. |
| 2003/0059631 | A1 | 3/2003 | Al-Lamee |
| 2003/0065254 | A1 | 4/2003 | Schulman et al. |
| 2003/0065257 | A1 | 4/2003 | Mault et al. |
| 2003/0065273 | A1 | 4/2003 | Mault et al. |
| 2003/0065274 | A1 | 4/2003 | Mault et al. |
| 2003/0065275 | A1 | 4/2003 | Mault et al. |
| 2003/0065308 | A1 | 4/2003 | Lebel et al. |
| 2003/0070548 | A1 | 4/2003 | Clausen |
| 2003/0076082 | A1 | 4/2003 | Morgan et al. |
| 2003/0078481 | A1 | 4/2003 | McIvor et al. |
| 2003/0078560 | A1 | 4/2003 | Miller et al. |
| 2003/0097082 | A1 | 5/2003 | Purdy et al. |
| 2003/0100040 | A1 | 5/2003 | Bonnecaze et al. |
| 2003/0100821 | A1 | 5/2003 | Heller et al. |
| 2003/0105407 | A1 | 6/2003 | Pearce et al. |
| 2003/0108976 | A1 | 6/2003 | Braig et al. |
| 2003/0117296 | A1 | 6/2003 | Seely |
| 2003/0125612 | A1 | 7/2003 | Fox et al. |
| 2003/0125613 | A1 | 7/2003 | Enegren et al. |
| 2003/0130616 | A1 | 7/2003 | Steil et al. |
| 2003/0134347 | A1 | 7/2003 | Heller et al. |
| 2003/0135100 | A1 | 7/2003 | Kim et al. |
| 2003/0135333 | A1 | 7/2003 | Aceti et al. |
| 2003/0138674 | A1 | 7/2003 | Zeikus et al. |
| 2003/0153820 | A1 | 8/2003 | Berner et al. |
| 2003/0153821 | A1 | 8/2003 | Berner et al. |
| 2003/0158472 | A1 | 8/2003 | Sohrab |
| 2003/0158707 | A1 | 8/2003 | Doi |
| 2003/0168338 | A1 | 9/2003 | Gao et al. |
| 2003/0175806 | A1 | 9/2003 | Rule et al. |
| 2003/0176183 | A1 | 9/2003 | Drucker et al. |
| 2003/0176933 | A1 | 9/2003 | Lebel et al. |
| 2003/0181794 | A1 | 9/2003 | Rini et al. |
| 2003/0181851 | A1 | 9/2003 | Mann et al. |
| 2003/0181852 | A1 | 9/2003 | Mann et al. |
| 2003/0187338 | A1 | 10/2003 | Say et al. |
| 2003/0187525 | A1 | 10/2003 | Mann et al. |
| 2003/0188427 | A1 | 10/2003 | Say et al. |
| 2003/0191376 | A1 | 10/2003 | Samuels et al. |
| 2003/0191431 | A1 | 10/2003 | Mann et al. |
| 2003/0195403 | A1 | 10/2003 | Berner et al. |
| 2003/0195462 | A1 | 10/2003 | Mann et al. |
| 2003/0199744 | A1 | 10/2003 | Buse et al. |
| 2003/0199791 | A1 | 10/2003 | Boecker et al. |
| 2003/0199903 | A1 | 10/2003 | Boecker et al. |
| 2003/0208110 | A1 | 11/2003 | Mault et al. |
| 2003/0208113 | A1 | 11/2003 | Mault et al. |
| 2003/0208133 | A1 | 11/2003 | Mault |
| 2003/0208409 | A1 | 11/2003 | Mault |
| 2003/0211625 | A1 | 11/2003 | Cohan |
| 2003/0212317 | A1 | 11/2003 | Kovatchev et al. |
| 2003/0212346 | A1 | 11/2003 | Yuzhakov et al. |
| 2003/0212347 | A1 | 11/2003 | Sohrab |
| 2003/0212364 | A1 | 11/2003 | Mann et al. |
| 2003/0212379 | A1 | 11/2003 | Bylund et al. |
| 2003/0217966 | A1 | 11/2003 | Tapsak et al. |
| 2003/0225437 | A1 | 12/2003 | Ferguson |
| 2003/0226695 | A1 | 12/2003 | Mault |
| 2003/0229514 | A2 | 12/2003 | Brown |
| 2003/0232370 | A1 | 12/2003 | Trifiro |
| 2003/0235817 | A1 | 12/2003 | Bartkowiak et al. |
| 2004/0010207 | A1 | 1/2004 | Flaherty et al. |
| 2004/0011671 | A1 | 1/2004 | Shults et al. |
| 2004/0015063 | A1 | 1/2004 | DeNuzzio et al. |
| 2004/0015134 | A1 | 1/2004 | Lavi et al. |
| 2004/0018486 | A1 | 1/2004 | Dunn et al. |

(56) References Cited

U.S. PATENT DOCUMENTS

2004/0024327 A1 2/2004 Brodnick
2004/0030285 A1 2/2004 Lavi et al.
2004/0030294 A1 2/2004 Mahurkar
2004/0039256 A1 2/2004 Kawatahara et al.
2004/0039298 A1 2/2004 Abreu
2004/0039406 A1 2/2004 Jessen
2004/0040840 A1 3/2004 Mao et al.
2004/0045879 A1 3/2004 Shults et al.
2004/0054263 A1 3/2004 Moerman et al.
2004/0059201 A1 3/2004 Ginsberg
2004/0068230 A1 4/2004 Estes et al.
2004/0069164 A1 4/2004 Nakamura et al.
2004/0072357 A1 4/2004 Stiene et al.
2004/0073095 A1 4/2004 Causey, III et al.
2004/0074785 A1 4/2004 Holker
2004/0078219 A1 4/2004 Kaylor
2004/0096959 A1 5/2004 Stiene et al.
2004/0106857 A1 6/2004 Gough
2004/0106858 A1 6/2004 Say et al.
2004/0106859 A1 6/2004 Say et al.
2004/0108226 A1 6/2004 Polychronakos et al.
2004/0122353 A1 6/2004 Shahmirian et al.
2004/0122489 A1 6/2004 Mazar et al.
2004/0133131 A1 7/2004 Kuhn et al.
2004/0133164 A1 7/2004 Funderburk et al.
2004/0138588 A1 7/2004 Saikley et al.
2004/0143173 A1 7/2004 Reghabi et al.
2004/0152187 A1 8/2004 Haight et al.
2004/0152622 A1 8/2004 Keith et al.
2004/0153585 A1 8/2004 Kawatahara et al.
2004/0162473 A1 8/2004 Sohrab
2004/0164961 A1 8/2004 Bal et al.
2004/0167383 A1 8/2004 Kim et al.
2004/0167801 A1 8/2004 Say et al.
2004/0171921 A1 9/2004 Say et al.
2004/0172284 A1 9/2004 Sullivan et al.
2004/0173472 A1 9/2004 Jung et al.
2004/0176913 A1 9/2004 Kawatahara et al.
2004/0186362 A1 9/2004 Brauker et al.
2004/0186365 A1 9/2004 Jin et al.
2004/0193025 A1 9/2004 Steil et al.
2004/0193090 A1 9/2004 Lebel et al.
2004/0199059 A1 10/2004 Brauker et al.
2004/0202576 A1 10/2004 Aceti et al.
2004/0204687 A1 10/2004 Mogensen et al.
2004/0219664 A1 11/2004 Heller et al.
2004/0225338 A1 11/2004 Lebel et al.
2004/0236200 A1 11/2004 Say et al.
2004/0236251 A1 11/2004 Roe et al.
2004/0248204 A1 12/2004 Moerman
2004/0249250 A1 12/2004 McGee et al.
2004/0249253 A1 12/2004 Racchini et al.
2004/0249254 A1 12/2004 Racchini et al.
2004/0249999 A1 12/2004 Connolly et al.
2004/0253736 A1 12/2004 Stout et al.
2004/0254429 A1 12/2004 Yang
2004/0254433 A1 12/2004 Bandis et al.
2004/0254434 A1 12/2004 Goodnow et al.
2004/0260363 A1 12/2004 Arx et al.
2004/0263354 A1 12/2004 Mann et al.
2005/0003470 A1 1/2005 Nelson et al.
2005/0004439 A1 1/2005 Shin et al.
2005/0006122 A1 1/2005 Burnette
2005/0010087 A1 1/2005 Banet et al.
2005/0010265 A1 1/2005 Baru Fassio et al.
2005/0010269 A1 1/2005 Lebel et al.
2005/0027177 A1 2/2005 Shin et al.
2005/0027179 A1 2/2005 Berner et al.
2005/0027180 A1 2/2005 Goode, Jr. et al.
2005/0027181 A1 2/2005 Goode, Jr. et al.
2005/0027182 A1 2/2005 Siddiqui et al.
2005/0027462 A1 2/2005 Goode, Jr. et al.
2005/0027463 A1 2/2005 Goode, Jr. et al.
2005/0031689 A1 2/2005 Shults et al.
2005/0033132 A1 2/2005 Shults et al.
2005/0038332 A1 2/2005 Saidara et al.
2005/0038680 A1 2/2005 McMahon
2005/0043598 A1 2/2005 Goode, Jr. et al.
2005/0043894 A1 2/2005 Fernandez
2005/0049473 A1 3/2005 Desai et al.
2005/0051427 A1 3/2005 Brauker et al.
2005/0051440 A1 3/2005 Simpson et al.
2005/0054909 A1 3/2005 Petisce et al.
2005/0056551 A1 3/2005 White et al.
2005/0056552 A1 3/2005 Simpson et al.
2005/0090607 A1 4/2005 Tapsak et al.
2005/0096519 A1 5/2005 DeNuzzio et al.
2005/0101847 A1 5/2005 Routt et al.
2005/0103625 A1 5/2005 Rhodes et al.
2005/0112169 A1 5/2005 Brauker et al.
2005/0113653 A1 5/2005 Fox et al.
2005/0113657 A1 5/2005 Alarcon et al.
2005/0113658 A1 5/2005 Jacobson et al.
2005/0115832 A1 6/2005 Simpson et al.
2005/0118726 A1 6/2005 Schultz et al.
2005/0121322 A1 6/2005 Say et al.
2005/0124873 A1 6/2005 Shults et al.
2005/0131346 A1 6/2005 Douglas
2005/0133368 A1 6/2005 Davies et al.
2005/0137471 A1 6/2005 Haar et al.
2005/0139489 A1 6/2005 Davies et al.
2005/0143635 A1 6/2005 Kamath et al.
2005/0143636 A1 6/2005 Zhang et al.
2005/0143675 A1 6/2005 Neel et al.
2005/0148003 A1 7/2005 Keith et al.
2005/0154271 A1 7/2005 Rasdal et al.
2005/0161346 A1 7/2005 Simpson et al.
2005/0171503 A1 8/2005 Van Den Berghe et al.
2005/0171513 A1 8/2005 Mann et al.
2005/0173245 A1 8/2005 Feldman et al.
2005/0176136 A1 8/2005 Burd et al.
2005/0177036 A1 8/2005 Shults et al.
2005/0181012 A1 8/2005 Saint et al.
2005/0182306 A1 8/2005 Sloan et al.
2005/0182451 A1 8/2005 Griffin et al.
2005/0183954 A1 8/2005 Hitchcock et al.
2005/0187720 A1 8/2005 Goode, Jr. et al.
2005/0192557 A1 9/2005 Brauker et al.
2005/0195930 A1 9/2005 Spital et al.
2005/0199494 A1 9/2005 Say et al.
2005/0203360 A1 9/2005 Brauker et al.
2005/0203707 A1 9/2005 Tsutsui et al.
2005/0211571 A1 9/2005 Schulein et al.
2005/0214892 A1 9/2005 Kovatchev et al.
2005/0215871 A1 9/2005 Feldman et al.
2005/0215872 A1 9/2005 Berner et al.
2005/0239154 A1 10/2005 Feldman et al.
2005/0239156 A1 10/2005 Drucker et al.
2005/0242479 A1 11/2005 Petisce et al.
2005/0245795 A1 11/2005 Goode, Jr. et al.
2005/0245799 A1 11/2005 Brauker et al.
2005/0251083 A1 11/2005 Carr-Brendel et al.
2005/0261563 A1 11/2005 Zhou et al.
2005/0261660 A1 11/2005 Choi
2005/0267780 A1 12/2005 Ray et al.
2005/0271546 A1 12/2005 Gerber et al.
2005/0271547 A1 12/2005 Gerber et al.
2005/0272640 A1 12/2005 Doyle, III et al.
2005/0272985 A1 12/2005 Kotulla et al.
2005/0272989 A1 12/2005 Shah et al.
2005/0277164 A1 12/2005 Drucker et al.
2005/0287620 A1 12/2005 Heller et al.
2006/0001538 A1 1/2006 Kraft et al.
2006/0001550 A1 1/2006 Mann et al.
2006/0001551 A1 1/2006 Kraft et al.
2006/0003398 A1 1/2006 Heller et al.
2006/0004271 A1 1/2006 Peyser et al.
2006/0007017 A1 1/2006 Mann et al.
2006/0015020 A1 1/2006 Neale et al.
2006/0015024 A1 1/2006 Brister et al.
2006/0016700 A1 1/2006 Brister et al.
2006/0019327 A1 1/2006 Brister et al.
2006/0020186 A1 1/2006 Brister et al.
2006/0020187 A1 1/2006 Brister et al.

(56) References Cited

U.S. PATENT DOCUMENTS

2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0025663 A1 2/2006 Talbot et al.
2006/0031094 A1 2/2006 Cohen et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0036187 A1 2/2006 Vos et al.
2006/0040402 A1 2/2006 Brauker et al.
2006/0047215 A1 3/2006 Newman et al.
2006/0052679 A1 3/2006 Kotulla et al.
2006/0058602 A1 3/2006 Kwiatkowski et al.
2006/0063218 A1 3/2006 Bartkowiak et al.
2006/0068208 A1 3/2006 Tapsak et al.
2006/0074564 A1 4/2006 Bartkowiak et al.
2006/0086624 A1 4/2006 Tapsak et al.
2006/0093556 A1 5/2006 Gonda et al.
2006/0100588 A1 5/2006 Brunnberg et al.
2006/0155180 A1 7/2006 Brister et al.
2006/0173444 A1 8/2006 Choy et al.
2006/0183984 A1 8/2006 Dobbles et al.
2006/0183985 A1 8/2006 Brister et al.
2006/0189856 A1 8/2006 Petisce et al.
2006/0189863 A1 8/2006 Peyser et al.
2006/0195029 A1 8/2006 Shults et al.
2006/0198864 A1 9/2006 Shults et al.
2006/0200019 A1 9/2006 Petisce et al.
2006/0200020 A1 9/2006 Brister et al.
2006/0200022 A1 9/2006 Brauker et al.
2006/0211921 A1 9/2006 Brauker et al.
2006/0222566 A1 10/2006 Brauker et al.
2006/0224108 A1 10/2006 Brauker et al.
2006/0235285 A1 10/2006 Brister et al.
2006/0247985 A1 11/2006 Liamos et al.
2006/0258761 A1 11/2006 Boock et al.
2006/0258929 A1 11/2006 Goode, Jr. et al.
2006/0270922 A1 11/2006 Brauker et al.
2006/0270923 A1 11/2006 Brauker et al.
2007/0016381 A1 1/2007 Kamath et al.
2007/0017805 A1 1/2007 Hodges et al.
2007/0027381 A1 2/2007 Stafford
2007/0027384 A1 2/2007 Brister et al.
2007/0027385 A1 2/2007 Brister et al.
2007/0032706 A1 2/2007 Kamath et al.
2007/0032717 A1 2/2007 Brister et al.
2007/0032718 A1 2/2007 Shults et al.
2007/0038044 A1 2/2007 Dobbles et al.
2007/0045902 A1 3/2007 Brauker et al.
2007/0049873 A1 3/2007 Hansen et al.
2007/0060814 A1 3/2007 Stafford
2007/0066873 A1 3/2007 Kamath et al.
2007/0078320 A1 4/2007 Stafford
2007/0078321 A1 4/2007 Mazza et al.
2007/0093704 A1 4/2007 Brister et al.
2007/0106135 A1 5/2007 Sloan et al.
2007/0149873 A1 6/2007 Say et al.
2007/0149874 A1 6/2007 Say et al.
2007/0151869 A1 7/2007 Heller et al.
2007/0161879 A1 7/2007 Say et al.
2007/0161880 A1 7/2007 Say et al.
2007/0163880 A1 7/2007 Woo et al.
2007/0173711 A1 7/2007 Shah et al.
2007/0179370 A1 8/2007 Say et al.
2007/0179372 A1 8/2007 Say et al.
2007/0191699 A1 8/2007 Say et al.
2007/0191700 A1 8/2007 Say et al.
2007/0197889 A1 8/2007 Brister et al.
2007/0197890 A1 8/2007 Boock et al.
2007/0200254 A1 8/2007 Curry
2007/0202672 A1 8/2007 Curry
2007/0203408 A1 8/2007 Say et al.
2007/0203410 A1 8/2007 Say et al.
2007/0203411 A1 8/2007 Say et al.
2007/0203966 A1 8/2007 Brauker et al.
2007/0208244 A1 9/2007 Brauker et al.
2007/0208245 A1 9/2007 Brauker et al.
2007/0208246 A1 9/2007 Brauker et al.
2007/0208247 A1 9/2007 Say et al.
2007/0213610 A1 9/2007 Say et al.
2007/0213611 A1 9/2007 Simpson et al.
2007/0215491 A1 9/2007 Heller et al.
2007/0218097 A1 9/2007 Heller et al.
2007/0232879 A1 10/2007 Brister et al.
2007/0235331 A1 10/2007 Simpson et al.
2007/0244380 A1 10/2007 Say et al.
2007/0249919 A1 10/2007 Say et al.
2007/0249920 A1 10/2007 Say et al.
2007/0249922 A1 10/2007 Peyser et al.
2007/0259217 A1 11/2007 Logan
2008/0021436 A1 1/2008 Wolpert et al.
2008/0021666 A1 1/2008 Goode, Jr. et al.
2008/0033254 A1 2/2008 Kamath et al.
2008/0033271 A1 2/2008 Say et al.
2008/0045824 A1 2/2008 Tapsak et al.
2008/0071156 A1 3/2008 Brister et al.
2008/0076997 A1 3/2008 Peyser et al.
2008/0083617 A1 4/2008 Simpson et al.
2008/0086039 A1 4/2008 Heller et al.
2008/0086040 A1 4/2008 Heller et al.
2008/0086041 A1 4/2008 Heller et al.
2008/0086042 A1 4/2008 Brister et al.
2008/0086043 A1 4/2008 Heller et al.
2008/0086044 A1 4/2008 Brister et al.
2008/0086273 A1 4/2008 Shults et al.
2008/0091094 A1 4/2008 Heller et al.
2008/0091095 A1 4/2008 Heller et al.
2008/0091096 A1 4/2008 Say et al.
2008/0108942 A1 5/2008 Brister et al.
2008/0154101 A1 6/2008 Jain et al.
2008/0167543 A1 7/2008 Say et al.
2008/0183061 A1 7/2008 Goode, Jr. et al.
2008/0183399 A1 7/2008 Goode, Jr. et al.
2008/0187655 A1 8/2008 Markle et al.
2008/0188722 A1 8/2008 Markle et al.
2008/0188725 A1 8/2008 Markle et al.
2008/0188731 A1 8/2008 Brister et al.
2008/0189051 A1 8/2008 Goode, Jr. et al.
2008/0194935 A1 8/2008 Brister et al.
2008/0194936 A1 8/2008 Goode, Jr. et al.
2008/0194937 A1 8/2008 Goode, Jr. et al.
2008/0194938 A1 8/2008 Brister et al.
2008/0195232 A1 8/2008 Carr-Brendel et al.
2008/0195967 A1 8/2008 Goode, Jr. et al.
2008/0197024 A1 8/2008 Simpson et al.
2008/0200788 A1 8/2008 Brister et al.
2008/0200789 A1 8/2008 Brister et al.
2008/0200791 A1 8/2008 Simpson et al.
2008/0208025 A1 8/2008 Shults et al.
2008/0210557 A1 9/2008 Heller et al.
2008/0214914 A1 9/2008 Say et al.
2008/0214915 A1 9/2008 Brister et al.
2008/0214918 A1 9/2008 Brister et al.
2008/0228051 A1 9/2008 Shults et al.
2008/0228054 A1 9/2008 Shults et al.
2008/0242961 A1 10/2008 Brister et al.
2008/0262329 A1 10/2008 Say et al.
2008/0262469 A1 10/2008 Brister et al.
2008/0269672 A1 10/2008 Say et al.
2008/0275313 A1 11/2008 Brister et al.
2008/0287764 A1 11/2008 Rasdal et al.
2008/0287765 A1 11/2008 Rasdal et al.
2008/0287766 A1 11/2008 Rasdal et al.
2008/0296155 A1 12/2008 Shults et al.
2008/0305009 A1 12/2008 Gamsey et al.
2008/0305506 A1 12/2008 Suri
2008/0306368 A1 12/2008 Goode, Jr. et al.
2008/0306434 A1 12/2008 Dobbles et al.

(56) References Cited

U.S. PATENT DOCUMENTS

| | | | |
|---|---|---|---|
| 2008/0306435 | A1 | 12/2008 | Kamath et al. |
| 2008/0306444 | A1 | 12/2008 | Brister et al. |
| 2008/0319292 | A1 | 12/2008 | Say et al. |
| 2009/0011449 | A1 | 1/2009 | Karinka et al. |
| 2009/0012379 | A1 | 1/2009 | Goode, Jr. et al. |
| 2009/0018418 | A1 | 1/2009 | Markle et al. |
| 2009/0018424 | A1 | 1/2009 | Kamath et al. |
| 2009/0018426 | A1 | 1/2009 | Markle et al. |
| 2009/0030294 | A1 | 1/2009 | Petisce et al. |
| 2009/0030297 | A1 | 1/2009 | Miller et al. |
| 2009/0036758 | A1 | 2/2009 | Brauker et al. |
| 2009/0036763 | A1 | 2/2009 | Brauker et al. |
| 2009/0043181 | A1 | 2/2009 | Brauker et al. |
| 2009/0043182 | A1 | 2/2009 | Brauker et al. |
| 2009/0043525 | A1 | 2/2009 | Brauker et al. |
| 2009/0043541 | A1 | 2/2009 | Brauker et al. |
| 2009/0043542 | A1 | 2/2009 | Brauker et al. |
| 2009/0045055 | A1 | 2/2009 | Rhodes et al. |
| 2009/0061528 | A1 | 3/2009 | Suri |
| 2009/0062633 | A1 | 3/2009 | Brauker et al. |
| 2009/0062634 | A1 | 3/2009 | Say et al. |
| 2009/0062635 | A1 | 3/2009 | Brauker et al. |
| 2009/0069655 | A1 | 3/2009 | Say et al. |
| 2009/0069656 | A1 | 3/2009 | Say et al. |
| 2009/0069657 | A1 | 3/2009 | Say et al. |
| 2009/0069658 | A1 | 3/2009 | Say et al. |
| 2009/0076356 | A1 | 3/2009 | Simpson et al. |
| 2009/0076360 | A1 | 3/2009 | Brister et al. |
| 2009/0076361 | A1 | 3/2009 | Kamath et al. |
| 2009/0081803 | A1 | 3/2009 | Gamsey et al. |
| 2009/0089999 | A1 | 4/2009 | Say et al. |
| 2009/0093696 | A1 | 4/2009 | Say et al. |
| 2009/0099432 | A1 | 4/2009 | Say et al. |
| 2009/0099434 | A1 | 4/2009 | Liu et al. |
| 2009/0099435 | A1 | 4/2009 | Say et al. |
| 2009/0099436 | A1 | 4/2009 | Brister et al. |
| 2009/0124877 | A1 | 5/2009 | Goode, Jr. et al. |
| 2009/0124878 | A1 | 5/2009 | Goode, Jr. et al. |
| 2009/0124879 | A1 | 5/2009 | Brister et al. |
| 2009/0124964 | A1 | 5/2009 | Leach et al. |
| 2009/0131768 | A1 | 5/2009 | Simpson et al. |
| 2009/0131769 | A1 | 5/2009 | Leach et al. |
| 2009/0131776 | A1 | 5/2009 | Simpson et al. |
| 2009/0131777 | A1 | 5/2009 | Simpson et al. |
| 2009/0137886 | A1 | 5/2009 | Shariati et al. |
| 2009/0137887 | A1 | 5/2009 | Shariati et al. |
| 2009/0143659 | A1 | 6/2009 | Li et al. |
| 2009/0143660 | A1 | 6/2009 | Brister et al. |
| 2009/0156919 | A1 | 6/2009 | Brister et al. |
| 2009/0156924 | A1 | 6/2009 | Shariati et al. |
| 2009/0163781 | A1 | 6/2009 | Say et al. |
| 2009/0163788 | A1 | 6/2009 | Say et al. |
| 2009/0163789 | A1 | 6/2009 | Say et al. |
| 2009/0163790 | A1 | 6/2009 | Brister et al. |
| 2009/0163791 | A1 | 6/2009 | Brister et al. |
| 2009/0171179 | A1 | 7/2009 | Say et al. |
| 2009/0173628 | A1 | 7/2009 | Say et al. |
| 2009/0177054 | A1 | 7/2009 | Say et al. |
| 2009/0177055 | A1 | 7/2009 | Say et al. |
| 2009/0177056 | A1 | 7/2009 | Say et al. |
| 2009/0177057 | A1 | 7/2009 | Say et al. |
| 2009/0177058 | A1 | 7/2009 | Say et al. |
| 2009/0177059 | A1 | 7/2009 | Say et al. |
| 2009/0177060 | A1 | 7/2009 | Say et al. |
| 2009/0177061 | A1 | 7/2009 | Say et al. |
| 2009/0177062 | A1 | 7/2009 | Say et al. |
| 2009/0177063 | A1 | 7/2009 | Say et al. |
| 2009/0177064 | A1 | 7/2009 | Say et al. |
| 2009/0177065 | A1 | 7/2009 | Say et al. |
| 2009/0177066 | A1 | 7/2009 | Say et al. |
| 2009/0177143 | A1 | 7/2009 | Markle et al. |
| 2009/0178459 | A1 | 7/2009 | Li et al. |
| 2009/0182212 | A1 | 7/2009 | Say et al. |
| 2009/0182213 | A1 | 7/2009 | Say et al. |
| 2009/0182214 | A1 | 7/2009 | Say et al. |
| 2009/0182215 | A1 | 7/2009 | Say et al. |
| 2009/0182217 | A1 | 7/2009 | Li et al. |
| 2009/0187088 | A1 | 7/2009 | Say et al. |
| 2009/0187089 | A1 | 7/2009 | Say et al. |
| 2009/0187090 | A1 | 7/2009 | Say et al. |
| 2009/0187091 | A1 | 7/2009 | Say et al. |
| 2009/0187092 | A1 | 7/2009 | Say et al. |
| 2009/0187093 | A1 | 7/2009 | Say et al. |
| 2009/0187094 | A1 | 7/2009 | Say et al. |
| 2009/0187095 | A1 | 7/2009 | Say et al. |
| 2009/0192366 | A1 | 7/2009 | Mensinger et al. |
| 2009/0192368 | A1 | 7/2009 | Say et al. |
| 2009/0192369 | A1 | 7/2009 | Say et al. |
| 2009/0192370 | A1 | 7/2009 | Say et al. |
| 2009/0192371 | A1 | 7/2009 | Say et al. |
| 2009/0192372 | A1 | 7/2009 | Say et al. |
| 2009/0192373 | A1 | 7/2009 | Say et al. |
| 2009/0192374 | A1 | 7/2009 | Say et al. |
| 2009/0192375 | A1 | 7/2009 | Say et al. |
| 2009/0192376 | A1 | 7/2009 | Say et al. |
| 2009/0192377 | A1 | 7/2009 | Say et al. |
| 2009/0192378 | A1 | 7/2009 | Say et al. |
| 2009/0192379 | A1 | 7/2009 | Say et al. |
| 2009/0192380 | A1 | 7/2009 | Shariati et al. |
| 2009/0192722 | A1 | 7/2009 | Shariati et al. |
| 2009/0192724 | A1 | 7/2009 | Brauker et al. |
| 2009/0192745 | A1 | 7/2009 | Kamath et al. |
| 2009/0192751 | A1 | 7/2009 | Kamath et al. |
| 2009/0198115 | A1 | 8/2009 | Say et al. |
| 2009/0198116 | A1 | 8/2009 | Say et al. |
| 2009/0198175 | A1 | 8/2009 | Say et al. |
| 2009/0203978 | A1 | 8/2009 | Say et al. |
| 2009/0203981 | A1 | 8/2009 | Brauker et al. |
| 2009/0204341 | A1 | 8/2009 | Brauker et al. |
| 2009/0209838 | A1 | 8/2009 | Say et al. |
| 2009/0216100 | A1 | 8/2009 | Ebner et al. |
| 2009/0216101 | A1 | 8/2009 | Say et al. |
| 2009/0216103 | A1 | 8/2009 | Brister et al. |
| 2009/0227940 | A1 | 9/2009 | Say et al. |
| 2009/0227941 | A1 | 9/2009 | Say et al. |
| 2009/0228214 | A1 | 9/2009 | Say et al. |
| 2009/0240120 | A1 | 9/2009 | Mensinger et al. |
| 2009/0240128 | A1 | 9/2009 | Mensinger et al. |
| 2009/0240193 | A1 | 9/2009 | Mensinger et al. |
| 2009/0242399 | A1 | 10/2009 | Kamath et al. |
| 2009/0242425 | A1 | 10/2009 | Kamath et al. |
| 2009/0247855 | A1 | 10/2009 | Boock et al. |
| 2009/0247856 | A1 | 10/2009 | Boock et al. |
| 2009/0264719 | A1 | 10/2009 | Markle et al. |
| 2009/0287073 | A1 | 11/2009 | Boock et al. |
| 2009/0287074 | A1 | 11/2009 | Shults et al. |
| 2009/0299155 | A1 | 12/2009 | Yang et al. |
| 2009/0299156 | A1 | 12/2009 | Simpson et al. |
| 2009/0299162 | A1 | 12/2009 | Brauker et al. |
| 2009/0299276 | A1 | 12/2009 | Brauker et al. |
| 2010/0010324 | A1 | 1/2010 | Brauker et al. |
| 2010/0010331 | A1 | 1/2010 | Brauker et al. |
| 2010/0010332 | A1 | 1/2010 | Brauker et al. |
| 2010/0016687 | A1 | 1/2010 | Brauker et al. |
| 2010/0016698 | A1 | 1/2010 | Rasdal et al. |
| 2010/0022855 | A1 | 1/2010 | Brauker et al. |
| 2010/0030038 | A1 | 2/2010 | Brauker et al. |
| 2010/0030053 | A1 | 2/2010 | Goode, Jr. et al. |
| 2010/0030484 | A1 | 2/2010 | Brauker et al. |
| 2010/0030485 | A1 | 2/2010 | Brauker et al. |
| 2010/0036215 | A1 | 2/2010 | Goode, Jr. et al. |
| 2010/0036216 | A1 | 2/2010 | Goode, Jr. et al. |
| 2010/0036222 | A1 | 2/2010 | Goode, Jr. et al. |
| 2010/0036223 | A1 | 2/2010 | Goode, Jr. et al. |
| 2010/0036224 | A1 | 2/2010 | Goode, Jr. et al. |
| 2010/0036225 | A1 | 2/2010 | Goode, Jr. et al. |
| 2010/0041971 | A1 | 2/2010 | Goode, Jr. et al. |
| 2010/0045465 | A1 | 2/2010 | Brauker et al. |
| 2010/0049024 | A1 | 2/2010 | Saint et al. |
| 2010/0063373 | A1 | 3/2010 | Kamath et al. |
| 2010/0076283 | A1 | 3/2010 | Simpson et al. |
| 2010/0081908 | A1 | 4/2010 | Dobbles et al. |
| 2010/0081910 | A1 | 4/2010 | Brister et al. |
| 2010/0087724 | A1 | 4/2010 | Brauker et al. |

(56) References Cited

U.S. PATENT DOCUMENTS

2010/0094111 A1 4/2010 Heller et al.
2010/0096259 A1 4/2010 Zhang et al.
2010/0099970 A1 4/2010 Shults et al.
2010/0099971 A1 4/2010 Shults et al.
2010/0119693 A1 5/2010 Tapsak et al.
2010/0121169 A1 5/2010 Petisce et al.
2010/0145172 A1 6/2010 Petisce et al.
2010/0160760 A1 6/2010 Shults et al.
2010/0161269 A1 6/2010 Kamath et al.
2010/0168540 A1 7/2010 Kamath et al.
2010/0168541 A1 7/2010 Kamath et al.
2010/0168542 A1 7/2010 Kamath et al.
2010/0168543 A1 7/2010 Kamath et al.
2010/0168544 A1 7/2010 Kamath et al.
2010/0168545 A1 7/2010 Kamath et al.
2010/0168546 A1 7/2010 Kamath et al.
2010/0168657 A1 7/2010 Kamath et al.
2010/0174157 A1 7/2010 Brister et al.
2010/0174158 A1 7/2010 Kamath et al.
2010/0174163 A1 7/2010 Brister et al.
2010/0174164 A1 7/2010 Brister et al.
2010/0174165 A1 7/2010 Brister et al.
2010/0174166 A1 7/2010 Brister et al.
2010/0174167 A1 7/2010 Kamath et al.
2010/0174168 A1 7/2010 Goode et al.
2010/0179399 A1 7/2010 Goode et al.
2010/0179400 A1 7/2010 Brauker et al.
2010/0179401 A1 7/2010 Rasdal et al.
2010/0179402 A1 7/2010 Goode et al.
2010/0179404 A1 7/2010 Kamath et al.
2010/0179405 A1 7/2010 Goode et al.
2010/0179406 A1 7/2010 Goode et al.
2010/0179407 A1 7/2010 Goode et al.
2010/0179408 A1 7/2010 Kamath et al.
2010/0179409 A1 7/2010 Kamath et al.
2010/0185065 A1 7/2010 Goode et al.
2010/0185069 A1 7/2010 Brister et al.
2010/0185070 A1 7/2010 Brister et al.
2010/0185071 A1 7/2010 Simpson et al.
2010/0185072 A1 7/2010 Goode et al.
2010/0185073 A1 7/2010 Goode et al.
2010/0185074 A1 7/2010 Goode et al.
2010/0185075 A1 7/2010 Brister et al.
2010/0191082 A1 7/2010 Brister et al.
2010/0198035 A1 8/2010 Kamath et al.
2010/0198036 A1 8/2010 Kamath et al.
2010/0204555 A1 8/2010 Shults et al.
2010/0204559 A1 8/2010 Shults et al.
2010/0212583 A1 8/2010 Brister et al.
2010/0214104 A1 8/2010 Goode, Jr. et al.
2010/0217106 A1 8/2010 Goode, Jr. et al.
2010/0217555 A1 8/2010 Kamath et al.
2010/0217557 A1 8/2010 Kamath et al.
2010/0223013 A1 9/2010 Kamath et al.
2010/0223022 A1 9/2010 Kamath et al.
2010/0223023 A1 9/2010 Kamath et al.
2010/0228109 A1 9/2010 Kamath et al.
2010/0228497 A1 9/2010 Kamath et al.
2010/0234707 A1 9/2010 Goode, Jr. et al.
2010/0234796 A1 9/2010 Kamath et al.
2010/0235106 A1 9/2010 Kamath et al.
2010/0240975 A1 9/2010 Goode, Jr. et al.
2010/0240976 A1 9/2010 Goode, Jr. et al.
2010/0261987 A1 10/2010 Kamath et al.
2010/0274107 A1 10/2010 Boock et al.
2010/0280341 A1 11/2010 Boock et al.
2010/0286496 A1 11/2010 Simpson et al.
2010/0298684 A1 11/2010 Leach et al.
2010/0305869 A1 12/2010 Brauker et al.
2010/0324403 A1 12/2010 Brister et al.
2010/0331644 A1 12/2010 Neale et al.
2010/0331648 A1 12/2010 Kamath et al.
2010/0331655 A1 12/2010 Kamath et al.
2010/0331656 A1 12/2010 Mensinger et al.
2010/0331657 A1 12/2010 Mensinger et al.
2011/0004085 A1 1/2011 Mensinger et al.
2011/0009727 A1 1/2011 Mensinger et al.
2011/0024043 A1 2/2011 Boock et al.
2011/0024307 A1 2/2011 Simpson et al.
2011/0027127 A1 2/2011 Simpson et al.
2011/0027453 A1 2/2011 Boock et al.
2011/0027458 A1 2/2011 Boock et al.
2011/0028815 A1 2/2011 Simpson et al.
2011/0028816 A1 2/2011 Simpson et al.
2011/0046467 A1 2/2011 Simpson et al.

FOREIGN PATENT DOCUMENTS

CN 1735375 2/2006
CN 100407988 8/2008
DE 2903216 8/1979
DE 227029 9/1985
DE 3934299 10/1990
DE 4234553 1/1995
DE 4401400 7/1995
EP 0010375 4/1980
EP 0026995 4/1981
EP 0048090 3/1982
EP 0078636 5/1983
EP 0080304 6/1983
EP 0096228 12/1983
EP 0096288 12/1983
EP 0098592 1/1984
EP 0107634 5/1984
EP 0125139 11/1984
EP 0127958 12/1984
EP 0136362 4/1985
EP 0170375 2/1986
EP 0177743 4/1986
EP 0184909 6/1986
EP 0206218 12/1986
EP 0230472 8/1987
EP 0241309 10/1987
EP 0245073 11/1987
EP 0255291 2/1988
EP 0278647 8/1988
EP 0284518 9/1988
EP 0320109 6/1989
EP 0353328 2/1990
EP 0359831 3/1990
EP 0368209 5/1990
EP 0368290 5/1990
EP 0390390 10/1990
EP 0396788 11/1990
EP 0400918 12/1990
EP 0453283 10/1991
EP 0470290 2/1992
EP 0476980 3/1992
EP 0504835 9/1992
EP 0512122 11/1992
EP 0534074 3/1993
EP 0535898 4/1993
EP 0539625 5/1993
EP 0563795 10/1993
EP 0561966 10/1994
EP 0286118 1/1995
EP 0653718 5/1995
EP 0727891 8/1996
EP 0776628 6/1997
EP 0800082 10/1997
EP 0817809 1/1998
EP 0838230 4/1998
EP 0880936 12/1998
EP 0885932 12/1998
EP 0967788 12/1999
EP 0970655 1/2000
EP 0995805 4/2000
EP 1034734 9/2000
EP 1048264 11/2000
EP 1077634 2/2001
EP 1078258 2/2001
EP 1355568 10/2003
EP 2187555 5/2010
EP 2201969 6/2010

(56) References Cited

FOREIGN PATENT DOCUMENTS

| | | |
|---|---|---|
| EP | 2305107 | 4/2011 |
| EP | 2305108 | 4/2011 |
| FR | 2656423 | 6/1991 |
| FR | 2760962 | 9/1998 |
| GB | 1394171 | 5/1975 |
| GB | 1442303 | 7/1976 |
| GB | 1579690 | 11/1980 |
| GB | 1599241 | 9/1981 |
| GB | 2073891 | 10/1981 |
| GB | 2149918 | 6/1985 |
| GB | 2154003 | 8/1985 |
| GB | 2194892 | 3/1988 |
| GB | 2204408 | 11/1988 |
| GB | 2225637 | 6/1990 |
| GB | 2254436 | 10/1992 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |
| JP | 60-210243 | 10/1985 |
| JP | 61-090050 | 5/1986 |
| JP | 62-083649 | 4/1987 |
| JP | 62-083849 | 4/1987 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-259457 | 10/1988 |
| JP | 63-294799 | 12/1988 |
| JP | 63-317757 | 12/1988 |
| JP | 63-317758 | 12/1988 |
| JP | 1-114746 | 5/1989 |
| JP | 1-114747 | 5/1989 |
| JP | 1-124060 | 5/1989 |
| JP | 1-134244 | 5/1989 |
| JP | 1-156658 | 6/1989 |
| JP | 2-062958 | 3/1990 |
| JP | 2-120655 | 5/1990 |
| JP | 2-287145 | 11/1990 |
| JP | 2-310457 | 12/1990 |
| JP | 3-026956 | 2/1991 |
| JP | 3-028752 | 2/1991 |
| JP | 3-202764 | 9/1991 |
| JP | 4-215739 | 8/1992 |
| JP | 5-072171 | 3/1993 |
| JP | 5-196595 | 8/1993 |
| JP | 6-190050 | 7/1994 |
| JP | 6-277201 | 10/1994 |
| JP | 7-055757 | 3/1995 |
| JP | 7-072585 | 3/1995 |
| JP | 7-275227 | 10/1995 |
| JP | 8-154903 | 6/1996 |
| JP | 8-285814 | 11/1996 |
| JP | 8-285815 | 11/1996 |
| JP | 9-021778 | 1/1997 |
| JP | 9-101280 | 4/1997 |
| JP | 9-285459 | 11/1997 |
| JP | 9-512200 | 12/1997 |
| JP | 10-170471 | 6/1998 |
| JP | 11-153575 | 6/1999 |
| JP | 11-192886 | 7/1999 |
| JP | 11-225103 | 8/1999 |
| JP | 11-275059 | 10/1999 |
| JP | 2000-000231 | 1/2000 |
| JP | 2000-500380 | 1/2000 |
| JP | 2000-060826 | 2/2000 |
| JP | 2000-098045 | 4/2000 |
| JP | 2000-101478 | 4/2000 |
| JP | 2000-116628 | 4/2000 |
| JP | 2000-349689 | 12/2000 |
| JP | 2002-189015 | 7/2002 |
| JP | 2003-108679 | 4/2003 |
| JP | 2004-520898 | 7/2004 |
| JP | 2007-203092 | 8/2007 |
| JP | 2008-062072 | 3/2008 |
| SU | 1281988 | 1/1987 |
| WO | WO-85/05119 | 11/1985 |
| WO | WO-86/00513 | 1/1986 |
| WO | WO-86/05339 | 9/1986 |
| WO | WO-87/00513 | 1/1987 |
| WO | WO-87/06040 | 10/1987 |
| WO | WO-89/02246 | 3/1989 |
| WO | WO-89/02720 | 4/1989 |
| WO | WO-89/05119 | 6/1989 |
| WO | WO-89/08713 | 9/1989 |
| WO | WO-90/00367 | 1/1990 |
| WO | WO-90/00738 | 1/1990 |
| WO | WO-90/05300 | 5/1990 |
| WO | WO-90/05910 | 5/1990 |
| WO | WO-90/10861 | 9/1990 |
| WO | WO-90/13021 | 11/1990 |
| WO | WO-91/01680 | 2/1991 |
| WO | WO-91/04704 | 4/1991 |
| WO | WO-91/15993 | 10/1991 |
| WO | WO-92/04153 | 3/1992 |
| WO | WO-92/07525 | 5/1992 |
| WO | WO-92/10584 | 6/1992 |
| WO | WO-92/13271 | 8/1992 |
| WO | WO-93/05703 | 4/1993 |
| WO | WO-93/14693 | 8/1993 |
| WO | WO-93/19701 | 10/1993 |
| WO | WO-93/23744 | 11/1993 |
| WO | WO-94/20602 | 9/1994 |
| WO | WO-94/22367 | 10/1994 |
| WO | WO-94/27140 | 11/1994 |
| WO | WO-95/06240 | 3/1995 |
| WO | WO-95/07109 | 3/1995 |
| WO | WO-96/01611 | 1/1996 |
| WO | WO-96/07908 | 3/1996 |
| WO | WO-96/14026 | 5/1996 |
| WO | WO-96/25089 | 8/1996 |
| WO | WO-96/30431 | 10/1996 |
| WO | WO-96/32076 | 10/1996 |
| WO | WO-96/35370 | 11/1996 |
| WO | WO-96/36296 | 11/1996 |
| WO | WO-96/37066 | 11/1996 |
| WO | WO-97/01986 | 1/1997 |
| WO | WO-97/02847 | 1/1997 |
| WO | WO-97/06727 | 2/1997 |
| WO | WO-97/19344 | 5/1997 |
| WO | WO-97/20207 | 6/1997 |
| WO | WO-97/28737 | 8/1997 |
| WO | WO-97/41421 | 11/1997 |
| WO | WO-97/42882 | 11/1997 |
| WO | WO-97/42883 | 11/1997 |
| WO | WO-97/42886 | 11/1997 |
| WO | WO-97/42888 | 11/1997 |
| WO | WO-97/43962 | 11/1997 |
| WO | WO-97/46868 | 12/1997 |
| WO | WO-98/09167 | 3/1998 |
| WO | WO-98/10699 | 3/1998 |
| WO | WO-98/19159 | 5/1998 |
| WO | WO-98/24358 | 6/1998 |
| WO | WO-98/24366 | 6/1998 |
| WO | WO-98/52045 | 11/1998 |
| WO | WO-98/52293 | 11/1998 |
| WO | WO-98/56293 | 12/1998 |
| WO | WO-99/05966 | 2/1999 |
| WO | WO-99/13574 | 3/1999 |
| WO | WO-99/32883 | 7/1999 |
| WO | WO-99/48419 | 9/1999 |
| WO | WO-99/56613 | 11/1999 |
| WO | WO-99/58051 | 11/1999 |
| WO | WO-99/58973 | 11/1999 |
| WO | WO-00/13580 | 3/2000 |
| WO | WO-00/18294 | 4/2000 |
| WO | WO-00/19887 | 4/2000 |

(56) References Cited

FOREIGN PATENT DOCUMENTS

| | | |
|---|---|---|
| WO | WO-00/20626 | 4/2000 |
| WO | WO-00/32098 | 6/2000 |
| WO | WO-00/33065 | 6/2000 |
| WO | WO-00/49940 | 8/2000 |
| WO | WO-00/59370 | 10/2000 |
| WO | WO-00/59373 | 10/2000 |
| WO | WO-00/62664 | 10/2000 |
| WO | WO-00/62665 | 10/2000 |
| WO | WO-00/74753 | 12/2000 |
| WO | WO-00/78210 | 12/2000 |
| WO | WO-00/78992 | 12/2000 |
| WO | WO-01/12158 | 2/2001 |
| WO | WO-01/20019 | 3/2001 |
| WO | WO-01/20334 | 3/2001 |
| WO | WO-01/24038 | 4/2001 |
| WO | WO-01/33216 | 5/2001 |
| WO | WO-01/34243 | 5/2001 |
| WO | WO-01/43660 | 6/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/58348 | 8/2001 |
| WO | WO-01/67009 | 9/2001 |
| WO | WO-01/68901 | 9/2001 |
| WO | WO-01/69222 | 9/2001 |
| WO | WO-01/88524 | 11/2001 |
| WO | WO-01/88534 | 11/2001 |
| WO | WO-02/16905 | 2/2002 |
| WO | WO-02/17210 | 2/2002 |
| WO | WO-02/24065 | 3/2002 |
| WO | WO-02/058537 | 8/2002 |
| WO | WO-02/078512 | 10/2002 |
| WO | WO-02/082989 | 10/2002 |
| WO | WO-02/100266 | 12/2002 |
| WO | WO-03/072269 | 9/2003 |
| WO | WO-03/076893 | 9/2003 |
| WO | WO-03/082091 | 10/2003 |
| WO | WO-03/101862 | 12/2003 |
| WO | WO-2004/061420 | 7/2004 |
| WO | WO-2005/041766 | 5/2005 |
| WO | WO-2005/065542 | 7/2005 |
| WO | WO-2005/089103 | 9/2005 |
| WO | WO-2005/026689 | 10/2005 |
| WO | WO-2006/105146 | 10/2006 |
| WO | WO-2006/119084 | 11/2006 |
| WO | WO-2007/002189 | 1/2007 |
| WO | WO-2007/016399 | 2/2007 |
| WO | WO-2007/027381 | 3/2007 |
| WO | WO-2007/027788 | 3/2007 |
| WO | WO-2007/051139 | 5/2007 |
| WO | WO-2007/053832 | 5/2007 |
| WO | WO-2007/056638 | 5/2007 |
| WO | WO-2007/120363 | 10/2007 |
| WO | WO-2009/029662 | 3/2009 |
| WO | WO-2011/002692 | 1/2011 |
| WO | WO-2011/002693 | 1/2011 |

OTHER PUBLICATIONS

Abel, P. U., et al., "Biosensors for In Vivo Glucose Measurement: Can We Cross the Experimental Stage", *Biosensors and Bioelectronics*, vol. 17, 2002, pp. 1059-1070.

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of The Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, 1994, pp. 319-325.

Anderson, L. B., et al., "Thin-Layer Electrochemistry: Steady-State Methods of Studying Rate Processes", *Journal of ElectroAnalytical Chemistry*, vol. 10, 1965, pp. 295-305.

Armour, J. C., et al., "Application of Chronic Intravascular Blood Glucose Sensor in Dogs", *Diabetes*, vol. 39, 1990, pp. 1519-1526.

Asberg, P., et al., "Hydrogels of a Conducting Conjugated Polymer as 3-D Enzyme Electrode", *Biosensors & Bioelectronics*, vol. 19, 2003, pp. 199-207.

Atanasov, P., et al., "Biosensor for Continuous Glucose Monitoring", *Biotechnology and Bioengineering*, vol. 43, 1994, pp. 262-266.

Atanasov, P., et al., "Implantation of a Refillable Glucose Monitoring-Telemetry Device", *Biosensors & Bioelectronics*, vol. 12, No. 7, 1997, pp. 669-680.

Aussedat, B., et al., "A User-Friendly Method for Calibrating a Subcutaneous Glucose Sensor-Based Hypoglycaemic Alarm", *Biosensors & Bioelectronics*, vol. 12, No. 11, 1997, pp. 1061-1071.

Baker, D. A., et al., "Dynamic Concentration Challenges for Biosensor Characterization", *Biosensors & Bioelectronics*, vol. 8, 1993, pp. 433-441.

Baker, D. A., et al., "Dynamic Delay and Maximal Dynamic Error in Continuous Biosensors", *Analytical Chemistry*, vol. 68, No. 8, 1996, pp. 1292-1297.

Bani Amer, M. M., "An Accurate Amperometric Glucose Sensor Based Glucometer with Eliminated Cross-Sensitivity", *Journal of Medical Engineering & Technology*, vol. 26, No. 5, 2002, pp. 208-213.

Bard, A. J., et al., *Electrochemical Methods*, 1980, pp. 173-175.

Bartlett, P. N., et al., "Covalent Binding of Electron Relays to Glucose Oxidase", *Journal of the Chemical Society, Chemical Communications*, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/88, pp. 359-379.

Beach, R. D., et al., "Subminiature Implantable Potentiostat and Modified Commercial Telemetry Device for Remote Glucose Monitoring", *IEEE Transactions on Instrumentation and Measurement*, vol. 28, No. 6, 1999, pp. 1239-1245.

Beech, W. A., "AX.25 Link Access Protocol for Amateur packet radio", *Tucson Amateur Packet Radio Corporation*, 1998, pp. 1-133.

Bellucci, F., et al., "Electrochemical Behaviour of Graphite-Epoxy Composite Materials (GECM) in Aqueous Salt Solutions", *Journal of Applied Electrochemistry*, vol. 16, 1986, pp. 15-22.

Bennion, N., et al., "Alternate Site Glucose Testing: A Crossover Design", *Diabetes Technology & Therapeutics*, vol. 4, No. 1, 2002, pp. 25-33.

Biermann, E., et al., "How Would Patients Behave if They Were Continually Informed of Their Blood Glucose Levels? A Simulation Study Using a 'Virtual' Patient", *Diabetes Technology & Therapeutics*, vol. 10, No. 3, 2008, pp. 178-187.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Bindra, D. S., et al., "Pulsed Amperometric Detection of Glucose in Biological Fluids at a Surface-Modified Gold Electrode", *Analytical Chemistry*, vol. 61, No. 22, 1989, pp. 2566-2570.

Bisenberger, M., et al., "A Triple-Step Potential Waveform at Enzyme Multisensors with Thick-Film Gold Electrodes for Detection of Glucose and Sucrose", *Sensors and Actuators B*, vol. 28, 1995, pp. 181-189.

Bland, J. M., et al., "A Note on the Use of the Intraclass Correlation Coefficient in the Evaluation of Agreement Between Two Methods of Measurement", *Computers in Biology and Medicine*, vol. 20, No. 5, 1990, pp. 337-340.

(56) References Cited

OTHER PUBLICATIONS

Bland, J. M., et al., "Statistical Methods for Assessing Agreement Between Two Methods of Clinical Measurement", *The Lancet*, 1986, pp. 307-310.
Blank, T. B., et al., "Clinical Results From a Non-Invasive Blood Clucose Monitor", *Optical Diagnostics and Sensing of Biological Fluids and Glucose and Cholesterol Monitoring II, Proceedings of SPIE*, vol. 4624, 2002, pp. 1-10.
Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.
Bode, B. W., "Clinical Utility of the Continuous Glucose Monitoring System", *Diabetes Technology & Therapeutics*, vol. 2, Sup. 1, 2000, pp. S35-S41.
Bode, B. W., et al., "Continuous Glucose Monitoring Used to Adjust Diabetes Therapy Improves Glycosylated Hemoglobin: A Pilot Study", *Diabetes Research and Clinical Practice*, vol. 46, 1999, pp. 183-190.
Bode, B. W., et al., "Using the Continuous Glucose Monitoring System to Improve the Management of Type I Diabetes", *Diabetes Technology & Therapeutics*, vol. 2, Sup. 1, 2000, pp. S43-S48.
Boedeker Plastics, Inc., "Polyethylene Specifications", Web Page of Boedeker.com, 2007, pp. 1-3.
Bolinder, J., et al., "Microdialysis Measurement of the Absolute Glucose Concentration in Subcutaneous Adipose Tissue Allowing Glucose Monitoring in Diabetic Patients", *Diabetologia*, vol. 35, 1992, pp. 1177-1180.
Bolinder, J., et al., "Self-Monitoring of Blood Glucose in Type I Diabetic Patients: Comparison with Continuous Microdialysis Measurements of Glucose in Subcutaneous Adipose Tissue During Ordinary Life Conditions", *Diabetes Care*, vol. 20, No. 1, 1997, pp. 64-70.
Bott, A. W., "A Comparison of Cyclic Voltammetry and Cyclic Staircase Voltammetry", *Current Separations*, vol. 16, No. 1, 1997, pp. 23-26.
Bott, A. W., "Electrochemical Methods for the Determination of Glucose", *Current Separations*, vol. 17, No. 1, 1998, pp. 25-31.
Bowman, L., et al., "The Packaging of Implantable Integrated Sensors", *IEEE Transactions on Biomedical Engineering*, vol. 33, No. 2, 1986, pp. 248-255.
Brandt, J., et al., "Covalent Attachment of Proteins to Polysaccharide Carriers by Means of Benzoquinone", *Biochimica et Biophysica Acta*, vol. 386, 1975, pp. 196-202.
Brauker, J., et al., "Sustained Expression of High Levels of Human Factor IX from Human Cells Implanted Within an Immunoisolation Device into Athymic Rodents", *Human Gene Therapy*, vol. 9, No. 6, 1998, pp. 879-888.
Bremer, T. M., et al., "Benchmark Data from the Literature for Evaluation of New Glucose Sensing Technologies", *Diabetes Technology & Therapeutics*, vol. 3, No. 3, 2001, pp. 409-418.
Bremer, T., et al., "Is Blood Glucose Predictable from Previous Values?", *Diabetes*, vol. 48, 1999, pp. 445-451.
Brooks, S. L., et al., "Development of an On-Line Glucose Sensor for Fermentation Monitoring", *Biosensors*, vol. 3, 1987/88, pp. 45-56.
Brownlee, M., et al., "A Glucose-Controlled Insulin-Delivery System: Semisynthetic Insulin Bound to Lectin", *Science*, vol. 206, 1979, 1190-1191.
Cai, Q., et al., "A Wireless, Remove Query Glucose Biosensor Based on a pH-Sensitive Polymer", *Analytical Chemistry*, vol. 76, No. 14, 2004, pp. 4038-4043.
Candas, B., et al., "An Adaptive Plasma Glucose Controller Based on a Nonlinear Insulin/Glucose Model", *IEEE Transactions on Biomedical Engineering*, vol. 41, No. 2, 1994, pp. 116-124.
Cass, A. E., et al., "Ferricinum Ion As an Electron Acceptor for Oxido-Reductases", *Journal of ElectroAnalytical Chemistry*, vol. 190, 1985, pp. 117-127.
Cass, A. E., et al., "Ferrocene-Medicated Enzyme Electrode for Amperometric Determination of Glucose", *Analytical Chemistry*, vol. 56, No. 4, 1984, 667-671.
Castner, J. F., et al., "Mass Transport and Reaction Kinetic Parameters Determined Electrochemically for Immobilized Glucose Oxidase", *Biochemistry*, vol. 23 No. 10, 1984, 2203-2210.
Chen, J. C., et al., "A Comparison of MAC Protocols for Wireless Local Networks Based on battery Power Consumption", *IEEE*, 1998, pp. 150-157.
Chen, T., et al., "Defining the Period of Recovery of the Glucose Concentration After Its Local Perturbation by the Impantation of a Miniature Sensor", *Clinical Chemistry and Laboratory Medicine*, vol. 40, No. 8, 2002, pp. 486-489.
Chia, C. W., et al., "Glucose Sensors: Toward Closed Loop Insulin Delivery", *Endocrinology and Metabolism Clinics of North America*, vol. 33, 2004, pp. 175-195.
Choleau, C., et al., "Calibration of a Subcutaneous Amperometric Glucose Sensor Implanted for 7 Days in Diabetic Patients Part 2: Superiority of the One-Point Calibration Method", *Biosensors and Bioelectronics*, vol. 17, 2002, pp. 647-654.
Choleau, C., et al., "Calibration of a Subcutaneous Amperometric Glucose Sensor Part 1: Effect of Measurement Uncertainties on the Determination of Sensor Sensitivity and Background Current", *Biosensors and Bioelectronics*, vol. 17, 2002, pp. 641-646.
Claremont, D. J., et al., "Biosensors for Continuous in Vivo Glucose Monitoring", *Proceedings of the Annual International Conference of the IEEE Engineering in Medicine and Biology Society*, vol. 10, 1988.
Clark Jr., L. C., et al., "Differential Anodic Enzyme Polarography for the Measurement of Glucose", *Oxygen Transport to Tissue: Instrumentation, Methods, and Physiology*, 1973, pp. 127-133.
Clark Jr., L. C., et al., "Electrode Systems for Continuous Monitoring in Cardiovascular Surgery", *Annals New York Academy of Sciences*, 1962, pp. 29-45.
Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.
Clarke, W. L., et al., "Evaluating Clinical Accuracy of Systems for Self-Monitoring of Blood Glucose", *Diabetes Care*, vol. 10, No. 5, 1987, pp. 622-628.
Cox, D. J., et al., "Accuracy of Perceiving Blood Glucose in IDDM", *Diabetes Care*, vol. 8, No. 6, 1985, pp. 529-536.
Csoregi, E., et al., "Amperometric Microbiosensors for Detection of Hydrogen Peroxide and Glucose Based on Peroxidase-Modified Carbon Fibers", *Electroanalysis*, vol. 6, 1994, pp. 925-933.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.
Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.
D'Arrigo, G., et al., "Porous-Si Based Bio Reactors for Glucose Monitoring and Drugs Production", *Proceedings of SPIE: Microfluids, BioMEMS, and Medical Microsystems*, vol. 4982, 2003, pp. 178-184.
Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.
Davies, M. L., et al., "Polymer Membranes in Clinical Sensor Applications", *Biomaterials*, vol. 13, No. 14, 1992, pp. 971-978.
Davis, G., "Electrochemical Techniques for the Development of Amperometric Biosensors", *Biosensors*, vol. 1, 1985, pp. 161-178.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

(56) References Cited

OTHER PUBLICATIONS

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.
Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.
Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.
Dixon, B. M., et al., "Characterization In Vitro and In Vivo of the Oxygen Dependence of an Enzyme/Polymer Biosensors for Monitoring Brain Glucose", *Journal of Neuroscience Methods*, vol. 119, 2002, pp. 135-142.
*Eighth Annual Diabetes Technology Meeting Abstracts*, Nov. 13-15, 2008, pp. Al -A182.
El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.
Ellis, C. D., et al., "Selectivity and Directed Charge Transfer through an Electroactive Metallopolymer Film", *Journal of the American Chemical Society*, vol. 103, No. 25, 1981, pp. 7480-7483.
El-Sa'Ad, L., et al., "Moisture Absorption by Epoxy Resins: The Reverse Thermal Effect", *Journal of Materials Science*, vol. 25, No. 8, 1990, pp. 3577-3582.
Engstrom, R. C., "Electrochemical Pretreatment of Glassy Carbon Electrodes", *Analytical Chemistry*, vol. 54, No. 13, 1982, pp. 2310-2314.
Engstrom, R. C., et al., "Characterization of Electrochemically Pretreated Glassy Carbon Electrodes", *Analytical Chemistry*, vol. 56, No. 2, 1984, pp. 136-141.
Ernst, H., et al., "Reliable Glucose Monitoring Through the Use of Microsystem Technology", *Analytical and Bioanalytical Chemistry*, vol. 373, 2002, pp. 758-761.
Fabietti, P. G., et al. "Clinical Validation of a New Control-Oriented Model of Insulin and Glucose Dynamics in Subjects with Type 1 Diabetes", *Diabetes Technology & Therapeutics*, vol. 9, No. 4, 2007, pp. 327-338.
Fare, T. L., et al., "Functional Characterization of a Conducting Polymer-Based Immunoassay System", *Biosensors & Bioelectronics*, vol. 13, No. 3-4, 1998, pp. 459-470.
Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.
Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.
Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.
Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society*, Faraday Transactions 1, vol. 82, 1986, pp. 1259-1264.
Foulds, N. C., et al , "Immobilization of Glucose Oxidase in Ferrocene-Modified Pyrrole Polymers", *Analytical Chemistry*, vol. 60, No. 22, 1988, pp. 2473-2478.
Frew, J. E., et al., "Electron-Transfer Biosensors", *Philosophical Transactions of the Royal Society of London*, vol. 316, 1987, pp. 95-106.
Frohnauer, M. K., et al., "Graphical Human Insulin Time-Activity Profiles Using Standardized Definitions", *Diabetes Technology & Therapeutics*, vol. 3, No. 3, 2001, pp. 419-429.
Frost, M. C., et al., "Implantable Chemical Sensors for Real-Time Clinical Monitoring: Progress and Challenges", *Current Opinion in Chemical Biology*, vol. 6, 2002, pp. 633-641.
Garg, S. K., et al., "Correlation of Fingerstick Blood Glucose Measurements with GlucoWatch Biographer Glucose Results in Young Subjects with Type 1 Diabetes", *Diabetes Care*,vol. 22, No. 10, 1999, pp. 1708-1714.
Garg, S. K., et al., "Improved Glucose Excursions Using an Implantable Real-Time Continuous Glucose Sensor in Adults with Type 1 Diabetes", *Diabetes Care*, vol. 27, No. 3, 2004, pp. 734-738.
Geller, R. L., et al., "Use of an Immunoisolation Device for Cell Transplantation and Tumor Immunotherapy", *Annals of the New York Academy of Sciences*, vol. 831, 1997, pp. 438-451.
Gerritsen, M., "Problems Associated with Subcutaneously Implanted Glucose Sensors", *Diabetes Care*, vol. 23, No. 2, 2000, pp. 143-145.
Gerritsen, M., et al., "Influence of Inflammatory Cells and Serum on the Performance of Implantable Glucose Sensors", *Journal of Biomedical materials Research*, vol. 54, 2001, pp. 69-75.
Gerritsen, M., et al., "Performance of Subcutaneously Implanted glucose Sensors for Continuous Monitoring", *The Netherlands Journal of Medicine*, vol. 54, 1999, pp. 167-179.
Gilligan, B. J., et al., "Evaluation of a Subcutaneous Glucose Sensor Out to 3 Months in a Dog Model", *Diabetes Care*, vol. 17, No. 8, 1994, pp. 882-887.
Gilligan, B. J., et al., "Feasibility of Continuous Long-Term Glucose Monitoring from a Subcutaneous Glucose Sensor in Humans", *Diabetes Technology & Therapeutics*, vol. 6, No. 3, 2004, pp. 378-386.
Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.
Gorton, L., et al., "Selective Detection in Flow Analysis Based on the Combination of Immobilized Enzymes and Chemically Modified Electrodes", *Analytica Chimica Acta*, vol. 250, 1991, pp. 203-248.
Gough, D. A., et al , "Immobilized Glucose Oxidase in Implantable Glucose Sensor Technology", *Diabetes Technology & Therapeutics*, vol. 2, No. 3, 2000, pp. 377-380.
Gough, D. A., et al., "The Implantable Glucose Sensor: An Example of Bioengineering Design", *Introduction to Bioengineering*, Chapter 3, 2001, pp. 57-66.
Graham, N. B., "Poly(ethylene oxide) and Related Hydrogels," *Hydrogels in Medicine and Pharmacy*, vol. II: Polymers, Chapter 4, 1987, pp. 95-113.
Grant, R., et al., *Grant & Hackh's Chemical Dictionary*, 1987, pp. 88, 89, 389, 390, 398.
Gregg, B. A., et al., "Cross-Linked Redox Gels Containing Glucose Oxidase for Amperometric Bionsensor Applications", *Analytical Chemistry*, vol. 62, No. 3, 1990, pp. 258-263.
Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.
Gross, T. M., et al., "Efficacy and Reliability of the Continuous Glucose Monitoring System", *Diabetes Technology & Therapeutics*, vol. 2, Sup. 1, 2000, pp. S19-S26.
Gross, T. M., et al., "Performance Evaluation of the MiniMed® Continuous Glucose Monitoring System During Patient Home Use", *Diabetes Technology & Therapeutics*, vol. 2, No. 1, 2000, pp. 49-56.
Guerci, B., et al., "Clinical Performance of CGMS in Type 1 Diabetic Patients Treated by Continuous Subcutaneous Insulin Infusion Using Insulin Analogs", *Diabetes Care*, vol. 26, 2003, pp. 582-589.
Gunasingham, et al., "Electrochemically Modulated Optrode for Glucose", *Biosensors & Bioelectronics*, vol. 7, 1992, pp. 353-359.

(56) References Cited

OTHER PUBLICATIONS

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.
Hall, S. B., et al., "Electrochemical Oxidation of Hydrogen Peroxide at Platinum Electrodes: Part I: An Absorption-Controlled Mechanism", *Electrochimica Acta*, vol. 43, No. 5-6, 1998, pp. 579-588.
Hall, S. B., et al., "Electrochemical Oxidation of Hydrogen Peroxide at Platinum Electrodes: Part II: Effect of Potential", *Electrochimica Acta*, vol. 43, No. 14-15, 1998, pp. 2015-2024.
Hall, S. B., et al., "Electrochemical Oxidation of Hydrogen Peroxide at Platinum Electrodes: Part III: Effect of Temperature", *Electrochimica Acta*, vol. 44, 1999, pp. 2455-2462.
Hall, S. B., et al., "Electrochemical Oxidation of Hydrogen Peroxide at Platinum Electrodes: Part IV: Phosphate Buffer Dependence", *Electrochimica Acta*, vol. 44, 1999, pp. 4573-4582.
Hall, S. B., et al., "Electrochemical Oxidation of Hydrogen Peroxide at Platinum Electrodes: Part V: Inhibition by Chloride", *Electrochimica Acta*, vol. 45, 2000, pp. 3573-3579.
Hamilton, "Hamilton Needle Gauge Index", www.hamiltoncompany.com.
Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.
Hawkridge, F. M., et al., "Indirect Coulometric Titration of Biological Electron Transport Components", *Analytical Chemistry*, vol. 45, No. 7, 1973, pp. 1021-1027.
Heise, T., et al., "Hypoglycemia Warning Signal and Glucose Sensors: Requirements and Concepts", *Diabetes Technology & Therapeutics*, vol. 5, No. 4, 2003, pp. 563-571.
Heller, A., "Electrical Connection Enzyme Redox Centers to Electrodes", *Journal of Physical Chemistry*, vol. 96, No. 9, 1990, pp. 3579-3587.
Heller, A., "Electrical Wiring of Redox Enzymes", *Accounts of Chemical Research*, vol. 23, No. 5, 1990, 128-134.
Heller, A., "Implanted Electrochemical Glucose Sensors for the Management of Diabetes", *Annual Review of Biomedical Engineering*, vol. 1, 1999, pp. 153-175.
Heller, A., "Plugging Metal Connectors into Enzymes", *Nature Biotechnology*, vol. 21, No. 6, 2003, pp. 631-632.
Heller, A., et al., "Amperometric Biosensors Based on Three-Dimensional Hydrogel-Forming Epoxy Networks", *Sensors and Actuators B*, vol. 13-14, 1993, pp. 180-183.
Hicks, J. M., "In Situ Monitoring", *Clinical Chemistry*, vol. 31, No. 12, 1985, pp. 1931-1935.
Hitchman, M. L., "Measurement of Dissolved Oxygen: Chapter 3: Principles of Voltammetry", *Chemical Analysis*, vol. 49, 1978, pp. 34-123.
Hrapovic, S., et al., "Picoamperometric Detection of Glucose at Ultrasmall Platinum-Based Biosensors: Preparation and Characterization", *Analytical Chemistry*, vol. 75, No. 14, 2003, pp. 3308-3315.
Hu, Y., et al., "A Needle-Type Enzyme-Based Lactate Sensor for In Vivo Monitoring", *Analytica Chimica Acta*, vol. 281, 1993, pp. 503-511.
Huang, C. J., et al., "Electrochemical Generation of Oxygen", *Electrochemistry Research laboratory*, 1972, pp. 1-115.
Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.
Ianniello, R. M., et al , "Immobilized Enzyme Chemically Modified Electrode as an Amperometric Sensor", *Analytical Chemistry*, vol. 53, No. 13, 1981, pp. 2090-2095.
Ikeda, T., et al., "Artificial Pancreas—Investigation of the Stability of Glucose Sensors Using a Telemetry System" (English language translation of abstract), *Jpn. J. Artif. Organs*, vol. 19, No. 2, 1990, 889-892.
Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.
Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Ishikawa, M., et al., "Initial Evaluation of a 290-μm Diameter Subcutaneous Glucose Sensor: Glucose Monitoring with a Biocompatible, Flexible-Wire, Enzyme-Based Amperometric Microsensor in Diabetic and Nondiabetic Humans", *Journal of Diabetes and Its Complication*, vol. 12, 1998, pp. 295-301.
Jablecki, M., et al., "Simulations of the Frequency Response of Implantable Glucose Sensors", *Analytical Chemistry*, vol. 72, No. 8, 2000, pp. 1853-1859.
Jaremko, J., et al., "Advances Toward the Implantable Artificial Pancreas for Treatment of Diabetes", *Diabetes Care*, vol. 21, No. 3, 1998, pp. 444-450.
Jensen, M. B., et al., "Fast Wave Forms for Pulsed Electrochemical Dectection of Glucose by Incorporation of Reductive Desorption of Oxidation Products", *Analytical Chemistry*, vol. 69, No. 9, 1997, pp. 1776-1781.
Jeutter, D. C., "A Transcutaneous Implanted Battery Recharging and Biotelemeter Power Switching System", *IEEE Transactions on Biomedical Engineering*, vol. 29, No. 5, 1982, pp. 314-321.
Jobst, G., et al., "Thin-Film Microbiosensors for Glucose-Lactate Monitoring", *Analytical Chemistry*, vol. 68, No. 18, 1996, pp. 3173-3179.
Johnson, J. M., et al., "Potential-Dependent Enzymatic Activity in an Enzyme Thin-Layer Cell", *Analytical Chemistry*, vol. 54, No. 8, 1982, pp. 1377-1383.
Johnson, K. W., "Reproducible Electrodeposition of Biomolecules for the Fabrication of Miniature Electroenzymatic Biosensors", *Sensors and Actuators B*, vol. 5, 1991, pp. 85-89.
Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.
Johnson, P. C., "Peripheral Circulation", John Wiley & Sons, 1978, pp. 198.
Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.
Josowicz, M., et al., "Electrochemical Pretreatment of Thin Film Platinum Electrodes", *Journal of the Electrochemical Society*, vol. 135 No. 1, 1988, pp. 112-115.
Jovanovic, L., "The Role of Continuous Glucose Monitoring in Gestational Diabetes Mellitus", *Diabetes Technology & Therapeutics*, vol. 2, Sup. 1, 2000, pp. S67-S71.
Jungheim, K., et al., "How Rapid Does Glucose Concentration Change in Daily Life of Patients with Type 1 Diabetes?", *Second Annual Diabetes Technology Meeting*, 2002, pp. A61-A62.
Jungheim, K., et al., "Risky Delay of Hypoglycemia Detection by Glucose Monitoring at the Arm", *Diabetes Care*, vol. 24, No. 7, 2001, pp. 1303-1304.
Kamath, A., et al., "Calibration of a Continuous Glucose Monitor: Effect of Glucose Rate of Change", *Eighth Annual Diabetes Technology Meeting Abstracts*, Nov. 13-15, 2008, pp. A88.
Kang, S. K., et al., "In Vitro and Short-Term in Vivo Characteristics of a Kel-F Thin Film Modified Glucose Sensor", *Analytical Sciences*, vol. 19, 2003, pp. 1481-1486.
Kaplan, S. M., "Wiley Electrical and Electronics Engineering Dictionary", *IEEE Press*, 2004, pp. 141, 142, 548, 549.
Kargol, M., et al., "Studies on the Structural Properties of Porous Membranes: Measurement of Linear Dimensions of Solutes", *Biophysical Chemistry*, vol. 91, 2001, pp. 263-271.

(56) References Cited

OTHER PUBLICATIONS

Katakis, I., et al., "Electrostatic Control of the Electron Transfer Enabling Binding of Recombinant Glucose Oxidase and Redox Polyelectrolytes", *Journal of the American Chemical Society*vol. 116, No. 8, 1994, pp. 3617-3618.
Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.
Kaufman, F. R., "Role of the Continuous Glucose Monitoring System in Pediatric Patients", *Diabetes Technology & Therapeutics*, vol. 2, Sup. 1, 2000, pp. S49-S52.
Kawagoe, J. L., et al., "Enzyme-Modified Organic Conducting Salt Microelectrode", *Analytical Chemistry*, vol. 63, No. 24, 1991, pp. 2961-2965.
Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.
Kenausis, G., et al., "'Wiring' of Glucose Oxidase and Lactate Oxidase Within a Hydrogel Made with Poly(vinyl pyridine) complexed with $[0s(4,4'\text{-dimethoxy-}2,2'\text{-bipyridine})_2C1]^{+/2+}$", *Journal of the Chemical Society, Faraday Transactions*, vol. 92, No. 20, 1996, pp. 4131-4136.
Kerner, W., "Implantable Glucose Sensors: Present Status and Future Developments", *Experimental and Clinical Endocrinology & Diabetes*, vol. 109, Supplement 2, 2001, pp. S341-S346.
Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.
Korf, J., et al., "Monitoring of Glucose and Lactate Using Microdialysis: Applications in Neonates and Rat Brain," *Developmental Neuroscience*, vol. 15, 1993, pp. 240-246.
Koschinsky, T., et al., "New Approach to Technical and Clinical Evaluation of Devices for Self-Monitoring of Blood Glucose", *Diabetes Care*, vol. 11, No. 9, 1988, pp. 619-629.
Koschinsky, T., et al., "Sensors for Glucose Monitoring: Technical and Clinical Aspects" *Diabetes Metabolism Research and Reviews*, vol. 17, 2001, pp. 113-123.
Koudelka, M., et al., "In-Vivo Behaviour of Hypodermically Implanted Microfabricated Glucose Sensors", *Biosensors & Bioelectronics*, vol. 6, 1991, pp. 31-36.
Koudelka, M., et al., "Planar Amperometric Enzyme-Based Glucose Microelectrode", *Sensors and Actuators*, vol. 18, 1989, pp. 157-165.
Kovatchev, B. P., et al., "Evaluating the Accuracy of Continuous Glucose-Monitoring Sensors", *Diabetes Care*, vol. 27, No. 8, 2004, pp. 1922-1928.
Kraver, K. L., et al., "A Mixed-Signal Sensor Interface Microinstrument", *Sensors and Actuators A*, vol. 91, 2001, pp. 266-277.
Krouwer, J. S., "Setting Performance Goals and Evaluating Total Analytical error for Diagnostic Assays", *Clinical Chemistry*, vol. 48, No. 6, 2002, pp. 919-927.
Kruger, D., et al., "Psychological Motivation and Patient Education: A Role for Continuous Glucose Monitoring", *Diabetes Technology & Therapeutics*, vol. 2, Sup. 1, 2000, pp. S93-S97.
Kulys, J., et al., "Mediatorless Peroxidase Electrode and Preparation of Bienzyme Sensors", *Bioelectrochemistry and Bioenergetics*, vol. 24, 1990, pp. 305-311.
Kurnik, R. T., et al., "Application of the Mixtures of Experts Algorithm for Signal Processing in a Noninvasive Glucose Monitoring System" *Sensors and Actuators B*, vol. 60, 1990, pp. 19-26.
Kusano, H., "Glucose Enzyme Electrode with Percutaneous Interface Which Operates Independently of Dissolved Oxygen", *Clinical Physics and Physiological Measurement*, vol. 10, No. 1, 1989, pp. 1-9.
Lacourse, W. R., et al., "Optimization of Waveforms for Pulsed Amperometric Detection of Carbohydrates Based on Pulsed Voltammetry", *Analytical Chemistry*, vol. 65, No. 1, 1993, pp. 50-55.
Lager, W., et al., "Implantable Electrocatalytic Glucose Sensor", *Hormone Metabolic Research*, vol. 26, 1994, pp. 526-530.
Laurell, T., "A Continuous Glucose Monitoring System Based on Microdialysis", *Journal of Medical Engineering & Technology*, vol. 16, No. 5, 1992, pp. 187-193.
Lee, E., et al., "Effects of Size, Void Volume, and Pore Connectivity on Tissue Responses to Porous Silicone Implants", *Transactions on the Twenty-Fifth Annual Meeting of the Society for Biomaterials*, vol. 22, 1999, pp. 171.
Lerner, H., et al., "An Implantable Electrochemical Glucose Sensor", *Annals of the New York Academy of Sciences*, vol. 428, 1984, pp. 263-278.
Lewis, R. J., ed., "2-hydroxyethyl methacrylate", *Hawley's Condensed Chemical Dictionary*, Twelfth Edition, 1993, pp. 596.
Leypoldt, J. K., et al., "Model of a Two-Substrate Enzyme Electrode for Glucose", *Analytical Chemistry*, vol. 56, No. 14, 1984, pp. 2896-2904.
Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.
Liu, W., et al., "A Neuro-Stimulus Chip with Telemetry Unit for Retinal Prosthetic Device", *IEEE Journal of Solid-State Circuits*, vol. 35, No. 10, 2000, pp. 1487-1497.
Lohn, A., et al., "A Knowledge-Based System for Real-Time Validation of Calibrations and Measurements", *Chemometrics and Intelligent Laboratory Systems*, vol. 46, 1999, pp. 57-66.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Luong, J. H. T., et al., "Solubilization of Multiwall Carbon Nanotubes by 3-Aminopropyltriethoxysilane Towards the Fabrication of Electrochemical Biosensors with Promoted Electron Transfer". *Electroanalysis*, vol. 16, No. 1-2, 2004, pp. 132-139.
Lynch, S. M., et al., "Estimation-Based Model Predictive Control of Blood Glucose in Type I Diabetics: A Simulation Study", *Proceedings of the IEEE 27$^{th}$ Annual Northeast Bioengineering Conference*, 2001, pp. 79-80.
Lynn, P. A., "Recursive Digital Filters for Biological Signals", *Medical and Biological Engineering*, vol. 9, 1971, pp. 37-43.
Maidan, R., et al., "Elimination of Electrooxidizable Interferant-Produced Currents in Amperometric Biosensors", *Analytical Chemistry*, vol. 64, No. 23, 1992, pp. 2889-2896.
Makale, M. T., et al., "Tissue Window Chamber System for Validation of Implanted Oxygen Sensors", *American Journal of Physiology: Heart and Circulatory Physiology*, vol. 284, 2003, pp. H2288-H2294.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
Mancy, K. H., et al., "A Galvanic Cell Oxygen Analyzer", *Journal of Electroanalytical Chemistry*, vol. 4, 1962, pp. 65-92.
Maran, A., et al., "Continuous Glucose Monitoring in Diabetic Patients", *Diabetes Care*, vol. 25, No. 2, 2002, pp. 347-352.
March, W. F., "Dealing the Delay", *Diabetes Technology & Therapeutics*, vol. 4, No. 1, 2002, pp. 49-50.
Marko-Varga, G., et al., "Enzyme-Based Biosensor as a Selective Detection Unit in Column Liquid Chromatography", *Journal of Chromatography A*, vol. 660, 1994, pp. 153-167.
Martin, R. F., "General Deming Regression for Estimating Systematic Bias and Its Confidence Interval in Method-Comparison Studies", *Clinical Chemistry*, vol. 46, No. 1, 2000, pp. 100-104.
Mastrototaro, J. J., "The MiniMed Continuous Glucose Monitoring System", *Diabetes Technology & Therapeutics*, vol. 2, Sup. 1, 2000, pp. S13-S18.
Mastrototaro, J. J., et al., "An Electroenzymatic Glucose Sensor Fabricated on a Flexible Substrate", *Sensors and Actuators B*, vol. 5, 1991, pp. 139-144.
Mastrototaro, J. J., et al., "Reproducibility of the Continuous Glucose Monitoring System Matches Previous Reports and the Intended Use of the Product" and "Response to Mastrototaro and Gross", *Diabetes Care*, vol. 26, No. 1, 2003, pp. 256-257.

(56) References Cited

OTHER PUBLICATIONS

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.
Mazze, R. S., et al., "Characterizing Glucose Exposure for Individuals with Normal Glucose Tolerance Using Continuous Glucose Monitoring and Ambulatory Glucose Profile Analysis", *Diabetes Technology & Therapeutics*, vol. 10, No. 3, 2008, pp. 149-159.
McCartney, L. J., et al., "Near-Infrared Fluorescence Lifetime Assay for Serum Glucose Based on Allophycocyanin-Labeled Concanavalin A", *Analytical Biochemistry*, vol. 292, 2001, pp. 216-221.
McGarraugh, G., et al., "Glucose Measurements Using Blood Extracted from the Forearm and the Finger", *TheraSense, Inc.*, 2000, 16 pp. 1-16.
McGarraugh, G., et al., "Physiological Influences on Off-Finger Glucose Testing", *Diabetes Technology & Therapeutics*, vol. 3, No. 3, 2001, pp. 367-376.
McGrath, M. J., et al., "The Use of Differential Measurements with a Glucose Biosensor for Interference Compensation During Glucose Determinations by Flow Injection Analysis", *Biosensors & Bioelectronics*, vol. 10, 1995, pp. 937-943.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.
Memoli, A., et al., "A Comparison Between Different Immobilized Glucoseoxidase-Based Electrodes", *Journal of Pharmaceutical and Biomedical Analysis*, vol. 29, 2002, pp. 1045-1052.
Metzger, M., et al., "Reproducibility of Glucose Measurements Using the Glucose Sensor", *Diabetes Care*, vol. 25, No. 6, 2002, pp. 1185-1191.
Miller, K. M., et al., "Generation of IL1-like Activity in Response to Biomedical Polymer Implants: A Comparison of In Vitro and In Vivo Models", *Journal of Biomedical Materials Research*, vol. 23, 1989, pp. 1007-1026.
Miller, K. M., et al., "Human Monocyte/Macrophage Activation and Interleukin 1 Generation by Biomedical Polymers", *Journal of Biomedical Materials Research*, vol. 22, 1988, pp. 713-731.
Miller, K. M., et al., "In Vitro Stimulation of Fibroblast Activity by Factors Generated from Human Monocytes Activated by Biomedical Polymers", *Journal of Biomedical Materials Research*, vol. 23, 1989, pp. 911-930.
Minimed Technologies, "Tape Tips and Other Infusion Site Information", 1995.
Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.
Moatti-Sirat, D., et al., "Evaluating In Vitro and In Vivo the Interference of Ascorbate and Acetaminophen on Glucose Detection by a Needle-Type Glucose Sensor", *Biosensors & Bioelectronics*, vol. 7, 1992, pp. 345-352.
Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.
Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.
Monsod, T. P., et al., "Do Sensor Glucose Levels Accurately Predict Plasma Glucose Concentrations During Hypoglycemia and Hyperinsulinemia?" *Diabetes Care*, vol. 25, No. 5, 2002, pp. 889-893.
Moussy, F., et al., "A Miniaturized Nafion-Based Glucose Sensor: In Vitro and In Vivo Evaluation in Dogs", *The International Journal of Artificial Organs*, vol. 17, No. 2, 1994, pp. 88-94.
Mowery, K. A., et al., "Preparation and Characterization of Hydrophobic Polymeric Films that are Thromboresistant via Nitric Oxide Release", *Biomaterials*, vol. 21, 2000, pp. 9-21.
Murphy, S. M., et al., "Polymer Membranes in Clinical Sensor Applications", *Biomaterials*, vol. 13, No. 14, 1992, pp. 979-990.
Nagy, G., et al., "A New Type of Enzyme Electrode: The Ascorbic Acid Eliminator Electrode", *Life Sciences*, vol. 31, No. 23, 1982, pp. 2611-2616.
Nakamura, S., et al., "Effect of Periodate Oxidation on the Structure and Properties of Glucose Oxidase", *Biochimica et Biophysica Acta.*, vol. 445, 1976, pp. 294-308.
Nam, Y. S., et al., "A Novel Fabrication Method of Macroporous Biodegradable Polymer Scaffolds Using Gas Foaming Salt as a Porogen Additive", *Journal of Biomedical Materials Research*, vol. 53, 2000, pp. 1-7.
Nappholz, T. A., "Programmers for Implants: A Need for Radical Change", *18th Annual International Conference of the IEEE Engineering in Medicine and Biology Society*, Amsterdam, 1996, pp. 1274-1275.
Narasimham, K., et al., "p-Benzoquinone Activation of Metal Oxide Electrodes for Attachment of Enzymes", *Enzyme and Microbial Technology*, vol. 7, 1985, pp. 283-286.
Neuburger, G. G., et al., "Pulsed Amperometric Detection of Carbohydrates at Gold Electrodes with a Two-Step Potential Waveform", *Analytical Chemistry*, vol. 59, No. 1, 1987, pp. 150-154.
Ohara, T. J., "Osmium Bipyridyl Redox Polymers Used in Enzyme Electrodes", *Platinum Metals Review*, vol. 39, No. 2, 1995, pp. 54-62.
Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.
Ohara, T. J., et al., "Glucose Electrodes Based on Cross-Linked $[Os(bpy)_2Cl]^{+/2+}$Complexed Poly(1-Vinylimidazole) Films", *Analytical Chemistry*, vol. 65, No. 23, 1993, pp. 3512-3517.
Okuda, J., et al., "Mutarotase Effect on Micro Determinations of D-Glucose and Its Anomers with β-D-Glucose Oxidase", *Analytical Biochemistry*, vol. 43, 1971, pp. 312-315.
Olievier, C. N., et al., "In Vivo Measurement of Carbon Dioxide Tension with a Miniature Electrodes", *Pflugers Archiv: European Journal of Physiology*, vol. 373, 1978, pp. 269-272.
Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.
Palleschi, G., et al., "A Study of Interferences in Glucose Measurements in Blood by Hydrogen Peroxide Based Glucose Probes", *Analytical Biochemistry*, vol. 159, 1986, pp. 114-121.
Palmisano, F., et al., "Simultaneous Monitoring of Glucose and Lactate by an Interference and Cross-Talk Free Dual Electrode Amperometric Biosensor Based on Electropolymerized Thin Films", *Biosensors & Bioelectronics*, vol. 15, 2000, pp. 531-539.
Pankratov, I., et al., "Sol-Gel Derived Renewable-Surface Biosensors", *Journal of ElectroAnalytical Chemistry*, vol. 393, 1995, pp. 35-41.
Panteleon, A. E., et al., "The Role of the Independent Variable to Glucose Sensor Calibration", *Diabetes Technology & Therapeutics*, vol. 5, No. 3, 2003, pp. 401-410.
Park, T., et al., "Sol-Gel-based Amperometric Glucose Biosensor Incorporating an Osmium Redox Polymer as Mediator", *Analytical Communications*, vol. 33, 1996, pp. 271-273.
Parker, R. S., et al., "A Model-Based Algorithm for Blood Glucose Control in Type I Diabetic Patients", *IEEE Transactions on Biomedical Engineering*, vol. 46, No. 2, 1999, pp. 148-157.
Patel, H., et al., "Amperometric Glucose Sensors Based on Ferrocene Containing Polymeric Electron Transfer Systems—A Preliminary Report", *Biosensors and Bioelectronics*, vol. 18, 2003, pp. 1073-1076.
Pathak, C., et al., "Rapid Photopolymerization of Immunoprotective Gels in Contact with Cells and Tissue", *Journal of the American Chemical Society*, vol. 114, No. 21, 1992, pp. 8311-8312.

(56) References Cited

OTHER PUBLICATIONS

Petrou, P. S., et al., "Microdevice with Integrated Dialysis Probe and Biosensor Array for Continuous Multi-Analyte Monitoring", *Biosensors & Bioelectronics*, vol. 18, 2003, pp. 613-619.
Pichert, J. W., et al., "Issues for the Coming Age of Continuous Glucose Monitoring", *The Diabetic Educator*, vol. 26, No. 6, 2000, pp. 969-980.
Pickup, J. C., et al., "Responses and Calibration of Amperometric Glucose Sensors Implanted in the Subcutaneous Tissue of Man", *Acta Diabetologica*, vol. 30, 1993, pp. 143-148.
Pickup, J., "Developing Glucose Sensors for In Vivo Use", *Tibtech*, vol. 11, 1993, pp. 285-291.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pickup, J., et al., "Potentially-Implantable, Amperometric Glucose Sensors with Mediated Electron Transfer: Improving the Operating Stability", *Biosensors*, vol. 4, 1989, pp. 109-119.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Pitzer, K. R., et al., "Detection of Hypoglycemia with the GlucoWatch Biographer", *Diabetes Care*, vol. 24, No. 5, 2001, pp. 881-885.
Poirier, J. Y., et al., "Clinical and Statistical Evaluation of Self-Monitoring Blood Glucose Meters", *Diabetes Care*, vol. 21, No. 11, 1998, pp. 1919-1924.
Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.
Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.
Poitout, V., et al., "In Vitro and In Vivo Evaluation in Dogs of a Miniaturized Glucose Sensor", *ASAIO Transactions*, vol. 37, No. 3, 1991, pp. M298-M300.
Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.
Poscia, A., et al., "A Microdialysis Technique for Continuous Subcutaneous Glucose Monitoring in Diabetic Patients (Part 1)", *Biosensors & Bioelectronics*, vol. 18, 2003, pp. 891-898.
Postlethwaite, T. A., et al., "Interdigitated Array Electrode as an Alternative to the Rotated Ring—Disk Electrode for Determination of the Reaction Products of Dioxygen Reduction", *Analytical Chemistry*, vol. 68, No. 17, 1996, pp. 2951-2958.
Prabhu, V. G., et al., "Electrochemical Studies of Hydrogen Peroxide at a Platinum Disc Electrode", *Electrochimica Acta*, vol. 26, No. 6, 1981, pp. 725-729.
Quinn, C. A. P., et al., "Biocompatible, Glucose-Permeable Hydrogel for in Situ Coating of Implantable Biosensors", *Biomaterials*, vol. 18, No. 24, 1997, pp. 1665-1670.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Ratner, B. D., "Reducing Capsular Thickness and Enhancing Angeiogenesis Around Implant Drug Release Systems", *Journal of Controlled Release*, vol. 78, 2002, pp. 211-218.
Reach, G., "Which Threshold to Detect Hypoglycemia?", *Diabetes Care*, vol. 24, No. 5, 2001, pp. 803-804.
Reach, G., et al., "A Method of Evaluating In Vivo the Functional Characteristics of Glucose Sensors", *Biosensors 2*, 1986, pp. 211-220.
Reach, G., et al., "Can Continuous Glucose Monitoring Be Used for the Treatment of Diabetes?", *Analytical Chemistry*, vol. 64, No. 6, 1992, pp. 381-386.
Reach, G., et al., "Letters to the Editor: Re: Diabetes Technology & Therapeutics, 2000; 2:49-56", *Diabetes Technology & Therapeutics*, vol. 3, No. 1, 2001, pp. 129-131.
Rebrin, K., et al., "Automated Feedback Control of Subcutaneous Glucose Concentration in Diabetic Dogs", *Diabetologia*, vol. 32, 1989, pp. 573-576.
Rebrin, K., et al., "Subcutaneous Glucose Predicts Plasma Glucose Independent of Insulin: Implications for Continuous Monitoring", *The American Physiological Society*, 1999, pp. E561-E571.
Reusch, W., "Other Topics: Organometallic Chemistry: Organometallic Compounds: Main Group Organometallic Compounds", *Virtual Textbook of Organic Chemistry*, 1999, Rev. 2007, 25 pages.
Rhodes, R. K., et al., "Prediction of Pocket-Portable and Implantable Glucose Enzyme Electrode Performance from Combined Species Permeability and Digital Simulation Analysis", *Analytical Chemistry*, vol. 66, No. 9, 1994, pp. 1520-1529.
Rigla, M, et al., "Real-Time Continuous Glucose Monitoring Together with Telemedical Assistance Improves Glycemic Control and Glucose Stability in Pump-Treated Patients", *Diabetes Technology & Therapeutics*, vol. 10, No. 3, 2008, pp. 194-199.
Rinken, T., et al., "Calibration of Glucose Biosensors by Using Pre-Study State Kinetic Data", *Biosensors & Bioelectronics*, vol. 13, 1998, pp. 801-807.
Roe, J. N., et al., "Bloodless Glucose Measurements", *Critical Review in Therapeutic Drug Carrier Systems*, vol. 15, Issue 3, 1998, pp. 199-241.
Sacks (ED), "Guidelines and Recommendations for Laboratory Analysis in the Diagnosis and Management of Diabetes Mellitus," *The National Academy of Clinical Biochemistry Presents Laboratory Medicine Practice Guidelines*vol. 13, 2002, pp. 8-11, 21-23, 52-56, 63.
Sakakida, M., et al., "Development of Ferrocene-Mediated Needle-Type Glucose Sensor as a Measure of True Subcutaneous Tissue Glucose Concentrations", *Artifical Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Samuels, G. J., et al., "An Electrode-Supported Oxidation Catalyst Based on Ruthenium (IV). pH 'Encapsulation' in a Polymer Film", *Journal of the American Chemical Society*, vol. 103, No. 2, 1981, pp. 307-312.
Sansen, W., et al., "A Smart Sensor for the Voltammetric Measurement of Oxygen or Glucose Concentrations", *Sensors and Actuators B1*, 1990, pp. 298-302.
Sansen, W., et al., "Chapter 12: Glucose Sensor with Telemetry System", *Implantable Sensor for Closed-Loop Prosthetic Systems*, 1985, pp. 167-175.
Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.
Scheller, F. W., et al., "Second Generation Biosensors," *Biosensors & Bioelectronics*, vol. 6, 1991, pp. 245-253.
Scheller, F., et al., "Enzyme Electrodes and Their Application", *Philosophical Transactions of The Royal Society of London B*, vol. 316, 1987, pp. 85-94.
Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.
Schmidt, F. J., et al., "Calibration of a Wearable Glucose Sensor", *The International Journal of Artificial Organs*, vol. 15, No. 1, 1992, pp. 55-61.

(56) References Cited

OTHER PUBLICATIONS

Schmidt, F. J., et al., "Glucose Concentration in Subcutaneous Extracellular Space", *Diabetes Care*, vol. 16, No. 5, 1993, pp. 695-700.
Schmidtke, D. W., et al., "Accuracy of the One-Point In Vivo Calibration of 'Wired' Glucose Oxidase Electrodes Implanted in Jugular Veins of Rats in Periods of Rapid Rise and Decline of the Glucose Concentration", *Analytical Chemistry*, vol. 70, No. 10, 1998, pp. 2149-2155.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Schoemaker, M., et al., "The SCHM1 System: Subcutaneous Continuous Glucose Monitoring Based on Microdialysis Technique", *Diabetes Technology & Therapeutics*, vol. 5, No. 4, 2003, pp. 599-608.
Schwarz, M., et al., "Micro Implantable Visual Prostheses", *1st Annual International IEEE-EMBS Special Topic Conference on Microtechnologies in Medicine & Biology*, Lyon, France, 2000, pp. 461-465.
Selam, J. L., "Management of Diabetes with Glucose Sensors and Implantable Insulin Pumps: From the Dream of the 60s to the Realities of the 90s", *American Society for Artificial Internal Organs Journal*, 1997, pp. 137-142.
Service, F. J., et al., "Mean Amplitude of Glycemic Excursions, a Measure of Diabetic Instability", *Diabetes*, vol. 19, No. 9, 1970, pp. 644-655.
Service, R. F., "Can Sensors Make a Home in the Body?", *Science*, vol. 297, 2002, pp. 962-963.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetic Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sieminski, A. L., et al., "Biomaterial-Microvasculature Interactions", *Biomaterials*, vol. 21, 2000, pp. 2233-2241.
Sittampalam, G., et al., "Surface-Modified Electrochemical Detector for Liquid Chromatography", *Analytical Chemistry*, vol. 55, No. 9, 1983, pp. 1608-1610.
Skoog, D. A., et al., "Evaluation of Analytical Data,"*Fundamentals of Analytical Chemistry*, 1966, pp. 55.
Skyler, J. S., "The Economic Burden of Diabetes and the Benefits of Improved Glycemic Control: The Potential Role of a Continuous Glucose Monitoring System", *Diabetes Technology & Therapeutics*, vol. 2, Sup. 1, 2000, pp. S7-S12.
Soegijoko, S., et al., "External Artificial Pancreas: A New Control Unit Using Microprocessor", *Hormone and Metabolic Research Supplement Series*, vol. 12, 1982, pp. 165-169.
Sokol, L., et al , "Immobilized-Enzyme Rate-Determination Method for Glucose Analysis", *Clinical Chemistry*, vol. 26, No. 1, 1980, pp. 89-92.
Sokolov, S., et al., "Metrological Opportunities of the Dynamic Mode of Operating an Enzyme Amperometric Biosensor", *Medical Engineering and Physics*, vol. 17, No. 6, 1995, pp. 471-476.
Sproule, B. A., et al., "Fuzzy Pharmacology: Theory and Applications", *Trends in Pharmacological Sciences* vol. 23, No. 9, 2002, pp. 412-417.
Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.
Sriyudthsak, M., et al., "Enzyme-Epoxy Membrane Based Glucose Analyzing System and Medical Applications", *Biosensors & Bioelectronics*, vol. 11, No. 8, 1996, pp. 735-742.
*Stedman's Medical Dictionary*, 26th Edition,1995, pp. 665.
Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27-31.
Sternberg, F., et al., "Calibration Problems of Subcutaneous Glucosensors when Applied 'In-Situ' in Man", *Hormone and Metabolic Research*, vol. 26, 1994, pp. 523-526.
Sternberg, F., et al., "Does Fall in Tissue Glucose Precede Fall in Blood Glucose?" *Diabetologia*, vol. 29, 1996, pp. 609-612.
Sternberg, R., et al., "Covalent Enzyme Coupling on Cellulose Acetate Membranes for Glucose Sensor Development", *Analytical Chemistry*, vol. 60 No. 24, 1988, pp. 2781-2786.
Sternberg, R., et al., "Study and Development of Multilayer Needle-Type Enzyme-Based Glucose Microsensors", *Biosensors*, vol. 4, 1988, pp. 27-40.
Street, J. O., et al., "A Note on Computing Robust Regression Estimates Via Interactively Reweighted Least Squares", *The American Statistician*, vol. 42, No. 2, 1988, pp. 152-154.
Suaning, G. J., et al., "CMOS Neurostimulation ASIC with 100 Channels, Scaleable Output, and Bidirectional Radio-Frequency Telemetry" *IEEE Transactions on Biomedical Engineering*, vol. 48, No. 2, 2001, pp. 248-260.
Suekane, M , "Immobilization of Glucose Isomerase", *Zettschrift fur Allgemeine Mikrobiologie*, vol. 22, No. 8, 1982, pp. 565-576.
Tajima, S., et al., "Simultaneous Determination of Glucose and 1,5-Anydroglucitol", *Chemical Abstracts*, vol. 111, No. 25, 1989, pp. 394.
Takamura, A., et al., Drug release from Poly(vinyl alcohol) Gel Prepared by Freeze-Thaw Procedure, *Journal of Controlled Release*, vol. 20, 1992, pp. 21-27.
Tamura, T., et al., "Preliminary Study of Continuous Glucose Monitoring with a Microdialysis Technique and a Null Method—a Numerical Analysis", *Frontiers Medical and Biological Engineering*, vol. 10, No. 2, 2000, pp. 147-156.
Tanenberg, R. J., et al., "Continuous Glucose Monitoring System: A New Approach to the Diagnosis of Diabetes Gastroparesis", *Diabetes Technology & Therapeutics*, vol. 2, Sup. 1, 2000, pp. S73-S80.
Tang, L, et al., "Fibrin(ogen) Mediates Acute Inflammatory Response to Biomaterials", *Journal of Experimental Medicine*, vol. 178, 1993, pp. 2147-2156.
Tang, L., et al., "Inflammatory Responses to Biomaterials", *American Journal of Clinical Pathology*, vol. 103, No. 4, 1995, pp. 466-471.
Tang, L., et al., "Mast Cells Mediate Acute Inflammatory Responses to Implanted Biomaterials", *Proceedings of the National Academy of Sciences USA*, vol. 95, 1998, pp. 8841-8846.
Tang, L., et al., "Molecular Determinants of Acute Inflammatory Responses to Biomaterials", *Journal of Clinical Investigation*, vol. 97, No. 5, 1996, pp. 1329-1334.
Tang, Z., et al., "Data Transmission from an Implantable Biotelemeter by Load-Shift Keying Using Circuit Configuration Modulator", *IEEE Transactions on Biomedical Engineering*, vol. 42, No. 5, 1995, pp. 524-528.
Tarasevich, M. R., "Bioelectrocatalysis", *Comprehensive Treatise of Electrochemistry*, vol. 10, 1985, pp. 231-295.

(56) References Cited

OTHER PUBLICATIONS

Tatsuma, T., et al., "Enzyme Monolayer—and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)C1]$^{+/2+}$", *Journal of ElectroAnalytical Chemistry*, vol. 396, 1995, pp. 511-515.

Thome-Duret, V., et al., "Continuous Glucose Monitoring in the Free-Moving Rat", *Metabolism*, vol. 47, No. 7, 1998, pp. 799-803.

Thome-Duret, V., et al., "Modification of the Sensitivity of Glucose Sensor Implanted into Subcutaneous Tissue", *Diabetes & Metabolism*, vol. 22, No. 3, 1996, pp. 174-178.

Thompson, M., et al., "In Vivo Probes: Problems and Perspectives", *Clinical Biochemistry*, vol. 19, 1986, pp. 255-261.

Tibell, A., et al., "Survival of Macroencapsulated Allogeneic Parathyriod Tissue One Year After Transplantation in Nonimmunosuppressed Humans", *Cell Transplantation*, vol. 10, No. 7, 2001, pp. 591-599.

Tierney, M. J., "The GlucoWatch® Biographer: A Frequent, Automatic and Noninvasive Glucose Monitor", *Annals of Medicine*, vol. 32, 2000, pp. 632-641.

Tierney, M. J., et al., "Effect of Acetaminophen on the Accuracy of Glucose Measurements Obtained with the GlucoWatch Biographer", *Diabetes Technology & Therapeutics*, vol. 2, No. 2, 2000, pp. 199-207.

Tilbury, J. B., et al., "Receiver Operating Characteristic Analysis for Intelligent Medical Systems—A New Approach for Finding Confidence Intervals", *IEEE Transactions on Biomedical Engineering*, vol. 47, No. 7, 2000, pp. 952-963.

Trajanoski, Z., et al., "Neural Predictive Controller for Insulin Delivery Using the Subcutaneous Route", *IEEE Transactions on Biomedical Engineering*, vol. 45, No. 9, 1998, pp. 1122-1134.

Trecroci, D., "A Glimpse Into the Future: Continuous Monitoring of Glucose with a Microfiber", *Diabetes Interview*, 2002, pp. 42-43.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for In Vivo Electrochemistry", *Analytical Letters*, vol. 24, No. 6, 1991, pp. 935-945.

U.S. Department of Health and Human Services, "Off-The-Shelf-Software Use in Medical Devices", *Guidance for Industry, FDA Reviewers and Compliance on*, 1999, pp. 1-26.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "A Subcutaneous Glucose Sensor with Improved Longevity, Dynamic Range, and Stability of Calibration", *Diabetes Care*, vol. 23, No. 2, 2000, pp. 208-214.

Updike, S. J., et al., "Continuous Glucose Monitor Based on an Immobilized Enzyme Electrode Detector", *The Journal of Laboratory and Clinical Medicine*, vol. 93, No. 4, 1979, pp. 518-527.

Updike, S. J., et al., "Enzymatic Glucose Sensors: Improved Long-Term Performance In Vitro and In Vivo", *American Society for Artificial Internal Organs Journal*, 1994, pp. 157-163.

Updike, S. J., et al., "Implanting the Glucose Enzyme Electrode: Problems, Progress, and Alternative Solutions", *Diabetes Care*, vol. 5, No. 3, 1982, pp. 207-212.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Updike, S. J., et al., "The Enzyme Electrode", *Nature*, vol. 214, 1967, pp. 986-988.

Urban, G., et al., "Miniaturized Thin-Film Biosensors Using Covalently Immobilized Glucose Oxidase", *Biosensors & Bioelectronics*, vol. 6, 1991, pp. 555-562.

Valdes, T. I., et al., "In Vitro and In Vivo Degradation of Glucose Oxidase Enzyme Used for an Implantable Glucose Biosensor", *Diabetes Technology & Therapeutics*, vol. 2, No. 3, 2000, pp. 367-376.

Varalli, M., et al., "A Microdialysis Technique for Continuous Subcutaneous Glucose Monitoring in Diabetic Patients (Part 2)", *Biosensors & Bioelectronics*, vol. 18, 2003, pp. 899-905.

Velho, G., et al., "In Vitro and In Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biomedica Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wade Jr., L. G., "Chapter 17: Reactions of Aromatic Compounds", *Organic Chemistry*, Sixth Edition, 2006, pp. 762-763.

Wagner, J. G., et al., "Continuous Amperometric Monitoring of Glucose in a Brittle Diabetic Chimpanzee with a Miniature Subcutaneous Electroide", *Proceedings of the National Academy of Sciences USA*, 1998, pp. 6379-6382.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Highly Selective Membrane-Free, Mediator-Free Glucose Biosensor", *Analytical Chemistry*, vol. 66, No. 21, 1994, pp. 3600-3606.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Wang, X., et al., "Improved Ruggedness for Membrane-Based Amperometric Sensors Using a Pulsed Amperometric Method", *Analytical Chemistry*, vol. 69, No. 21, 1997, pp. 4482-4489.

Ward, W. K., et al., "A New Amperometric Glucose Microsensor: In Vitro and Short-Term in Vivo Evaluation", *Biosensors & Bioelectronics*, vol. 17, 2002, pp. 181-189.

Ward, W. K., et al., "Assessment of Chronically Implanted Subcutaneous Glucose Sensors in Dogs: The Effect of Surrounding Fluid Masses", *American Society fro Artificial Internal Organs Journal*, 1999, pp. 555-561.

Ward, W. K., et al., "Rise in Background Current Over Time in a Subcutaneous Glucose Sensor in the Rabbit: Relevance to Calibration and Accuracy", *Biosensors & Bioelectronics*, vol. 15, 2000, pp. 53-61.

(56) References Cited

OTHER PUBLICATIONS

Ward, W. K., et al., "Understanding Spontaneous Output Fluctuations of an Amperometric Glucose Sensor: Effect of Inhalation Anesthesia and Use of a Nonenzyme Containing Electrode", *American Society for Artificial Internal Organs Journal*, 2000, pp. 540-546.
Wientjes, K. J. C., *Development of a Glucose Sensor for Diabetic Patients*, 2000, pp. vii-xiii.
Wilkins, E., et al., "Glucose Monitoring: State of the Art and Future Possibilities", *Medical Engineering and Physics*, vol. 18, No. 4, 1995, pp. 273-288.
Wilkins, E., et al., "Integrated Implantable Device for Long-Term Glucose Monitoring", *Biosensors & Bioelectronics*, vol. 10, 1995, pp. 485-494.
Williams, D. L., et al., "Electrochemical-Enzymatic Analysis of Blood Glucose and Lactate", *Analytical Chemistry*, vol. 42, No. 1, 1970, pp. 118-121.
Wilson, G. S., et al., "Enzyme-Based Biosensors for In Vivo Measurements", *Chemical Reviews*, vol. 100, No. 7, 2000, pp. 2693-2704.
Wilson, G. S., et al., "Progress Toward the Development of an Implantable Sensor for Glucose", *Clinical Chemistry*, vol. 38, No. 9, 1992, pp. 1613-1617.
Wood, W. D., et al., ", Hermetic Sealing with Epoxy", *Mechanical Engineering*, 1990, pp. 46-48.
Wu, H., et al., "In Situ Electrochemical Oxygen Generation with an Immunoisolation Device", *Annals of the New York Academy of Sciences*, vol. 875, 1999, pp. 105-125.
Yabuki, S., et al., "Electro-Conductive Enzyme Membrane", *Journal of the Chemical Communications*, 1989, pp. 945-946.
Yang, C., et al., "A Comparison of Physical Properties and Fuel Cell Performance of Nation and Zirconium Phosphate/Nafion Composite Membranes," *Journal of Membrane Science*, vol. 237, 2004, pp. 145-161.
Yang, L., et al., "Determination of Oxidase Enzyme Substrates Using Cross-Flow Thin-Layer Amperometry", *Electroanalysis*, vol. 8, No. 8-9, 1996, pp. 716-721.
Yang, Q., et al., "Development of Needle-Type Glucose Sensor with High Selectivity", *Sensors and Actuators B*, vol. 46, 1998, pp. 249-256.
Yang, S., et al., "A Glucose Biosensor Based on an Oxygen Electrode: In-Vitro Performances in Model Buffer Solution and in Blood Plasma", *Biomedical Instrumentation & Technology*, vol. 30, No. 1, 1996, pp. 55-61.
Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.
Yao, T., "A Chemically-Modified Enzyme Membrane Electrode as an Amperometric Glucose Sensor", *Analytica Chimica Acta*, vol. 148, 1983, pp. 27-33.
Ye, L., et al., "High Current Density 'Wired' Quinoprotein Glucose Dehydrogenase Electrode", *Analytical Chemistry*, vol. 65, No. 3, 1993, pp. 238-241.
Yildiz, A., et al., "Evaluation of an Improved Thin-Layer Electrode", *Analytical Chemistry*, vol. 40, No. 7, 1968, pp. 1018-1024.
Zamzow, K., et al., "New Wearable Continuous Blood Glucose Monitor (BGM) and Artificial Pancreas (AP)", *Diabetes*, vol. 39, 1990, pp. 5A-20A.
Zavalkoff, S. R., et al., "Evaluation of Conventional Blood Glucose Monitoring as an Indicator of Integrated Glucose Values Using a Continuous Subcutaneous Sensor", *Diabetes Care*, vol. 25, No. 9, 2002, pp. 1603-1606.
Zhang, Y., et al., "Application of Cell Culture Toxicity Tests to the Development of Implantable Biosensors", *Biosensors & Bioelectronics*, vol. 6, 1991, pp. 653-661.
Zhang, Y., et al., "Elimination of the Acetaminophen Interference in an Implantable Glucose Sensor", *Analytical Chemistry*, vol. 66, No. 7, 1994, pp. 1183-1188.
Zhu, J., et al., "Planar Amperometric Glucose Sensor Based on Glucose Oxidase Immobilized by Chitosan Film on Prussian Blue Layer", *Sensors*, vol. 2, 2002, pp. 127-136.
Canadian Patent Application No. 2,433,144, Examiner's Report mailed Nov. 2, 2010.
Canadian Patent Application No. 2,433,144, Examiner's Report mailed Sep. 8, 2008.
Chinese Patent Application No. 01822786.4, Office Action mailed Feb. 2, 2007.
Chinese Patent Application No. 01822786.4, Office Action mailed Sep. 21, 2007.
European Patent Application No. 01994499.0, Examination Report mailed Dec. 7, 2006.
European Patent Application No. 01994499.0, Examination Report mailed Feb. 10, 2009.
European Patent Application No. 01994499.0, Examination Report mailed Oct. 11, 2007.
European Patent Application No. 09010614.7, Examination Report mailed Aug. 8, 2012.
European Patent Application No. 09010614.7, Extended European Search Report mailed Mar. 2, 2010.
European Patent Application No. 10012409.8, Extended European Search Report mailed Mar. 15, 2011.
European Patent Application No. 10012414.8, Extended European Search Report mailed Mar. 15, 2011.
Japanese Patent Application No. 2002-558875, Office Action mailed Sep. 26, 2006.
Japanese Patent Application No. 2007-270411, original language and translation of Office Action mailed Aug. 17, 2010.
Japanese Patent Application No. 2007-270411, original language and translation of Office Action mailed Jun. 21, 2011.
PCT Application No. PCT/US2001/050832, International Preliminary Examination Report mailed Nov. 4, 2003.
PCT Application No. PCT/US2001/050832, International Search Report mailed Dec. 17, 2002.
PCT Application No. PCT/US2003/041640, International Preliminary Examination Report mailed 11 Jul. 2005.
U.S. Appl. No. 09/753,746, Notice of Allowance mailed Oct. 9, 2002.
U.S. Appl. No. 09/753,746, Office Action mailed Jul. 3, 2002.
U.S. Appl. No. 10/336,195, Office Action mailed Apr. 29, 2005.
U.S. Appl. No. 10/336,195, Office Action mailed Dec. 28, 2007.
U.S. Appl. No. 10/336,195, Office Action mailed Feb. 6, 2006.
U.S. Appl. No. 10/336,195, Office Action mailed Jul. 16, 2008.
U.S. Appl. No. 10/336,195, Office Action mailed Jun. 17, 2004.
U.S. Appl. No. 10/336,195, Office Action mailed Mar. 25, 2009.
U.S. Appl. No. 10/336,195, Office Action mailed Nov. 10, 2009.
U.S. Appl. No. 10/336,195, Office Action mailed Oct. 26, 2006.
U.S. Appl. No. 11/928,574, Office Action mailed Dec. 30, 2009.
U.S. Appl. No. 11/928,574, Office Action mailed Jul. 21, 2010.
U.S. Appl. No. 11/928,668, Office Action mailed Apr. 1, 2010.
U.S. Appl. No. 11/928,668, Office Action mailed Dec. 23, 2010.
U.S. Appl. No. 11/928,795, Office Action mailed May 12, 2011.
U.S. Appl. No. 11/928,795, Office Action mailed Sep. 15, 2010.
U.S. Appl. No. 11/928,968, Office Action mailed Apr. 28, 2010.
U.S. Appl. No. 11/928,968, Office Action mailed Jul. 22, 2009.
U.S. Patent Reexamination Application No. 90/007,903, Advisory Action mailed Nov. 20, 2008.
U.S. Patent Reexamination Application No. 90/007,903, Decision on Appeal mailed Jan. 18, 2011.
U.S. Patent Reexamination Application No. 90/007,903, Examiner's Answer to Appeal Brief mailed Oct. 2, 2009.
U.S. Patent Reexamination Application No. 90/007,903, Office Action mailed Feb. 13, 2008.
U.S. Patent Reexamination Application No. 90/007,903, Office Action mailed Sep. 19, 2008.
U.S. Patent Reexamination Application No. 90/007,903, Order Granting Request for Reexamination mailed Mar. 27, 2006.
U.S. Patent Reexamination Application No. 90/007,903, Request for Reexamination of U.S. Patent No. 6,565,509 filed Jan. 25, 2006.
U.S. Patent Reexamination Application No. 90/007,910, Advisory Action mailed Feb. 6, 2009.
U.S. Patent Reexamination Application No. 90/007,910, Advisory Action mailed Jul. 30, 2009.
U.S. Patent Reexamination Application No. 90/007,910, Decision on Appeal mailed Jan. 18, 2011.

(56) References Cited

OTHER PUBLICATIONS

U.S. Patent Reexamination Application No. 90/007,910, Examiner's Answer to Appeal Brief mailed Nov. 19, 2009.
U.S. Patent Reexamination Application No. 90/007,910, Office Action mailed Feb. 13, 2008.
U.S. Patent Reexamination Application No. 90/007,910, Office Action mailed Oct. 2, 2008.
U.S. Patent Reexamination Application No. 90/007,910, Order Granting Request for Reexamination mailed Mar. 27, 2006.
U.S. Patent Reexamination Application No. 90/007,910, Request for Reexamination of U.S. Patent No. 6,175,752 filed Feb. 1, 2006.
U.S. Patent Reexamination Application No. 90/007,913, Request for Reexamination of U.S. Patent No. 6,284,478 filed Feb. 1, 2006.
U.S. Patent Reexamination Application No. 90/007,914, Request for Reexamination of U.S. Patent No. 6,329,161 filed Feb. 1, 2006.
U.S. Patent Reexamination Application No. 90/008,172, Request for Reexamination of U.S. Patent No. 6,990,366 filed Aug. 16, 2006.
U.S. Patent Reexamination Application No. 90/008,173, Request for Reexamination of U.S. Patent No. 6,134,461 filed Aug. 16, 2006.
U.S. Patent Reexamination Application No. 90/008,234, Request for Reexamination of U.S. Patent No. 5,899,855 filed Oct. 31, 2006.
U.S. Patent Reexamination Application No. 90/008,457, Notice of Intent to Issue Reexamination Certificate mailed Mar. 13, 2008.
U.S. Patent Reexamination Application No. 90/008,457, Order Granting Request for Reexamination mailed Feb. 23, 2007.
U.S. Patent Reexamination Application No. 90/008,457, Request for Reexamination of U.S. Patent No. 6,990,366 filed Jan. 23, 2007.
U.S. Patent Reexamination Application No. 90/008,665, Request for Reexamination of U.S. Patent No. 6,284,478 filed May 25, 2007.
U.S. Patent Reexamination Application No. 90/008,713, Request for Reexamination of U.S. Patent No. 6,329,161 filed Jul. 25, 2007.
U.S. Patent Reexamination Application No. 90/008,909, Request for Reexamination of U.S. Patent No. 5,899,855 filed Dec. 11, 2007.
U.S. Patent Reexamination Application No. 90/008,928, Request for Reexamination of U.S. Patent No. 6,134,461 filed Nov. 16, 2007.
U.S. Patent Reexamination Application No. 90/009,104 & 90/009,328, Notice of Intent to Issue Reexamination Certificate mailed Nov. 20, 2009.
U.S. Patent Reexamination Application No. 90/009,104 & 90/009,328, Office Action mailed Aug. 4, 2009.
U.S. Patent Reexamination Application No. 90/009,104 & 90/009,328, Office Action mailed Sep. 30, 2009.
U.S. Patent Reexamination Application No. 90/009,104, Office Action mailed Oct. 16, 2008.
U.S. Patent Reexamination Application No. 90/009,104, Order Granting Request for Reexamination mailed Jun. 5, 2008.
U.S. Patent Reexamination Application No. 90/009,104, Request for Reexamination of U.S. Patent No. 6,990,366 filed Apr. 8, 2008.
U.S. Patent Reexamination Application No. 90/009,270, Order Denying Request for Reexamination mailed Dec. 1, 2008.
U.S. Patent Reexamination Application No. 90/009,270, Request for Reexamination of U.S. Patent No. 6,175,752 filed Sep. 8, 2008.
U.S. Patent Reexamination Application No. 90/009,279, Order Denying Request for Reexamination mailed Dec. 1, 2008.
U.S. Patent Reexamination Application No. 90/009,279, Request for Reexamination of U.S. Patent No. 6,565,509 filed Sep. 17, 2008.
U.S. Patent Reexamination Application No. 90/009,328, Order Granting Request for Reexamination mailed Dec. 9, 2008.
U.S. Patent Reexamination Application No. 90/009,328, Request for Reexamination of U.S. Patent No. 6,990,366 filed Nov. 10, 2008.
U.S. Patent Reexamination Application No. 90/009,352, Request for Reexamination of U.S. Patent No. 5,899,855 filed Dec. 4, 2008.
U.S. Patent Reexamination Application No. 90/009,390, Office Action mailed Aug. 23, 2010.
U.S. Patent Reexamination Application No. 90/009,390, Office Action mailed Nov. 26, 2010.
U.S. Patent Reexamination Application No. 90/009,390, Order Granting Request for Reexamination mailed May 1, 2009.
U.S. Patent Reexamination Application No. 90/009,390, Request for Reexamination of U.S. Patent No. 6,565,509 filed Jan. 21, 2009.
U.S. Patent Reexamination Application No. 90/009,472, Office Action mailed Sep. 6, 2012.
U.S. Patent Reexamination Application No. 90/009,472, Replacement Request for Reexamination of U.S. Patent No. 6,284,478 filed Sep. 3, 2009.
U.S. Patent Reexamination Application No. 90/009,472, Request for Reexamination of U.S. Patent No. 6,284,478 filed May 27, 2009.
U.S. Patent Reexamination Application No. 90/009,488, Replacement Request for Reexamination of U.S. Patent No. 6,329,161 filed Jul. 31, 2009.
U.S. Patent Reexamination Application No. 90/009,488, Request for Reexamination of U.S. Patent No. 6,329,161 filed Jun. 10, 2009.
U.S. Patent Reexamination Application No. 90/009,497, Notice of Intent to Issue Reexamination Certificate mailed Aug. 23, 2010.
U.S. Patent Reexamination Application No. 90/009,497, Order Granting Request for Reexamination mailed Jul. 30, 2009.
U.S. Patent Reexamination Application No. 90/009,497, Request for Reexamination of U.S. Patent No. 6,175,752 filed Jun. 17, 2009.
U.S. Patent Reexamination Application No. 90/009,620, Request for Reexamination of U.S. Patent No. 6,329,161 filed Oct. 27, 2009.
U.S. Patent Reexamination Application No. 90/009,763, Request for Reexamination of U.S. Patent No. 6,134,461 filed Jun. 18, 2010.
U.S. Patent Reexamination Application No. 90/010,791, Notice of Intent to Issue Reexamination Certificate mailed May 17, 2011.
U.S. Patent Reexamination Application No. 90/010,791, Office Action mailed Dec. 17, 2010.
U.S. Patent Reexamination Application No. 90/010,791, Office Action mailed May 28, 2010.
U.S. Patent Reexamination Application No. 90/010,791, Order Granting Request for Reexamination mailed Feb. 22, 2010.
U.S. Patent Reexamination Application No. 90/010,791, Request for Reexamination of U.S. Patent No. 6,990,366 filed Dec. 22, 2009.
U.S. Patent Reexamination Application No. 90/010,835, Request for Reexamination of U.S. Patent No. 6,134,461 filed Jan. 27, 2010.
U.S. Patent Reexamination Application No. 90/011,317, Replacement Request for Reexamination of U.S. Patent No. 6,484,046 filed Jan. 14, 2011.
U.S. Patent Reexamination Application No. 90/011,317, Request for Reexamination of U.S. Patent No. 6,484,046 filed Nov. 5, 2010.
U.S. Patent Reexamination Application No. 90/011,346, Request for Reexamination of U.S. Patent No. 6,103,033 filed Nov. 19, 2010.
U.S. Patent Reexamination Application No. 90/011,730, Notice of Intent to Issue Reexam Certificate for U.S. Patent No. 6,990,366 mailed Apr. 5, 2012.
U.S. Patent Reexamination Application No. 90/011,730, Office Action mailed Jan. 11, 2012.
U.S. Patent Reexamination Application No. 90/011,730, Order Granting Request for Reexamination of U.S. Patent No. 6,990,366 mailed Aug. 24, 2011.
U.S. Patent Reexamination Application No. 90/011,730, Request for Reexamination of U.S. Patent No. 6,990,366 filed Jun. 3, 2011.
U.S. Patent Reexamination Application No. 95/002,113, Order Denying Request for Reexamination of U.S. Patent No. 6,990,366 mailed Nov. 13, 2012.
U.S. Patent Reexamination Application No. 95/002,113, Request for Reexamination of U.S. Patent No. 6,990,366 filed Aug. 30, 2012.
U.S. Patent Reexamination Application No. 95/002,162, Order Denying Request for Reexamination of U.S. Patent No. 8,175,673 mailed Nov. 13, 2012.
U.S. Patent Reexamination Application No. 95/002,162, Request for Reexamination of U.S. Patent No. 8,175,673 filed Sep. 7, 2012.

42
55
65
50
49
52
57
58
60
51
58
3A
3A
67
53

FIG. 19A
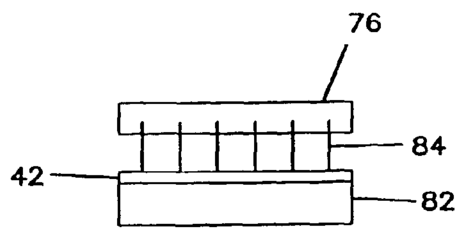
FIG. 19B
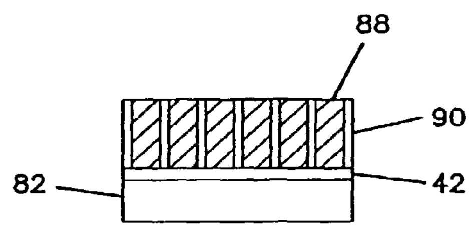
FIG. 19C
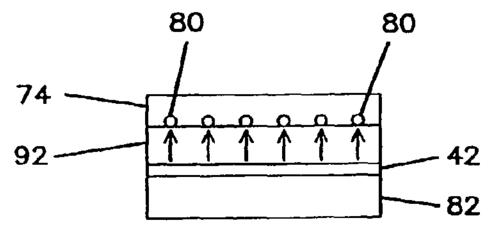
FIG. 19D
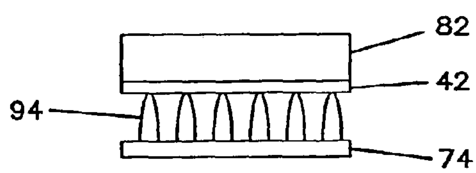
FIG. 19E
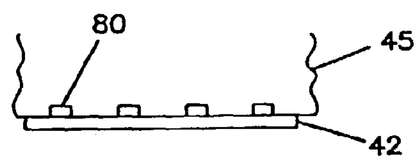
FIG. 19F
45
80
42

CONTROL_BUS
290
FREQ
270
÷ N
DATA_BUS
280
200
LOOP CONTROL
240
PD
210
CHG PMP
212
LF
214
VCO
216
÷ M
218
220
TOTALIZER
250
A
260
F OUT
MODULATION CONTROL
230

ANALYTE MONITORING DEVICE AND METHODS OF USE

RELATED APPLICATIONS

The present application is a continuation of U.S. patent application Ser. No. 10/336,195 filed Jan. 3, 2003, which is a continuation of U.S. patent application Ser. No. 09/753,746 filed Jan. 2, 2001 and issued as U.S. Pat. No. 6,560,471 on May 6, 2003, the disclosures of each of which are herein incorporated by reference for all purposes.

FIELD OF THE INVENTION

The present invention is, in general, directed to devices and methods for the in vivo monitoring of an analyte, such as glucose or lactate. More particularly, the present invention relates to devices and methods for the in vivo monitoring of an analyte using an electrochemical sensor to provide information to a patient about the level of the analyte.

BACKGROUND OF THE INVENTION

The monitoring of the level of glucose or other analytes, such as lactate or oxygen, in certain individuals is vitally important to their health. High or low levels of glucose or other analytes may have detrimental effects. The monitoring of glucose is particularly important to individuals with diabetes, as they must determine when insulin is needed to reduce glucose levels in their bodies or when additional glucose is needed to raise the level of glucose in their bodies.

A conventional technique used by many diabetics for personally monitoring their blood glucose level includes the periodic drawing of blood, the application of that blood to a test strip, and the determination of the blood glucose level using calorimetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many diabetics find the periodic testing inconvenient and they sometimes forget to test their glucose level or do not have time for a proper test. In addition, some individuals wish to avoid the pain associated with the test. These situations may result in hyperglycemic or hypoglycemic episodes.

An in vivo glucose sensor that continuously or automatically monitors the individual's glucose level would enable individuals to more easily monitor their glucose, or other analyte, levels.

A variety of devices have been developed for continuous or automatic monitoring of analytes, such as glucose, in the blood stream or interstitial fluid. A number of these devices use electrochemical sensors which are directly implanted into a blood vessel or in the subcutaneous tissue of a patient. However, these devices are often difficult to reproducibly and inexpensively manufacture in large numbers. In addition, these devices are typically large, bulky, and/or inflexible, and many cannot be used effectively outside of a controlled medical facility, such as a hospital or a doctor's office, unless the patient is restricted in his activities.

Some devices include a sensor guide which rests on or near the skin of the patient and may be attached to the patient to hold the sensor in place. These sensor guides are typically bulky and do not allow for freedom of movement. In addition, the sensor guides or the sensors include cables or wires for connecting the sensor to other equipment to direct the signals from the sensors to an analyzer. The size of the sensor guides and presence of cables and wires hinders the convenient use of these devices for everyday applications. There is a need for a small, compact device that can operate the sensor and provide signals to an analyzer without substantially restricting the movements and activities of a patient.

The patient's comfort and the range of activities that can be performed while the sensor is implanted are important considerations in designing extended-use sensors for continuous or automatic in vivo monitoring of the level of an analyte, such as glucose. There is a need for a small, comfortable device which can continuously monitor the level of an analyte, such as glucose, while still permitting the patient to engage in normal activities. Continuous and/or automatic monitoring of the analyte can provide a warning to the patient when the level of the analyte is at or near a threshold level. For example, if glucose is the analyte, then the monitoring device might be configured to warn the patient of current or impending hyperglycemia or hypoglycemia. The patient can then take appropriate actions.

SUMMARY OF THE INVENTION

Generally, the present invention relates to methods and devices for the continuous and/or automatic in vivo monitoring of the level of an analyte using a subcutaneously implantable sensor. Many of these devices are small and comfortable when used, thereby allowing a wide range of activities. One embodiment is a sensor control unit having a housing adapted for placement on skin. The housing is also adapted to receive a portion of an electrochemical sensor. The sensor control unit includes two or more conductive contacts disposed on the housing and configured for coupling to two or more contact pads on the sensor. A transmitter is disposed in the housing and coupled to the plurality of conductive contacts for transmitting data obtained using the sensor. The sensor control unit may also include a variety of optional components, such as, for example, adhesive for adhering to the skin, a mounting unit, a receiver, a processing circuit, a power supply (e.g., a battery), an alarm system, a data storage unit, a watchdog circuit, and a temperature measurement circuit. Other optional components are described below.

Another embodiment of the invention is a sensor assembly that includes the sensor control unit described above. The sensor assembly also includes a sensor having at least one working electrode and at least one contact pad coupled to the working electrode or electrodes. The sensor may also include optional components, such as, for example, a counter electrode, a counter/reference electrode, a reference electrode, and a temperature probe. Other components and options for the sensor are described below.

A further embodiment of the invention is an analyte monitoring system that includes the sensor control unit described above. The analyte monitoring system also includes a sensor that has at least one working electrode and at least one contact pad coupled to the working electrode or electrodes. The analyte monitoring system also includes a display unit that has a receiver for receiving data from the sensor control unit and a display coupled to the receiver for displaying an indication of the level of an analyte. The display unit may optionally include a variety of components, such as, for example, a transmitter, an analyzer, a data storage unit, a watchdog circuit, an input device, a power supply, a clock, a lamp, a pager, a telephone interface, a computer interface, an alarm or alarm system, a radio, and a calibration unit. Further components and options for the display unit are described below. In addition, the analyte monitoring system or a component of the analyte monitoring system may optionally include a processor capable of determining a drug or treatment protocol and/or a drug delivery system.

Yet another embodiment of the invention is an insertion kit for inserting an electrochemical sensor into a patient. The insertion kit includes an inserter. A portion of the inserter has a sharp, rigid, planer structure adapted to support the sensor during insertion of the electrochemical sensor. The insertion kit also includes an insertion gun having a port configured to accept the electrochemical sensor and the inserter. The insertion gun has a driving mechanism for driving the inserter and electrochemical sensor into the patient, and a retraction mechanism for removing the inserter while leaving the sensor within the patient.

Another embodiment is a method of using an electrochemical sensor. A mounting unit is adhered to the skin of a patient. An insertion gun is aligned with a port on the mounting unit. The electrochemical sensor is disposed within the insertion gun and then the electrochemical sensor is inserted into the skin of the patient using the insertion gun. The insertion gun is removed and a housing of the sensor control unit is mounted on the mounting base. A plurality of conductive contacts disposed on the housing is coupled to a plurality of contact pads disposed on the electrochemical sensor to prepare the sensor for use.

One embodiment of the invention is a method for detecting failures in an implanted analyte-responsive sensor. An analyte-responsive sensor is implanted into a patient. The analyte-responsive sensor includes N working electrodes, where N is an integer and is two or greater, and a common counter electrode. Signals generated at one of the N working electrodes and at the common counter electrode are then obtained and the sensor is determined to have failed if the signal from the common counter electrode is not N times the signal from one of the working electrodes, within a predetermined threshold limit.

Yet another embodiment is a method of calibrating an electrochemical sensor having one or more working electrodes implanted in a patient. A signal is generated from each of the working electrodes. Several conditions are tested to determine if calibration is appropriate. First, the signals from each of the one or more working electrodes should differ by less than a first threshold amount. Second, the signals from each of the one or more working electrodes should be within a predetermined range. And, third, a rate of change of the signals from each of the one or more working electrodes should be less than a second threshold amount. A calibration value is found assaying a calibration sample of a patient's body fluid. The calibration value is then related to at least one of the signals from the one or more working electrodes if the conditions described above are met.

A further embodiment is a method for monitoring a level of an analyte. A sensor is inserted into a skin of a patient and a sensor control unit is attached to the skin of the patient. Two or more conductive contacts on the sensor control unit are coupled to contact pads on the sensor. Then, using the sensor control unit, data is collected regarding a level of an analyte from signals generated by the sensor. The collected data is transmitted to a display unit and an indication of the level of the analyte is displayed on the display unit.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIGS. 19A, 19B, 19C, and 19D are cross-sectional views of four embodiments of conductive contacts disposed on an interior surface of a housing of an on-skin sensor control unit, according to the invention;

FIGS. 19E and 19F are cross-sectional views of two embodiments of conductive contacts disposed on an exterior surface of a housing of an on-skin sensor control unit, according to the invention;

DETAILED DESCRIPTION OF THE INVENTION

Figure 1:
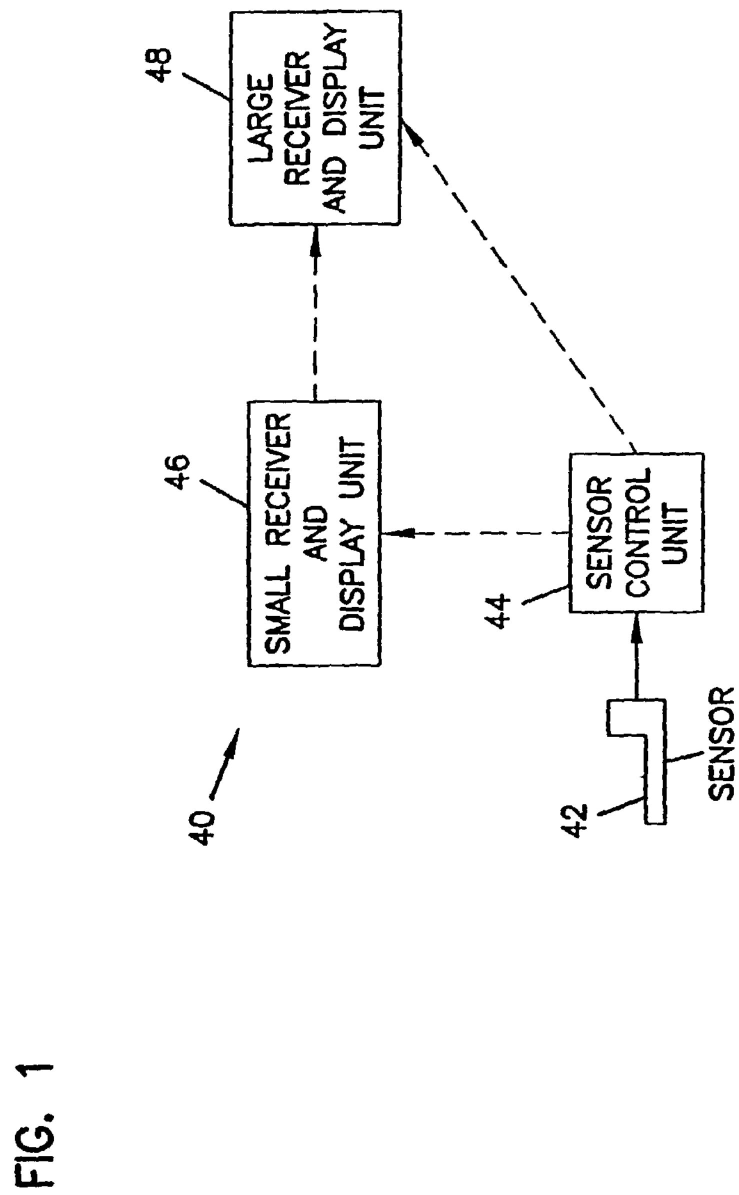
FIG. 1 is a block diagram of one embodiment of a subcutaneous analyte monitor using a subcutaneously implantable analyte sensor, according to the invention.

The present invention is applicable to an analyte monitoring system using an implantable sensor for the in vivo determination of a concentration of an analyte, such as glucose or lactate, in a fluid. The sensor can be, for example, subcutaneously implanted in a patient for the continuous or periodic monitoring an analyte in a patient's interstitial fluid. This can then be used to infer the glucose level in the patient's bloodstream. Other in vivo analyte sensors can be made, according to the invention, for insertion into a vein, artery, or other portion of the body containing fluid. The analyte monitoring system is typically configured for monitoring the level of the analyte over a time period which may range from days to weeks or longer.

The following definitions are provided for terms used herein:

A "counter electrode" refers to an electrode paired with the working electrode, through which passes a current equal in magnitude and opposite in sign to the current passing through the working electrode. In the context of the invention, the term "counter electrode" is meant to include counter electrodes which also function as reference electrodes (i.e., a counter/reference electrode).

An "electrochemical sensor" is a device configured to detect the presence and/or measure the level of an analyte in a sample via electrochemical oxidation and reduction reactions on the sensor. These reactions are transduced to an electrical signal that can be correlated to an amount, concentration, or level of an analyte in the sample.

"Electrolysis" is the electrooxidation or electroreduction of a compound either directly at an electrode or via one or more electron transfer agents.

A compound is "immobilized" on a surface when it is entrapped on or chemically bound to the surface.

A "non-leachable" or "non-releasable" compound or a compound that is "non-leachably disposed" is meant to define a compound that is affixed on the sensor such that it does not substantially diffuse away from the working surface of the working electrode for the period in which the sensor is used (e.g., the period in which the sensor is implanted in a patient or measuring a sample).

Components are "immobilized" within a sensor, for example, when the components are covalently, ionically, or coordinatively bound to constituents of the sensor and/or are entrapped in a polymeric or sol-gel matrix or membrane which precludes mobility.

An "electron transfer agent" is a compound that carries electrons between the analyte and the working electrode, either directly, or in cooperation with other electron transfer agents. One example of an electron transfer agent is a redox mediator.

A "working electrode" is an electrode at which the analyte (or a second compound whose level depends on the level of the analyte) is electrooxidized or electroreduced with or without the agency of an electron transfer agent.

A "working surface" is that portion of the working electrode which is coated with or is accessible to the electron transfer agent and configured for exposure to an analyte-containing fluid.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both. In some embodiments of the sensor, the sensing layer is non-leachably disposed in proximity to or on the working electrode.

A "non-corroding" conductive material includes non-metallic materials, such as carbon and conductive polymers.

Analyte Sensor Systems

The analyte monitoring systems of the present invention can be utilized under a variety of conditions. The particular configuration of a sensor and other units used in the analyte monitoring system may depend on the use for which the analyte monitoring system is intended and the conditions under which the analyte monitoring system will operate. One embodiment of the analyte monitoring system includes a sensor configured for implantation into a patient or user. For example, implantation of the sensor may be made in the arterial or venous systems for direct testing of analyte levels in blood. Alternatively, a sensor may be implanted in the interstitial tissue for determining the analyte level in interstitial fluid. This level may be correlated and/or converted to analyte levels in blood or other fluids. The site and depth of implantation may affect the particular shape, components, and configuration of the sensor. Subcutaneous implantation may be preferred, in some cases, to limit the depth of implantation of the sensor. Sensors may also be implanted in other regions of the body to determine analyte levels in other fluids. Examples of suitable sensor for use in the analyte monitoring systems of the invention are described in U.S. patent application Ser. No. 09/034,372, issued as U.S. Pat. No. 6,134,461, incorporated herein by reference.

One embodiment of the analyte monitoring system 40 for use with an implantable sensor 42, and particularly for use with a subcutaneously implantable sensor, is illustrated in block diagram form in FIG. 1. The analyte monitoring system 40 includes, at minimum, a sensor 42, a portion of which is configured for implantation (e.g., subcutaneous, venous, or arterial implantation) into a patient, and a sensor control unit 44. The sensor 42 is coupled to the sensor control unit 44 which is typically attached to the skin of a patient. The sensor control unit 44 operates the sensor 42, including, for example, providing a voltage across the electrodes of the sensor 42 and collecting signals from the sensor 42. The sensor control unit 44 may evaluate the signals from the sensor 42 and/or transmit the signals to one or more optional receiver/display units 46, 48 for evaluation. The sensor control unit 44 and/or the receiver/display units 46, 48 may display or otherwise communicate the current level of the analyte. Furthermore, the sensor control unit 44 and/or the receiver/display units 46, 48 may indicate to the patient, via, for example, an audible, visual, or other sensory-stimulating alarm, when the level of the analyte is at or near a threshold level. In some embodiments, an electrical shock can be delivered to the patient as a warning through one of the electrodes or the optional temperature probe of the sensor. For example, if glucose is monitored then an alarm may be used to alert the patient to a hypoglycemic or hyperglycemic glucose level and/or to impending hypoglycemia or hyperglycemia.

The Sensor

Figure 2:
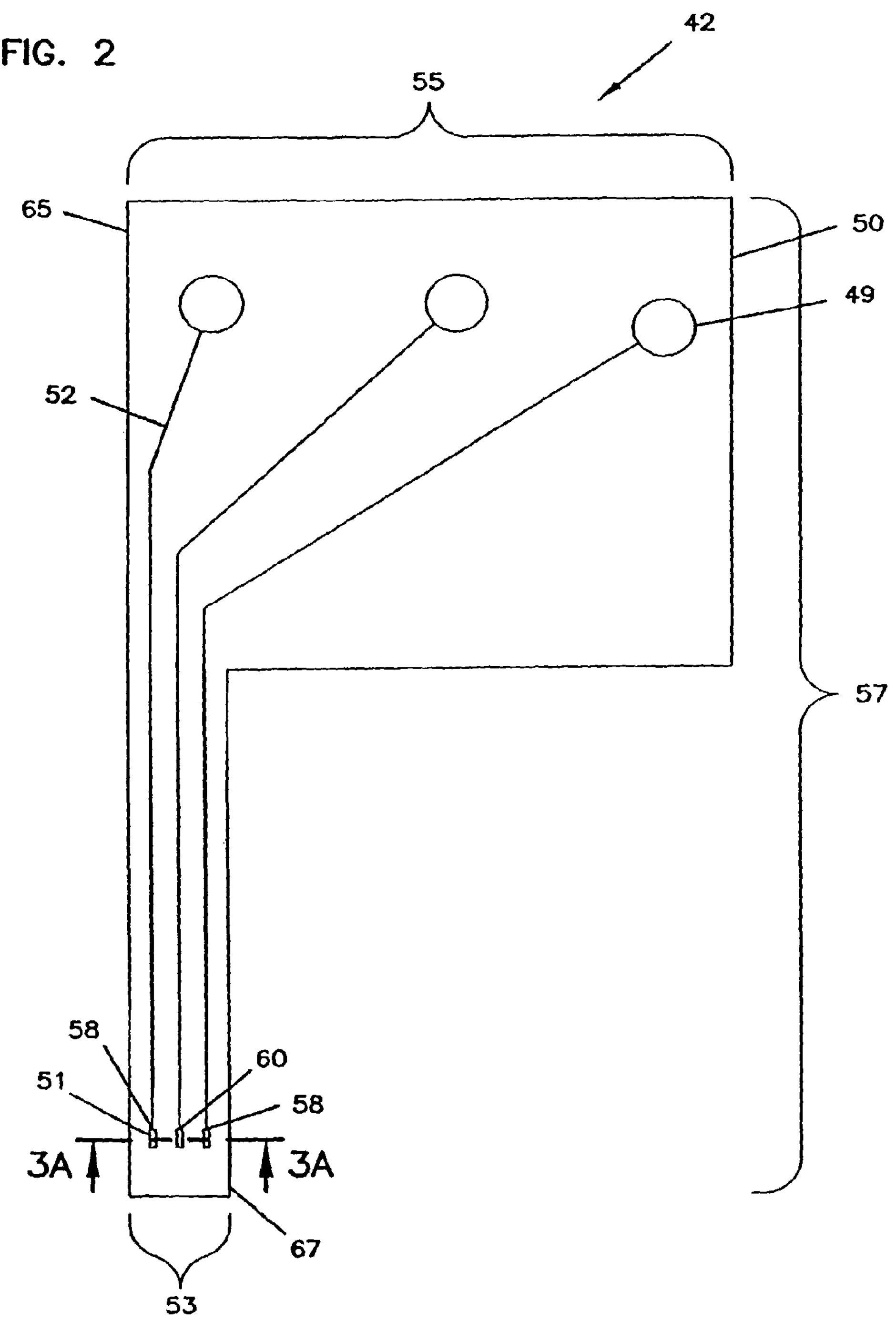
FIG. 2 is a top view of one embodiment of an analyte sensor, according to the invention.

A sensor 42 includes at least one working electrode 58 formed on a substrate 50, as shown in FIG. 2. The sensor 42 may also include at least one counter electrode 60 (or counter/reference electrode) and/or at least one reference electrode 62 (see FIG. 8). The counter electrode 60 and/or reference electrode 62 may be formed on the substrate 50 or may be separate units. For example, the counter electrode and/or reference electrode may be formed on a second substrate which is also implanted in the patient or, for some embodiments of the implantable sensors, the counter electrode and/or reference electrode may be placed on the skin of the patient with the working electrode or electrodes being implanted into the patient. The use of an on-the-skin counter and/or reference electrode with an implantable working electrode is described in U.S. Pat. No. 5,593,852, incorporated herein by reference.

The working electrode or electrodes 58 are formed using conductive traces 52 disposed on the substrate 50. The counter electrode 60 and/or reference electrode 62 (see FIG. 3B), as well as other optional portions of the sensor 42, such as a temperature probe 66 (see FIG. 8), may also be formed using conductive traces 52 disposed on the substrate 50. These conductive traces 52 may be formed over a smooth surface of the substrate 50 or within channels 54 (see FIG. 3A) formed by, for example, embossing, indenting or otherwise creating a depression in the substrate 50.

A sensing layer 64 (see FIGS. 3A and 3B) is often formed proximate to or on at least one of the working electrodes 58 to facilitate the electrochemical detection of the analyte and the determination of its level in the sample fluid, particularly if the analyte cannot be electrolyzed at a desired rate and/or with a desired specificity on a bare electrode. The sensing layer 64 may include an electron transfer agent to transfer electrons directly or indirectly between the analyte and the working electrode 58. The sensing layer 64 may also contain a catalyst to catalyze a reaction of the analyte. The components of the sensing layer may be in a fluid or gel that is proximate to or in contact with the working electrode 58. Alternatively, the components of the sensing layer 64 may be disposed in a polymeric or sol-gel matrix that is proximate to or on the working electrode 58. Preferably, the components of the sensing layer 64 are non-leachably disposed within the sensor 42. More preferably, the components of the sensor 42 are immobilized within the sensor 42.

In addition to the electrodes 58, 60, 62 and the sensing layer 64, the sensor 42 may also include a temperature probe 66 (see FIGS. 6 and 8), a mass transport limiting layer 74 (see FIG. 9), a biocompatible layer 75 (see FIG. 9), and/or other optional components, as described below. Each of these items enhances the functioning of and/or results from the sensor 42, as discussed below.

The Substrate

The substrate 50 may be formed using a variety of non-conducting materials, including, for example, polymeric or plastic materials and ceramic materials. Suitable materials for a particular sensor 42 may be determined, at least in part, based on the desired use of the sensor 42 and properties of the materials.

In some embodiments, the substrate is flexible. For example, if the sensor 42 is configured for implantation into a patient, then the sensor 42 may be made flexible (although rigid sensors may also be used for implantable sensors) to reduce pain to the patient and damage to the tissue caused by the implantation of and/or the wearing of the sensor 42. A flexible substrate 50 often increases the patient's comfort and allows a wider range of activities. Suitable materials for a flexible substrate 50 include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors 42 are made using a relatively rigid substrate 50 to, for example, provide structural support against bending or breaking Examples of rigid materials that may be used as the substrate 50 include poorly conducting ceramics, such as aluminum oxide and silicon dioxide. One advantage of an implantable sensor 42 having a rigid substrate is that the sensor 42 may have a sharp point and/or a sharp edge to aid in implantation of a sensor 42 without an additional insertion device.

It will be appreciated that for many sensors 42 and sensor applications, both rigid and flexible sensors will operate adequately. The flexibility of the sensor 42 may also be controlled and varied along a continuum by changing, for example, the composition and/or thickness of the substrate 50.

In addition to considerations regarding flexibility, it is often desirable that implantable sensors 42 should have a substrate 50 which is non-toxic. Preferably, the substrate 50 is approved by one or more appropriate governmental agencies or private groups for in vivo use.

Figure 12:
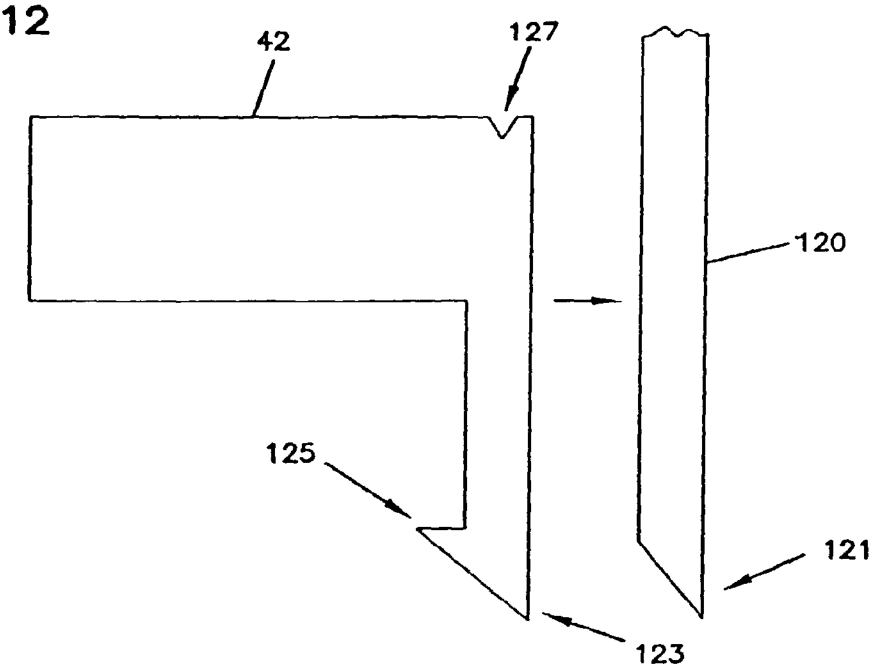
FIG. 12 is an expanded side view of one embodiment of a sensor and an insertion device, according to the invention.

The sensor 42 may include optional features to facilitate insertion of an implantable sensor 42, as shown in FIG. 12. For example, the sensor 42 may be pointed at the tip 123 to ease insertion. In addition, the sensor 42 may include a barb 125 which assists in anchoring the sensor 42 within the tissue of the patient during operation of the sensor 42. However, the barb 125 is typically small enough that little damage is caused to the subcutaneous tissue when the sensor 42 is removed for replacement.

Although the substrate 50 in at least some embodiments has uniform dimensions along the entire length of the sensor 42, in other embodiments, the substrate 50 has a distal end 67 and a proximal end 65 with different widths 53, 55, respectively, as illustrated in FIG. 2. In these embodiments, the distal end 67 of the substrate 50 may have a relatively narrow width 53. For sensors 42 which are implantable into the subcutaneous tissue or another portion of a patient's body, the narrow width 53 of the distal end 67 of the substrate 50 may facilitate the implantation of the sensor 42. Often, the narrower the width of the sensor 42, the less pain the patient will feel during implantation of the sensor and afterwards.

For subcutaneously implantable sensors 42 which are designed for continuous or periodic monitoring of the analyte during normal activities of the patient, a distal end 67 of the sensor 42 which is to be implanted into the patient has a width 53 of 2 mm or less, preferably 1 mm or less, and more preferably 0.5 mm or less. If the sensor 42 does not have regions of different widths, then the sensor 42 will typically have an overall width of, for example, 2 mm, 1.5 mm, 1 mm, 0.5 mm, 0.25 mm, or less. However, wider or narrower sensors may be used. In particular, wider implantable sensors may be used for insertion into veins or arteries or when the movement of the patient is limited, for example, when the patient is confined in bed or in a hospital.

Returning to FIG. 2, the proximal end 65 of the sensor 42 may have a width 55 larger than the distal end 67 to facilitate the connection between contact pads 49 of the electrodes and contacts on a control unit. The wider the sensor 42 at this point, the larger the contact pads 49 can be made. This may reduce the precision needed to properly connect the sensor 42 to contacts on the control unit (e.g., sensor control unit 44 of FIG. 1). However, the maximum width of the sensor 42 may be constrained so that the sensor 42 remains small for the convenience and comfort of the patient and/or to fit the desired size of the analyte monitor. For example, the proximal end 65 of a subcutaneously implantable sensor 42, such as the sensor 42 illustrated in FIG. 1, may have a width 55 ranging from 0.5 mm to 15 mm, preferably from 1 mm to 10 mm, and more preferably from 3 mm to 7 mm. However, wider or narrower sensors may be used in this and other in vivo applications.

The thickness of the substrate 50 may be determined by the mechanical properties of the substrate material (e.g., the strength, modulus, and/or flexibility of the material), the desired use of the sensor 42 including stresses on the substrate 50 arising from that use, as well as the depth of any channels or indentations formed in the substrate 50, as discussed below. Typically, the substrate 50 of a subcutaneously implantable sensor 42 for continuous or periodic monitoring of the level of an analyte while the patient engages in normal activities has a thickness of 50 to 500 μm and preferably 100 to 300 μm. However, thicker and thinner substrates 50 may be used, particularly in other types of in vivo sensors 42.

The length of the sensor 42 may have a wide range of values depending on a variety of factors. Factors which influence the length of an implantable sensor 42 may include the depth of implantation into the patient and the ability of the patient to manipulate a small flexible sensor 42 and make connections between the sensor 42 and the sensor control unit 44. A subcutaneously implantable sensor 42 for the analyte monitor illustrated in FIG. 1 may have a length ranging from 0.3 to 5 cm, however, longer or shorter sensors may be used. The length of the narrow portion of the sensor 42 (e.g., the portion which is subcutaneously inserted into the patient), if the sensor 42 has narrow and wide portions, is typically about 0.25 to 2 cm in length. However, longer and shorter portions may be used. All or only a part of this narrow portion may be subcutaneously implanted into the patient. The lengths of other implantable sensors 42 will vary depending, at least in part, on the portion of the patient into which the sensor 42 is to be implanted or inserted.

Conductive Traces

At least one conductive trace 52 is formed on the substrate for use in constructing a working electrode 58. In addition, other conductive traces 52 may be formed on the substrate 50 for use as electrodes (e.g., additional working electrodes, as well as counter, counter/reference, and/or reference electrodes) and other components, such as a temperature probe. The conductive traces 52 may extend most of the distance along a length 57 of the sensor 50, as illustrated in FIG. 2, although this is not necessary. The placement of the conductive traces 52 may depend on the particular configuration of the analyte monitoring system (e.g., the placement of control unit contacts and/or the sample chamber in relation to the sensor 42). For implantable sensors, particularly subcutaneously implantable sensors, the conductive traces typically extend close to the tip of the sensor 42 to minimize the amount of the sensor that must be implanted.

The conductive traces 52 may be formed on the substrate 50 by a variety of techniques, including, for example, photolithography, screen printing, or other impact or non-impact printing techniques. The conductive traces 52 may also be formed by carbonizing conductive traces 52 in an organic (e.g., polymeric or plastic) substrate 50 using a laser. A description of some exemplary methods for forming the sensor 42 is provided in U.S. patent application Ser. No. 09/034,422, issued as U.S. Pat. No. 6,103,033, incorporated herein by reference.

Figure 3A:
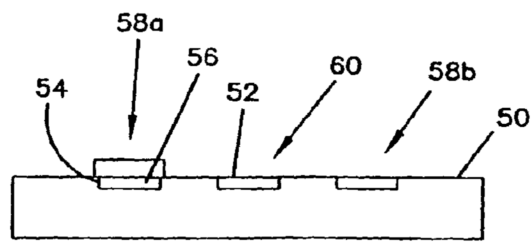
FIG. 3A is a cross-sectional view of the analyte sensor of FIG. 2.

Another method for disposing the conductive traces 52 on the substrate 50 includes the formation of recessed channels 54 in one or more surfaces of the substrate 50 and the subsequent filling of these recessed channels 54 with a conductive material 56, as shown in FIG. 3A. The recessed channels 54 may be formed by indenting, embossing, or otherwise creating a depression in the surface of the substrate 50. Exemplary methods for forming channels and electrodes in a surface of a substrate can be found in U.S. patent application Ser. No. 09/034,422, issued as U.S. Pat. No. 6,103,033. The depth of the channels is typically related to the thickness of the substrate 50. In one embodiment, the channels have depths in the range of about 12.5 to 75 μm (0.5 to 3 mils), and preferably about 25 to 50 μm (1 to 2 mils).

The conductive traces are typically formed using a conductive material 56 such as carbon (e.g., graphite), a conductive polymer, a metal or alloy (e.g., gold or gold alloy), or a metallic compound (e.g., ruthenium dioxide or titanium dioxide). The formation of films of carbon, conductive polymer, metal, alloy, or metallic compound are well-known and include, for example, chemical vapor deposition (CVD), physical vapor deposition, sputtering, reactive sputtering, printing, coating, and painting. The conductive material 56 which fills the channels 54 is often formed using a precursor material, such as a conductive ink or paste. In these embodiments, the conductive material 56 is deposited on the substrate 50 using methods such as coating, painting, or applying the material using a spreading instrument, such as a coating blade. Excess conductive material between the channels 54 is then removed by, for example, running a blade along the substrate surface.

In one embodiment, the conductive material 56 is a part of a precursor material, such as a conductive ink, obtainable, for example, from Ercon, Inc. (Wareham, Mass.), Metech, Inc. (Elverson, Pa.), E.I. du Pont de Nemours and Co. (Wilmington, Del.), Emca-Remex Products (Montgomeryville, Pa.), or MCA Services (Melbourn, Great Britain). The conductive ink is typically applied as a semiliquid or paste which contains particles of the carbon, metal, alloy, or metallic compound and a solvent or dispersant. After application of the conductive ink on the substrate 50 (e.g., in the channels 54), the solvent or dispersant evaporates to leave behind a solid mass of conductive material 56.

In addition to the particles of carbon, metal, alloy, or metallic compound, the conductive ink may also contain a binder. The binder may optionally be cured to further bind the conductive material 56 within the channel 54 and/or on the substrate 50. Curing the binder increases the conductivity of the conductive material 56. However, this is typically not necessary as the currents carried by the conductive material 56 within the conductive traces 52 are often relatively low (usually less than 1 μA and often less than 100 nA). Typical binders include, for example, polyurethane resins, cellulose derivatives, elastomers, and highly fluorinated polymers. Examples of elastomers include silicones, polymeric dienes, and acrylonitrile-butadiene-styrene (ABS) resins. One example of a fluorinated polymer binder is Teflon® (DuPont, Wilmington, Del.). These binders are cured using, for example, heat or light, including ultraviolet (UV) light. The appropriate curing method typically depends on the particular binder which is used.

Often, when a liquid or semiliquid precursor of the conductive material 56 (e.g., a conductive ink) is deposited in the channel 54, the precursor fills the channel 54. However, when the solvent or dispersant evaporates, the conductive material 56 which remains may lose volume such that the conductive material 56 may or may not continue to fill the channel 54. Preferred conductive materials 56 do not pull away from the substrate 50 as they lose volume, but rather decrease in height within the channel 54. These conductive materials 56 typically adhere well to the substrate 50 and therefore do not pull away from the substrate 50 during evaporation of the solvent or dispersant. Other suitable conductive materials 56 either adhere to at least a portion of the substrate 50 and/or contain another additive, such as a binder, which adheres the conductive material 56 to the substrate 50. Preferably, the conductive material 56 in the channels 54 is non-leachable, and more preferably immobilized on the substrate 50. In some embodiments, the conductive material 56 may be formed by multiple applications of a liquid or semiliquid precursor interspersed with removal of the solvent or dispersant.

In another embodiment, the channels 54 are formed using a laser. The laser carbonizes the polymer or plastic material. The carbon formed in this process is used as the conductive material 56. Additional conductive material 56, such as a conductive carbon ink, may be used to supplement the carbon formed by the laser.

In a further embodiment, the conductive traces 52 are formed by pad printing techniques. For example, a film of conductive material is formed either as a continuous film or as a coating layer deposited on a carrier film. This film of conductive material is brought between a print head and the substrate 50. A pattern on the surface of the substrate 50 is made using the print head according to a desired pattern of conductive traces 52. The conductive material is transferred by pressure and/or heat from the film of conductive material to the substrate 50. This technique often produces channels (e.g., depressions caused by the print head) in the substrate 50. Alternatively, the conductive material is deposited on the surface of the substrate 50 without forming substantial depressions.

In other embodiments, the conductive traces 52 are formed by non-impact printing techniques. Such techniques include electrophotography and magnetography. In these processes, an image of the conductive traces 52 is electrically or magnetically formed on a drum. A laser or LED may be used to electrically form an image. A magnetic recording head may be used to magnetically form an image. A toner material (e.g., a conductive material, such as a conductive ink) is then attracted to portions of the drum according to the image. The toner material is then applied to the substrate by contact between the drum and the substrate. For example, the substrate may be rolled over the drum. The toner material may then be dried and/or a binder in the toner material may be cured to adhere the toner material to the substrate.

Another non-impact printing technique includes ejecting droplets of conductive material onto the substrate in a desired pattern. Examples of this technique include ink jet printing and piezo jet printing. An image is sent to the printer which then ejects the conductive material (e.g., a conductive ink) according to the pattern. The printer may provide a continuous stream of conductive material or the printer may eject the conductive material in discrete amounts at the desired points.

Yet another non-impact printing embodiment of forming the conductive traces includes an ionographic process. In the this process, a curable, liquid precursor, such as a photopolymerizable acrylic resin (e.g., Solimer 7501 from Cubital, Bad Kreuznach, Germany) is deposited over a surface of a substrate 50. A photomask having a positive or negative image of the conductive traces 52 is then used to cure the liquid precursor. Light (e.g., visible or ultraviolet light) is directed through the photomask to cure the liquid precursor and form a solid layer over the substrate according to the image on the photomask. Uncured liquid precursor is removed leaving behind channels 54 in the solid layer. These channels 54 can then be filled with conductive material 56 to form conductive traces 52.

Conductive traces 52 (and channels 54, if used) can be formed with relatively narrow widths, for example, in the range of 25 to 250 μm, and including widths of, for example, 250 μm, 150 μm, 100 μm, 75 μm, 50 μm, 25 μm or less by the methods described above. In embodiments with two or more conductive traces 52 on the same side of the substrate 50, the conductive traces 52 are separated by distances sufficient to prevent conduction between the conductive traces 52. The edge-to-edge distance between the conductive traces is preferably in the range of 25 to 250 μm and may be, for example, 150 μm, 100 μm, 75 μm, 50 μm, or less. The density of the conductive traces 52 on the substrate 50 is preferably in the range of about 150 to 700 μm/trace and may be as small as 667 μm/trace or less, 333 μm/trace or less, or even 167 μm/trace or less.

The working electrode 58 and the counter electrode 60 (if a separate reference electrode is used) are often made using a conductive material 56, such as carbon. Suitable carbon conductive inks are available from Ercon, Inc. (Wareham, Mass.), Metech, Inc. (Elverson, Pa.), E.I. du Pont de Nemours and Co. (Wilmington, Del.), Emca-Remex Products (Montgomeryville, Pa.), or MCA Services (Melbourn, Great Britain). Typically, the working surface 51 of the working electrode 58 is at least a portion of the conductive trace 52 that is in contact with the analyte-containing fluid (e.g., implanted in the patient).

The reference electrode 62 and/or counter/reference electrode are typically formed using conductive material 56 that is a suitable reference material, for example silver/silver chloride or a non-leachable redox couple bound to a conductive material, for example, a carbon-bound redox couple. Suitable silver/silver chloride conductive inks are available from Ercon, Inc. (Wareham, Mass.), Metech, Inc. (Elverson, Pa.), E.I. du Pont de Nemours and Co. (Wilmington, Del.), Emca- Remex Products (Montgomeryville, Pa.), or MCA Services (Melbourn, Great Britain). Silver/silver chloride electrodes illustrate a type of reference electrode that involves the reaction of a metal electrode with a constituent of the sample or body fluid, in this case, $Cl^-$.

Suitable redox couples for binding to the conductive material of the reference electrode include, for example, redox polymers (e.g., polymers having multiple redox centers.) It is preferred that the reference electrode surface be non-corroding so that an erroneous potential is not measured. Preferred conductive materials include less corrosive metals, such as gold and palladium. Most preferred are non-corrosive materials including non-metallic conductors, such as carbon and conducting polymers. A redox polymer can be adsorbed on or covalently bound to the conductive material of the reference electrode, such as a carbon surface of a conductive trace 52. Non-polymeric redox couples can be similarly bound to carbon or gold surfaces.

A variety of methods may be used to immobilize a redox polymer on an electrode surface. One method is adsorptive immobilization. This method is particularly useful for redox polymers with relatively high molecular weights. The molecular weight of a polymer may be increased, for example, by cross-linking Another method for immobilizing the redox polymer includes the functionalization of the electrode surface and then the chemical bonding, often covalently, of the redox polymer to the functional groups on the electrode surface. One example of this type of immobilization begins with a poly(4-vinylpyridine). The polymer's pyridine rings are, in part, complexed with a reducible/oxidizable species, such as $[Os(bpy)_2Cl]^{+/2+}$ where bpy is 2,2'-bipyridine. Part of the pyridine rings are quaternized by reaction with 2-bromoethylamine. The polymer is then crosslinked, for example, using a diepoxide, such as polyethylene glycol diglycidyl ether.

Carbon surfaces can be modified for attachment of a redox species or polymer, for example, by electroreduction of a diazonium salt. As an illustration, reduction of a diazonium salt formed upon diazotization of p-aminobenzoic acid modifies a carbon surface with phenylcarboxylic acid functional groups. These functional groups can then be activated by a carbodiimide, such as 1-ethyl-3-(3-dimethylaminopropyl)-carbodiimide hydrochloride. The activated functional groups are then bound with an amine-functionalized redox couple, such as the quaternized osmium-containing redox polymer described above or 2-aminoethylferrocene, to form the redox couple.

Similarly, gold can be functionalized by an amine, such as cystamine. A redox couple such as $[Os(bpy)_2(pyridine\text{-}4\text{-}carboxylate)Cl]^{0/+}$ is activated by 1-ethyl-3-(3-dimethylaminopropyl)-carbodiimide hydrochloride to form a reactive O-acylisourea which reacts with the gold-bound amine to form an amide.

In one embodiment, in addition to using the conductive traces 52 as electrodes or probe leads, two or more of the conductive traces 52 on the substrate 50 are used to give the patient a mild electrical shock when, for example, the analyte level exceeds a threshold level. This shock may act as a warning or alarm to the patient to initiate some action to restore the appropriate level of the analyte.

The mild electrical shock is produced by applying a potential between any two conductive traces 52 that are not otherwise connected by a conductive path. For example, two of the electrodes 58, 60, 62 or one electrode 58, 60, 62 and the temperature probe 66 may be used to provide the mild shock. Preferably, the working electrode 58 and the reference electrode 62 are not used for this purpose as this may cause some damage to the chemical components on or proximate to the particular electrode (e.g., the sensing layer on the working electrode or the redox couple on the reference electrode).

The current used to produce the mild shock is typically 0.1 to 1 mA. Higher or lower currents may be used, although care should be taken to avoid harm to the patient. The potential between the conductive traces is typically 1 to 10 volts. However, higher or lower voltages may be used depending, for example, on the resistance of the conductive traces 52, the distance between the conductive traces 52 and the desired amount of current. When the mild shock is delivered, potentials at the working electrode 58 and across the temperature probe 66 may be removed to prevent harm to those components caused by unwanted conduction between the working electrode 58 (and/or temperature probe 66, if used) and the conductive traces 52 which provide the mild shock.

Contact Pads

Typically, each of the conductive traces 52 includes a contact pad 49. The contact pad 49 may simply be a portion of the conductive trace 52 that is indistinguishable from the rest of the trace 52 except that the contact pad 49 is brought into contact with the conductive contacts of a control unit (e.g., the sensor control unit 44 of FIG. 1). More commonly, however, the contact pad 49 is a region of the conductive trace 52 that has a larger width than other regions of the trace 52 to facilitate a connection with the contacts on the control unit. By making the contact pads 49 relatively large as compared with the width of the conductive traces 52, the need for precise registration between the contact pads 49 and the contacts on the control unit is less critical than with small contact pads.

The contact pads 49 are typically made using the same material as the conductive material 56 of the conductive traces 52. However, this is not necessary. Although metal, alloys, and metallic compounds may be used to form the contact pads 49, in some embodiments, it is desirable to make the contact pads 49 from a carbon or other non-metallic material, such as a conducting polymer. In contrast to metal or alloy contact pads, carbon and other non-metallic contact pads are not easily corroded if the contact pads 49 are in a wet, moist, or humid environment. Metals and alloys may corrode under these conditions, particularly if the contact pads 49 and contacts of the control unit are made using different metals or alloys. However, carbon and non-metallic contact pads 49 do not significantly corrode, even if the contacts of the control device are metal or alloy.

One embodiment of the invention includes a sensor 42 having contact pads 49 and a control unit 44 having conductive contacts (not shown). During operation of the sensor 42, the contact pads 49 and conductive contacts are in contact with each other. In this embodiment, either the contact pads 49 or the conductive contacts are made using a non-corroding, conductive material. Such materials include, for example, carbon and conducting polymers. Preferred non-corroding materials include graphite and vitreous carbon. The opposing contact pad or conductive contact is made using carbon, a conducting polymer, a metal, such as gold, palladium, or platinum group metal, or a metallic compound, such as ruthenium dioxide. This configuration of contact pads and conductive contacts typically reduces corrosion. Preferably, when the sensor is placed in a 3 mM, and more preferably, in a 100 mM, NaCl solution, the signal arising due to the corrosion of the contact pads and/or conductive contacts is less than 3% of the signal generated by the sensor when exposed to concentration of analyte in the normal physiological range. For at least some subcutaneous glucose sensors, the current generated by analyte in a normal physiological range ranges from 3 to 500 nA.

Figure 10:
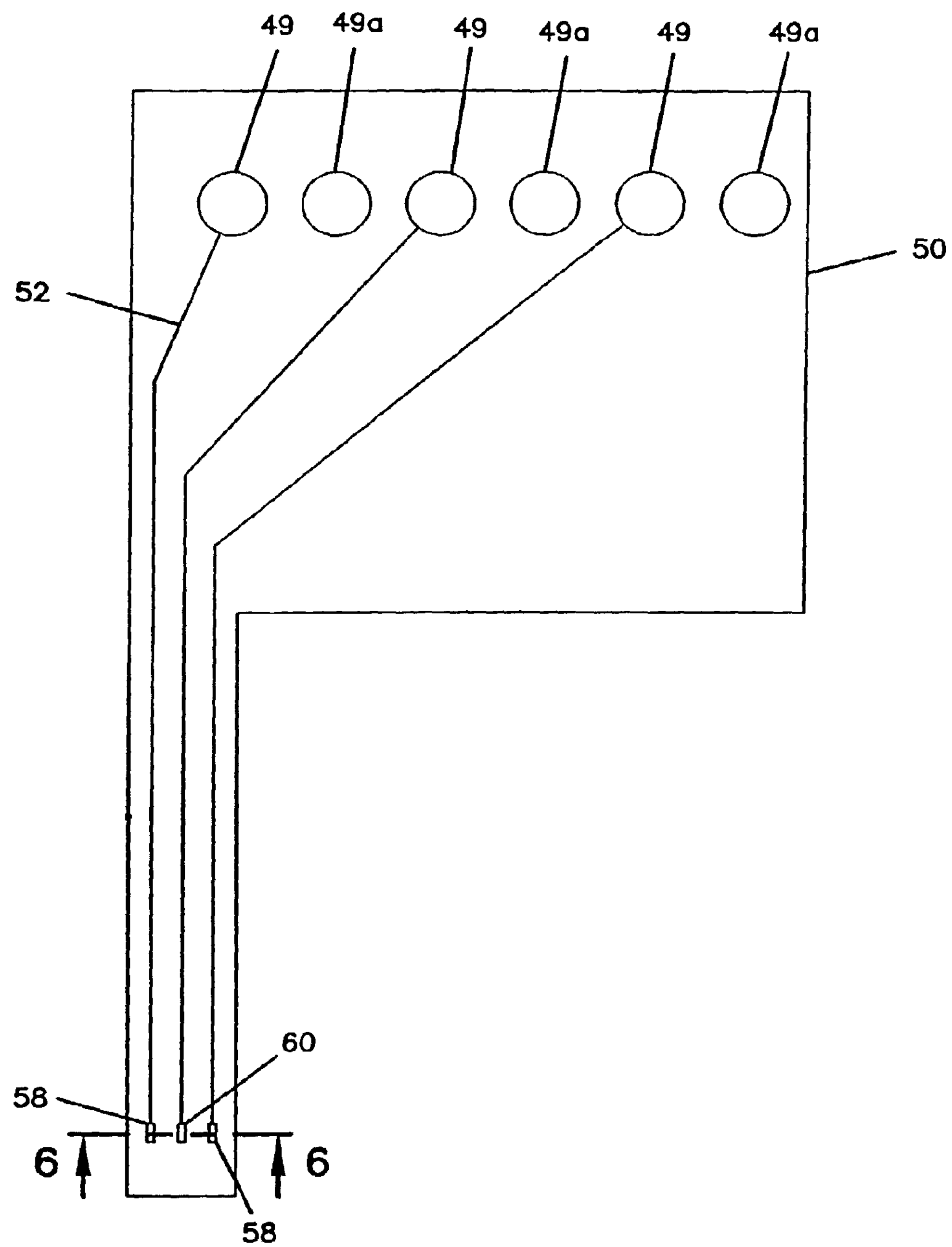
FIG. 10 is a top view of the analyte sensor of FIG. 6.
Figure 11:
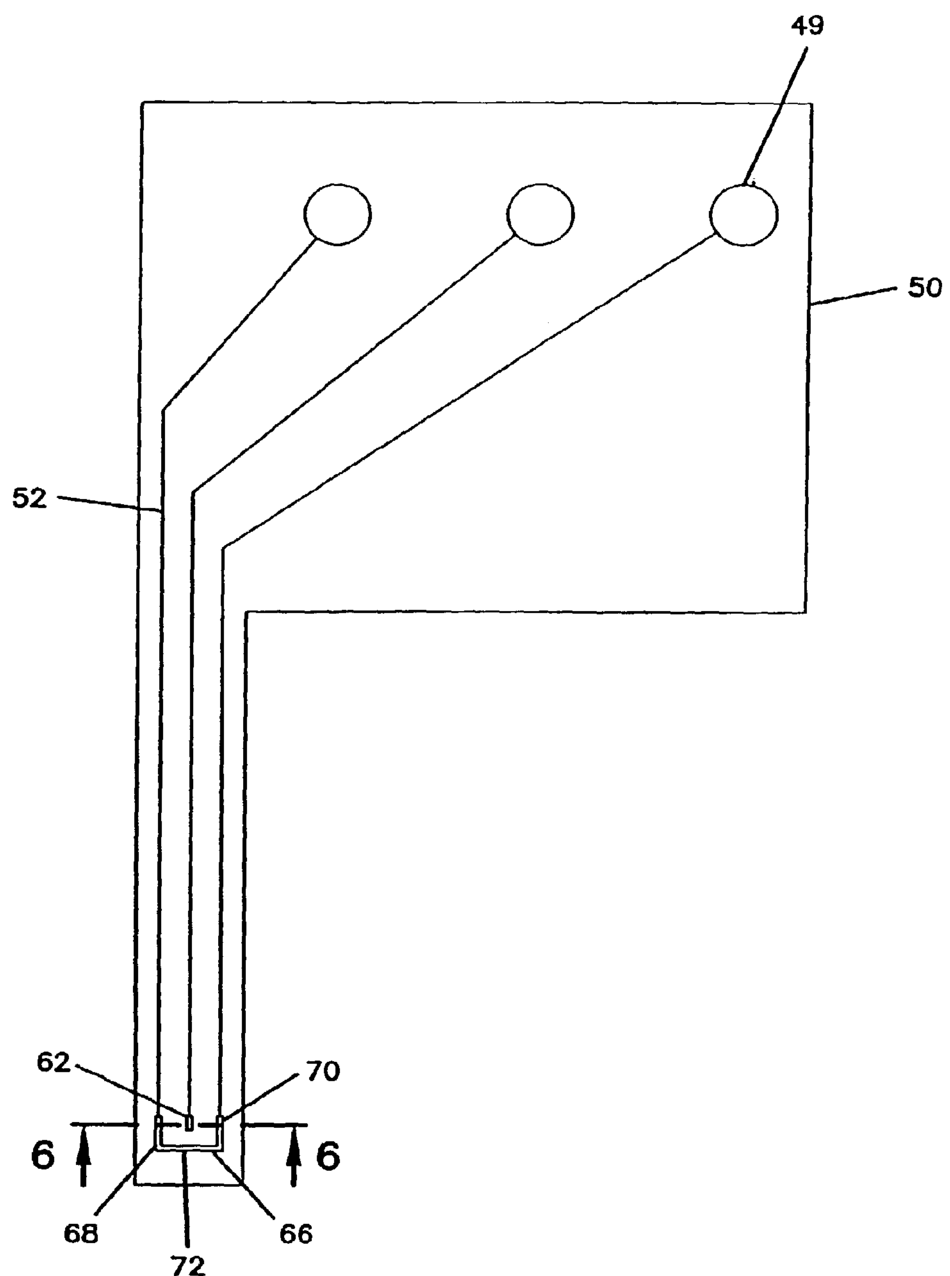
FIG. 11 is a bottom view of the analyte sensor of FIG. 6.

Each of the electrodes 58, 60, 62, as well as the two probe leads 68, 70 of the temperature probe 66 (described below), are connected to contact pads 49 as shown in FIGS. 10 and 11. In one embodiment (not shown), the contact pads 49 are on the same side of the substrate 50 as the respective electrodes or temperature probe leads to which the contact pads 49 are attached.

In other embodiments, the conductive traces 52 on at least one side are connected through vias in the substrate to contact pads 49*a* on the opposite surface of the substrate 50, as shown in FIGS. 10 and 11. An advantage of this configuration is that contact between the contacts on the control unit and each of the electrodes 58, 60, 62 and the probe leads 68, 70 of the temperature probe 66 can be made from a single side of the substrate 50.

In yet other embodiments (not shown), vias through the substrate are used to provide contact pads on both sides of the substrate 50 for each conductive trace 52. The vias connecting the conductive traces 52 with the contact pads 49*a* can be formed by making holes through the substrate 50 at the appropriate points and then filling the holes with conductive material 56.

Exemplary Electrode Configurations

Figure 3B:
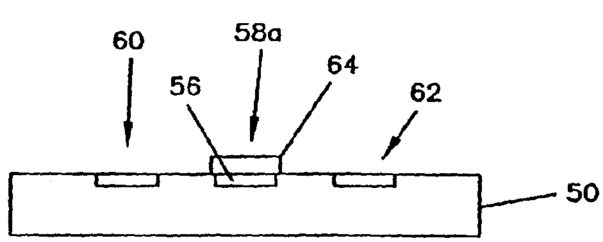
FIG. 3B is a cross-sectional view of another embodiment of an analyte sensor, according to the invention.

A number of exemplary electrode configurations are described below, however, it will be understood that other configurations may also be used. In one embodiment, illustrated in FIG. 3A, the sensor 42 includes two working electrodes 58*a*, 58*b* and one counter electrode 60, which also functions as a reference electrode. In another embodiment, the sensor includes one working electrode 58*a*, one counter electrode 60, and one reference electrode 62, as shown in FIG. 3B. Each of these embodiments is illustrated with all of the electrodes formed on the same side of the substrate 50.

Alternatively, one or more of the electrodes may be formed on an opposing side of the substrate 50. This may be convenient if the electrodes are formed using two different types of conductive material 56 (e.g., carbon and silver/silver chloride). Then, at least in some embodiments, only one type of conductive material 56 needs to be applied to each side of the substrate 50, thereby reducing the number of steps in the manufacturing process and/or easing the registration constraints in the process. For example, if the working electrode 58 is formed using a carbon-based conductive material 56 and the reference or counter/reference electrode is formed using a silver/silver chloride conductive material 56, then the working electrode and reference or counter/reference electrode may be formed on opposing sides of the substrate 50 for ease of manufacture.

Figure 6:
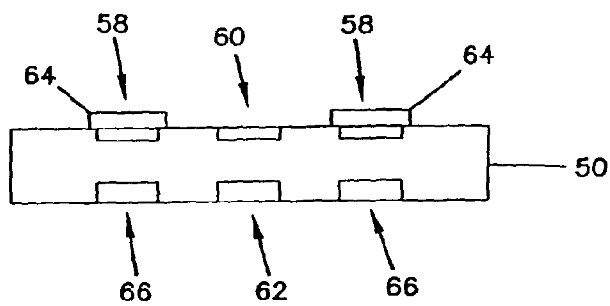
FIG. 6 is a cross-sectional view of a fifth embodiment of an analyte sensor, according to the invention.
Figure 7:
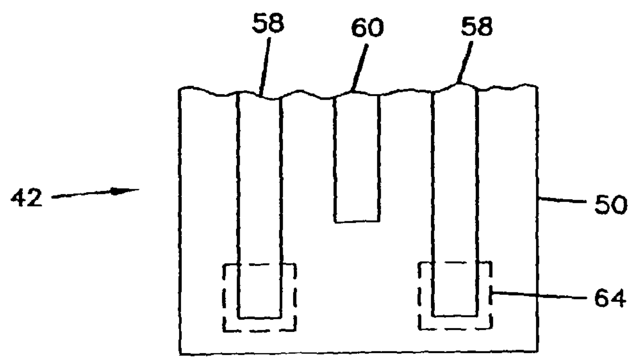
FIG. 7 is an expanded top view of a tip-portion of the analyte sensor of FIG. 6.
Figure 8:
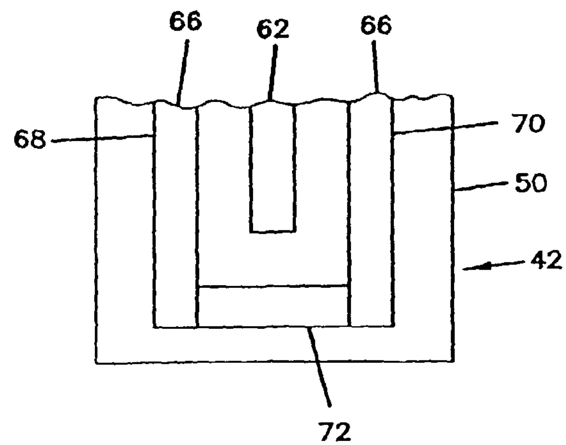
FIG. 8 is an expanded bottom view of a tip-portion of the analyte sensor of FIG. 6.

In another embodiment, two working electrodes 58 and one counter electrode 60 are formed on one side of the substrate 50 and one reference electrode 62 and two temperature probes 66 are formed on an opposing side of the substrate 50, as illustrated in FIG. 6. The opposing sides of the tip of this embodiment of the sensor 42 are illustrated in FIGS. 7 and 8.

Sensing Layer

Some analytes, such as oxygen, can be directly electrooxidized or electroreduced on the working electrode 58. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode 58. For these analytes, each working electrode 58 has a sensing layer 64 formed proximate to or on a working surface of the working electrode 58. Typically, the sensing layer 64 is formed near or on only a small portion of the working electrode 58, often near a tip of the sensor 42. This limits the amount of material needed to form the sensor 42 and places the sensing layer 64 in the best position for contact with the analyte-containing fluid (e.g., a body fluid, sample fluid, or carrier fluid).

The sensing layer 64 includes one or more components designed to facilitate the electrolysis of the analyte. The sensing layer 64 may include, for example, a catalyst to catalyze a reaction of the analyte and produce a response at the working electrode 58, an electron transfer agent to indirectly or directly transfer electrons between the analyte and the working electrode 58, or both.

The sensing layer 64 may be formed as a solid composition of the desired components (e.g., an electron transfer agent and/or a catalyst). These components are preferably non-leachable from the sensor 42 and more preferably are immobilized on the sensor 42. For example, the components may be immobilized on a working electrode 58. Alternatively, the components of the sensing layer 64 may be immobilized within or between one or more membranes or films disposed over the working electrode 58 or the components may be immobilized in a polymeric or sol-gel matrix. Examples of immobilized sensing layers are described in U.S. Pat. Nos. 5,262,035, 5,264,104, 5,264,105, 5,320,725, 5,593,852, and 5,665,222, U.S. patent application Ser. No. 08/540,789, and PCT Patent Application No. US1998/002403 entitled "Electrochemical Analyte Sensors Using Thermostable Soybean Peroxidase", filed on Feb. 11, 1998, published as WO-1998/035053, incorporated herein by reference.

In some embodiments, one or more of the components of the sensing layer 64 may be solvated, dispersed, or suspended in a fluid within the sensing layer 64, instead of forming a solid composition. The fluid may be provided with the sensor 42 or may be absorbed by the sensor 42 from the analyte-containing fluid. Preferably, the components which are solvated, dispersed, or suspended in this type of sensing layer 64 are non-leachable from the sensing layer. Non-leachability may be accomplished, for example, by providing barriers (e.g., the electrode, substrate, membranes, and/or films) around the sensing layer which prevent the leaching of the components of the sensing layer 64. One example of such a barrier is a microporous membrane or film which allows diffusion of the analyte into the sensing layer 64 to make contact with the components of the sensing layer 64, but reduces or eliminates the diffusion of the sensing layer components (e.g., an electron transfer agent and/or a catalyst) out of the sensing layer 64.

A variety of different sensing layer configurations can be used. In one embodiment, the sensing layer 64 is deposited on the conductive material 56 of a working electrode 58*a*, as illustrated in FIGS. 3A and 3B. The sensing layer 64 may extend beyond the conductive material 56 of the working electrode 58*a*. In some cases, the sensing layer 64 may also extend over the counter electrode 60 or reference electrode 62 without degrading the performance of the glucose sensor. For those sensors 42 which utilize channels 54 within which the conductive material 56 is deposited, a portion of the sensing layer 64 may be formed within the channel 54 if the conductive material 56 does not fill the channel 54.

A sensing layer 64 in direct contact with the working electrode 58*a* may contain an electron transfer agent to transfer electrons directly or indirectly between the analyte and the working electrode, as well as a catalyst to facilitate a reaction of the analyte. For example, a glucose, lactate, or oxygen electrode may be formed having a sensing layer which contains a catalyst, such as glucose oxidase, lactate oxidase, or laccase, respectively, and an electron transfer agent that facilitates the electrooxidation of the glucose, lactate, or oxygen, respectively.

Figure 4A:
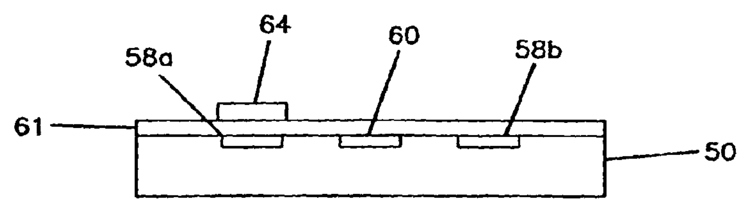
FIG. 4A is a cross-sectional view of a third embodiment of an analyte sensor, according to the invention.

In another embodiment, the sensing layer 64 is not deposited directly on the working electrode 58*a*. Instead, the sensing layer 64 is spaced apart from the working electrode 58*a*, as illustrated in FIG. 4A, and separated from the working electrode 58*a* by a separation layer 61. The separation layer 61 typically includes one or more membranes or films. In addition to separating the working electrode 58*a* from the sensing layer 64, the separation layer 61 may also act as a mass transport limiting layer or an interferent eliminating layer, as described below.

Typically, a sensing layer 64, which is not in direct contact with the working electrode 58*a*, includes a catalyst that facilitates a reaction of the analyte. However, this sensing layer 64 typically does not include an electron transfer agent that transfers electrons directly from the working electrode 58*a* to the analyte, as the sensing layer 64 is spaced apart from the working electrode 58*a*. One example of this type of sensor is a glucose or lactate sensor which includes an enzyme (e.g., glucose oxidase or lactate oxidase, respectively) in the sensing layer 64. The glucose or lactate reacts with a second compound (e.g., oxygen) in the presence of the enzyme. The second compound is then electrooxidized or electroreduced at the electrode. Changes in the signal at the electrode indicate changes in the level of the second compound in the fluid and are proportional to changes in glucose or lactate level and, thus, correlate to the analyte level.

Figure 4B:
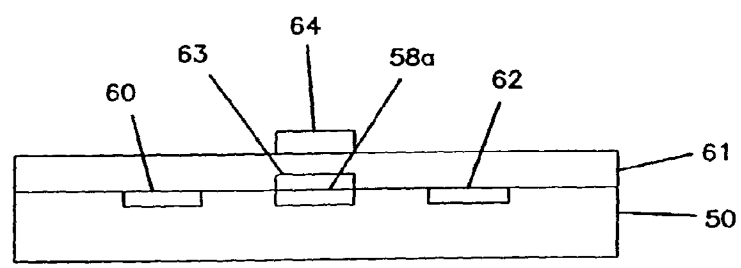
FIG. 4B is a cross-sectional view of a fourth embodiment of an analyte sensor, according to the invention.
Figure 5:
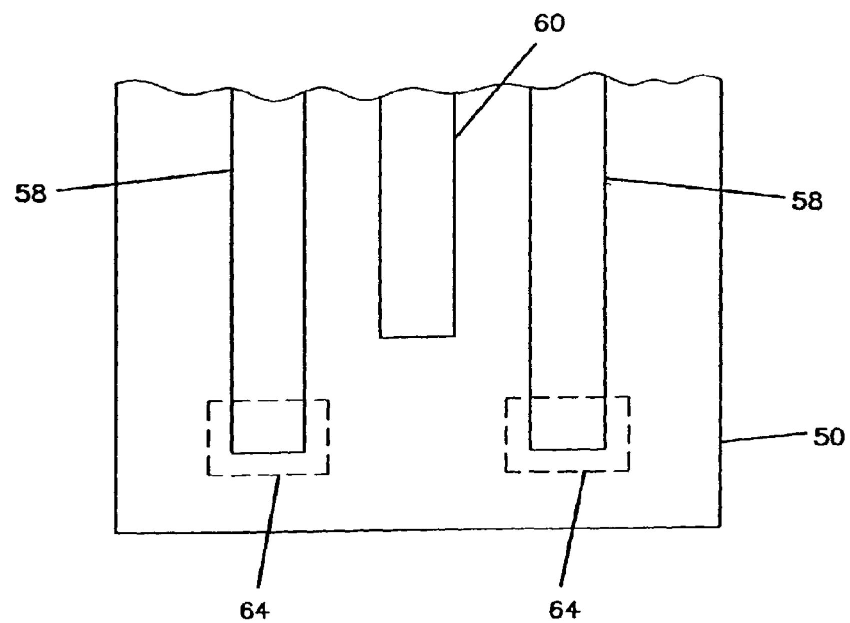
FIG. 5 is an expanded top view of a tip portion of the analyte sensor of FIG. 2.

In another embodiment, two sensing layers 63, 64 are used, as shown in FIG. 4B. Each of the two sensing layers 63, 64 may be independently formed on the working electrode 58*a* or in proximity to the working electrode 58*a*. One sensing layer 64 is typically, although not necessarily, spaced apart from the working electrode 58*a*. For example, this sensing layer 64 may include a catalyst which catalyzes a reaction of the analyte to form a product compound. The product compound is then electrolyzed in the second sensing layer 63 which may include an electron transfer agent to transfer electrons between the working electrode 58*a* and the product compound and/or a second catalyst to catalyze a reaction of the product compound to generate a signal at the working electrode 58*a*.

For example, a glucose or lactate sensor may include a first sensing layer 64 which is spaced apart from the working electrode and contains an enzyme, for example, glucose oxidase or lactate oxidase. The reaction of glucose or lactate in the presence of the appropriate enzyme forms hydrogen peroxide. A second sensing layer 63 is provided directly on the working electrode 58*a* and contains a peroxidase enzyme and an electron transfer agent to generate a signal at the electrode in response to the hydrogen peroxide. The level of hydrogen peroxide indicated by the sensor then correlates to the level of glucose or lactate. Another sensor which operates similarly can be made using a single sensing layer with both the glucose or lactate oxidase and the peroxidase being deposited in the single sensing layer. Examples of such sensors are described in U.S. Pat. No. 5,593,852, U.S. patent application Ser. No. 08/540,789, issued as U.S. Pat. No. 5,665,222, and PCT Patent Application No. US1998/002403 entitled "Electrochemical Analyte Sensors Using Thermostable Soybean Peroxidase", filed on Feb. 11, 1998, published as WO-1998/035053, incorporated herein by reference.

In some embodiments, one or more of the working electrodes 58*b* do not have a corresponding sensing layer 64, as shown in FIGS. 3A and 4A, or have a sensing layer (not shown) which does not contain one or more components (e.g., an electron transfer agent or catalyst) needed to electrolyze the analyte. The signal generated at this working electrode 58*b* typically arises from interferents and other sources, such as ions, in the fluid, and not in response to the analyte (because the analyte is not electrooxidized or electroreduced). Thus, the signal at this working electrode 58*b* corresponds to a background signal. The background signal can be removed from the analyte signal obtained from other working electrodes 58*a* that are associated with fully-functional sensing layers 64 by, for example, subtracting the signal at working electrode 58*b* from the signal at working electrode 58*a*.

Sensors having multiple working electrodes 58*a* may also be used to obtain more precise results by averaging the signals or measurements generated at these working electrodes 58*a*. In addition, multiple readings at a single working electrode 58*a* or at multiple working electrodes may be averaged to obtain more precise data.

Electron Transfer Agent

In many embodiments, the sensing layer 64 contains one or more electron transfer agents in contact with the conductive material 56 of the working electrode 58, as shown in FIGS. 3A and 3B. In some embodiments of the invention, there is little or no leaching of the electron transfer agent away from the working electrode 58 during the period in which the sensor 42 is implanted in the patient. A diffusing or leachable (i.e., releasable) electron transfer agent often diffuses into the analyte-containing fluid, thereby reducing the effectiveness of the electrode by reducing the sensitivity of the sensor over time. In addition, a diffusing or leaching electron transfer agent in an implantable sensor 42 may also cause damage to the patient. In these embodiments, preferably, at least 90%, more preferably, at least 95%, and, most preferably, at least 99%, of the electron transfer agent remains disposed on the sensor after immersion in the analyte-containing fluid for 24 hours, and, more preferably, for 72 hours. In particular, for an implantable sensor, preferably, at least 90%, more preferably, at least 95%, and most preferably, at least 99%, of the electron transfer agent remains disposed on the sensor after immersion in the body fluid at 37° C. for 24 hours, and, more preferably, for 72 hours.

In some embodiments of the invention, to prevent leaching, the electron transfer agents are bound or otherwise immobilized on the working electrode 58 or between or within one or more membranes or films disposed over the working electrode 58. The electron transfer agent may be immobilized on the working electrode 58 using, for example, a polymeric or sol-gel immobilization technique. Alternatively, the electron transfer agent may be chemically (e.g., ionically, covalently, or coordinatively) bound to the working electrode 58, either directly or indirectly through another molecule, such as a polymer, that is in turn bound to the working electrode 58.

Application of the sensing layer 64 on a working electrode 58*a* is one method for creating a working surface for the working electrode 58*a*, as shown in FIGS. 3A and 3B. The electron transfer agent mediates the transfer of electrons to electrooxidize or electroreduce an analyte and thereby permits a current flow between the working electrode 58 and the counter electrode 60 via the analyte. The mediation of the electron transfer agent facilitates the electrochemical analysis of analytes which are not suited for direct electrochemical reaction on an electrode.

In general, the preferred electron transfer agents are electroreducible and electrooxidizable ions or molecules having redox potentials that are a few hundred millivolts above or below the redox potential of the standard calomel electrode (SCE). Preferably, the electron transfer agents are not more reducing than about −150 mV and not more oxidizing than about +400 mV versus SCE.

The electron transfer agent may be organic, organometallic, or inorganic. Examples of organic redox species are quinones and species that in their oxidized state have quinoid structures, such as Nile blue and indolphenol. Some quinones and partially oxidized quinhydrones react with functional groups of proteins such as the thiol groups of cysteine, the amine groups of lysine and arginine, and the phenolic groups of tyrosine which may render those redox species unsuitable for some of the sensors of the present invention because of the presence of the interfering proteins in an analyte-containing fluid. Usually substituted quinones and molecules with quinoid structure are less reactive with proteins and are preferred. A preferred tetrasubstituted quinone usually has carbon atoms in positions 1, 2, 3, and 4.

In general, electron transfer agents suitable for use in the invention have structures or charges which prevent or substantially reduce the diffusional loss of the electron transfer agent during the period of time that the sample is being analyzed. The preferred electron transfer agents include a redox species bound to a polymer which can in turn be immobilized on the working electrode. The bond between the redox species and the polymer may be covalent, coordinative, or ionic. Useful electron transfer agents and methods for producing them are described in U.S. Pat. Nos. 5,264,104; 5,356,786; 5,262,035; and 5,320,725, incorporated herein by reference. Although any organic or organometallic redox species can be bound to a polymer and used as an electron transfer agent, the preferred redox species is a transition metal compound or complex. The preferred transition metal compounds or complexes include osmium, ruthenium, iron, and cobalt compounds or complexes. The most preferred are osmium compounds and complexes. It will be recognized that many of the redox species described below may also be used, typically without a polymeric component, as electron transfer agents in a carrier fluid or in a sensing layer of a sensor where leaching of the electron transfer agent is acceptable.

One type of non-releasable polymeric electron transfer agent contains a redox species covalently bound in a polymeric composition. An example of this type of mediator is poly(vinylferrocene).

Another type of non-releasable electron transfer agent contains an ionically-bound redox species. Typically, this type of mediator includes a charged polymer coupled to an oppositely charged redox species. Examples of this type of mediator include a negatively charged polymer such as Nafion® (DuPont) coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. The preferred ionically-bound redox species is a highly charged redox species bound within an oppositely charged redox polymer.

In another embodiment of the invention, suitable non-releasable electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

The preferred electron transfer agents are osmium transition metal complexes with one or more ligands, each ligand having a nitrogen-containing heterocycle such as 2,2'-bipyridine, 1,10-phenanthroline, or derivatives thereof. Furthermore, the preferred electron transfer agents also have one or more ligands covalently bound in a polymer, each ligand having at least one nitrogen-containing heterocycle, such as pyridine, imidazole, or derivatives thereof. These preferred electron transfer agents exchange electrons rapidly between each other and the working electrodes 58 so that the complex can be rapidly oxidized and reduced.

One example of a particularly useful electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Preferred derivatives of 2,2'-bipyridine for complexation with the osmium cation are 4,4'-dimethyl-2,2'-bipyridine and mono-, di-, and polyalkoxy-2,2'-bipyridines, such as 4,4'-dimethoxy-2,2'-bipyridine. Preferred derivatives of 1,10-phenanthroline for complexation with the osmium cation are 4,7-dimethyl-1,10-phenanthroline and mono, di-, and polyalkoxy-1,10-phenanthrolines, such as 4,7-dimethoxy-1,10-phenanthroline. Preferred polymers for complexation with the osmium cation include polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole. Most preferred are electron transfer agents with osmium complexed to a polymer or copolymer of poly(1-vinyl imidazole).

The preferred electron transfer agents have a redox potential ranging from −100 mV to about +150 mV versus the standard calomel electrode (SCE). Preferably, the potential of the electron transfer agent ranges from −100 mV to +150 mV and more preferably, the potential ranges from −50 mV to +50 mV. The most preferred electron transfer agents have osmium redox centers and a redox potential ranging from +50 mV to −150 mV versus SCE.

Catalyst

The sensing layer 64 may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone glucose dehydrogenase (PQQ)), or oligosaccharide dehydrogenase, may be used when the analyte is glucose. A lactate oxidase or lactate dehydrogenase may be used when the analyte is lactate. Laccase may be used when the analyte is oxygen or when oxygen is generated or consumed in response to a reaction of the analyte.

Preferably, the catalyst is non-leachably disposed on the sensor, whether the catalyst is part of a solid sensing layer in the sensor or solvated in a fluid within the sensing layer. More preferably, the catalyst is immobilized within the sensor (e.g., on the electrode and/or within or between a membrane or film) to prevent unwanted leaching of the catalyst away from the working electrode 58 and into the patient. This may be accomplished, for example, by attaching the catalyst to a polymer, cross linking the catalyst with another electron transfer agent (which, as described above, can be polymeric), and/or providing one or more barrier membranes or films with pore sizes smaller than the catalyst.

As described above, a second catalyst may also be used. This second catalyst is often used to catalyze a reaction of a product compound resulting from the catalyzed reaction of the analyte. The second catalyst typically operates with an electron transfer agent to electrolyze the product compound to generate a signal at the working electrode. Alternatively, the second catalyst may be provided in an interferent-eliminating layer to catalyze reactions that remove interferents, as described below.

One embodiment of the invention is an electrochemical sensor in which the catalyst is mixed or dispersed in the conductive material 56 which forms the conductive trace 52 of a working electrode 58. This may be accomplished, for example, by mixing a catalyst, such as an enzyme, in a carbon ink and applying the mixture into a channel 54 on the surface of the substrate 50. Preferably, the catalyst is immobilized in the channel 53 so that it cannot leach away from the working electrode 58. This may be accomplished, for example, by curing a binder in the carbon ink using a curing technique appropriate to the binder. Curing techniques include, for example, evaporation of a solvent or dispersant, exposure to ultraviolet light, or exposure to heat. Typically, the mixture is applied under conditions that do not substantially degrade the catalyst. For example, the catalyst may be an enzyme that is heat-sensitive. The enzyme and conductive material mixture should be applied and cured, preferably, without sustained periods of heating. The mixture may be cured using evaporation or UV curing techniques or by the exposure to heat that is sufficiently short that the catalyst is not substantially degraded.

Another consideration for in vivo analyte sensors is the thermostability of the catalyst. Many enzymes have only limited stability at biological temperatures. Thus, it may be necessary to use large amounts of the catalyst and/or use a catalyst that is thermostable at the necessary temperature (e.g., 37° C. or higher for normal body temperature). A thermostable catalyst may be defined as a catalyst which loses less than 5% of its activity when held at 37° C. for at least one hour, preferably, at least one day, and more preferably at least three days. One example of a thermostable catalyst is soybean peroxidase. This particular thermostable catalyst may be used in a glucose or lactate sensor when combined either in the same or separate sensing layers with glucose or lactate oxidase or dehydrogenase. A further description of thermostable catalysts and their use in electrochemical inventions is found in U.S. Pat. No. 5,665,222 U.S. patent application Ser. No. 08/540,789, and PCT Application No. US98/02403 entitled "Electrochemical Analyte Sensors Using Thermostable Soybean Peroxidase", filed on Feb. 11, 1998, published as WO-1998/035053.

Electrolysis of the Analyte

To electrolyze the analyte, a potential (versus a reference potential) is applied across the working and counter electrodes 58, 60. The minimum magnitude of the applied potential is often dependent on the particular electron transfer agent, analyte (if the analyte is directly electrolyzed at the electrode), or second compound (if a second compound, such as oxygen or hydrogen peroxide, whose level is dependent on the analyte level, is directly electrolyzed at the electrode). The applied potential usually equals or is more oxidizing or reducing, depending on the desired electrochemical reaction, than the redox potential of the electron transfer agent, analyte, or second compound, whichever is directly electrolyzed at the electrode. The potential at the working electrode is typically large enough to drive the electrochemical reaction to or near completion.

The magnitude of the potential may optionally be limited to prevent significant (as determined by the current generated in response to the analyte) electrochemical reaction of interferents, such as urate, ascorbate, and acetaminophen. The limitation of the potential may be obviated if these interferents have been removed in another way, such as by providing an interferent-limiting barrier, as described below, or by including a working electrode 58*b* (see FIG. 3A) from which a background signal may be obtained.

When a potential is applied between the working electrode 58 and the counter electrode 60, an electrical current will flow. The current is a result of the electrolysis of the analyte or a second compound whose level is affected by the analyte. In one embodiment, the electrochemical reaction occurs via an electron transfer agent and the optional catalyst. Many analytes B are oxidized (or reduced) to products C by an electron transfer agent species A in the presence of an appropriate catalyst (e.g., an enzyme). The electron transfer agent A is then oxidized (or reduced) at the electrode. Electrons are collected by (or removed from) the electrode and the resulting current is measured. This process is illustrated by reaction equations (1) and (2) (similar equations may be written for the reduction of the analyte B by a redox mediator A in the presence of a catalyst):

$$nA(ox) + B \xrightarrow{catalyst} nA(red) + C \quad (1)$$

$$nA(red) \xrightarrow{electrode} nA(ox) + ne^- \quad (2)$$

As an example, an electrochemical sensor may be based on the reaction of a glucose molecule with two non-leachable ferricyanide anions in the presence of glucose oxidase to produce two non-leachable ferrocyanide anions, two hydrogen ions, and gluconolactone. The amount of glucose present is assayed by electrooxidizing the non-leachable ferrocyanide anions to non-leachable ferricyanide anions and measuring the current.

In another embodiment, a second compound whose level is affected by the analyte is electrolyzed at the working electrode. In some cases, the analyte D and the second compound, in this case, a reactant compound E, such as oxygen, react in the presence of the catalyst, as shown in reaction equation (3).

$$D + E \xrightarrow{catalyst} F + G \quad (3)$$

The reactant compound E is then directly oxidized (or reduced) at the working electrode, as shown in reaction equation (4)

$$nE(red) \xrightarrow{electrode} nE(ox) + ne^- \quad (4)$$

Alternatively, the reactant compound E is indirectly oxidized (or reduced) using an electron transfer agent H (optionally in the presence of a catalyst), that is subsequently reduced or oxidized at the electrode, as shown in reaction equations (5) and (6).

$$nH(ox) + E \rightarrow nH(red) + I \quad (5)$$

$$nH(red) \xrightarrow{electrode} nH(ox) + ne^- \quad (6)$$

In either case, changes in the concentration of the reactant compound, as indicated by the signal at the working electrode, correspond inversely to changes in the analyte (i.e., as the level of analyte increase then the level of reactant compound and the signal at the electrode decreases.)

In other embodiments, the relevant second compound is a product compound F, as shown in reaction equation (3). The product compound F is formed by the catalyzed reaction of analyte D and then be directly electrolyzed at the electrode or indirectly electrolyzed using an electron transfer agent and, optionally, a catalyst. In these embodiments, the signal arising from the direct or indirect electrolysis of the product compound F at the working electrode corresponds directly to the level of the analyte (unless there are other sources of the product compound). As the level of analyte increases, the level of the product compound and signal at the working electrode increases.

Those skilled in the art will recognize that there are many different reactions that will achieve the same result; namely the electrolysis of an analyte or a compound whose level depends on the level of the analyte. Reaction equations (1) through (6) illustrate non-limiting examples of such reactions.

Temperature Probe

A variety of optional items may be included in the sensor. One optional item is a temperature probe 66 (FIGS. 8 and 11). The temperature probe 66 may be made using a variety of known designs and materials. One exemplary temperature probe 66 is formed using two probe leads 68, 70 connected to each other through a temperature-dependent element 72 that is formed using a material with a temperature-dependent characteristic. An example of a suitable temperature-dependent characteristic is the resistance of the temperature-dependent element 72.

The two probe leads 68, 70 are typically formed using a metal, an alloy, a semimetal, such as graphite, a degenerate or highly doped semiconductor, or a small-band gap semiconductor. Examples of suitable materials include gold, silver, ruthenium oxide, titanium nitride, titanium dioxide, indium doped tin oxide, tin doped indium oxide, or graphite. The temperature-dependent element 72 is typically made using a fine trace (e.g., a conductive trace that has a smaller cross-section than that of the probe leads 68, 70) of the same conductive material as the probe leads, or another material such as a carbon ink, a carbon fiber, or platinum, which has a temperature-dependent characteristic, such as resistance, that provides a temperature-dependent signal when a voltage source is attached to the two probe leads 68, 70 of the temperature probe 66. The temperature-dependent characteristic of the temperature-dependent element 72 may either increase or decrease with temperature. Preferably, the temperature dependence of the characteristic of the temperature-dependent element 72 is approximately linear with temperature over the expected range of biological temperatures (about 25 to 45° C.), although this is not required.

Typically, a signal (e.g., a current) having an amplitude or other property that is a function of the temperature can be obtained by providing a potential across the two probe leads 68, 70 of the temperature probe 66. As the temperature changes, the temperature-dependent characteristic of the temperature-dependent element 72 increases or decreases with a corresponding change in the signal amplitude. The signal from the temperature probe 66 (e.g., the amount of current flowing through the probe) may be combined with the signal obtained from the working electrode 58 by, for example, scaling the temperature probe signal and then adding or subtracting the scaled temperature probe signal from the signal at the working electrode 58. In this manner, the temperature probe 66 can provide a temperature adjustment for the output from the working electrode 58 to offset the temperature dependence of the working electrode 58.

One embodiment of the temperature probe includes probe leads 68, 70 formed as two spaced-apart channels with a temperature-dependent element 72 formed as a cross-channel connecting the two spaced-apart channels, as illustrated in FIG. 8. The two spaced-apart channels contain a conductive material, such as a metal, alloy, semimetal, degenerate semiconductor, or metallic compound. The cross-channel may contain the same material (provided the cross-channel has a smaller cross-section than the two spaced-apart channels) as the probe leads 68, 70. In other embodiments, the material in the cross-channel is different than the material of the probe leads 68, 70.

One exemplary method for forming this particular temperature probe includes forming the two spaced-apart channels and then filling them with the metallic or alloyed conductive material. Next, the cross-channel is formed and then filled with the desired material. The material in the cross-channel overlaps with the conductive material in each of the two spaced-apart channels to form an electrical connection.

For proper operation of the temperature probe 66, the temperature-dependent element 72 of the temperature probe 66 cannot be shorted by conductive material formed between the two probe leads 68, 70. In addition, to prevent conduction between the two probe leads 68, 70 by ionic species within the body or sample fluid, a covering may be provided over the temperature-dependent element 72, and preferably over the portion of the probe leads 68, 70 that is implanted in the patient. The covering may be, for example, a non-conducting film disposed over the temperature-dependent element 72 and probe leads 68, 70 to prevent the ionic conduction. Suitable non-conducting films include, for example, Kapton™ polyimide films (DuPont, Wilmington, Del.).

Another method for eliminating or reducing conduction by ionic species in the body or sample fluid is to use an ac voltage source connected to the probe leads 68, 70. In this way, the positive and negative ionic species are alternately attracted and repelled during each half cycle of the ac voltage. This results in no net attraction of the ions in the body or sample fluid to the temperature probe 66. The maximum amplitude of the ac current through the temperature-dependent element 72 may then be used to correct the measurements from the working electrodes 58.

The temperature probe can be placed on the same substrate as the electrodes. Alternatively, a temperature probe may be placed on a separate substrate. In addition, the temperature probe may be used by itself or in conjunction with other devices.

Another embodiment of a temperature probe utilizes the temperature dependence of the conductivity of a solution (e.g., blood or interstitial fluid). Typically, the conductivity of an electrolyte-containing solution is dependent on the temperature of the solution, assuming that the concentration of electrolytes is relatively constant. Blood, interstitial fluid, and other bodily fluids are solutions with relatively constant levels of electrolytes. Thus, a sensor 42 can include two or more conductive traces (not shown) which are spaced apart by a known distance. A portion of these conductive traces is exposed to the solution and the conductivity between the exposed portions of the conductive traces is measured using known techniques (e.g., application of a constant or known current or potential and measurement of the resulting potential or current, respectively, to determine the conductivity).

A change in conductivity is related to a change in temperature. This relation can be modeled using linear, quadratic, exponential, or other relations. The parameters for this relationship typically do not vary significantly between most people. The calibration for the temperature probe can be determined by a variety of methods, including, for example, calibration of each sensor 42 using an independent method of determining temperature (e.g., a thermometer, an optical or electrical temperature detector, or the temperature probe 66, described above) or calibrating one sensor 42 and using that calibration for all other sensors in a batch based on uniformity in geometry.

Biocompatible Layer

Figure 9:
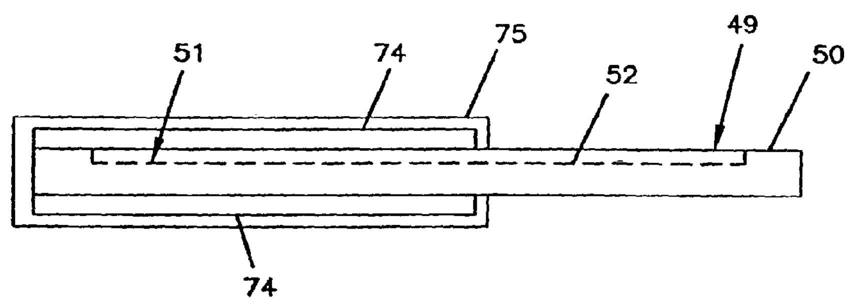
FIG. 9 is a side view of the analyte sensor of FIG. 2.

An optional biocompatible film layer 75 is formed over at least that portion of the sensor 42 which is subcutaneously inserted into the patient, as shown in FIG. 9. This optional biocompatible film layer 75 may serve one or more functions. The biocompatible film layer 75 prevents the penetration of large biomolecules into the electrodes. This is accomplished by using a biocompatible film layer 75 having a pore size that is smaller than the biomolecules that are to be excluded. Such biomolecules may foul the electrodes and/or the sensing layer 64 thereby reducing the effectiveness of the sensor 42 and altering the expected signal amplitude for a given analyte concentration. The fouling of the working electrodes 58 may also decrease the effective life of the sensor 42. The biocompatible layer 75 may also prevent protein adhesion to the sensor 42, formation of blood clots, and other undesirable interactions between the sensor 42 and body.

For example, the sensor may be completely or partially coated on its exterior with a biocompatible coating. A preferred biocompatible coating is a hydrogel which contains at least 20 wt. % fluid when in equilibrium with the analyte-containing fluid. Examples of suitable hydrogels are described in U.S. Pat. No. 5,593,852, incorporated herein by reference, and include crosslinked polyethylene oxides, such as polyethylene oxide tetraacrylate.

Interferent-Eliminating Layer

An interferent-eliminating layer (not shown) may be included in the sensor 42. The interferent-eliminating layer may be incorporated in the biocompatible layer 75 or in the mass transport limiting layer 74 (described below) or may be a separate layer. Interferents are molecules or other species that are electroreduced or electrooxidized at the electrode, either directly or via an electron transfer agent, to produce a false signal. In one embodiment, a film or membrane prevents the penetration of one or more interferents into the region around the working electrodes 58. Preferably, this type of interferent-eliminating layer is much less permeable to one or more of the interferents than to the analyte.

The interferent-eliminating layer may include ionic components, such as Nafion®, incorporated into a polymeric matrix to reduce the permeability of the interferent-eliminating layer to ionic interferents having the same charge as the ionic components. For example, negatively charged compounds or compounds that form negative ions may be incorporated in the interferent-eliminating layer to reduce the permeation of negative species in the body or sample fluid.

Another example of an interferent-eliminating layer includes a catalyst for catalyzing a reaction which removes interferents. One example of such a catalyst is a peroxidase. Hydrogen peroxide reacts with interferents, such as acetaminophen, urate, and ascorbate. The hydrogen peroxide may be added to the analyte-containing fluid or may be generated in situ, by, for example, the reaction of glucose or lactate in the presence of glucose oxidase or lactate oxidase, respectively. Examples of interferent eliminating layers include a peroxidase enzyme crosslinked (a) using gluteraldehyde as a crosslinking agent or (b) oxidation of oligosaccharide groups in the peroxidase glycoenzyme with $NaIO_4$, followed by coupling of the aldehydes formed to hydrazide groups in a polyacrylamide matrix to form hydrazones are describe in U.S. Pat. Nos. 5,262,305 and 5,356,786, incorporated herein by reference.

Mass Transport Limiting Layer

A mass transport limiting layer 74 may be included with the sensor to act as a diffusion-limiting barrier to reduce the rate of mass transport of the analyte, for example, glucose or lactate, into the region around the working electrodes 58. By limiting the diffusion of the analyte, the steady state concentration of the analyte in the proximity of the working electrode 58 (which is proportional to the concentration of the analyte in the body or sample fluid) can be reduced. This extends the upper range of analyte concentrations that can still be accurately measured and may also expand the range in which the current increases approximately linearly with the level of the analyte.

It is preferred that the permeability of the analyte through the film layer 74 vary little or not at all with temperature, so as to reduce or eliminate the variation of current with temperature. For this reason, it is preferred that in the biologically relevant temperature range from about 25° C. to about 45° C., and most importantly from 30° C. to 40° C., neither the size of the pores in the film nor its hydration or swelling change excessively. Preferably, the mass transport limiting layer is made using a film that absorbs less than 5 wt. % of fluid over 24 hours. This may reduce or obviate any need for a temperature probe. For implantable sensors, it is preferable that the mass transport limiting layer is made using a film that absorbs less than 5 wt. % of fluid over 24 hours at 37° C.

Particularly useful materials for the film layer 74 are membranes that do not swell in the analyte-containing fluid that the sensor tests. Suitable membranes include 3 to 20,000 nm diameter pores. Membranes having 5 to 500 nm diameter pores with well-defined, uniform pore sizes and high aspect ratios are preferred. In one embodiment, the aspect ratio of the pores is preferably two or greater and more preferably five or greater.

Well-defined and uniform pores can be made by track etching a polymeric membrane using accelerated electrons, ions, or particles emitted by radioactive nuclei. Most preferred are anisotropic, polymeric, track etched membranes that expand less in the direction perpendicular to the pores than in the direction of the pores when heated. Suitable polymeric membranes included polycarbonate membranes from Poretics (Livermore, Calif., catalog number 19401, 0.01 μm pore size polycarbonate membrane) and Corning Costar Corp. (Cambridge, Mass., Nucleopore™ brand membranes with 0.015 μm pore size). Other polyolefin and polyester films may be used. It is preferred that the permeability of the mass transport limiting membrane changes no more than 4%, preferably, no more than 3%, and, more preferably, no more than 2%, per ° C. in the range from 30° C. to 40° C. when the membranes resides in the subcutaneous interstitial fluid.

In some embodiments of the invention, the mass transport limiting layer 74 may also limit the flow of oxygen into the sensor 42. This can improve the stability of sensors 42 that are used in situations where variation in the partial pressure of oxygen causes non-linearity in sensor response. In these embodiments, the mass transport limiting layer 74 restricts oxygen transport by at least 40%, preferably at least 60%, and more preferably at least 80%, than the membrane restricts transport of the analyte. For a given type of polymer, films having a greater density (e.g., a density closer to that of the crystalline polymer) are preferred. Polyesters, such as polyethylene terephthalate, are typically less permeable to oxygen and are, therefore, preferred over polycarbonate membranes.

Anticlotting Agent

An implantable sensor may also, optionally, have an anticlotting agent disposed on a portion the substrate which is implanted into a patient. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor 42 that is to be implanted. The anticlotting agent may be applied, for example, by bath, spraying, brushing, or dipping. The anticlotting agent is allowed to dry on the sensor 42. The anticlotting agent may be immobilized on the surface of the sensor or it may be allowed to diffuse away from the sensor surface. Typically, the quantities of anticlotting agent disposed on the sensor are far below the amounts typically used for treatment of medical conditions involving blood clots and, therefore, have only a limited, localized effect.

Sensor Lifetime

The sensor 42 may be designed to be a replaceable component in an in vivo analyte monitor, and particularly in an implantable analyte monitor. Typically, the sensor 42 is capable of operation over a period of days. Preferably, the period of operation is at least one day, more preferably at least three days, and most preferably at least one week. The sensor 42 can then be removed and replaced with a new sensor. The lifetime of the sensor 42 may be reduced by the fouling of the electrodes or by the leaching of the electron transfer agent or catalyst. These limitations on the longevity of the sensor 42 can be overcome by the use of a biocompatible layer 75 or non-leachable electron transfer agent and catalyst, respectively, as described above.

Another primary limitation on the lifetime of the sensor 42 is the temperature stability of the catalyst. Many catalysts are enzymes, which are very sensitive to the ambient temperature and may degrade at temperatures of the patient's body (e.g., approximately 37° C. for the human body). Thus, robust enzymes should be used where available. The sensor 42 should be replaced when a sufficient amount of the enzyme has been deactivated to introduce an unacceptable amount of error in the measurements.

Insertion Device

An insertion device 120 can be used to subcutaneously insert the sensor 42 into the patient, as illustrated in FIG. 12. The insertion device 120 is typically formed using structurally rigid materials, such as metal or rigid plastic. Preferred materials include stainless steel and ABS (acrylonitrile-butadiene-styrene) plastic. In some embodiments, the insertion device 120 is pointed and/or sharp at the tip 121 to facilitate penetration of the skin of the patient. A sharp, thin insertion device may reduce pain felt by the patient upon insertion of the sensor 42. In other embodiments, the tip 121 of the insertion device 120 has other shapes, including a blunt or flat shape. These embodiments may be particularly useful when the insertion device 120 does not penetrate the skin but rather serves as a structural support for the sensor 42 as the sensor 42 is pushed into the skin.

Figure 13A:
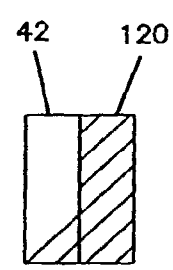
FIGS. 13A, 13B, 13C are cross-sectional views of three embodiments of the insertion device of FIG. 12.
Figure 13B:
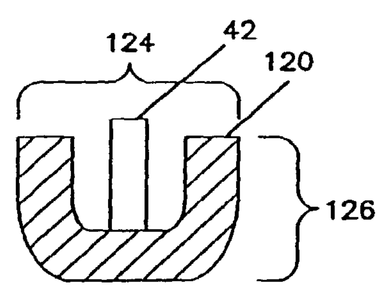
Figure 13C:
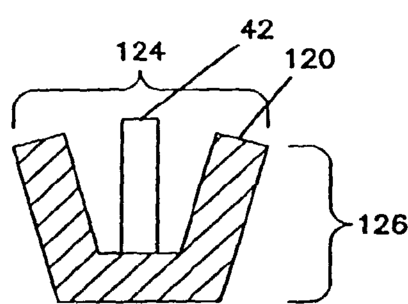

The insertion device 120 may have a variety of cross-sectional shapes, as shown in FIGS. 13A, 13B, and 13C. The insertion device 120 illustrated in FIG. 13A is a flat, planar, pointed strip of rigid material which may be attached or otherwise coupled to the sensor 42 to ease insertion of the sensor 42 into the skin of the patient, as well as to provide structural support to the sensor 42 during insertion. The insertion devices 120 of FIGS. 13B and 13C are U- or V-shaped implements that support the sensor 42 to limit the amount that the sensor 42 may bend or bow during insertion. The cross-sectional width 124 of the insertion devices 120 illustrated in FIGS. 13B and 13C is typically 1 mm or less, preferably 700 μm or less, more preferably 500 μm or less, and most preferably 300 μm or less. The cross-sectional height 126 of the insertion device 120 illustrated in FIGS. 13B and 13C is typically about 1 mm or less, preferably about 700 μm or less, and more preferably about 500 μm or less.

The sensor 42 itself may include optional features to facilitate insertion. For example, the sensor 42 may be pointed at the tip 123 to ease insertion, as illustrated in FIG. 12. In addition, the sensor 42 may include a barb 125 which helps retain the sensor 42 in the subcutaneous tissue of the patient. The barb 125 may also assist in anchoring the sensor 42 within the subcutaneous tissue of the patient during operation of the sensor 42. However, the barb 125 is typically small enough that little damage is caused to the subcutaneous tissue when the sensor 42 is removed for replacement. The sensor 42 may also include a notch 127 that can be used in cooperation with a corresponding structure (not shown) in the insertion device to apply pressure against the sensor 42 during insertion, but disengage as the insertion device 120 is removed. One example of such a structure in the insertion device is a rod (not shown) between two opposing sides of an insertion device 120 and at an appropriate height of the insertion device 120.

In operation, the sensor 42 is placed within or next to the insertion device 120 and then a force is provided against the insertion device 120 and/or sensor 42 to carry the sensor 42 into the skin of the patient. In one embodiment, the force is applied to the sensor 42 to push the sensor into the skin, while the insertion device 120 remains stationary and provides structural support to the sensor 42. Alternatively, the force is applied to the insertion device 120 and optionally to the sensor 42 to push a portion of both the sensor 42 and the insertion device 120 through the skin of the patient and into the subcutaneous tissue. The insertion device 120 is optionally pulled out of the skin and subcutaneous tissue with the sensor 42 remaining in the subcutaneous tissue due to frictional forces between the sensor 42 and the patient's tissue. If the sensor 42 includes the optional barb 125, then this structure may also facilitate the retention of the sensor 42 within the interstitial tissue as the barb catches in the tissue.

Figure 26:
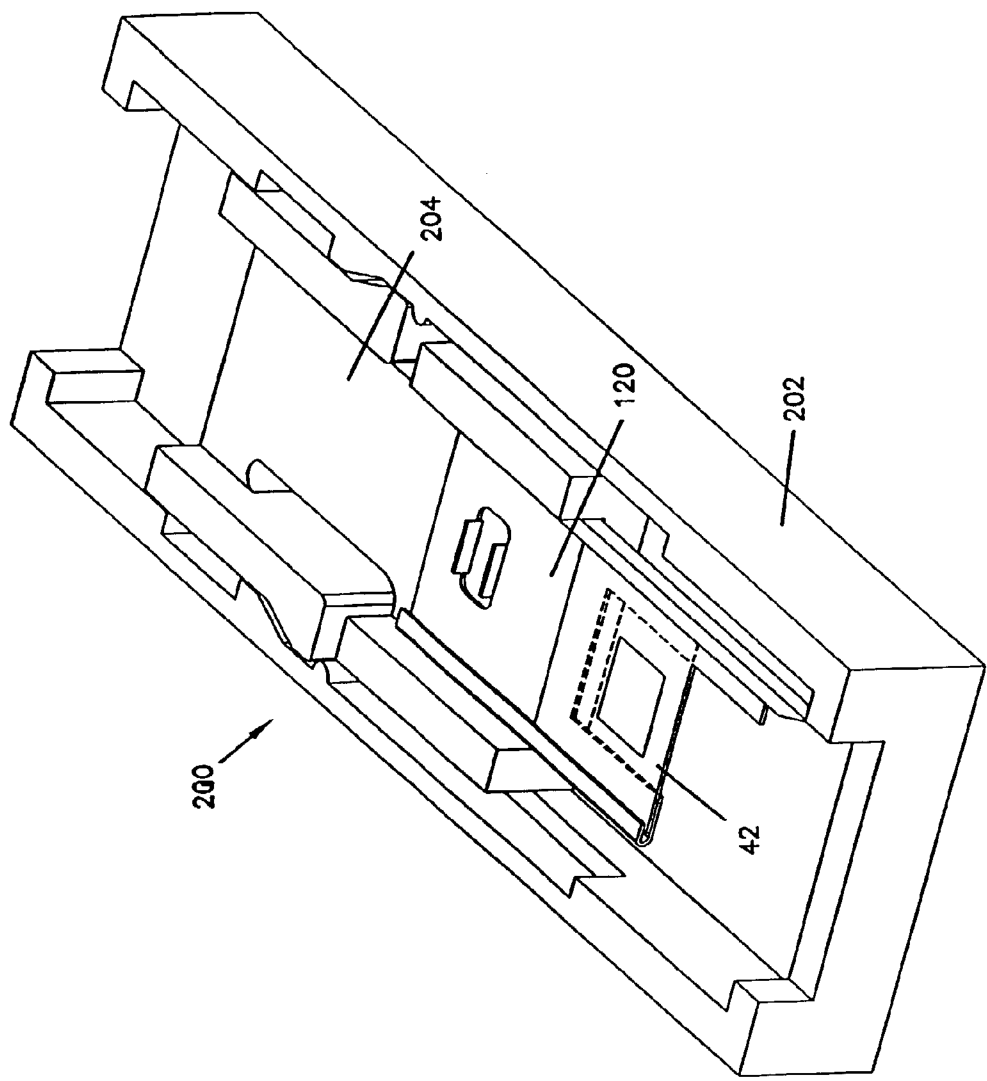
FIG. 26 is a perspective view of the internal structure of an insertion gun, according to the invention.

The force applied to the insertion device 120 and/or the sensor 42 may be applied manually or mechanically. Preferably, the sensor 42 is reproducibly inserted through the skin of the patient. In one embodiment, an insertion gun is used to insert the sensor. One example of an insertion gun 200 for inserting a sensor 42 is shown in FIG. 26. The insertion gun 200 includes a housing 202 and a carrier 204. The insertion device 120 is typically mounted on the carrier 204 and the sensor 42 is pre-loaded into the insertion device 120. The carrier 204 drives the sensor 42 and, optionally, the insertion device 120 into the skin of the patient using, for example, a cocked or wound spring, a burst of compressed gas, an electromagnet repelled by a second magnet, or the like, within the insertion gun 200. In some instances, for example, when using a spring, the carrier 204 and insertion device may be moved, cocked, or otherwise prepared to be directed towards the skin of the patient.

After the sensor 42 is inserted, the insertion gun 200 may contain a mechanism which pulls the insertion device 120 out of the skin of the patient. Such a mechanism may use a spring, electromagnet, or the like to remove the insertion device 120.

The insertion gun may be reusable. The insertion device 120 is often disposable to avoid the possibility of contamination. Alternatively, the insertion device 120 may be sterilized and reused. In addition, the insertion device 120 and/or the sensor 42 may be coated with an anticlotting agent to prevent fouling of the sensor 42.

In one embodiment, the sensor 42 is injected between 2 to 12 mm into the interstitial tissue of the patient for subcutaneous implantation. Preferably, the sensor is injected 3 to 9 mm, and more preferably 5 to 7 mm, into the interstitial tissue. Other embodiments of the invention, may include sensors implanted in other portions of the patient, including, for example, in an artery, vein, or organ. The depth of implantation varies depending on the desired implantation target.

Although the sensor 42 may be inserted anywhere in the body, it is often desirable that the insertion site be positioned so that the on-skin sensor control unit 44 can be concealed. In addition, it is often desirable that the insertion site be at a place on the body with a low density of nerve endings to reduce the pain to the patient. Examples of preferred sites for insertion of the sensor 42 and positioning of the on-skin sensor control unit 44 include the abdomen, thigh, leg, upper arm, and shoulder.

An insertion angle is measured from the plane of the skin (i.e., inserting the sensor perpendicular to the skin would be a 90° insertion angle). Insertion angles usually range from 10 to 90°, typically from 15 to 60°, and often from 30 to 45°.

On-Skin Sensor Control Unit

Figure 15:
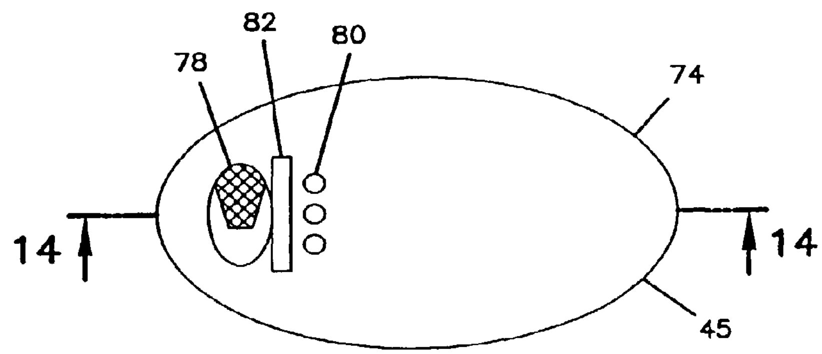
FIG. 15 is a top view of a base of the on-skin sensor control unit of FIG. 14.
Figure 16:
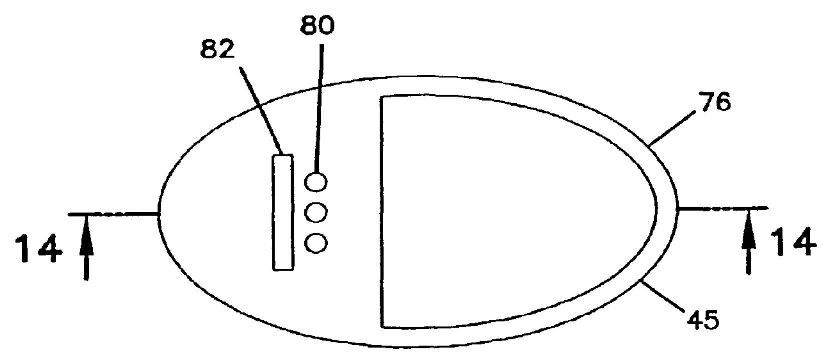
FIG. 16 is a bottom view of a cover of the on-skin sensor control unit of FIG. 14.
Figure 14:
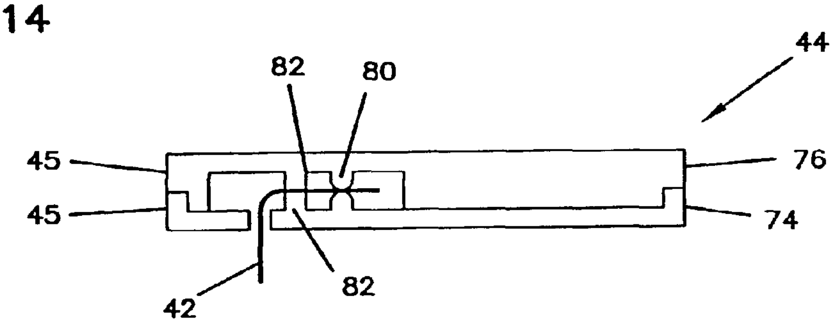
FIG. 14 is a cross-sectional view of one embodiment of a on-skin sensor control unit, according to the invention.

The on-skin sensor control unit 44 is configured to be placed on the skin of a patient. The on-skin sensor control unit 44 is optionally formed in a shape that is comfortable to the patient and which may permit concealment, for example, under a patient's clothing. The thigh, leg, upper arm, shoulder, or abdomen are convenient parts of the patient's body for placement of the on-skin sensor control unit 44 to maintain concealment. However, the on-skin sensor control unit 44 may be positioned on other portions of the patient's body. One embodiment of the on-skin sensor control unit 44 has a thin, oval shape to enhance concealment, as illustrated in FIGS. 14-16. However, other shapes and sizes may be used.

The particular profile, as well as the height, width, length, weight, and volume of the on-skin sensor control unit 44 may vary and depends, at least in part, on the components and associated functions included in the on-skin sensor control unit 44, as discussed below. For example, in some embodiments, the on-skin sensor control unit 44 has a height of 1.3 cm or less, and preferably 0.7 cm or less. In some embodiments, the on-skin sensor control unit 44 has a weight of 90 grams or less, preferably 45 grams or less, and more preferably 25 grams or less. In some embodiments, the on-skin sensor control unit 44 has a volume of about 15 $cm^3$ or less, preferably about 10 $cm^3$ or less, more preferably about 5 $cm^3$ or less, and most preferably about 2.5 $cm^3$ or less.

The on-skin sensor control unit 44 includes a housing 45, as illustrated in FIGS. 14-16. The housing 45 is typically formed as a single integral unit that rests on the skin of the patient. The housing 45 typically contains most or all of the electronic components, described below, of the on-skin sensor control unit 44. The on-skin sensor control unit 44 usually includes no additional cables or wires to other electronic components or other devices. If the housing includes two or more parts, then those parts typically fit together to form a single integral unit.

The housing 45 of the on-skin sensor control unit 44, illustrated in FIGS. 14-16, may be formed using a variety of materials, including, for example, plastic and polymeric materials, particularly rigid thermoplastics and engineering thermoplastics. Suitable materials include, for example, polyvinyl chloride, polyethylene, polypropylene, polystyrene, ABS polymers, and copolymers thereof. The housing 45 of the on-skin sensor control unit 44 may be formed using a variety of techniques including, for example, injection molding, compression molding, casting, and other molding methods. Hollow or recessed regions may be formed in the housing 45 of the on-skin sensor control unit 44. The electronic components of the on-skin sensor control unit 44, described below, and/or other items, such as a battery or a speaker for an audible alarm, may be placed in the hollow or recessed areas.

In some embodiments, conductive contacts 80 are provided on the exterior of the housing 45. In other embodiments, the conductive contacts 80 are provided on the interior of the housing 45, for example, within a hollow or recessed region.

In some embodiments, the electronic components and/or other items are incorporated into the housing 45 of the on-skin sensor control unit 44 as the plastic or polymeric material is molded or otherwise formed. In other embodiments, the electronic components and/or other items are incorporated into the housing 45 as the molded material is cooling or after the molded material has been reheated to make it pliable. Alternatively, the electronic components and/or other items may be secured to the housing 45 using fasteners, such as screws, nuts and bolts, nails, staples, rivets, and the like or adhesives, such as contact adhesives, pressure sensitive adhesives, glues, epoxies, adhesive resins, and the like. In some cases, the electronic components and/or other items are not affixed to the housing 45 at all.

In some embodiments, the housing 45 of the on-skin sensor control unit 44 is a single piece. The conductive contacts 80 may be formed on the exterior of the housing 45 or on the interior of the housing 45 provided there is a port 78 in the housing 45 through which the sensor 42 can be directed to access the conductive contacts 80.

In other embodiments, the housing 45 of the on-skin sensor control unit 44 is formed in at least two separate portions that fit together to form the housing 45, for example, a base 74 and a cover 76, as illustrated in FIGS. 14-16. The two or more portions of the housing 45 may be entirely separate from each other. Alternatively, at least some of the two or more portions of the housing 45 may be connected together, for example, by a hinge, to facilitate the coupling of the portions to form the housing 45 of the on-skin sensor control unit 44.

These two or more separate portions of the housing 45 of the on-skin sensor control unit 44 may have complementary, interlocking structures, such as, for example, interlocking ridges or a ridge on one component and a complementary groove on another component, so that the two or more separate components may be easily and/or firmly coupled together. This may be useful, particularly if the components are taken apart and fit together occasionally, for example, when a battery or sensor 42 is replaced. However, other fasteners may also be used to couple the two or more components together, including, for example, screws, nuts and bolts, nails, staples, rivets, or the like. In addition, adhesives, both permanent or temporary, may be used including, for example, contact adhesives, pressure sensitive adhesives, glues, epoxies, adhesive resins, and the like.

Typically, the housing 45 is at least water resistant to prevent the flow of fluids into contact with the components in the housing, including, for example, the conductive contacts 80. Preferably, the housing is waterproof. In one embodiment, two or more components of the housing 45, for example, the base 74 and the cover 76, fit together tightly to form a hermetic, waterproof, or water resistant seal so that fluids cannot flow into the interior of the on-skin sensor control unit 44. This may be useful to avoid corrosion currents and/or degradation of items within the on-skin sensor control unit 44, such as the conductive contacts, the battery, or the electronic components, particularly when the patient engages in such activities as showering, bathing, or swimming.

Water resistant, as used herein, means that there is no penetration of water through a water resistant seal or housing when immersed in water at a depth of one meter at sea level. Waterproof, as used herein, means that there is no penetration of water through the waterproof seal or housing when immersed in water at a depth of ten meters, and preferably fifty meters, at sea level. It is often desirable that the electronic circuitry, power supply (e.g., battery), and conductive contacts of the on-skin sensor control unit, as well as the contact pads of the sensor, are contained in a water resistant, and preferably, a waterproof, environment.

In addition to the portions of the housing 45, such as the base 74 and cover 76, there may be other individually-formed pieces of the on-skin sensor control unit 44, which may be assembled during or after manufacture. One example of an individually-formed piece is a cover for electronic components that fits a recess in the base 74 or cover 76. Another example is a cover for a battery provided in the base 74 or cover 76. These individually-formed pieces of the on-skin sensor control unit 44 may be permanently affixed, such as, for example, a cover for electronic components, or removably affixed, such as, for example, a removable cover for a battery, to the base 74, cover 76, or other component of the on-skin sensor control unit 44. Methods for affixing these individually formed pieces include the use of fasteners, such as screws, nuts and bolts, staples, nails, rivets, and the like, frictional fasteners, such as tongue and groove structures, and adhesives, such as contact adhesives, pressure sensitive adhesives, glues, epoxies, adhesive resins, and the like.

One embodiment of the on-skin sensor control unit 44 is a disposable unit complete with a battery for operating the unit. There are no portions of the unit that the patient needs to open or remove, thereby reducing the size of the unit and simplifying its construction. The on-skin sensor control unit 44 optionally remains in a sleep mode prior to use to conserve the battery's power. The on-skin sensor control unit 44 detects that it is being used and activates itself. Detection of use may be through a number of mechanisms. These include, for example, detection of a change in resistance across the electrical contacts, actuation of a switch upon mating the on-skin sensor control unit 44 with a mounting unit 77 (see FIGS. 27A and 28A). The on-skin sensor control unit 44 is typically replaced when it no longer operates within threshold limits, for example, if the battery or other power source does not generate sufficient power. Often this embodiment of the on-skin sensor control unit 44 has conductive contacts 80 on the exterior of the housing 45. Once the sensor 42 is implanted in the patient, the sensor control unit 44 is placed over the sensor 42 with the conductive contacts 80 in contact with the contact pads 49 of the sensor 42.

Figure 17:
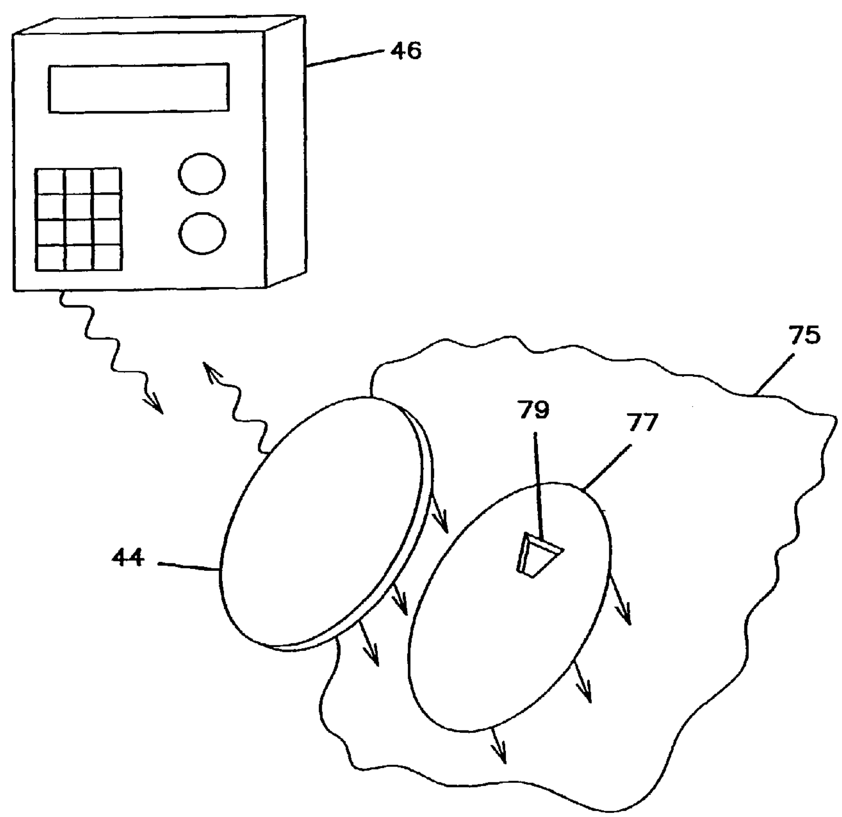
FIG. 17 is a perspective view of the on-skin sensor control unit of FIG. 14 on the skin of a patient.

The on-skin sensor control unit 44 is typically attached to the skin 75 of the patient, as illustrated in FIG. 17. The on-skin sensor control unit 44 may be attached by a variety of techniques including, for example, by adhering the on-skin sensor control unit 44 directly to the skin 75 of the patient with an adhesive provided on at least a portion of the housing 45 of the on-skin sensor control unit 44 which contacts the skin 75, by suturing the on-skin sensor control unit 44 to the skin 75 through suture openings (not shown) in the sensor control unit 44, or by strapping the on-skin sensor control unit 44 to the skin 75.

Another method of attaching the housing 45 of the on-skin sensor control unit 44 to the skin 75 includes using a mounting unit 77. The mounting unit 77 is often a part of the on-skin sensor control unit 44. One example of a suitable mounting unit 77 is a double-sided adhesive strip, one side of which is adhered to a surface of the skin of the patient and the other side is adhered to the on-skin sensor control unit 44. In this embodiment, the mounting unit 77 may have an optional opening 79 which is large enough to allow insertion of the sensor 42 through the opening 79. Alternatively, the sensor may be inserted through a thin adhesive and into the skin. Each of the aforementioned techniques for holding the on-skin sensor control unit 44 in a fixed orientation relative to the skin 75 may be used in conjunction with an embodiment of the present invention wherein the transmitter 98 is disposed upon the substrate 50. For example, the substrate 50 itself may be adhered to the skin 75, may be sutured to the skin, or may be strapped to the skin 75 using the aforementioned techniques and materials.

A variety of adhesives may be used to adhere the on-skin sensor control unit 44 to the skin 75 of the patient, either directly or using the mounting unit 77, including, for example, pressure sensitive adhesives (PSA) or contact adhesives. Preferably, an adhesive is chosen which is not irritating to all or a majority of patients for at least the period of time that a particular sensor 42 is implanted in the patient. Alternatively, a second adhesive or other skin-protecting compound may be included with the mounting unit so that a patient, whose skin is irritated by the adhesive on the mounting unit 77, can cover his skin with the second adhesive or other skin-protecting compound and then place the mounting unit 77 over the second adhesive or other skin-protecting compound. This should substantially prevent the irritation of the skin of the patient because the adhesive on the mounting unit 77 is no longer in contact with the skin, but is instead in contact with the second adhesive or other skin-protecting compound.

An alternate embodiment of the invention allows for the transmitter 98 to be disposed upon the sensor substrate 50. In this embodiment, the transmitter 98 is electrically coupled to at least one conductive trace disposed upon the substrate 50, so that the transmitter 98 is provided with a signal that is representative of an analyte level of bodily fluid. This arrangement provides the advantage of relieving the user of the analyte monitoring device from having to electrically connect the transmitter 98 to the sensor 42. This is advantageous because the mechanics involved in forming the aforementioned electrical connection may be difficult for a user to accomplish. Furthermore, if the user connects the sensor 42 to the transmitter, then the region of electrical connectivity would likely be designed for protection from moisture and contamination, causing the housing 45 to become more important to the operation of the device.

Figure 32:
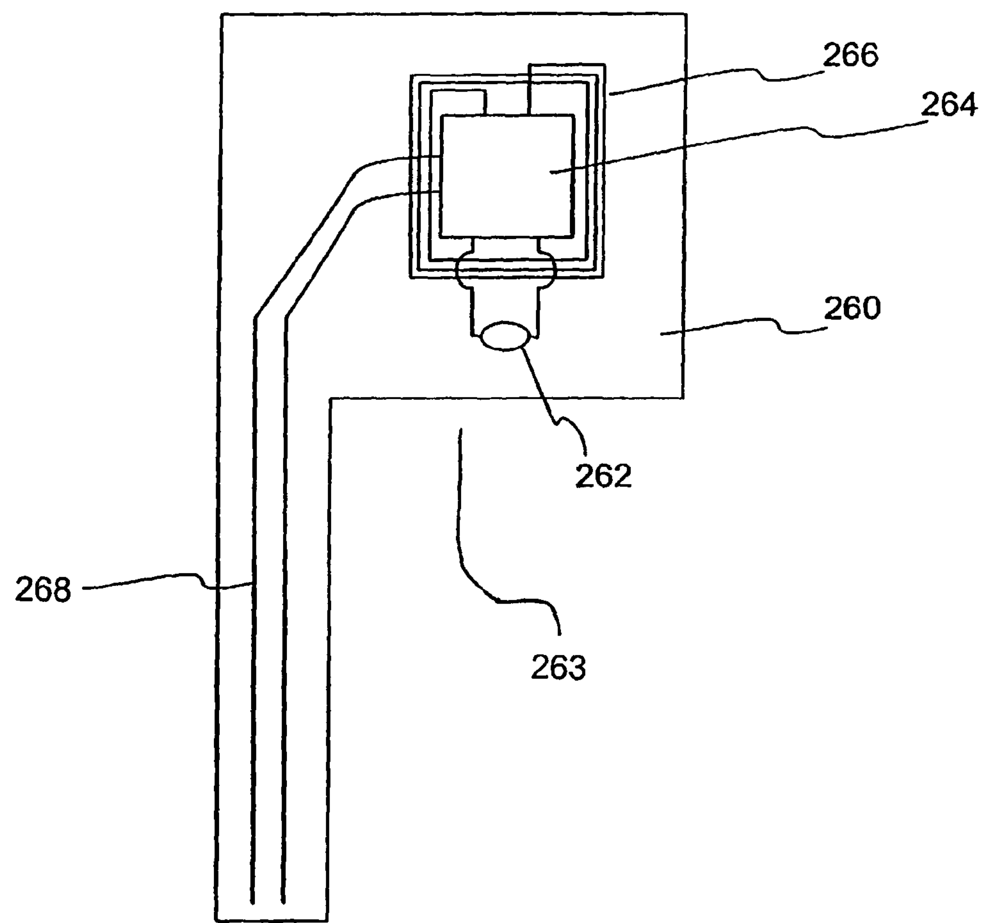
FIG. 32 depicts one possible embodiment of a transmitter disposed upon a substrate.

FIG. 32 depicts one possible embodiment of a transmitter 263 disposed upon a substrate 260. As can be seen from FIG. 32, substrate 260 has a conductive trace 268 disposed upon it, a portion of which is chemically enabled to form an electrochemical sensor. The substrate 260 may be flexible, thereby enhancing patient comfort. Such flexibility also reduces the risk of the substrate 260 shattering upon impact, potentially embedding a shard of the substrate within the user. Thus, flexibility enhances user safety. The transmitter 263 is comprised of an integrated circuit 264 designed to generate a transmission signal representative of the analyte level of the bodily fluid. In one embodiment, the integrated circuit 264 is comprised of: (1) an organizing circuit that emits, at intervals, data representative of the level of the analyte in the bodily fluid; (2) a modulator that modulates a carrier signal with the data emitted from the organizing circuit; and (3) an amplifier that amplifies the modulated carrier signal. Although FIG. 32 depicts a single integrated circuit 264, one skilled in the art would recognize that integrated circuit 264 may be embodied by a digital integrated circuit coupled to an analog integrated circuit. Integrated circuit 264 is powered by a battery 262 disposed upon substrate 260. The integrated circuit 264 is electrically coupled to conductive trace 268, to provide the integrated circuit 264 with a signal representative of an analyte level of a bodily fluid. The output of the integrated circuit 264 is a transmission signal, which is provided to an antenna 266 for transmission into the region of space surrounding the antenna 266. Antenna 266 may take on several forms. In one embodiment, antenna 266 is printed directly upon substrate 260. In an alternate embodiment, antenna 266 may take the form of a separate structure disposed upon substrate 260, such as a coil mounted upon substrate 260. Additionally, regardless of whether antenna 266 is embodied as either a separate structure or is printed upon the substrate 260, antenna 266 can be positioned on the reverse side of the substrate 260 from the transmitter 263.

It is important that transmitter 263 is protected from corrosive or contaminating influences. To this end, in one embodiment, transmitter 263 is encapsulated in a protective non-conductive coating, such as an epoxy.

A patient using the aforementioned embodiment wherein the transmitter 263 is disposed upon the substrate 260, may make use of the device by simply inserting the implantable portion of the sensor transcutaneously and fixing the unit to the skin. The sensor need not be connected by the patient to an on-skin sensor control unit (such as on-skin sensor control unit 44 in FIG. 17). Thus, the entire device becomes disposable, meaning that a user of the device is able to purchase the device as a single unit and dispose of it as such, after a period of use that may range from one to fourteen days, or more.

Other embodiments of the invention depicted in FIG. 32 exist. For example, although the battery 262 is shown as being mounted upon the substrate 260, the battery 262 may be a separate unit from the single-unit transmitter 263/substrate 260. In such an embodiment, the transmitter 263 is designed to mate with the battery 262, thereby providing electrical power to the transmitter 263. Thus, the transmitter 263/substrate 260 combination may be disposed of after a period of use, while the battery 262 may be reused with many separate transmitter 263/substrate 260 combinations, until its energy is depleted. If the battery 262 is embodied as a separate unit, the battery can be housed in a separate housing, designed to stabilize and protect the battery from impact, contamination and corrosion. Such a housing permits the battery 262 to mate with the transmitter 263, conforming to the geometry of the transmitter 263/substrate 260 combination and maintaining a minimal profile.

Returning to FIG. 17, when the sensor 42 is changed, the on-skin sensor control unit 44 may be moved to a different position on the skin 75 of the patient, for example, to avoid excessive irritation. Alternatively, the on-skin sensor control unit 44 may remain at the same place on the skin of the patient until it is determined that the unit 44 should be moved.

Figure 27A:
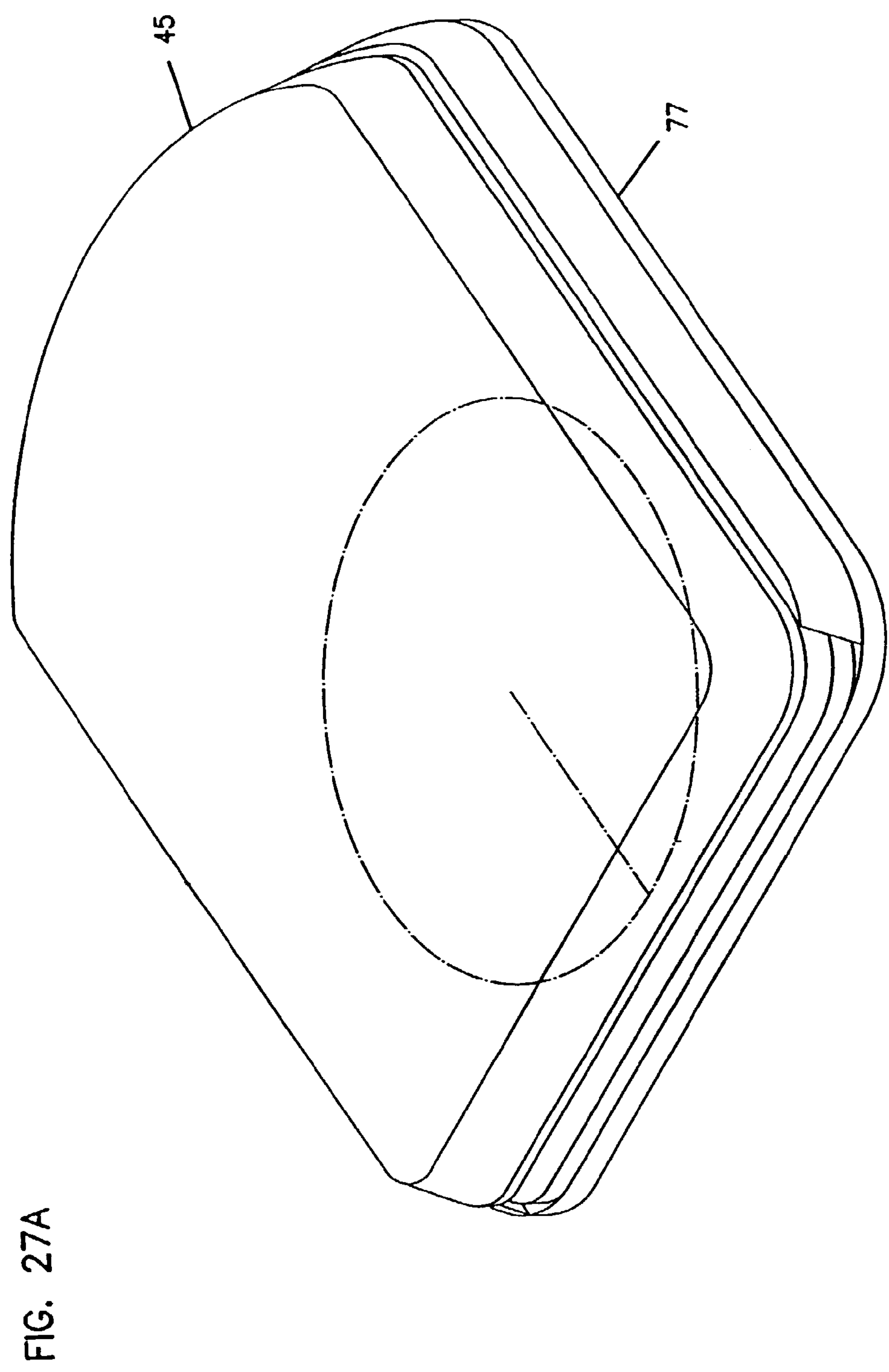
FIG. 27A is a top view of one embodiment of an on-skin sensor control unit, according to the invention.
Figure 27B:
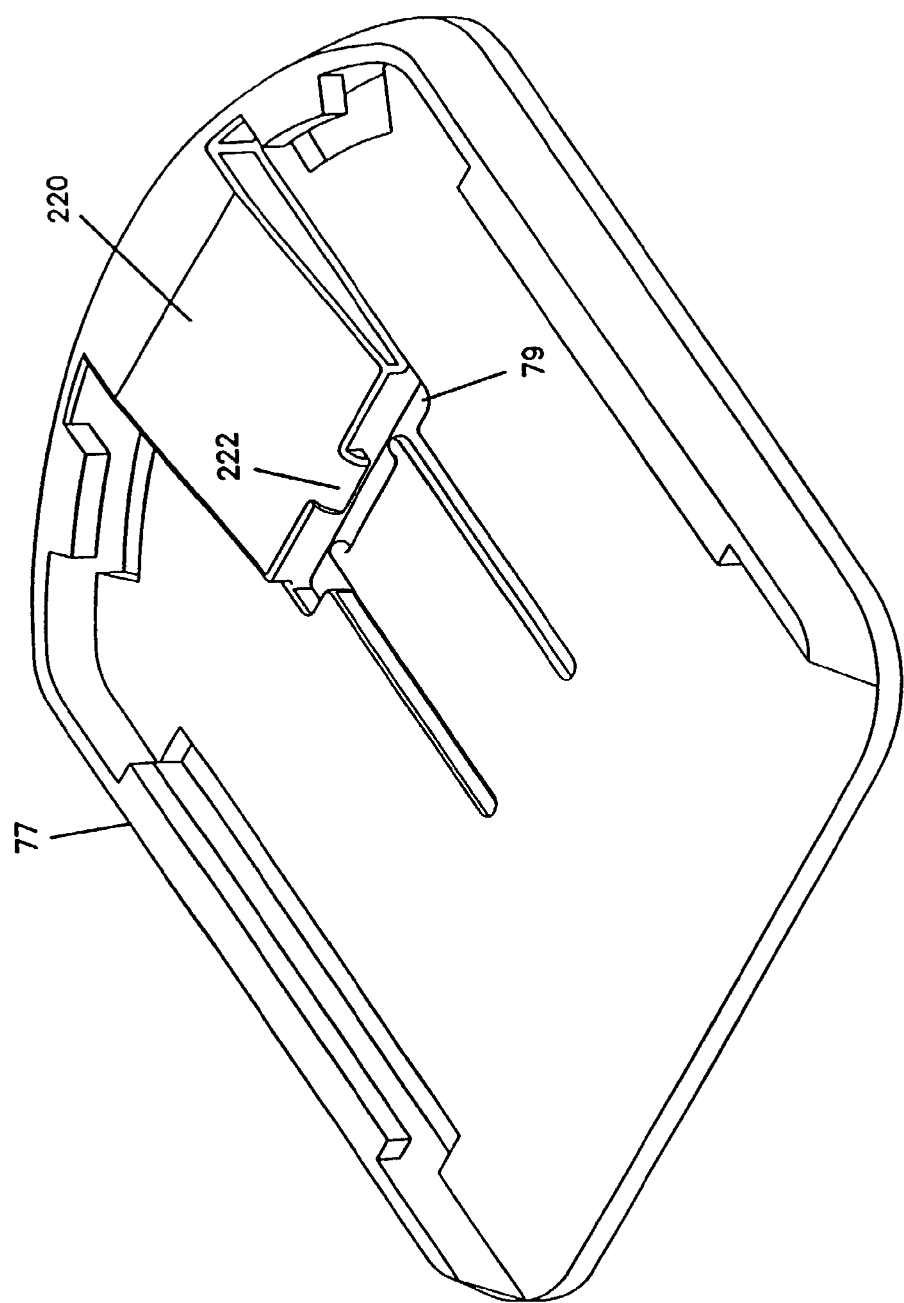
FIG. 27B is a top view of one embodiment of a mounting unit of the on-skin sensor control unit of FIG. 27A.

Another embodiment of a mounting unit 77 used in an on-skin sensor control unit 44 is illustrated in FIGS. 27A and 27B. The mounting unit 77 and a housing 45 of an on-skin sensor control unit 44 are mounted together in, for example, an interlocking manner, as shown in FIG. 27A. The mounting unit 77 is formed, for example, using plastic or polymer materials, including, for example, polyvinyl chloride, polyethylene, polypropylene, polystyrene, ABS polymers, and copolymers thereof. The mounting unit 77 may be formed using a variety of techniques including, for example, injection molding, compression molding, casting, and other molding methods.

The mounting unit 77 typically includes an adhesive on a bottom surface of the mounting unit 77 to adhere to the skin of the patient or the mounting unit 77 is used in conjunction with, for example, double-sided adhesive tape or the like. The mounting unit 77 typically includes an opening 79 through which the sensor 42 is inserted, as shown in FIG. 27B. The mounting unit 77 may also include a support structure 220 for holding the sensor 42 in place and against the conductive contacts 80 on the on-skin sensor control unit 42. The mounting unit 77, also, optionally, includes a positioning structure 222, such as an extension of material from the mounting unit 77, that corresponds to a structure (not shown), such as an opening, on the sensor 42 to facilitate proper positioning of the sensor 42, for example, by aligning the two complementary structures.

Figure 28A:
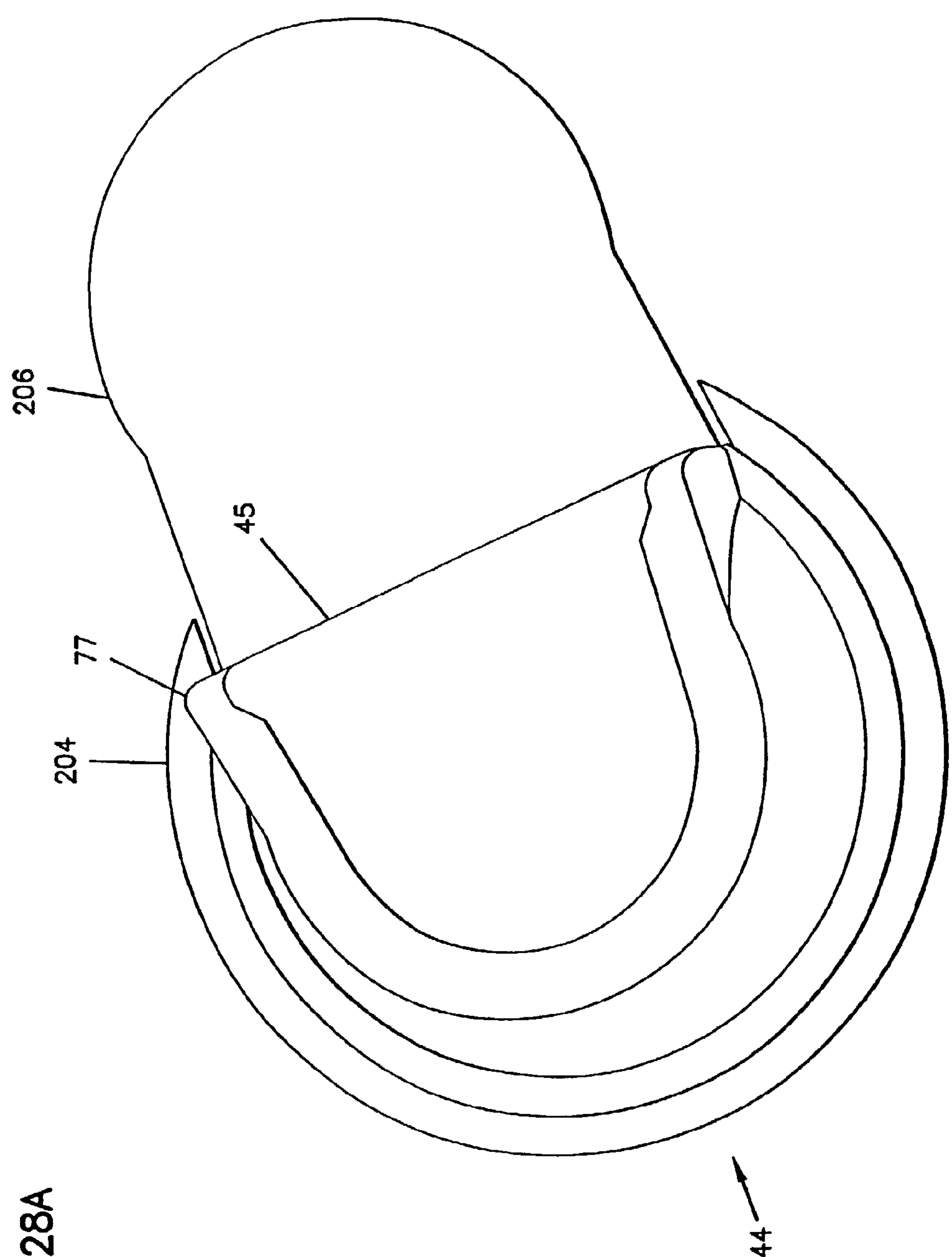
FIG. 28A is a top view of another embodiment of an on-skin sensor control unit after insertion of an insertion device and a sensor, according to the invention.
Figure 28B:
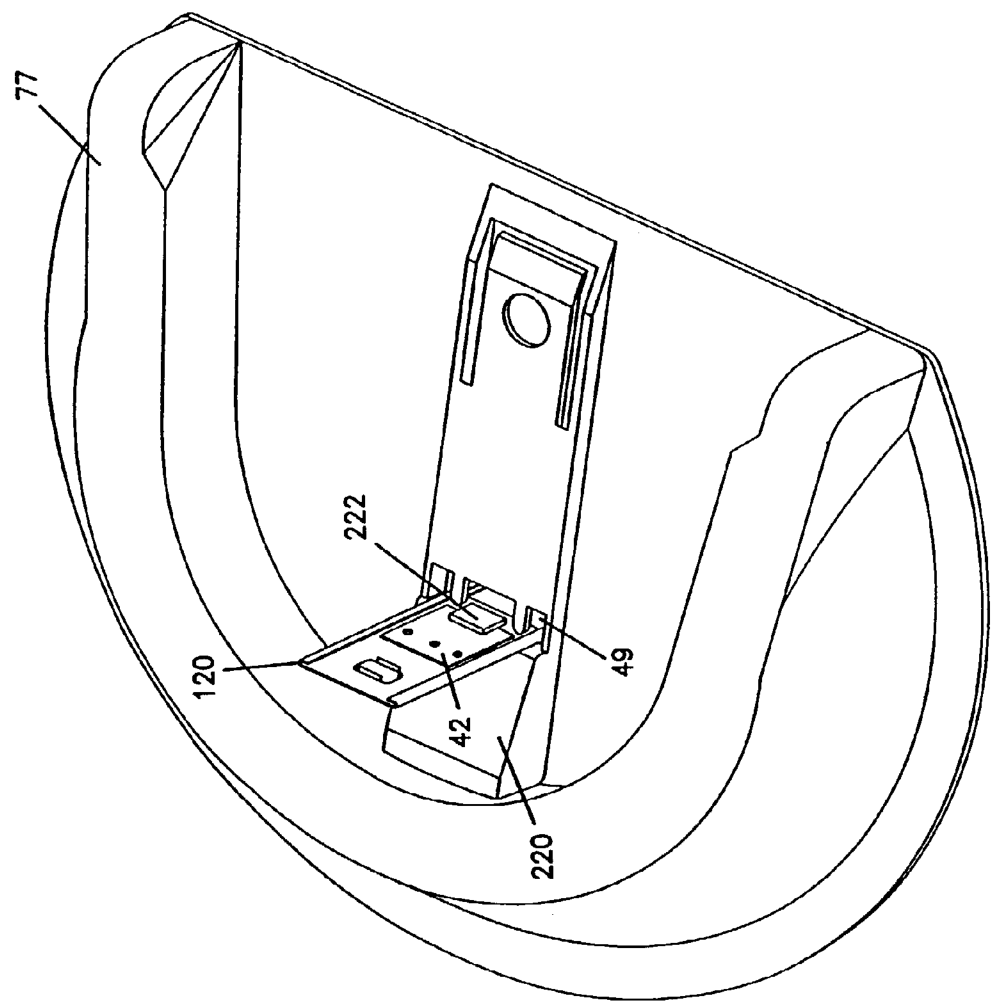
FIG. 28B is a top view of one embodiment of a mounting unit of the on-skin sensor control unit of FIG. 28A.
Figure 28C:
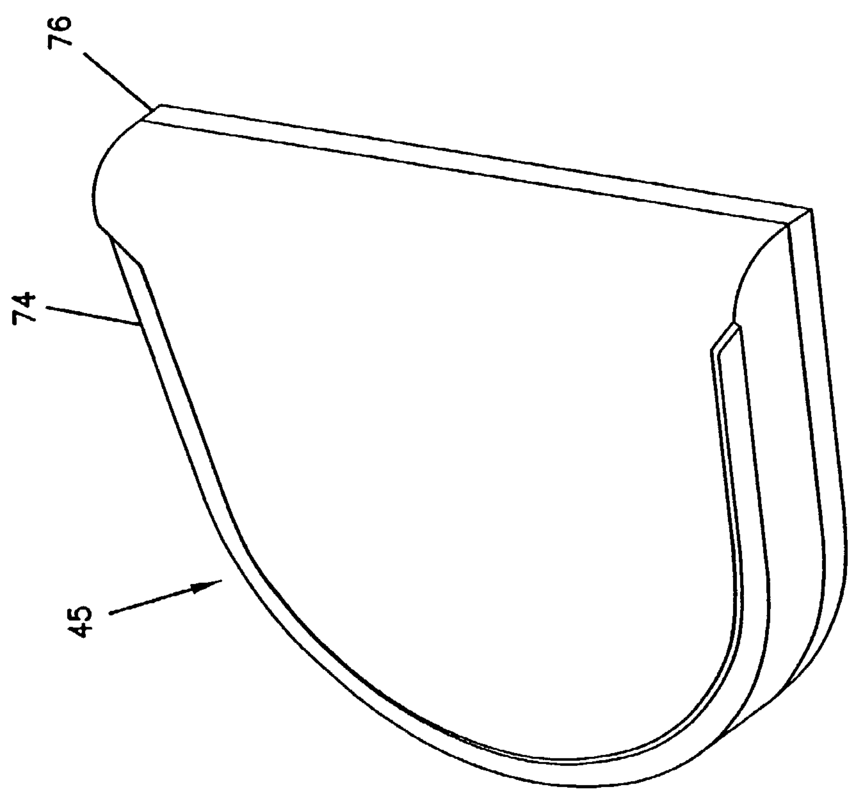
FIG. 28C is a top view of one embodiment of a housing for at least a portion of the electronics of the on-skin sensor control unit of FIG. 28A.
Figure 28D:
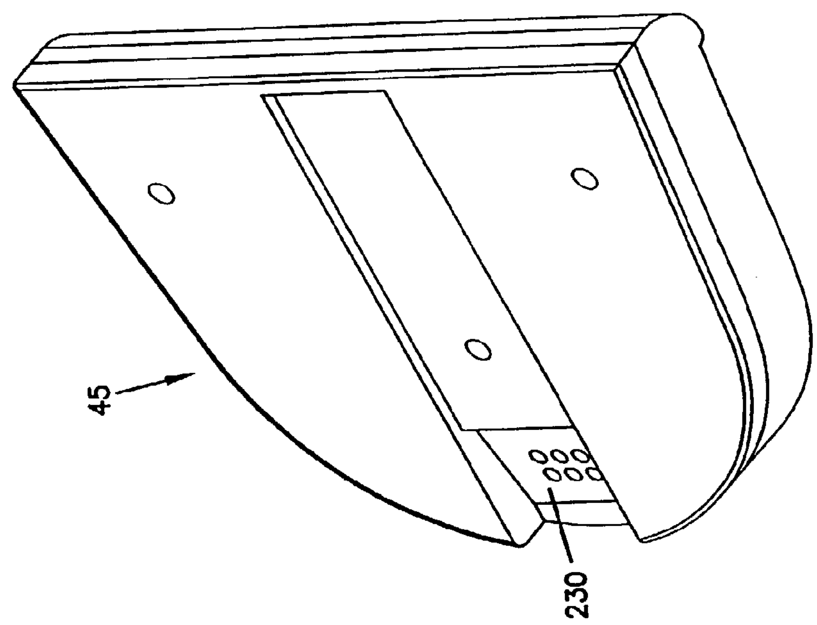
FIG. 28D is a bottom view of the housing of FIG. 28C.
Figure 28E:
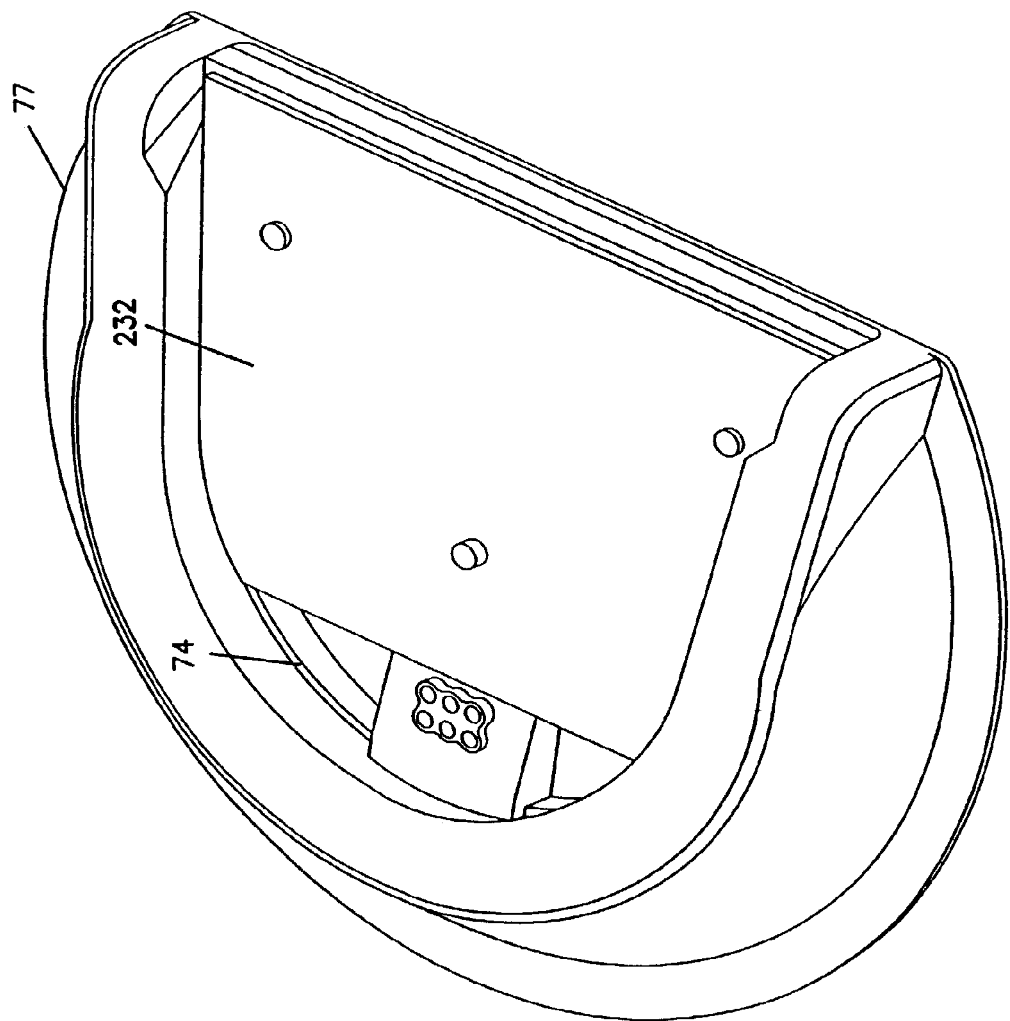
FIG. 28E is a top view of the on-skin sensor control unit of FIG. 28A with a cover of the housing removed.

In another embodiment, a coupled mounting unit 77 and housing 45 of an on-skin sensor control unit 44 is provided on an adhesive patch 204 with an optional cover 206 to protect and/or confine the housing 45 of the on-skin sensor control unit 44, as illustrated in FIG. 28A. The optional cover may contain an adhesive or other mechanism for attachment to the housing 45 and/or mounting unit 77. The mounting unit 77 typically includes an opening 49 through which a sensor 42 is disposed, as shown in FIG. 28B. The opening 49 may optionally be configured to allow insertion of the sensor 42 through the opening 49 using an insertion device 120 or insertion gun 200 (see FIG. 26). The housing 45 of the on-skin sensor control unit 44 has a base 74 and a cover 76, as illustrated in FIG. 28C. A bottom view of the housing 45, as shown in FIG. 28D, illustrates ports 230 through which conductive contacts (not shown) extend to connect with contact pads on the sensor 42. A board 232 for attachment of circuit components may optionally be provided within the on-skin sensor control unit 44, as illustrated in FIG. 28E.

In some embodiments, the adhesive on the on-skin sensor control unit 44 and/or on any of the embodiments of the mounting unit 77 is water resistant or waterproof to permit activities such as showering and/or bathing while maintaining adherence of the on-skin sensor control unit 44 to the skin 75 of the patient and, at least in some embodiments, preventing water from penetrating into the sensor control unit 44. The use of a water resistant or waterproof adhesive combined with a water resistant or waterproof housing 45 protects the components in the sensor control unit 44 and the contact between the conductive contacts 80 and the sensor 42 from damage or corrosion. An example of a non-irritating adhesive that repels water is Tegaderm (3M, St. Paul, Minn.).

In one embodiment, the on-skin sensor control unit 44 includes a sensor port 78 through which the sensor 42 enters the subcutaneous tissue of the patient, as shown in FIGS. 14 to 16. The sensor 42 may be inserted into the subcutaneous tissue of the patient through the sensor port 78. The on-skin sensor control unit 44 may then be placed on the skin of the patient with the sensor 42 being threaded through the sensor port 78. If the housing 45 of the sensor 42 has, for example, a base 74 and a cover 76, then the cover 76 may be removed to allow the patient to guide the sensor 42 into the proper position for contact with the conductive contacts 80.

Alternatively, if the conductive contacts 80 are within the housing 45 the patient may slide the sensor 42 into the housing 45 until contact is made between the contact pads 49 and the conductive contacts 80. The sensor control unit 44 may have a structure which obstructs the sliding of the sensor 42 further into the housing once the sensor 42 is properly positioned with the contact pads 49 in contact with the conductive contacts 80.

In other embodiments, the conductive contacts 80 are on the exterior of the housing 45 (see e.g., FIGS. 27A-27B and 28A-28E). In these embodiments, the patient guides the contacts pads 49 of the sensor 42 into contact with the conductive contacts 80. In some cases, a guiding structure may be provided on the housing 45 which guides the sensor 42 into the proper position. An example of such a structure includes a set of guiding rails extending from the housing 45 and having the shape of the sensor 42.

In some embodiments, when the sensor 42 is inserted using an insertion device 120 (see FIG. 12), the tip of the insertion device 120 or optional insertion gun 200 (see FIG. 26) is positioned against the skin or the mounting unit 77 at the desired insertion point. In some embodiments, the insertion device 120 is positioned on the skin without any guide. In other embodiments, the insertion device 120 or insertion gun 200 is positioned using guides (not shown) in the mounting unit 77 or other portion of the on-skin sensor control unit 44. In some embodiments, the guides, opening 79 in the mounting unit 77 and/or sensor port 78 in the housing 45 of the on-skin sensor control unit 44 have a shape which is complementary to the shape of the tip of the insertion device 120 and/or insertion gun 200 to limit the orientation of the insertion device 120 and/or insertion gun 200 relative to the opening 79 and/or sensor port 78. The sensor can then be subcutaneously inserted into the patient by matching the complementary shape of the opening 79 or sensor port 78 with the insertion device 120 and/or insertion gun 200.

In some embodiments, the shapes of a) the guides, opening 79, or sensor port 78, and (b) the insertion device 120 or insertion gun 200 are configured such that the two shapes can only be matched in a single orientation. This aids in inserting the sensor 42 in the same orientation each time a new sensor is inserted into the patient. This uniformity in insertion orientation may be required in some embodiments to ensure that the contact pads 49 on the sensor 42 are correctly aligned with appropriate conductive contacts 80 on the on-skin sensor control unit 44. In addition, the use of the insertion gun, as described above, may ensure that the sensor 42 is inserted at a uniform, reproducible depth.

The sensor 42 and the electronic components within the on-skin sensor control unit 44 are coupled via conductive contacts 80, as shown in FIGS. 14-16. The one or more working electrodes 58, counter electrode 60 (or counter/reference electrode), optional reference electrode 62, and optional temperature probe 66 are attached to individual conductive contacts 80. In the illustrated embodiment of FIGS. 14-16, the conductive contacts 80 are provided on the interior of the on-skin sensor control unit 44. Other embodiments of the on-skin sensor control unit 44 have the conductive contacts disposed on the exterior of the housing 45. The placement of the conductive contacts 80 is such that they are in contact with the contact pads 49 on the sensor 42 when the sensor 42 is properly positioned within the on-skin sensor control unit 44.

In the illustrated embodiment of FIGS. 14-16, the base 74 and cover 76 of the on-skin sensor control unit 44 are formed such that, when the sensor 42 is within the on-skin sensor control unit 44 and the base 74 and cover 76 are fitted together, the sensor 42 is bent. In this manner, the contact pads 49 on the sensor 42 are brought into contact with the conductive contacts 80 of the on-skin sensor control unit 44. The on-skin sensor control unit 44 may optionally contain a support structure 82 to hold, support, and/or guide the sensor 42 into the correct position.

Figure 18A:
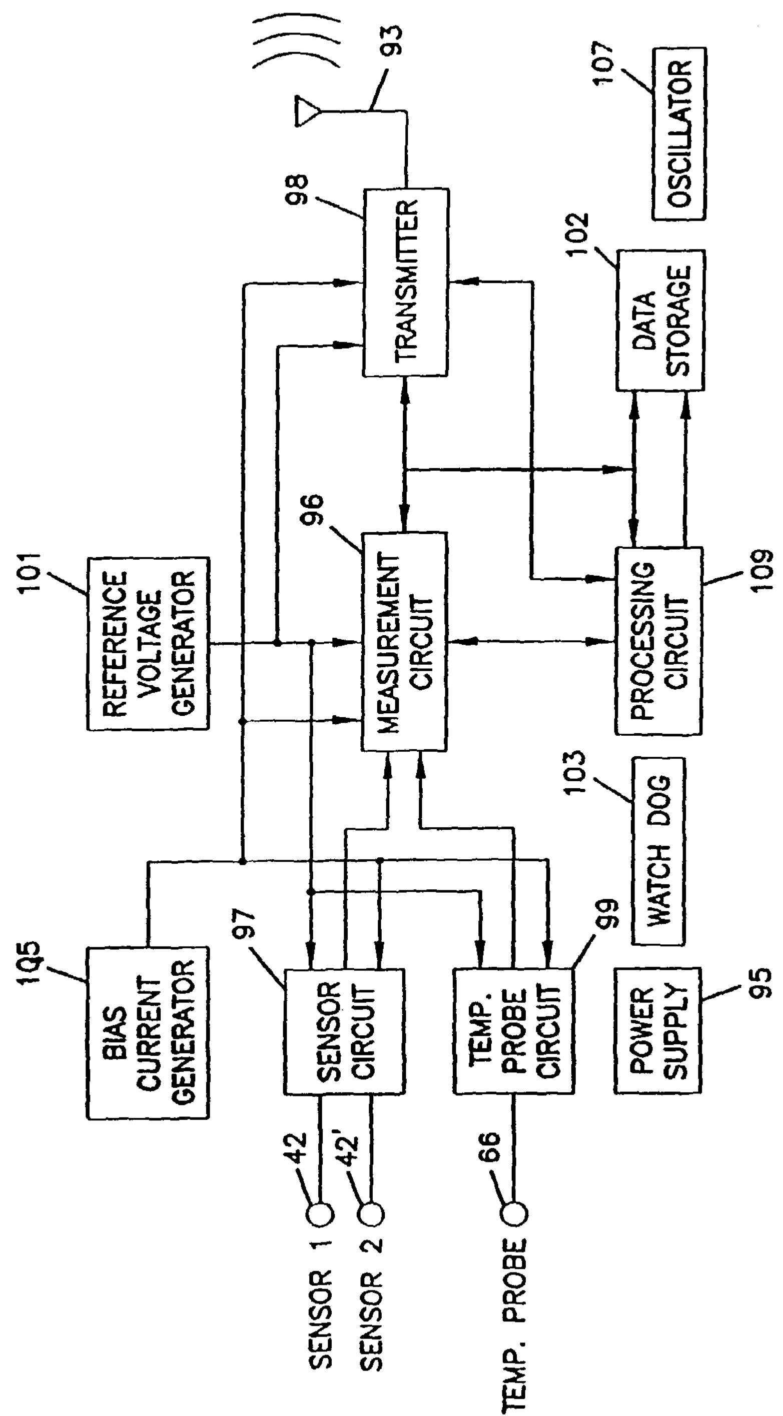
FIG. 18A is a block diagram of one embodiment of an on-skin sensor control unit, according to the invention.

Non-limiting examples of suitable conductive contacts 80 are illustrated in FIGS. 19A-19D. In one embodiment, the conductive contacts 80 are pins 84 or the like, as illustrated in FIG. 19A, which are brought into contact with the contact pads 49 on the sensor 42 when the components of the on-skin sensor control unit 44, for example, the base 74 and cover 76, are fitted together. A support 82 may be provided under the sensor 42 to promote adequate contact between the contact pads 49 on the sensor 42 and the pins 84. The pins are typically made using a conductive material, such as a metal or alloy, for example, copper, stainless steel, or silver. Each pin has a distal end that extends from the on-skin sensor control unit 44 for contacting the contact pads 49 on the sensor 42. Each pin 84 also has a proximal end that is coupled to a wire or other conductive strip that is, in turn, coupled to the rest of the electronic components (e.g., the power supply 95 and measurement circuit 96 of FIGS. 18A and 18B) within the on-skin sensor control unit 44. Alternatively, the pins 84 may be coupled directly to the rest of the electronics.

In another embodiment, the conductive contacts 80 are formed as a series of conducting regions 88 with interspersed insulating regions 90, as illustrated in FIG. 19B. The conducting regions 88 may be as large or larger than the contact pads 49 on the sensor 42 to alleviate registration concerns. However, the insulating regions 90 should have sufficient width so that a single conductive region 88 does not overlap with two contact pads 49 as determined based on the expected variation in the position of the sensor 42 and contact pads 49 with respect to the conductive contacts 80. The conducting regions 88 are formed using materials such as metals, alloys, or conductive carbon. The insulating regions 90 may be formed using known insulating materials including, for example, insulating plastic or polymer materials.

In a further embodiment, a unidirectional conducting adhesive 92 may be used between the contact pads 49 on the sensor 42 and conductive contacts 80 implanted or otherwise formed in the on-skin sensor control unit 44, as shown in FIG. 19C.

In yet another embodiment, the conductive contacts 80 are conductive members 94 that extend from a surface of the on-skin sensor control unit 44 to contact the contact pads 49, as shown in FIG. 19D. A variety of different shapes may be used for these members, however, they should be electrically insulated from each other. The conductive members 94 may be made using metal, alloy, conductive carbon, or conducting plastics and polymers.

Any of the exemplary conductive contacts 80 described above may extend from either the upper surface of the interior of the on-skin sensor control unit 44, as illustrated in FIG. 19A-19C, or from the lower surface of the interior of the on-skin sensor control unit 44, as illustrated in FIG. 19D, or from both the upper and lower surfaces of the interior of the on-skin sensor control unit 44, particularly when the sensor 42 has contact pads 49 on both sides of the sensor.

Conductive contacts 80 on the exterior of the housing 45 may also have a variety of shapes as indicated in FIGS. 19E and 19F. For example, the conductive contacts 80 may be embedded in (FIG. 19E) or extending out of (FIG. 19F) the housing 45.

The conductive contacts 80 are preferably made using a material which will not corrode due to contact with the contact pads 49 of the sensor 42. Corrosion may occur when two different metals are brought in contact. Thus, if the contact pads 49 are formed using carbon then the preferred conductive contacts 80 may be made using any material, including metals or alloys. However, if any of the contact pads 49 are made with a metal or alloy then the preferred conductive contacts 80 for coupling with the metallic contact pads are made using a non-metallic conductive material, such as conductive carbon or a conductive polymer, or the conductive contacts 80 and the contact pads 49 are separated by a non-metallic material, such as a unidirectional conductive adhesive.

In one embodiment, electrical contacts are eliminated between the sensor 42 and the on-skin sensor control unit 44. Power is transmitted to the sensor via inductive coupling, using, for example, closely space antennas (e.g., facing coils) (not shown) on the sensor and the on-skin sensor control unit. Changes in the electrical characteristics of the sensor control unit 44 (e.g., current) induce a changing magnetic field in the proximity of the antenna. The changing magnetic field induces a current in the antenna of the sensor. The close proximity of the sensor and on-skin sensor control unit results in reasonably efficient power transmission. The induced current in the sensor may be used to power potentiostats, operational amplifiers, capacitors, integrated circuits, transmitters, and other electronic components built into the sensor structure. Data is transmitted back to the sensor control unit, using, for example, inductive coupling via the same or different antennas and/or transmission of the signal via a transmitter on the sensor. The use of inductive coupling can eliminate electrical contacts between the sensor and the on-skin sensor control unit. Such contacts are commonly a source of noise and failure. Moreover, the sensor control unit may then be entirely sealed which may increase the waterproofing of the on-skin sensor control unit.

An exemplary on-skin sensor control unit 44 can be prepared and used in the following manner. A mounting unit 77 having adhesive on the bottom is applied to the skin. An insertion gun 200 (see FIG. 26) carrying the sensor 42 and the insertion device 120 is positioned against the mounting unit 77. The insertion gun 200 and mounting unit 77 are optionally designed such that there is only one position in which the two properly mate. The insertion gun 200 is activated and a portion of the sensor 42 and optionally a portion of the insertion device 120 are driven through the skin into, for example, the subcutaneous tissue. The insertion gun 200 withdraws the insertion device 200, leaving the portion of the sensor 42 inserted through the skin. The housing 45 of the on-skin control unit 44 is then coupled to the mounting unit 77. Optionally, the housing 45 and the mounting unit 77 are formed such that there is only one position in which the two properly mate. The mating of the housing 45 and the mounting unit 77 establishes contact between the contact pads 49 (see e.g., FIG. 2) on the sensor 42 and the conductive contacts 80 on the on-skin sensor control unit 44. Optionally, this action activates the on-skin sensor control unit 44 to begin operation.

Figure 33:
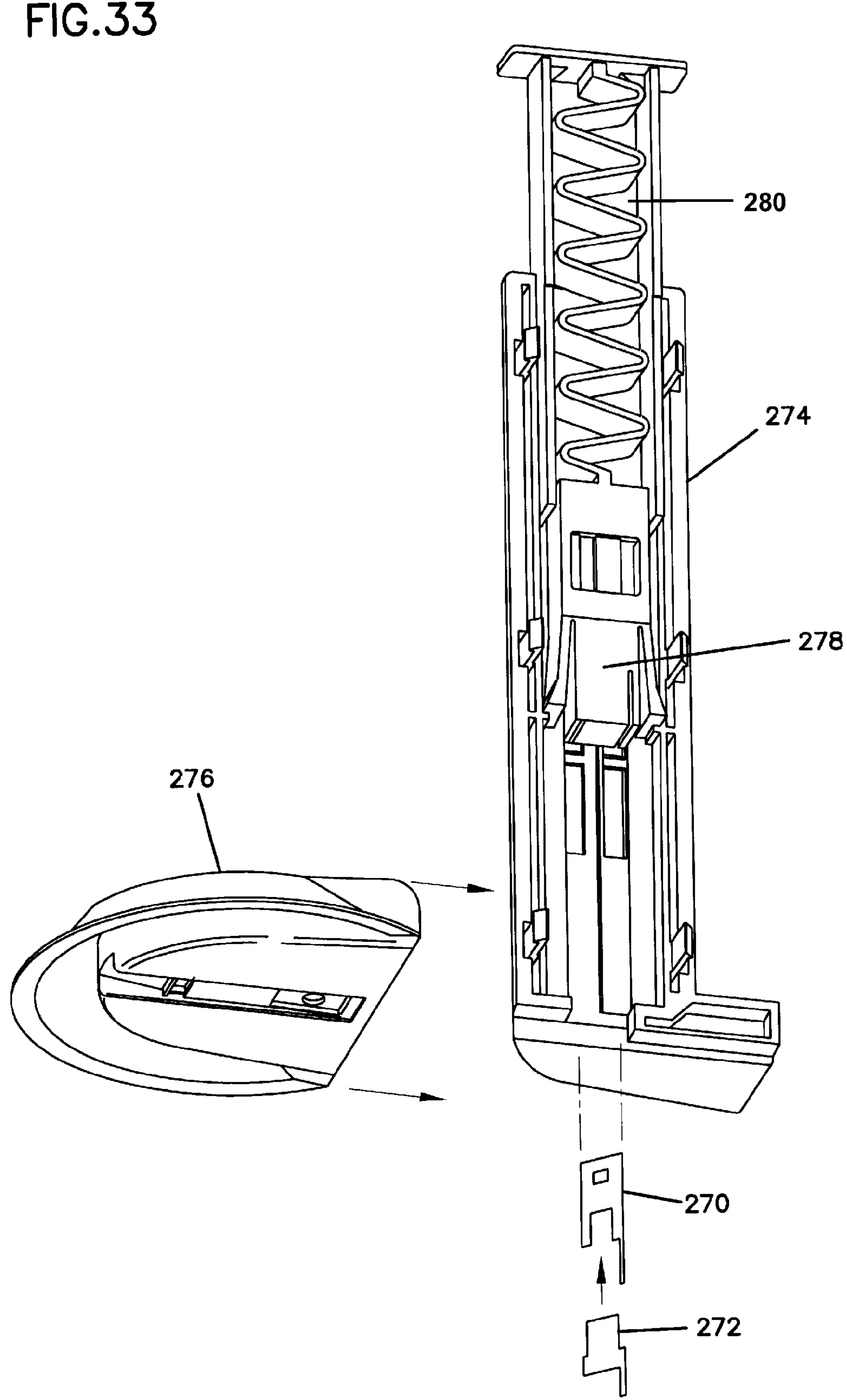
FIG. 33 depicts an insertion device, sensor, insertion gun and mounting unit, which can be assembled and sold together in an insertion kit While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

The insertion device, sensor, insertion gun and mounting unit can be manufactured, marketed, or sold as a unit. For example, FIG. 33 depicts an insertion device 270, sensor 272, insertion gun 274 and mounting unit 276, which can be assembled (as indicated by the arrows) and sold together in an insertion kit. In such an embodiment of an insertion kit, the insertion gun 274 can be packaged in a pre-loaded fashion, with an insertion device 270 and sensor 272 mated or otherwise coupled, the mated sensor 272 and insertion device 270 loaded upon the carrier 278 of the insertion gun, and with a mounting unit 276 already mated with the end of the insertion gun 274.

In one embodiment, the insertion gun 274 is packaged in a state where it is ready to thrust the sensor 272 (and perhaps insertion device 270) into subcutaneous tissue. For example, the insertion gun 274 can be packaged in a "cocked" state, such that the thrusting force used to introduce the sensor 272 into the subcutaneous tissue is stored in the device as potential energy (in the case of the embodiment depicted in FIG. 33, the insertion gun 274 would be "cocked" by compressing its spring 280, thus storing potential energy within the coils of the spring). Preferably, an insertion gun 274 packaged in such a manner employs a "safety", a barrier to prevent the release of the stored potential energy. The barrier is removed in order to permit the potential energy to be released. Within the context of the embodiment presented in FIG. 33, an example of a safety is a pin (not pictured) that impedes the spring from expanding, once compressed. Thus, an insertion kit so embodied can be obtained at a place of purchase, removed from its package, and used after removal of the safety, without necessitating additional steps. Alternatively, the insertion gun 274 can be packaged in the above-described pre-loaded configuration, but without being "cocked". Thus, an insertion kit with an "uncocked" insertion gun 274 can be obtained at a place of purchase, removed from its package, cocked, and used. To facilitate the insertion kit being ready to use with minimal user-exercised steps, the insertion kit can be sterilized prior to packaging. Examples of acceptable sterilizing techniques include exposing the elements of the insertion kit to gamma radiation or an e-beam.

On-Skin Control Unit Electronics

The on-skin sensor control unit 44 also typically includes at least a portion of the electronic components that operate the sensor 42 and the analyte monitoring device system 40. One embodiment of the electronics in the on-skin control unit 44 is illustrated as a block diagram in FIG. 18A. The electronic components of the on-skin sensor control unit 44 typically include a power supply 95 for operating the on-skin control unit 44 and the sensor 42, a sensor circuit 97 for obtaining signals from and operating the sensor 42, a measurement circuit 96 that converts sensor signals to a desired format, and a processing circuit 109 that, at minimum, obtains signals from the sensor circuit 97 and/or measurement circuit 96 and provides the signals to an optional transmitter 98. In some embodiments, the processing circuit 109 may also partially or completely evaluate the signals from the sensor 42 and convey the resulting data to the optional transmitter 98 and/or activate an optional alarm system 94 (see FIG. 18B) if the analyte level exceeds a threshold. The processing circuit 109 often includes digital logic circuitry.

The on-skin sensor control unit 44 may optionally contain a transmitter 98 for transmitting the sensor signals or processed data from the processing circuit 109 to a receiver/display unit 46, 48; a data storage unit 102 for temporarily or permanently storing data from the processing circuit 109; a temperature probe circuit 99 for receiving signals from and operating a temperature probe 66; a reference voltage generator 101 for providing a reference voltage for comparison with sensor-generated signals; and/or a watchdog circuit 103 that monitors the operation of the electronic components in the on-skin sensor control unit 44.

Moreover, the sensor control unit 44 often includes digital and/or analog components utilizing semiconductor devices, such as transistors. To operate these semiconductor devices, the on-skin control unit 44 may include other components including, for example, a bias control generator 105 to correctly bias analog and digital semiconductor devices, an oscillator 107 to provide a clock signal, and a digital logic and timing component 109 to provide timing signals and logic operations for the digital components of the circuit.

As an example of the operation of these components, the sensor circuit 97 and the optional temperature probe circuit 99 provide raw signals from the sensor 42 to the measurement circuit 96. The measurement circuit 96 converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit 109 may then, optionally, evaluate the data and provide commands to operate the electronics.

Figure 18B:
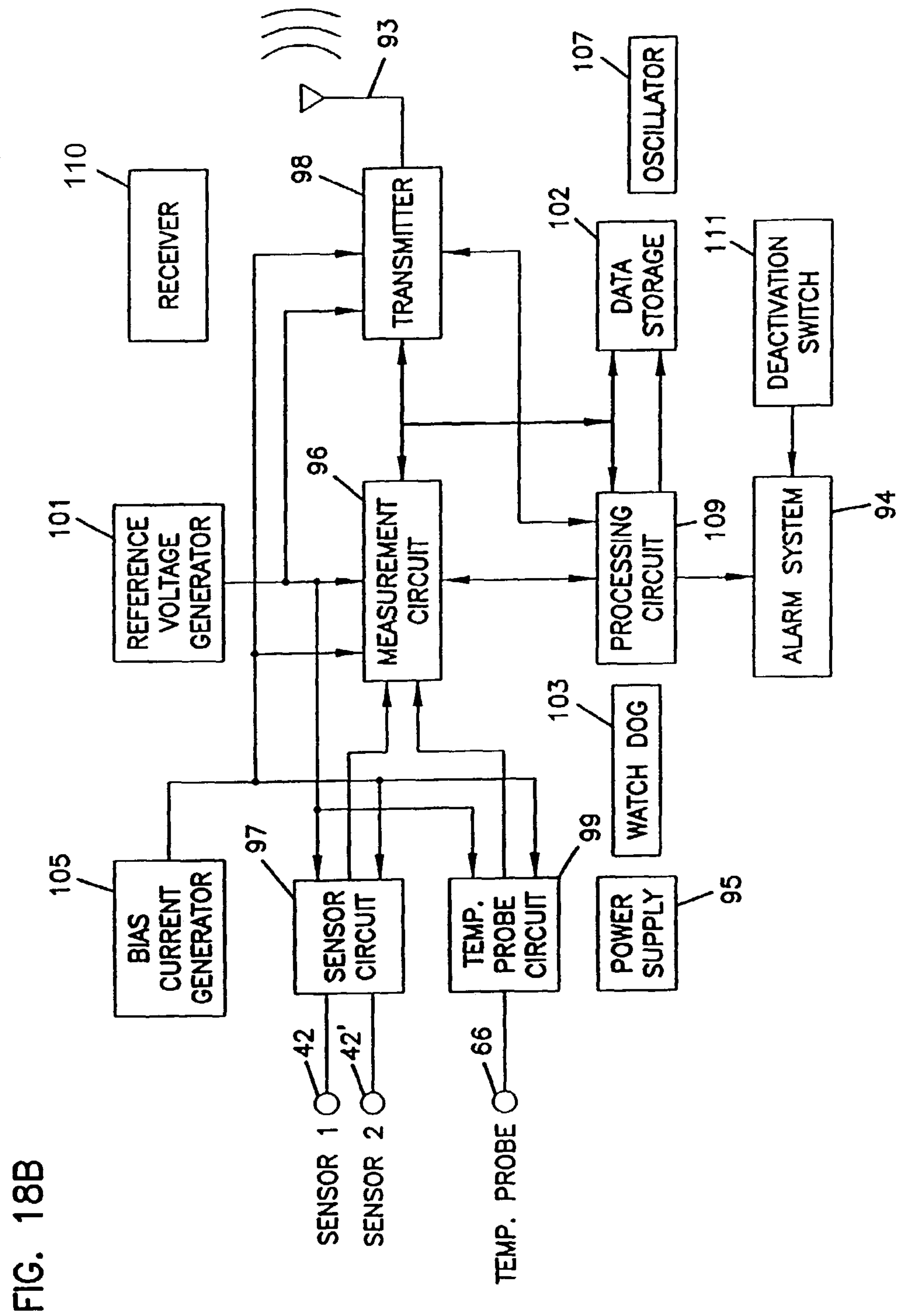
FIG. 18B is a block diagram of another embodiment of an on-skin sensor control unit, according to the invention.

FIG. 18B illustrates a block diagram of another exemplary on-skin sensor control unit 44 that also includes optional components such as a receiver 110 to receive, for example, calibration data; a calibration storage unit (not shown) to hold, for example, factory-set calibration data, calibration data obtained via the receiver 110 and/or operational signals received, for example, from a receiver/display unit 46, 48 or other external device; an alarm system 94 for warning the patient; and a deactivation switch 111 to turn off the alarm system.

Functions of the analyte monitoring system 40 and the sensor control unit 44 may be implemented using either software routines, hardware components, or combinations thereof. The hardware components may be implemented using a variety of technologies, including, for example, integrated circuits or discrete electronic components. The use of integrated circuits typically reduces the size of the electronics, which in turn may result in a smaller on-skin sensor control unit 44.

The electronics in the on-skin sensor control unit 44 and the sensor 42 are operated using a power supply 95. One example of a suitable power supply 95 is a battery, for example, a thin circular battery, such as those used in many watches, hearing aids, and other small electronic devices. Preferably, the battery has a lifetime of at least 30 days, more preferably, a lifetime of at least three months, and most preferably, a lifetime of at least one year. The battery is often one of the largest components in the on-skin control unit 44, so it is often desirable to minimize the size of the battery. For example, a preferred battery's thickness is 0.5 mm or less, preferably 0.35 mm or less, and most preferably 0.2 mm or less. Although multiple batteries may be used, it is typically preferred to use only one battery.

The sensor circuit 97 is coupled via the conductive contacts 80 of the sensor control unit 44 to one or more sensors 42, 42'. Each of the sensors represents, at minimum, a working electrode 58, a counter electrode 60 (or counter/reference electrode), and an optional reference electrode 62. When two or more sensors 42, 42' are used, the sensors typically have individual working electrodes 58, but may share a counter electrode 60, counter/reference electrode, and/or reference electrode 62.

The sensor circuit 97 receives signals from and operates the sensor 42 or sensors 42, 42'. The sensor circuit 97 may obtain signals from the sensor 42 using amperometric, coulometric, potentiometric, voltammetric, and/or other electrochemical techniques. The sensor circuit 97 is exemplified herein as obtaining amperometric signals from the sensor 42, however, it will be understood that the sensor circuit can be appropriately configured for obtaining signals using other electrochemical techniques. To obtain amperometric measurements, the sensor circuit 97 typically includes a potentiostat that provides a constant potential to the sensor 42. In other embodiments, the sensor circuit 97 includes an amperostat that supplies a constant current to the sensor 42 and can be used to obtain coulometric or potentiometric measurements.

The signal from the sensor 42 generally has at least one characteristic, such as, for example, current, voltage, or frequency, which varies with the concentration of the analyte. For example, if the sensor circuit 97 operates using amperometry, then the signal current varies with analyte concentration. The measurement circuit 96 may include circuitry which converts the information-carrying portion of the signal from one characteristic to another. For example, the measurement circuit 96 may include a current-to-voltage or current-to-frequency converter. The purpose of this conversion may be to provide a signal that is, for example, more easily transmitted, readable by digital circuits, and/or less susceptible to noise contributions.

Figure 20A:
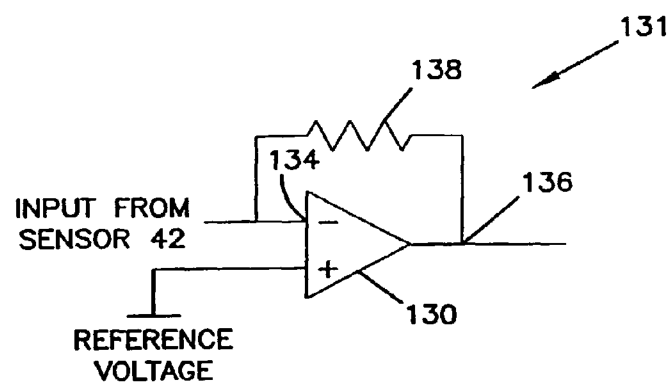
FIGS. 20A and 20B are schematic diagrams of two embodiments of a current-to-voltage converter for use in an analyte monitoring device, according to the invention.

One example of a standard current-to-voltage converter is provided in FIG. 20A. In this converter, the signal from the sensor 42 is provided at one input terminal 134 of an operational amplifier 130 ("op amp") and coupled through a resistor 138 to an output terminal 136. This particular current-to-voltage converter 131 may, however, be difficult to implement in a small CMOS chip because resistors are often difficult to implement on an integrated circuit. Typically, discrete resistor components are used. However, the used of discrete components increases the space needed for the circuitry.

Figure 20B:
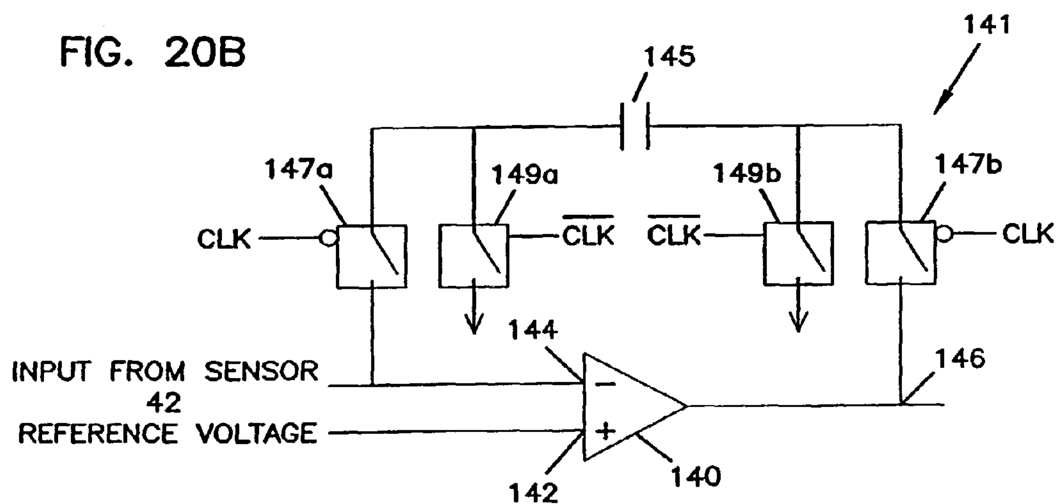

An alternative current-to-voltage converter 141 is illustrated in FIG. 20B. This converter includes an op amp 140 with the signal from the sensor 42 provided at input terminal 144 and a reference potential provided at input terminal 142. A capacitor 145 is placed between the input terminal 144 and the output terminal 146. In addition, switches 147*a*, 147*b*, 149*a*, and 149*b* are provided to allow the capacitor to charge and discharge at a rate determined by a clock (CLK) frequency. In operation, during one half cycle, switches 147*a* and 147*b* close and switches 149*a* and 149*b* open allowing the capacitor 145 to charge due to the attached potential V1. During the other half cycle, switches 147*a* and 147*b* open and switches 149*a* and 149*b* close to ground and allow the capacitor 145 to partially or fully discharge. The reactive impedance of the capacitor 145 is analogous to the resistance of the resistor 138 (see FIG. 20A), allowing the capacitor 145 to emulate a resistor. The value of this "resistor" depends on the capacitance of the capacitor 145 and the clock frequency. By altering the clock frequency, the reactive impedance ("resistance value") of the capacitor changes. The value of the impedance ("resistance") of the capacitor 145 may be altered by changing the clock frequency. Switches 147*a*, 147*b*, 149*a*, and 149*b* may be implemented in a CMOS chip using, for example, transistors.

A current-to-frequency converter may also be used in the measurement circuit 96. One suitable current-to-frequency converter includes charging a capacitor using the signal from the sensor 42. When the potential across the capacitor exceeds a threshold value, the capacitor is allowed to discharge. Thus, the larger the current from the sensor 42, the quicker the threshold potential is achieved. This results in a signal across the capacitor that has an alternating characteristic, corresponding to the charging and discharging of the capacitor, having a frequency which increases with an increase in current from the sensor 42.

In some embodiments, the analyte monitoring system 40 includes two or more working electrodes 58 distributed over one or more sensors 42. These working electrodes 58 may be used for quality control purposes. For example, the output signals and/or analyzed data derived using the two or more working electrodes 58 may be compared to determine if the signals from the working electrodes agree within a desired level of tolerance. If the output signals do not agree, then the patient may be alerted to replace the sensor or sensors. In some embodiments, the patient is alerted only if the lack of agreement between the two sensors persists for a predetermined period of time. The comparison of the two signals may be made for each measurement or at regular intervals. Alternatively or additionally, the comparison may be initiated by the patient or another person. Moreover, the signals from both sensors may be used to generate data or one signal may be discarded after the comparison.

Alternatively, if, for example, two working electrodes 58 have a common counter electrode 60 and the analyte concentration is measured by amperometry, then the current at the counter electrode 60 should be twice the current at each of the working electrodes, within a predetermined tolerance level, if the working electrodes are operating properly. If not, then the sensor or sensors should be replaced, as described above.

An example of using signals from only one working electrode for quality control includes comparing consecutive readings obtained using the single working electrode to determine if they differ by more than a threshold level. If the difference is greater than the threshold level for one reading or over a period of time or for a predetermined number of readings within a period of time then the patient is alerted to replace the sensor 42. Typically, the consecutive readings and/or the threshold level are determined such that all expected excursions of the sensor signal are within the desired parameters (i.e., the sensor control unit 44 does not consider true changes in analyte concentration to be a sensor failure).

The sensor control unit 44 may also optionally include a temperature probe circuit 99. The temperature probe circuit 99 provides a constant current through (or constant potential) across the temperature probe 66. The resulting potential (or current) varies according to the resistance of the temperature dependent element 72. Examples of devices which may be used as a temperature dependent element include a rectifier diode or a bipolar junction transistor. The threshold value of a rectifier diode decreases as the temperature of the diode increases. Thus, by gradually increasing the potential across a pn junction, temperature may be determined by measuring the forward voltage required to permit a given level of forward current through the pn junction. Similarly, the forward gain of a bipolar junction transistor is known to increase with temperature. Accordingly, temperature may be determined by biasing a bipolar junction transistor to produce a known collector current at a known calibration temperature. Deviance in collector current can be related to a discrepancy between the known calibration temperature and the actual temperature.

The temperature probe 66 can be configured to reside at the surface of the skin (so that the temperature dependent element 66 is in close proximity to, or preferably abutting, the skin surface). The benefit of such an arrangement is that such a temperature probe does not require implantation, thereby permitting the implantable portion of the substrate 50 to remain small in size—an advantageous property with respect to case of implantation and minimization of pain. In such an arrangement, skin surface temperature is measured, as opposed to temperature at the point of sensor chemistry. As will be discussed later, a compensation factor may be used to determine the temperature at the point of sensor chemistry based upon the measured temperature at the surface of the skin.

The output from the sensor circuit 97 and optional temperature probe circuit is coupled into a measurement circuit 96 that obtains signals from the sensor circuit 97 and optional temperature probe circuit 99 and, at least in some embodiments, provides output data in a form that, for example can be read by digital circuits. The signals from the measurement circuit 96 are sent to the processing circuit 109, which in turn may provide data to an optional transmitter 98. The processing circuit 109 may have one or more of the following functions: 1) transfer the signals from the measurement circuit 96 to the transmitter 98, 2) transfer signals from the measurement circuit 96 to the data storage circuit 102, 3) convert the information-carrying characteristic of the signals from one characteristic to another (when, for example, that has not been done by the measurement circuit 96), using, for example, a current-to-voltage converter, a current-to-frequency converter, or a voltage-to-current converter, 4) modify the signals from the sensor circuit 97 using calibration data and/or output from the temperature probe circuit 99, 5) determine a level of an analyte in the interstitial fluid, 6) determine a level of an analyte in the bloodstream based on the sensor signals obtained from interstitial fluid, 7) determine if the level, rate of change, and/or acceleration in the rate of change of the analyte exceeds or meets one or more threshold values, 8) activate an alarm if a threshold value is met or exceeded, 9) evaluate trends in the level of an analyte based on a series of sensor signals, 10) determine a dose of a medication, and 11) reduce noise and/or errors, for example, through signal averaging or comparing readings from multiple working electrodes 58.

Figure 29:
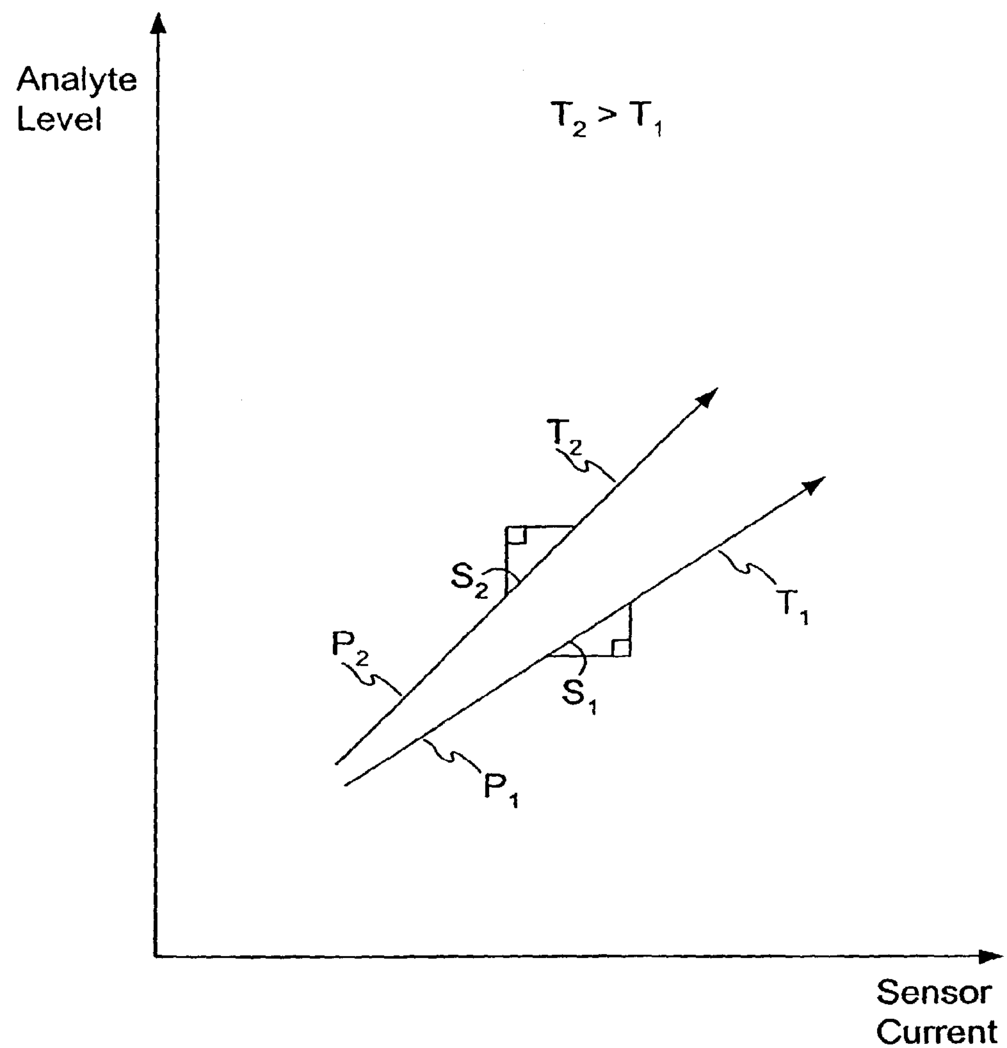
FIG. 29 depicts two sensor current-analyte level profiles at differing temperatures.

As depicted in FIG. 29, sensor current (or any other sensor characteristic, for that matter) varies directly with analyte level. Thus, at a given temperature, a particular sensor current-analyte level profile portrays the relationship between sensor current and analyte level. For example, at a given temperature, $T_1$, the sensor current-analyte level profile, $P_1$, represents that relationship. As depicted in FIG. 29, profile $P_1$ has a slope of $S_1$. Oftentimes, a particular profile is known to vary with a change in temperature in a predictable manner. For example, it is known that for each 1° C. rise in temperature from $T_1$, the slope of $S_1$ becomes steeper by a particular amount (perhaps 6% steeper for each 1° C. rise in temperature). This principle is illustrated in FIG. 29 by the depiction of a second sensor current-analyte level profile, $P_2$, which portrays the relationship between sensor current and analyte level at a second temperature, $T_2$. Because $T_2$ is greater than $T_1$, slope $S_2$ is greater than $S_1$. In some embodiments of the invention, processing circuit 109 is designed to account for this relationship by using the temperature information from measurement circuit 96 to adjust a known profile for a given temperature in a known manner when the sensed temperature varies from the aforementioned given temperature. For example, in one embodiment, processing circuit 109 comprises a microprocessor or application specific integrated circuit (ASIC) designed to adjust a known profile to be either more or less steep based upon a relationship of +/−6% slope for each +/−1° C. change in temperature. Alternately, this computation could take place in processing circuitry of the receiver/display device 256. If, as described above, the temperature probe 66 is positioned at the skin surface, the temperature information can be adjusted for the purpose of estimating temperature at the point of sensor chemistry. Skin surface temperature can be related to temperature at the point of sensor chemistry by a linear relationship. For example, in one embodiment, processing circuit 109 is configured and arranged to calculate an estimate of temperature at the point of sensor chemistry by assuming that a 5° change in temperature at the skin surface corresponds to an n° change in temperature at a particular depth below the skin surface (n can be an empirically determined value). Thus, with knowledge of the temperature at the skin surface and knowledge of the depth at which the sensor is implanted, temperature at the point of sensor chemistry may be obtained. Similarly, the estimation of the temperature at the point of sensor chemistry could take place in the processing circuitry of the receiver/display device 256.

The processing circuit 109 may be simple and perform only one or a small number of these functions or the processing circuit 109 may be more sophisticated and perform all or most of these functions. The size of the on-skin sensor control unit 44 may increase with the increasing number of functions and complexity of those functions that the processing circuit 109 performs. Many of these functions may not be performed by a processing circuit 109 in the on-skin sensor control unit 44, but may be performed by another analyzer 152 in the receiver/display units 46, 48 (see FIG. 22).

One embodiment of the measurement circuit 96 and/or processing circuit 109 provides as output data, the current flowing between the working electrode 58 and the counter electrode 60. The measurement circuit 96 and/or processing circuit 109 may also provide as output data a signal from the optional temperature probe 66 which indicates the temperature of the sensor 42. This signal from the temperature probe 66 may be as simple as a current through the temperature probe 66 or the processing circuit 109 may include a device that determines a resistance of the temperature probe 66 from the signal obtained from the measurement circuit 96 for correlation with the temperature of the sensor 42. The output data may then be sent to a transmitter 98 that then transmits this data to at least one receiver/display device 46,48.

Returning to the processing circuit 109, in some embodiments processing circuit 109 is more sophisticated and is capable of determining the analyte concentration or some measure representative of the analyte concentration, such as a current or voltage value. The processing circuit 109 may incorporate the signal of the temperature probe to make a temperature correction in the signal or analyzed data from the working electrode 58. This may include, for example, scaling the temperature probe measurement and adding or subtracting the scaled measurement to the signal or analyzed data from the working electrode 58. The processing circuit 109 may also incorporate calibration data which has been received from an external source or has been incorporated into the processing circuit 109, both of which are described below, to correct the signal or analyzed data from the working electrode 58. Additionally, the processing circuit 109 may include a correction algorithm for converting interstitial analyte level to blood analyte level. The conversion of interstitial analyte level to blood analyte level is described, for example, in Schmidtke, et al., "Measurement and Modeling of the Transient Difference Between Blood and Subcutaneous Glucose Concentrations in the Rat after Injection of Insulin", Proc. of the Nat'l Acad. of Science, 95, 294-299 (1998) and Quinn, et al., "Kinetics of Glucose Delivery to Subcutaneous Tissue in Rats Measured with 0.3 mm Amperometric Microsensors", Am. J. Physiol., 269 (Endocrinol. Metab. 32), E155-E161 (1995), incorporated herein by reference.

In some embodiments, the data from the processing circuit 109 is analyzed and directed to an alarm system 94 (see FIG. 18B) to warn the user. In at least some of these embodiments, a transmitter is not used as the sensor control unit performs all of the needed functions including analyzing the data and warning the patient.

However, in many embodiments, the data (e.g., a current signal, a converted voltage or frequency signal, or fully or partially analyzed data) from processing circuit 109 is transmitted to one or more receiver/display units 46, 48 using a transmitter 98 in the on-skin sensor control unit 44. The transmitter has an antenna 93, such as a wire or similar conductor, formed in the housing 45. The transmitter 98 is typically designed to transmit a signal up to about 2 meters or more, preferably up to about 5 meters or more, and more preferably up to about 10 meters or more, when transmitting to a small receiver/display unit 46, such as a palm-size, belt-worn receiver. The effective range is longer when transmitting to a unit with a better antenna, such as a bedside receiver. As described in detail below, suitable examples of receiver/display units 46, 48 include units that can be easily worn or carried or units that can be placed conveniently on, for example, a nightstand when the patient is sleeping.

The transmitter 98 may send a variety of different signals to the receiver/display units 46, 48, typically, depending on the sophistication of the processing circuit 109. For example, the processing circuit 109 may simply provide raw signals, for example, currents from the working electrodes 58, without any corrections for temperature or calibration, or the processing circuit 109 may provide converted signals which are obtained, for example, using a current-to-voltage converter 131 or 141 (see FIGS. 20A and 20B) or a current-to-frequency converter. The raw measurements or converted signals may then be processed by an analyzer 152 (see FIG. 22) in the receiver/display units 46, 48 to determine the level of an analyte, optionally using temperature and calibration corrections. In another embodiment, the processing circuit 109 corrects the raw measurements using, for example, temperature and/or calibration information and then the transmitter 98 sends the corrected signal, and optionally, the temperature and/or calibration information, to the receiver/display units 46, 48. In yet another embodiment, the processing circuit 109 calculates the analyte level in the interstitial fluid and/or in the blood (based on the interstitial fluid level) and transmits that information to the one or more receiver/display units 46, 48, optionally with any of the raw data and/or calibration or temperature information. In a further embodiment, the processing circuit 109 calculates the analyte concentration, but the transmitter 98 transmits only the raw measurements, converted signals, and/or corrected signals.

Figure 30:
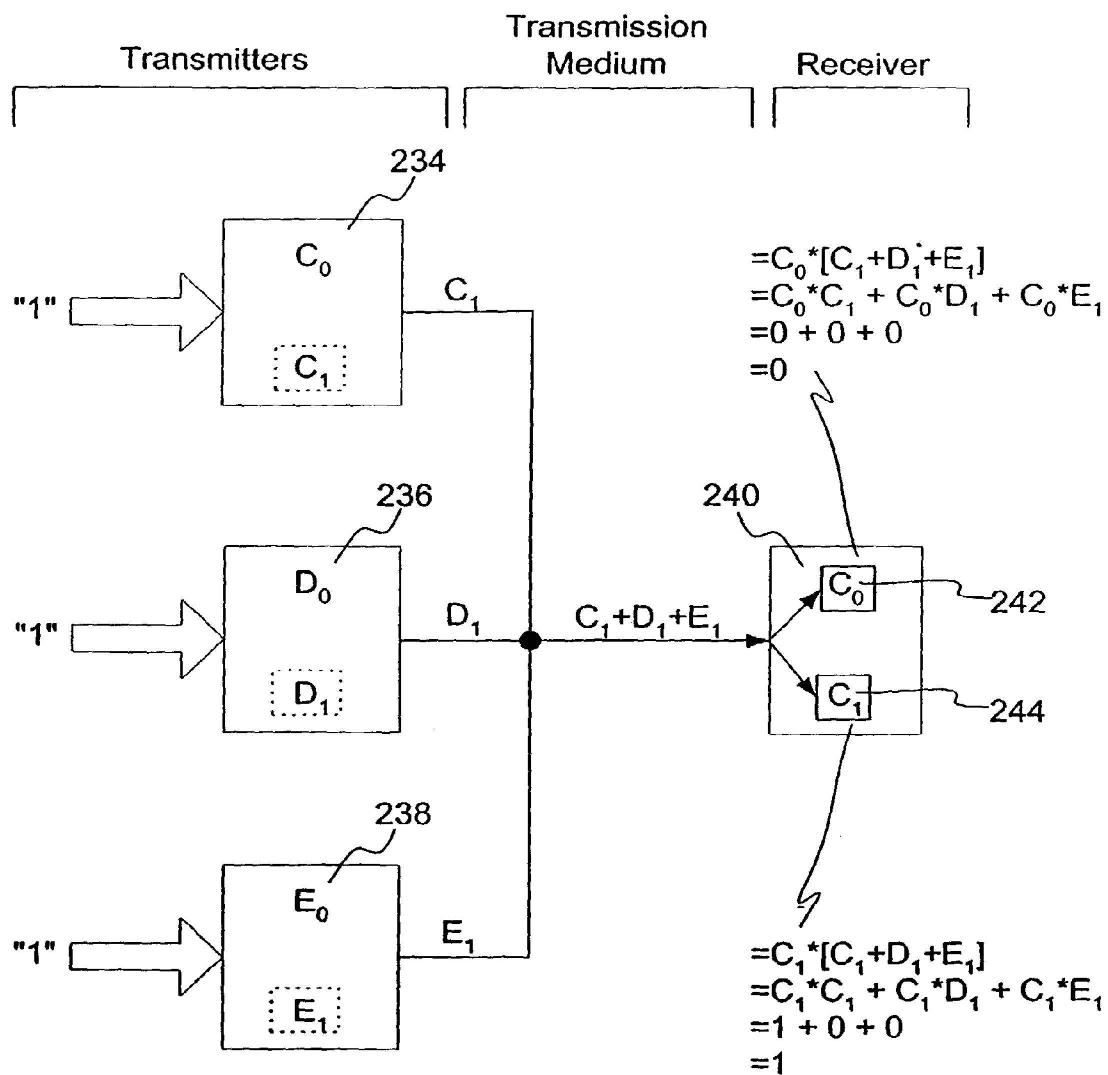
FIG. 30 depicts three code division multiple access (CDMA) transmitters simultaneously transmitting across a transmission medium to a CDMA receiver.

In one possible embodiment, the transmitter 98 is configured to employ code division multiple access (CDMA) transmission. CDMA transmission carries with it at least two benefits. First, the transmitted signal becomes more resistant to noise. Second, transmissions emanating from transmitters that employ CDMA technology can be discerned at the point of reception, although they were simultaneously transmitted upon the same carrier frequency. As shown in FIG. 30, CDMA transmitters 234, 236, 238 employ a set of spreading codes. In its simplest form, a CDMA transmitter (such as 234, 236, or 238) employs two spreading codes (a CDMA transmitter may, however, employ more than two spreading codes). A spreading code is a sequence of ones and zeros that is used to represent a shorter sequence of ones and zeros. For example, a simple CDMA transmitter employing two spreading codes would use one sequence of ones and zeros to represent a binary one and a different sequence of ones and zeros to represent a binary zero. Each one and zero that is represented as a longer sequence of ones and zeros is referred to as a "bit". Each one and zero within a spreading code is referred to as a "chip". Thus, a sequence of 64 chips can represent a single bit.

As illustrated in FIG. 30, a multiplicity of CDMA transmitters 234, 236, 238 can discernibly transmit (i.e., transmit within the same vicinity and yet be individually understood by a CDMA receiver), if each CDMA transmitter 234, 236, 238 employs a different spreading code, thereby representing a one or zero with a different sequence of chips. The transmitters 234, 236, 238 in FIG. 30 each employ two spreading codes, $C_0$, $C_1$, $D_0$, $D_1$, $E_0$ and $E_1$, respectively. Spreading codes subscripted with a zero are used to represent a "0" bit. Spreading codes subscripted with a one are used to represent a "1" bit. Each of the spreading codes are chosen so that they are pairwise orthogonal. Stated another way, the normalized inner product of any two spreading codes is zero:

$$(C_0 \cdot C_1)=(C_0 \cdot D_0)=(C_0 \cdot D_1)=(C_0 \cdot D_1)=(C_0 \cdot E_0)=0$$

$$(C_0 \cdot E1)=(C_1 \cdot D_0)=(C_1 \cdot D_1)=(C_1 \cdot E_0)=(C_1 \cdot E_1)=0$$

$$(D_0 \cdot D_1)=(D_0 \cdot E_0)=(D_0 \cdot E_1)=(D_1 \cdot E_0)=(D_1 \cdot E_1)=0$$

$$(E_0 \cdot E_1)=0$$

As can be seen from FIG. 30, if each of the transmitters simultaneously transmit a chip sequence representing a "1" bit, their transmissions combine according to the principles of superposition, meaning that the resultant combined transmission is equal to the sum of each of the chip sequences representing a "1" bit for each transmitter:

$$C_1+D_1+E_1$$

As can also be seen from FIG. 30, a CDMA receiver can be configured to receive the transmission emanating from a particular transmitter only. For example, in FIG. 30, receiver 240 is configured to receive transmissions exclusively from transmitter 234. Receiver 240 employs correlators 242, 244, which correlate the incoming signal against the spreading codes known to be used by transmitter 234. Correlator 242 produces an output of "0" when correlating against the combined transmission, indicating that a "0" bit was not detected as having been transmitted from transmitter 234:

$$\begin{aligned} C_0 \cdot [C_1 + D_1 + E_1] &= (C_0 \cdot C_1) + (C_0 \cdot D_1) + (C_0 \cdot E_1) \\ &= 0 + 0 + 0 \\ &= 0 \end{aligned}$$

Correlator 244 produces an output of "1" when correlating against the combined transmission, indicating that a "1" bit has been detected as having been transmitted from transmitter 234:

$$\begin{aligned} C_1 \cdot [C_1 + D_1 + E_1] &= (C_1 \cdot C_1) + (C_1 \cdot D_1) + (C_1 \cdot E_1) \\ &= 1 + 0 + 0 \\ &= 1 \end{aligned}$$

Note that the presence of signals D1 and E1 from transmitters 236 and 238 do not prevent receiver 240 from discerning the transmission from transmitter 234. This is because spreading codes serve to identify each transmitter. A method of manufacture may be employed, whereby each transmitter is assigned its own set of spreading codes, thereby uniquely identifying the transmitter. However, because the manufacturer is likely to run out of unique sets of spreading codes, these sets may be re-used out of necessity. Under a re-use scheme, a spreading code set would identify a particular transmission as having emanated from a smaller population of transmitters, but would not uniquely identify the particular transmitter.

A second method of manufacture may be employed, wherein a first set of spreading codes would be used to identify a first population of transmitters and a second set of spreading codes would be used to identify a second population of transmitters (and an $n^{th}$ set of spreading codes would be used to identify an $n^{th}$ population of transmitters). Each of the n sets of spreading codes is selected to utilize chip sequences not utilized by other spreading code sets. Further, each transmitter is coupled to an electrochemical sensor, to yield an analyte monitoring device. In order to uniquely identify each transmitter/analyte monitoring device, each transmitter may be programmed and/or configured to transmit a second identification signal. For example, a second identification signal could comprise: (1) an ID code; (2) a value representing the duration for which the associated sensor has been implanted; (3) a value representing the duration for which the associated sensor has been joined with the transmitter. In the latter two embodiments, the receiver is configured and arranged with circuitry that anticipates a value (a duration for which a sensor has been implanted, for example) from its associated transmitter as being within a certain tolerance. For example, assume a sensor that was paired with a receiver had been implanted three minutes earlier. The receiver can be programmed to exclude transmissions from transmitters using the correct set of spreading codes, by revealing that its associated sensor had been implanted for less than 2 minutes or more than 4 minutes.

By representing a "1" bit or a "0" bit as a longer sequence of chips, the spectral space consumed in transmission is increased. This effect is evident from the fact that the Nyquist rate of a chip sequence transmitted over a given period is higher than that for a bit sequence over the same period, because a greater number of ones and zeros must be transmitted when transmitting a chip sequence. For example, if 64 chips represent one bit, then 64 ones and zeros must be transmitted to represent a single bit, and the spectrum is spread by a factor of 64. The ratio of chips to bits is referred to as "processing gain." Generally, the higher the processing gain, the greater the number of transmitters that may discernibly transmit in a particular vicinity. The transmitters 234, 236, 238 employ a processing gain sufficient to permit at least two transmitters to discernibly transmit in the same region. More preferably, transmitters 234, 236, 238 employ a processing gain sufficient to permit at least four transmitters to discernibly transmit in the same region. More preferably yet, transmitters 234, 236, 238 employ a processing gain sufficient to permit at least eight transmitters to discernibly transmit in the same region. More preferably yet, transmitters 234, 236, 238 employ a processing gain sufficient to permit at least sixteen transmitters to discernibly transmit in the same region.

Figure 31:
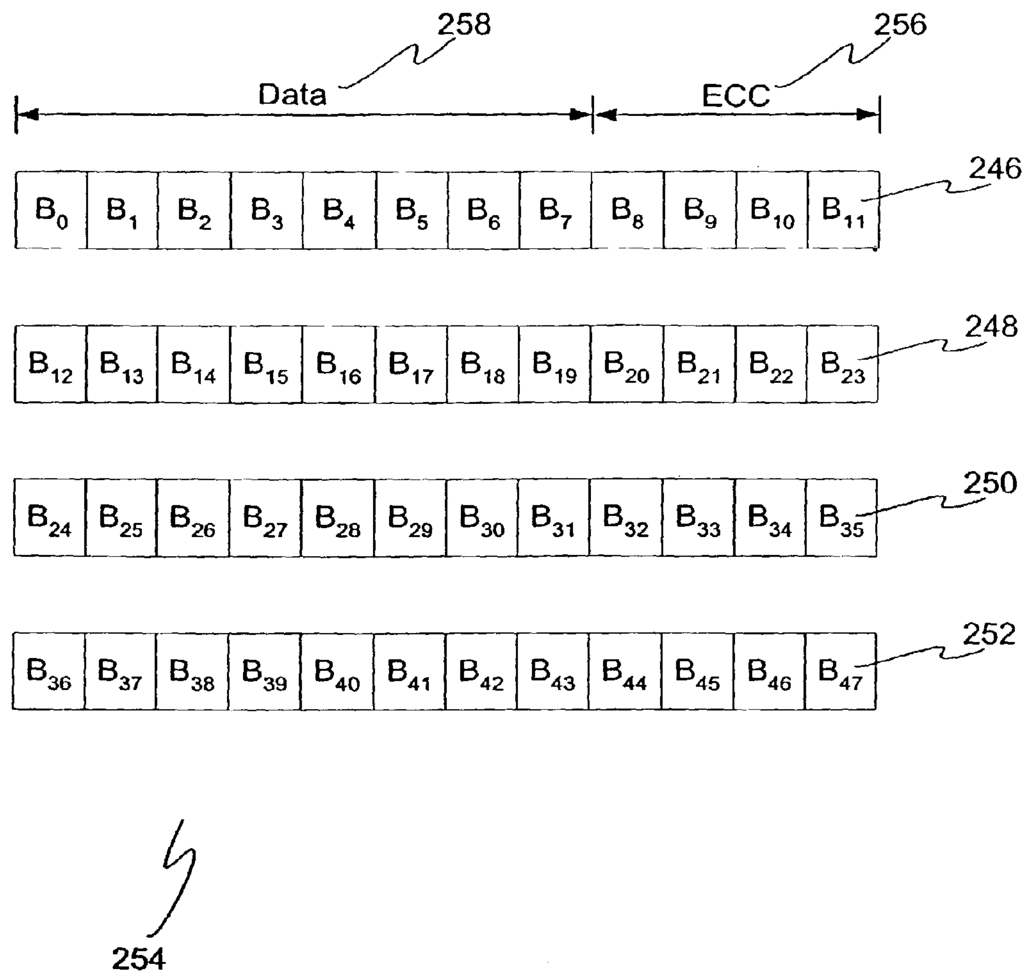
FIG. 31 depicts a data message that may be transmitted under an interleaved transmission scheme.

One possible difficulty that the transmitter 98 may encounter is the presence of interference in the broadcast medium. FIG. 31 illustrates the principle that transmitter 98 may be configured and arranged to transmit a data message in the form of a plurality of data words—the plurality of data words comprising a single data message—that are terminated by a series of error correction bits, which permit m-bit errors to be detected and n-bit errors to be corrected (the values of m and n being determined by the particular error correction scheme being employed). In FIG. 31, a data message 254 is depicted as being comprised of four data words 246, 248, 250, and 252. A data message 254 may be comprised of any number of data words 246, 248, 250, and 252, but is depicted as being comprised of four data words 246, 248, 250, and 252 for the illustrative purposes only. Each data word 246, 248, 250, and 252 is depicted as being comprised of 12 bits/chips $B_0$-$B_{47}$. Once again, although each data word 246, 248, 250, and 252 is depicted as being comprised of 12 bits/chips $B_0$-$B_{47}$, each data word 246, 248, 250, and 252 may be comprised of any number of bits/chips.

Data word 246 is depicted as being comprised of two separate fields 256, 258 of bits. The first eight bits 258 are depicted as being representative of data 258. Although the first eight bits 258 are depicted as being representative of data 258, any number of bits may represent data 258. The next four bits 256 are depicted as error correction bits 256. Although the next four bits 256 are depicted as error correction bits 256, any number of bits may represent error correction information 256. The error correction information 256 permits a receiver to detect errors of a given length, while correcting errors of a typically smaller size. The precise size of the error that may be detected or corrected depends upon the particular error correction scheme used. One example of a suitable error correction scheme is a Hamming code. For the sake of illustration, it will be assumed that the error correction information 256 is capable of correcting a two-bit error. For example, if two bits within data word 246 are corrupted, a receiver will be able to correct the data word to its original form, but a larger error would be uncorrectable.

For the sake of illustrating a potential vulnerability of this system, consider a word-by-word transmission sequence. Under such a transmission sequence, each data bit within a data word is transmitted sequentially, until the entire data word has been transmitted; the next word is then transmitted in the same sequential fashion (data is transmitted in the order $B_0$, $B_1$, $B_2$ . . . $B_{10}$, $B_{11}$, $B_{12}$ . . . ). One ramification of a word-by-word transmission sequence is that, assuming a transmission rate of x seconds per bit, an interference source persisting more than 2x seconds could result in an uncorrectable data error, because more than two bits within a data word could be corrupted. To ensure better resistance to this form of error, interleaving may be used.

Under a transmission sequence founded upon a principle of interleaving, transmitter 98 is configured and arranged to transmit the bits within a data word in a sequence other than sequential progression. For example, under one possible interleaved sequence, transmitter 98 is configured and arranged to: (1) assemble a plurality of data words into a data message, with at least one portion of one of the data words being derived from the analyte level of the body under monitor; and (2) transmit the first bit of each data word $B_0$, $B_{12}$, $B_{24}$ and $B_{36}$, followed by the second bit of each data word $B_1$, $B_{13}$, $B_{25}$ and $B_{37}$, proceeding in a similar bit-by-bit fashion until all four data words were transmitted. Thus, assuming a transmission rate of x seconds per bit, an interference source would have to persist for longer than 8x seconds (4 times as long as that required under a word-by-word transmission sequence) to possess the capacity to cause an uncorrectable error.

Figure 21:
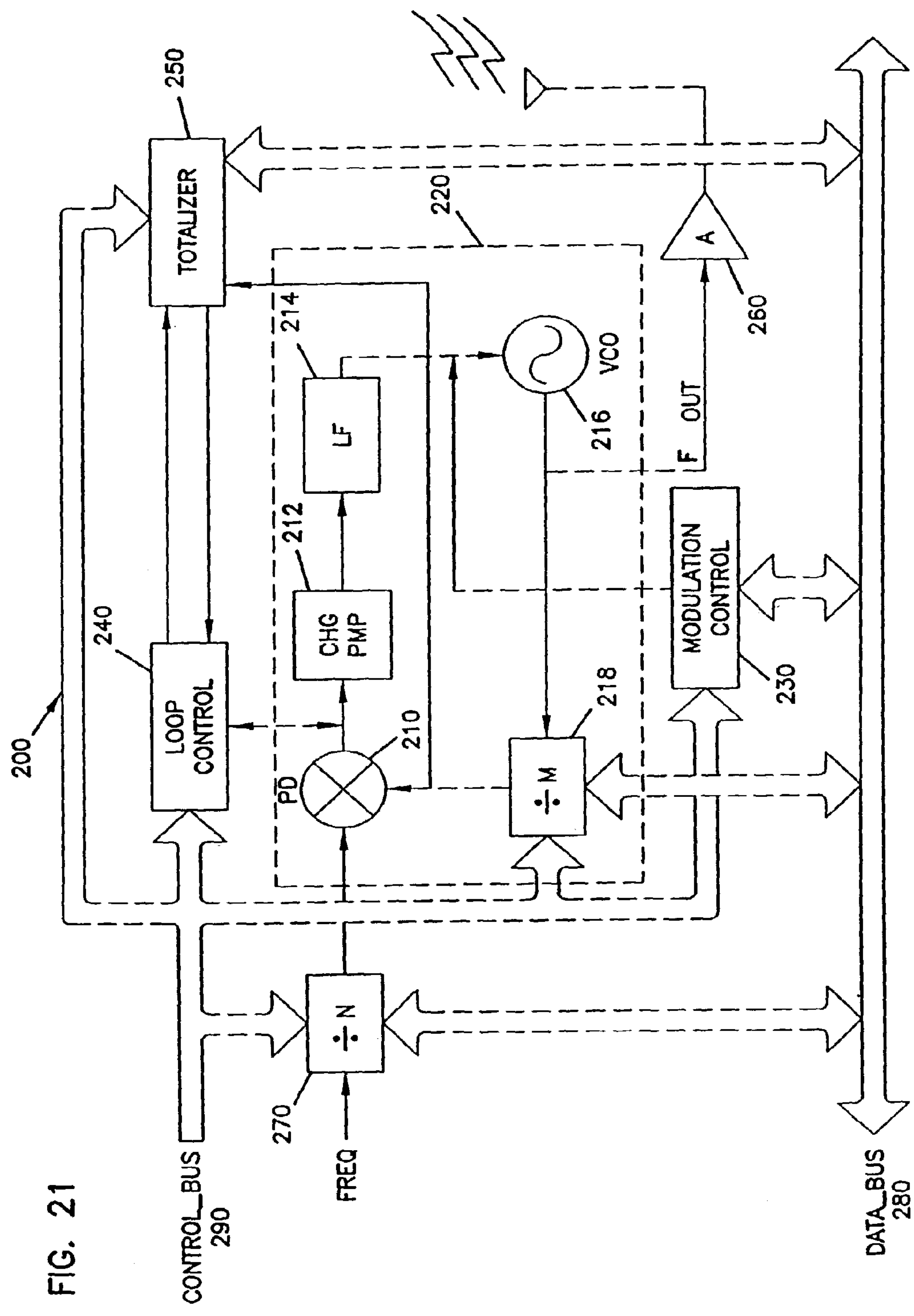
FIG. 21 is a block diagram of one embodiment of an open loop modulation system for use in an analyte monitoring device, according to the invention.

Another potential difficulty that may be experienced with the on-skin sensor control unit 44 is a change in the transmission frequency of the transmitter 98 over time. To overcome this potential difficulty, the transmitter may include optional circuitry that can return the frequency of the transmitter 98 to the desired frequency or frequency band. One example of suitable circuitry is illustrated in FIG. 21 as a block diagram of an open loop modulation system 200. The open loop modulation system 200 includes a phase detector (PD) 210, a charge pump (CHGPMP) 212, a loop filter (LF) 214, a voltage controlled oscillator (VCO) 216, and a divide by M circuit (÷M) 218 to form the phase-locked loop (PLL) 220.

The analyte monitoring device 40 uses an open loop modulation system 200 for RF communication between the transmitter 98 and a receiver of, for example, the one or more receiver/display units 46, 48. This open loop modulation system 200 is designed to provide a high reliability RF link between a transmitter and its associated receiver. The system employs frequency modulation (FM), and locks the carrier center frequency using a conventional phase-locked loop (PLL) 220. In operation, the phase-locked loop 220 is opened prior to the modulation. During the modulation the phase-locked loop 220 remains open for as long as the center frequency of the transmitter is within the receiver's bandwidth. When the transmitter detects that the center frequency is going to move outside of the receiver bandwidth, the receiver is signaled to stand by while the center frequency is captured. Subsequent to the capture, the transmission will resume. This cycle of capturing the center frequency, opening the phase-locked loop 220, modulation, and recapturing the center frequency will repeat for as many cycles as required.

The loop control 240 detects the lock condition of the phase-locked loop 220 and is responsible for closing and opening the phase-locked loop 220. The totalizer 250 in conjunction with the loop control 240, detects the status of the center frequency. The modulation control 230 is responsible for generating the modulating signal. A transmit amplifier 260 is provided to ensure adequate transmit signal power. The reference frequency is generated from a very stable signal source (not shown), and is divided down by N through the divide by N block (÷N) 270. Data and control signals are received by the open loop modulation system 200 via the DATA BUS 280, and the CONTROL BUS 290.

The operation of the open loop modulation system 200 begins with the phase-locked loop 220 in closed condition. When the lock condition is detected by the loop control 240, the phase-locked loop 220 is opened and the modulation control 230 begins generating the modulating signal. The totalizer 250 monitors the VCO frequency (divided by M), for programmed intervals. The monitored frequency is compared to a threshold programmed in the totalizer 250. This threshold corresponds to the 3 dB cut off frequencies of the receiver's intermediate frequency stage. When the monitored frequency approaches the thresholds, the loop control 240 is notified and a stand-by code is transmitted to the receiver and the phase-locked loop 220 is closed.

At this point the receiver is in the wait mode. The loop control 240 in the transmitter closes the phase-locked loop 220. Then, modulation control 230 is taken off line, the monitored value of the totalizer 250 is reset, and the phase-locked loop 220 is locked. When the loop control 240 detects a lock condition, the loop control 240 opens the phase-locked loop 220, the modulation control 230 is brought on line and the data transmission to the receiver will resume until the center frequency of the phase-locked loop 220 approaches the threshold values, at which point the cycle of transmitting the stand-by code begins. The ÷N 270 and ÷M 218 blocks set the frequency channel of the transmitter.

Accordingly, the open loop modulation system 200 provides a reliable low power FM data transmission for an analyte monitoring system. The open loop modulation system 200 provides a method of wide band frequency modulation, while the center frequency of the carrier is kept within receiver bandwidth. The effect of parasitic capacitors and inductors pulling the center frequency of the transmitter is corrected by the phase-locked loop 220. Further, the totalizer 250 and loop control 240 provide a new method of center frequency drift detection. Finally, the open loop modulation system 200 is easily implemented in CMOS process.

The rate at which the transmitter 98 transmits data may be the same rate at which the sensor circuit 97 obtains signals and/or the processing circuit 109 provides data or signals to the transmitter 98. Alternatively, the transmitter 98 may transmit data at a slower rate. In this case, the transmitter 98 may transmit more than one datapoint in each transmission. Alternatively, only one datapoint may be sent with each data transmission, the remaining data not being transmitted. Typically, data is transmitted to the receiver/display unit 46, 48 at least every hour, preferably, at least every fifteen minutes, more preferably, at least every five minutes, and most preferably, at least every one minute. However, other data transmission rates may be used. In some embodiments, the processing circuit 109 and/or transmitter 98 are configured to process and/or transmit data at a faster rate when a condition is indicated, for example, a low level or high level of analyte or impending low or high level of analyte. In these embodiments, the accelerated data transmission rate is typically at least every five minutes and preferably at least every minute.

In addition to a transmitter 98, an optional receiver 110 may be included in the on-skin sensor control unit 44. In some cases, the transmitter 98 is a transceiver, operating as both a transmitter and a receiver. The receiver 110 may be used to receive calibration data for the sensor 42. The calibration data may be used by the processing circuit 109 to correct signals from the sensor 42. This calibration data may be transmitted by the receiver/display unit 46, 48 or from some other source such as a control unit in a doctor's office. In addition, the optional receiver 110 may be used to receive a signal from the receiver/display units 46, 48, as described above, to direct the transmitter 98, for example, to change frequencies or frequency bands, to activate or deactivate the optional alarm system 94 (as described below), and/or to direct the transmitter 98 to transmit at a higher rate.

Calibration data may be obtained in a variety of ways. For instance, the calibration data may simply be factory-determined calibration measurements which can be input into the on-skin sensor control unit 44 using the receiver 110 or may alternatively be stored in a calibration data storage unit within the on-skin sensor control unit 44 itself (in which case a receiver 110 may not be needed). The calibration data storage unit may be, for example, a readable or readable/writeable memory circuit.

Alternative or additional calibration data may be provided based on tests performed by a doctor or some other professional or by the patient himself. For example, it is common for diabetic individuals to determine their own blood glucose concentration using commercially available testing kits. The results of this test is input into the on-skin sensor control unit 44 either directly, if an appropriate input device (e.g., a keypad, an optical signal receiver, or a port for connection to a keypad or computer) is incorporated in the on-skin sensor control unit 44, or indirectly by inputting the calibration data into the receiver/display unit 46, 48 and transmitting the calibration data to the on-skin sensor control unit 44.

Other methods of independently determining analyte levels may also be used to obtain calibration data. This type of calibration data may supplant or supplement factory-determined calibration values.

In some embodiments of the invention, calibration data may be required at periodic intervals, for example, every eight hours, once a day, or once a week, to confirm that accurate analyte levels are being reported. Calibration may also be required each time a new sensor 42 is implanted or if the sensor exceeds a threshold minimum or maximum value or if the rate of change in the sensor signal exceeds a threshold value. In some cases, it may be necessary to wait a period of time after the implantation of the sensor 42 before calibrating to allow the sensor 42 to achieve equilibrium. In some embodiments, the sensor 42 is calibrated only after it has been inserted. In other embodiments, no calibration of the sensor 42 is needed.

The on-skin sensor control unit 44 and/or receiver/display units 46, 48 may include an auditory or visual indicator that calibration data is needed, based, for example, on a predetermined periodic time interval between calibrations or on the implantation of a new sensor 42. The on-skin sensor control unit 44 and/or receiver/display units 46, 48 may also include an auditory or visual indicator to remind the patient that information, such as analyte levels, reported by the analyte monitoring device 40, may not be accurate because a calibration of the sensor 42 has not been performed within the predetermined periodic time interval and/or after implantation of a new sensor 42.

The processing circuit 109 of the on-skin sensor control unit 44 and/or an analyzer 152 of the receiver/display unit 46, 48 may determine when calibration data is needed and if the calibration data is acceptable. The on-skin sensor control unit 44 may optionally be configured to not allow calibration or to reject a calibration point if, for example, 1) a temperature reading from the temperature probe indicates a temperature that is not within a predetermined acceptable range (e.g., 30 to 42° C. or 32 to 40° C.) or that is changing rapidly (for example, 0.2° C./minute, 0.5° C./minute, or 0.7° C./minute or greater); 2) two or more working electrodes 58 provide uncalibrated signals that are not within a predetermined range (e.g., within 10% or 20%) of each other; 3) the rate of change of the uncalibrated signal is above a threshold rate (e.g., 0.25 mg/dL per minute or 0.5 mg/dL per minute or greater); 4) the uncalibrated signal exceeds a threshold maximum value (e.g., 5, 10, 20, or 40 nA) or is below a threshold minimum value (e.g., 0.05, 0.2, 0.5, or 1 nA); 5) the calibrated signal exceeds a threshold maximum value (e.g., a signal corresponding to an analyte concentration of 200 mg/dL, 250 mg/dL, or 300 mg/dL) or is below a threshold minimum value (e.g., a signal corresponding to an analyte concentration of 50 mg/dL, 65 mg/dL, or 80 mg/dL); and/or 6) an insufficient amount of time has elapsed since implantation (e.g., 10 minutes or less, 20 minutes or less, or 30 minutes or less).

The processing circuit 109 or an analyzer 152 may also request another calibration point if the values determined using the sensor data before and after the latest calibration disagree by more than a threshold amount, indicating that the calibration may be incorrect or that the sensor characteristics have changed radically between calibrations. This additional calibration point may indicate the source of the difference.

Referring back to FIG. 18A, the on-skin sensor control unit 44 may include an optional data storage unit 102 which may be used to hold data (e.g., measurements from the sensor or processed data) from the processing circuit 109 permanently or, more typically, temporarily. The data storage unit 102 may hold data so that the data can be used by the processing circuit 109 to analyze and/or predict trends in the analyte level, including, for example, the rate and/or acceleration of analyte level increase or decrease. The data storage unit 102 may also or alternatively be used to store data during periods in which a receiver/display unit 46, 48 is not within range. The data storage unit 102 may also be used to store data when the transmission rate of the data is slower than the acquisition rate of the data. For example, if the data acquisition rate is 10 points/min and the transmission is 2 transmissions/min, then one to five points of data could be sent in each transmission depending on the desired rate for processing datapoints. The data storage unit 102 typically includes a readable/writeable memory storage device and typically also includes the hardware and/or software to write to and/or read the memory storage device.

Referring back to FIG. 18A, the on-skin sensor control unit 44 may include an optional alarm system 104 that, based on the data from the processing circuit 109, warns the patient of a potentially detrimental condition of the analyte. For example, if glucose is the analyte, than the on-skin sensor control unit 44 may include an alarm system 94 that warns the patient of conditions such as hypoglycemia, hyperglycemia, impending hypoglycemia, and/or impending hyperglycemia. The alarm system 94 is triggered when the data from the processing circuit 109 reaches or exceeds a threshold value. Examples of threshold values for blood glucose levels are about 60, 70, or 80 mg/dL for hypoglycemia; about 70, 80, or 90 mg/dL for impending hypoglycemia; about 130, 150, 175, 200, 225, 250, or 275 mg/dL for impending hyperglycemia; and about 150, 175, 200, 225, 250, 275, or 300 mg/dL for hyperglycemia. The actual threshold values that are designed into the alarm system 94 may correspond to interstitial fluid glucose concentrations or electrode measurements (e.g., current values or voltage values obtained by conversion of current measurements) that correlate to the above-mentioned blood glucose levels. The analyte monitor device may be configured so that the threshold levels for these or any other conditions may be programmable by the patient and/or a medical professional.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the patient has entered a hyperglycemic state. As another example, a datapoint which correlates to a glucose level of 65 mg/dL exceeds a threshold value for hypoglycemia of 70 mg/dL because the datapoint indicates that the patient is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor 42. For glucose, the physiologically relevant measurement range is typically about 50 to 250 mg/dL, preferably about 40-300 mg/dL and ideally 30-400 mg/dL, of glucose in the interstitial fluid.

The alarm system 94 may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

The optional alarm system 94 may be configured to activate when a single data point meets or exceeds a particular threshold value. Alternatively, the alarm may be activated only when a predetermined number of datapoints spanning a predetermined amount of time meet or exceed the threshold value. As another alternative, the alarm may be activated only when the datapoints spanning a predetermined amount of time have an average value which meets or exceeds the threshold value. Each condition that can trigger an alarm may have a different alarm activation condition. In addition, the alarm activation condition may change depending on current conditions (e.g., an indication of impending hyperglycemia may alter the number of datapoints or the amount of time that is tested to determine hyperglycemia).

The alarm system 94 may contain one or more individual alarms. Each of the alarms may be individually activated to indicate one or more conditions of the analyte. The alarms may be, for example, auditory or visual. Other sensory-stimulating alarm systems may be used including alarm systems which heat, cool, vibrate, or produce a mild electrical shock when activated. In some embodiments, the alarms are auditory with a different tone, note, or volume indicating different conditions. For example, a high note might indicate hyperglycemia and a low note might indicate hypoglycemia. Visual alarms may use a difference in color, brightness, or position on the on-skin sensor control device 44 to indicate different conditions. In some embodiments, an auditory alarm system is configured so that the volume of the alarm increases over time until the alarm is deactivated.

In some embodiments, the alarm may be automatically deactivated after a predetermined time period. In other embodiments, the alarm may be configured to deactivate when the data no longer indicate that the condition which triggered the alarm exists. In these embodiments, the alarm may be deactivated when a single data point indicates that the condition no longer exists or, alternatively, the alarm may be deactivated only after a predetermined number of datapoints or an average of datapoints obtained over a given period of time indicate that the condition no longer exists.

In some embodiments, the alarm may be deactivated manually by the patient or another person in addition to or as an alternative to automatic deactivation. In these embodiments, a deactivation switch 111 is provided which when activated turns off the alarm. The switch 111 may be operatively engaged (or disengaged depending on the configuration of the switch) by, for example, operating an actuator on the on-skin sensor control unit 44 or the receiver/display unit 46, 48. In some cases, an actuator may be provided on two or more units 44, 46, 48, any of which may be actuated to deactivate the alarm. If the switch 111 and or actuator is provided on the receiver/display unit 46, 48 then a signal may be transmitted from the receiver/display unit 46, 48 to the receiver 110 on the on-skin sensor control unit 44 to deactivate the alarm.

A variety of switches 111 may be used including, for example, a mechanical switch, a reed switch, a Hall effect switch, a Gigantic Magnetic Ratio (GMR) switch (the resistance of the GMR switch is magnetic field dependent) and the like. Preferably, the actuator used to operatively engage (or disengage) the switch is placed on the on-skin sensor control unit 44 and configured so that no water can flow around the button and into the housing. One example of such a button is a flexible conducting strip that is completely covered by a flexible polymeric or plastic coating integral to the housing. In an open position the flexible conducting strip is bowed and bulges away from the housing. When depressed by the patient or another person, the flexible conducting strip is pushed directly toward a metal contact and completes the circuit to shut off the alarm.

For a reed or GMR switch, a piece of magnetic material, such as a permanent magnet or an electromagnet, in a flexible actuator that is bowed or bulges away from the housing 45 and the reed or GMR switch is used. The reed or GMR switch is activated (to deactivate the alarm) by depressing the flexible actuator bringing the magnetic material closer to the switch and causing an increase in the magnetic field within the switch.

In some embodiments of the invention, the analyte monitoring device 40 includes only an on-skin control unit 44 and a sensor 42. In these embodiments, the processing circuit 109 of the on-skin sensor control unit 44 is able to determine a level of the analyte and activate an alarm system 94 if the analyte level exceeds a threshold. The on-skin control unit 44, in these embodiments, has an alarm system 94 and may also include a display, such as those discussed below with respect to the receiver/display units 46, 48. Preferably, the display is an LCD or LED display. The on-skin control unit 44 may not have a transmitter, unless, for example, it is desirable to transmit data, for example, to a control unit in a doctor's office.

The on-skin sensor control unit 44 may also include a reference voltage generator 101 to provide an absolute voltage or current for use in comparison to voltages or currents obtained from or used with the sensor 42. An example of a suitable reference voltage generator is a band-gap reference voltage generator that uses, for example, a semiconductor material with a known band-gap. Preferably, the band-gap is temperature insensitive over the range of temperatures that the semiconductor material will experience during operation. Suitable semiconductor materials includes gallium, silicon and silicates.

A bias current generator 105 may be provided to correctly bias solid-state electronic components. An oscillator 107 may be provided to produce a clock signal that is typically used with digital circuitry.

The on-skin sensor control unit 44 may also include a watchdog circuit 103 that tests the circuitry, particularly, any digital circuitry in the control unit 44 to determine if the circuitry is operating correctly. Non-limiting examples of watchdog circuit operations include: a) generation of a random number by the watchdog circuit, storage of the number in a memory location, writing the number to a register in the watchdog circuit, and recall of the number to compare for equality; b) checking the output of an analog circuit to determine if the output exceeds a predetermined dynamic range; c) checking the output of a timing circuit for a signal at an expected pulse interval. Other examples of functions of a watchdog circuit are known in the art. If the watchdog circuit detects an error that watchdog circuit may activate an alarm and/or shut down the device.

Receiver/Display Unit

One or more receiver/display units 46, 48 may be provided with the analyte monitoring device 40 for easy access to the data generated by the sensor 42 and may, in some embodiments, process the signals from the on-skin sensor control unit 44 to determine the concentration or level of analyte in the subcutaneous tissue. Small receiver/display units 46 may be carried by the patient. These units 46 may be palm-sized and/or may be adapted to fit on a belt or within a bag or purse that the patient carries. One embodiment of the small receiver/display unit 46 has the appearance of a pager, for example, so that the user is not identified as a person using a medical device. Such receiver/display units may optionally have one-way or two-way paging capabilities.

Large receiver/display units 48 may also be used. These larger units 48 may be designed to sit on a shelf or nightstand. The large receiver/display unit 48 may be used by parents to monitor their children while they sleep or to awaken patients during the night. In addition, the large receiver/display unit 48 may include a lamp, clock, or radio for convenience and/or for activation as an alarm. One or both types of receiver/display units 46, 48 may be used.

Figure 22:
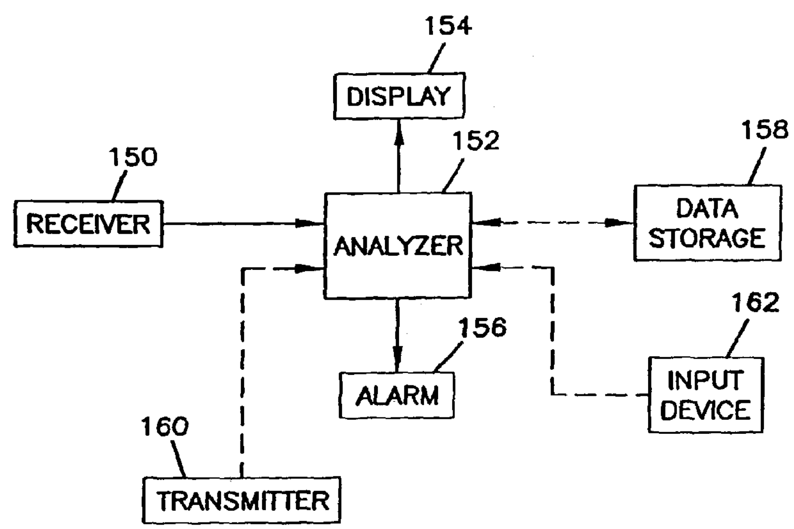
FIG. 22 is a block diagram of one embodiment of a receiver/display unit, according to the invention.

The receiver/display units 46, 48, as illustrated in block form at FIG. 22, typically include a receiver 150 to receive data from the on-skin sensor control unit 44, an analyzer 152 to evaluate the data, a display 154 to provide information to the patient, and an alarm system 156 to warn the patient when a condition arises. The receiver/display units 46, 48 may also optionally include a data storage device 158, a transmitter 160, and/or an input device 162. The receiver/display units 46,48 may also include other components (not shown), such as a power supply (e.g., a battery and/or a power supply that can receive power from a wall outlet), a watchdog circuit, a bias current generator, and an oscillator. These additional components are similar to those described above for the on-skin sensor control unit 44.

In one embodiment, a receiver/display unit 48 is a bedside unit for use by a patient at home. The bedside unit includes a receiver and one or more optional items, including, for example, a clock, a lamp, an auditory alarm, a telephone connection, and a radio. The bedside unit also has a display, preferably, with large numbers and/or letters that can be read across a room. The unit may be operable by plugging into an outlet and may optionally have a battery as backup. Typically, the bedside unit has a better antenna than a small palm-size unit, so the bedside unit's reception range is longer.

When an alarm is indicated, the bedside unit may activate, for example, the auditory alarm, the radio, the lamp, and/or initiate a telephone call. The alarm may be more intense than the alarm of a small palm-size unit to, for example, awaken or stimulate a patient who may be asleep, lethargic, or confused. Moreover, a loud alarm may alert a parent monitoring a diabetic child at night.

The bedside unit may have its own data analyzer and data storage. The data may be communicated from the on-skin sensor unit or another receiver/display unit, such as a palm-size or small receiver/display unit. Thus, at least one unit has all the relevant data so that the data can be downloaded and analyzed without significant gaps.

Optionally, the beside unit has an interface or cradle into which a small receiver/display unit may be placed. The bedside unit may be capable of utilizing the data storage and analysis capabilities of the small receiver/display unit and/or receive data from the small receiver/display unit in this position. The bedside unit may also be capable of recharging a battery of the small receiver/display unit.

The receiver 150 typically is formed using known receiver and antenna circuitry and is often tuned or tunable to the frequency or frequency band of the transmitter 98 in the on-skin sensor control unit 44. Typically, the receiver 150 is capable of receiving signals from a distance greater than the transmitting distance of the transmitter 98. The small receiver/display unit 46 can typically receive a signal from an on-skin sensor control unit 44 that is up to 2 meters, preferably up to 5 meters, and more preferably up to 10 meters or more, away. A large receiver/display unit 48, such as a bedside unit, can typically receive a receive a signal from an on-skin sensor control unit 44 that is up to 5 meters distant, preferably up to 10 meters distant, and more preferably up to 20 meters distant or more.

In one embodiment, a repeater unit (not shown) is used to boost a signal from an on-skin sensor control unit 44 so that the signal can be received by a receiver/display unit 46, 48 that may be distant from the on-skin sensor control unit 44. The repeater unit is typically independent of the on-skin sensor control unit 44, but, in some cases, the repeater unit may be configured to attach to the on-skin sensor control unit 44. Typically, the repeater unit includes a receiver for receiving the signals from the on-skin sensor control unit 44 and a transmitter for transmitting the received signals. Often the transmitter of the repeater unit is more powerful than the transmitter of the on-skin sensor control unit, although this is not necessary. The repeater unit may be used, for example, in a child's bedroom for transmitting a signal from an on-skin sensor control unit on the child to a receiver/display unit in the parent's bedroom for monitoring the child's analyte levels. Another exemplary use is in a hospital with a display/receiver unit at a nurse's station for monitoring on-skin sensor control unit(s) of patients.

The presence of other devices, including other on-skin sensor control units, may create noise or interference within the frequency band of the transmitter 98. This may result in the generation of false data. To overcome this potential difficulty, the transmitter 98 may also transmit a code to indicate, for example, the beginning of a transmission and/or to identify, preferably using a unique identification code, the particular on-skin sensor control unit 44 in the event that there is more than one on-skin sensor control unit 44 or other transmission source within range of the receiver/display unit 46, 48. The provision of an identification code with the data may reduce the likelihood that the receiver/display unit 46, 48 intercepts and interprets signals from other transmission sources, as well as preventing "crosstalk" with different on-skin sensor control units 44. The identification code may be provided as a factory-set code stored in the sensor control unit 44. Alternatively, the identification code may be randomly generated by an appropriate circuit in the sensor control unit 44 or the receiver/display unit 46, 48 (and transmitted to the sensor control unit 44) or the identification code may be selected by the patient and communicated to the sensor control unit 44 via a transmitter or an input device coupled to the sensor control unit 44.

Other methods may be used to eliminate "crosstalk" and to identify signals from the appropriate on-skin sensor control unit 44. In some embodiments, the transmitter 98 may use encryption techniques to encrypt the datastream from the transmitter 98. The receiver/display unit 46, 48 contains the key to decipher the encrypted data signal. The receiver/display unit 46, 48 then determines when false signals or "crosstalk" signals are received by evaluation of the signal after it has been deciphered. For example, the analyzer 152 in the one or more receiver/display units 46, 48 compares the data, such as current measurements or analyte levels, with expected measurements (e.g., an expected range of measurements corresponding to physiologically relevant analyte levels). Alternatively, an analyzer in the receiver/display units 46, 48 searches for an identification code in the decrypted data signal.

Another method to eliminate "crosstalk", which is typically used in conjunction with the identification code or encryption scheme, includes providing an optional mechanism in the on-skin sensor control unit 44 for changing transmission frequency or frequency bands upon determination that there is "crosstalk". This mechanism for changing the transmission frequency or frequency band may be initiated by the receiver/display unit automatically, upon detection of the possibility of cross-talk or interference, and/or by a patient manually. For automatic initiation, the receiver/display unit 46, 48 transmits a signal to the optional receiver 110 on the on-skin sensor control unit 44 to direct the transmitter 98 of the on-skin sensor control unit 44 to change frequency or frequency band.

Manual initiation of the change in frequency or frequency band may be accomplished using, for example, an actuator (not shown) on the receiver/display unit 46, 48 and/or on the on-skin sensor control unit 44 which a patient operates to direct the transmitter 98 to change frequency or frequency band. The operation of a manually initiated change in transmission frequency or frequency band may include prompting the patient to initiate the change in frequency or frequency band by an audio or visual signal from the receiver/display unit 46, 48 and/or on-skin sensor control unit 44.

As discussed in greater detail with reference to FIG. 30, each receiver 150 can reduce "crosstalk" by employing CDMA techniques in concert with a transmitter 98. A receiver 150 can correlate against a set of spreading codes known to be used by a particular transmitter 98, thereby eliminating crosstalk emanating from transmitters not employing that set of spreading codes. The ability of a particular transmitter 98/receiver 150 pair to reject crosstalk is dependent, in part, upon the processing gain. Generally, the higher the processing gain, the better the ability of the pair to reject crosstalk. In one embodiment, a receiver 150 employs a processing gain sufficient to permit at least two transmitters to discernibly transmit in the same region. In another embodiment, a receiver 150 can employ a processing gain sufficient to permit at least four transmitters to discernibly transmit in the same region. In yet another embodiment, a receiver can employ a processing gain sufficient to permit at least eight transmitters to discernibly transmit in the same region. In still another embodiment, a receiver can employ a processing gain sufficient to permit at least sixteen transmitters to discernibly transmit in the same region.

Returning to the receiver 150, the data received by the receiver 150 is then sent to an analyzer 152. The analyzer 152 may have a variety of functions, similar to the processor circuit 109 of the on-skin sensor control unit 44, including 1) modifying the signals from the sensor 42 using calibration data and/or measurements from the temperature probe 66, 2) determining a level of an analyte in the interstitial fluid, 3) determining a level of an analyte in the bloodstream based on the sensor measurements in the interstitial fluid, 4) determining if the level, rate of change, and/or acceleration in the rate of change of the analyte exceeds or meets one or more threshold values, 5) activating an alarm system 156 and/or 94 if a threshold value is met or exceeded, 6) evaluating trends in the level of an analyte based on a series of sensor signals, 7) determine a dose of a medication, and 8) reduce noise or error contributions (e.g., through signal averaging or comparing readings from multiple electrodes). The analyzer 152 may be simple and perform only one or a small number of these functions or the analyzer 152 may perform all or most of these functions.

Analyzer 152 can perform computations related to adjusting a detected analyte level to correct for the influence of temperature. As discussed with reference to FIG. 29, analyzer 152 can be designed to adjust a known sensor current-analyte level profile to be either more or less steep based upon a relationship of +/−6% slope for each +/−1° C. change in temperature. If a different temperature dependency is determined to exist, the analyzer 152 can be designed, programmed, or arranged to adjust the profile to mimic the determined dependency. The analyzer 152 may take the form of a microprocessor, digital logic or an ASIC, amongst other forms known to those skilled in the art.

Figure 23:
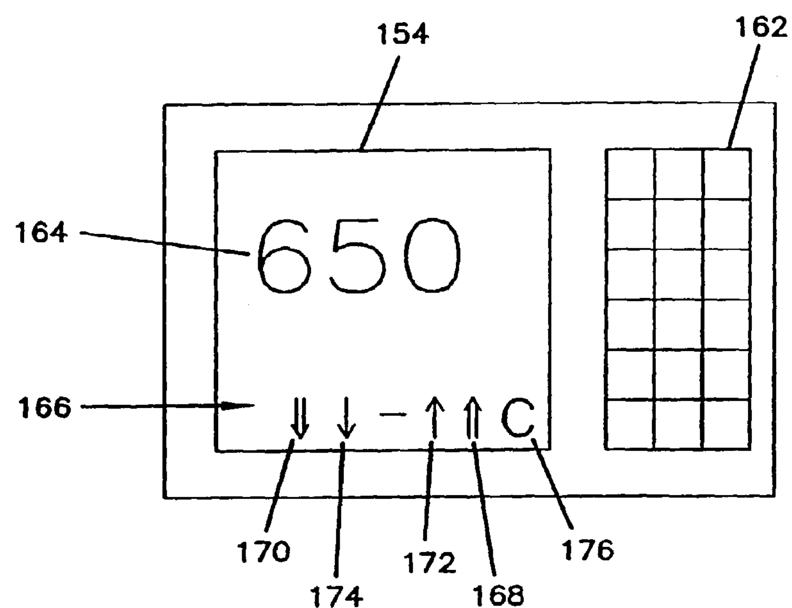
FIG. 23 is a front view of one embodiment of a receiver/display unit.

The output from the analyzer 152 is typically provided to a display 154. A variety of displays 154 may be used including cathode ray tube displays (particularly for larger units), LED displays, or LCD displays. The display 154 may be monochromatic (e.g., black and white) or polychromatic (i.e., having a range of colors). The display 154 may contain symbols or other indicators that are activated under certain conditions (e.g., a particular symbol may become visible on the display when a condition, such as hyperglycemia, is indicated by signals from the sensor 42). The display 154 may also contain more complex structures, such as LCD or LED alphanumeric structures, portions of which can be activated to produce a letter, number, or symbol. For example, the display 154 may include region 164 to display numerically the level of the analyte, as illustrated in FIG. 23. In one embodiment, the display 154 also provides a message to the patient to direct the patient in an action. Such messages may include, for example, “Eat Sugar”, if the patient is hypoglycemic, or “Take Insulin”, if the patient is hyperglycemic.

One example of a receiver/display unit 46, 48 is illustrated in FIG. 23. The display 154 of this particular receiver/display unit 46, 48 includes a portion 164 which displays the level of the analyte, for example, the blood glucose concentration, as determined by the processing circuit 109 and/or the analyzer 152 using signals from the sensor 42. The display also includes various indicators 166 which may be activated under certain conditions. For example, the indicator 168 of a glucose monitoring device may be activated if the patient is hyperglycemic. Other indicators may be activated in the cases of hypoglycemia (170), impending hyperglycemia (172), impending hypoglycemia (174), a malfunction, an error condition, or when a calibration sample is needed (176). In some embodiments, color coded indicators may be used. Alternatively, the portion 164 which displays the blood glucose concentration may also include a composite indicator 180 (see FIG. 24), portions of which may be appropriately activated to indicate any of the conditions described above.

Figure 24:
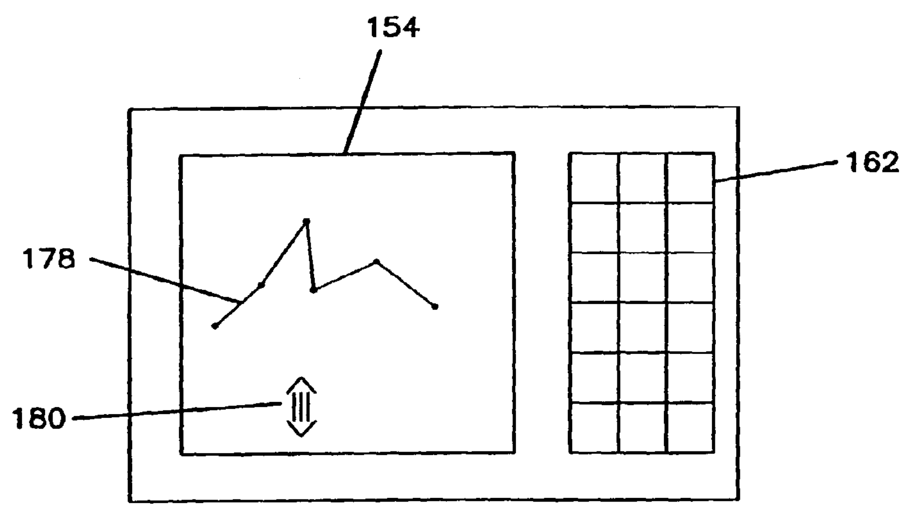
FIG. 24 is a front view of a second embodiment of a receiver/display unit.

The display 154 may also be capable of displaying a graph 178 of the analyte level over a period of time, as illustrated in FIG. 24. Examples of other graphs that may be useful include graphs of the rate of change or acceleration in the rate of change of the analyte level over time. In some embodiments, the receiver/display unit is configured so that the patient may choose the particular display (e.g., blood glucose concentration or graph of concentration versus time) that the patient wishes to view. The patient may choose the desired display mode by pushing a button or the like, for example, on an optional input device 162.

The receiver/display units 46, 48 also typically include an alarm system 156. The options for configuration of the alarm system 156 are similar to those for the alarm system 94 of the on-skin sensor control unit 44. For example, if glucose is the analyte, than the on-skin sensor control unit 44 may include an alarm system 156 that warns the patient of conditions such as hypoglycemia, hyperglycemia, impending hypoglycemia, and/or impending hyperglycemia. The alarm system 156 is triggered when the data from the analyzer 152 reaches or exceeds a threshold value. The threshold values may correspond to interstitial fluid glucose concentrations or sensor signals (e.g., current or converted voltage values) which correlate to the above-mentioned blood glucose levels.

The alarm system 156 may also, or alternatively, be activated when the rate or acceleration of an increase or decrease in analyte level reaches or exceeds a threshold value. For example, in the case of a subcutaneous glucose monitor, the alarm system 156 might be activated if the rate of change in glucose concentration exceeds a threshold value which might indicate that a hyperglycemic or hypoglycemic condition is likely to occur.

The alarm system 156 may be configured to activate when a single data point meets or exceeds a particular threshold value. Alternatively, the alarm may be activated only when a predetermined number of datapoints spanning a predetermined amount of time meet or exceed the threshold value. As another alternative, the alarm may be activated only when the datapoints spanning a predetermined amount of time have an average value which meets or exceeds the threshold value. Each condition that can trigger an alarm may have a different alarm activation condition. In addition, the alarm activation condition may change depending on current conditions (e.g., an indication of impending hyperglycemia may alter the number of datapoints or the amount of time that is tested to determine hyperglycemia).

The alarm system 156 may contain one or more individual alarms. Each of the alarms may be individually activated to indicate one or more conditions of the analyte. The alarms may be, for example, auditory or visual. Other sensory-stimulating alarm systems by be used including alarm systems 156 that direct the on-skin sensor control unit 44 to heat, cool, vibrate, or produce a mild electrical shock. In some embodiments, the alarms are auditory with a different tone, note, or volume indicating different conditions. For example, a high note might indicate hyperglycemia and a low note might indicate hypoglycemia. Visual alarms may also use a difference in color or brightness to indicate different conditions. In some embodiments, an auditory alarm system might be configured so that the volume of the alarm increases over time until the alarm is deactivated.

In some embodiments, the alarms may be automatically deactivated after a predetermined time period. In other embodiments, the alarms may be configured to deactivate when the data no longer indicate that the condition which triggered the alarm exists. In these embodiments, the alarms may be deactivated when a single data point indicates that the condition no longer exists or, alternatively, the alarm may be deactivated only after a predetermined number of datapoints or an average of datapoints obtained over a given period of time indicate that the condition no longer exists.

In yet other embodiments, the alarm may be deactivated manually by the patient or another person in addition to or as an alternative to automatic deactivation. In these embodiments, a switch is provided which when activated turns off the alarm. The switch may be operatively engaged (or disengaged depending on the configuration of the switch) by, for example, pushing a button on the receiver/display unit 46, 48. One configuration of the alarm system 156 has automatic deactivation after a period of time for alarms that indicate an impending condition (e.g., impending hypoglycemia or hyperglycemia) and manual deactivation of alarms which indicate a current condition (e.g., hypoglycemia or hyperglycemia).

The receiver/display units 46, 48 may also include a number of optional items. One item is a data storage unit 158. The data storage unit 158 may be desirable to store data for use if the analyzer 152 is configured to determine trends in the analyte level. The data storage unit 158 may also be useful to store data that may be downloaded to another receiver/display unit, such as a large display unit 48. Alternatively, the data may be downloaded to a computer or other data storage device in a patient’s home, at a doctor’s office, etc. for evaluation of trends in analyte levels. A port (not shown) may be provided on the receiver/display unit 46, 48 through which the stored data may be transferred or the data may be transferred using an optional transmitter 160. The data storage unit 158 may also be activated to store data when a directed by the patient via, for example, the optional input device 162. The data storage unit 158 may also be configured to store data upon occurrence of a particular event, such as a hyperglycemic or hypoglycemic episode, exercise, eating, etc. The storage unit 158 may also store event markers with the data of the particular event. These event markers may be generated either automatically by the display/receiver unit 46, 48 or through input by the patient.

The receiver/display unit 46, 48 may also include an optional transmitter 160 which can be used to transmit 1) calibration information, 2) a signal to direct the transmitter 98 of the on-skin sensor control unit 44 to change transmission frequency or frequency bands, and/or 3) a signal to activate an alarm system 94 on the on-skin sensor control unit 44, all of which are described above. The transmitter 160 typically operates in a different frequency band than the transmitter 98 of the on-skin sensor control unit 44 to avoid cross-talk between the transmitters 98, 160. Methods may be used to reduce cross-talk and the reception of false signals, as described above in connection with the transmitter 98 of the on-skin sensor control unit 44. In some embodiments, the transmitter 160 is only used to transmit signals to the sensor control unit 44 and has a range of less than one foot, and preferably less than six inches. This then requires the patient or another person to hold the receiver/display unit 46 near the sensor control unit 44 during transmission of data, for example, during the transmission of calibration information. Transmissions may also be performed using methods other than RF transmission, including optical or wire transmission.

In addition, in some embodiments of the invention, the transmitter 160 may be configured to transmit data to another receiver/display unit 46, 48 or some other receiver. For example, a small receiver/display unit 46 may transmit data to a large receiver/display unit 48, as illustrated in FIG. 1. As another example, a receiver/display unit 46, 48 may transmit data to a computer in the patient's home or at a doctor's office. Moreover, the transmitter 160, or a separate transmitter, may direct a transmission to another unit, or to a telephone or other communications device that alerts a doctor, or other individual, when an alarm is activated and/or if, after a predetermined time period, an activated alarm has not been deactivated, suggesting that the patient may require assistance. In some embodiments, the receiver/display unit is capable of one-way or two-way paging and/or is coupled to a telephone line to send and/or receive messages from another, such as a health professional monitoring the patient.

Another optional component for the receiver/display unit 46, 48 is an input device 162, such as a keypad or keyboard. The input device 162 may allow numeric or alphanumeric input. The input device 162 may also include buttons, keys, or the like which initiate functions of and/or provide input to the analyte monitoring device 40. Such functions may include initiating a data transfer, manually changing the transmission frequency or frequency band of the transmitter 98, deactivating an alarm system 94, 156, inputting calibration data, and/or indicating events to activate storage of data representative of the event.

Another embodiment of the input device 162 is a touch screen display. The touch screen display may be incorporated into the display 154 or may be a separate display. The touch screen display is activated when the patient touches the screen at a position indicated by a "soft button" which corresponds to a desired function. Touch screen displays are well known.

In addition, the analyte monitoring device 40 may include password protection to prevent the unauthorized transmission of data to a terminal or the unauthorized changing of settings for the device 40. A patient may be prompted by the display 154 to input the password using the input device 162 whenever a password-protected function is initiated.

Another function that may be activated by the input device 162 is a deactivation mode. The deactivation mode may indicate that the receiver/display unit 46, 48 should no longer display a portion or all of the data. In some embodiments, activation of the deactivation mode may even deactivate the alarm systems 94, 156. Preferably, the patient is prompted to confirm this particular action. During the deactivation mode, the processing circuit 109 and/or analyzer 152 may stop processing data or they may continue to process data and not report it for display and may optionally store the data for later retrieval.

Alternatively, a sleep mode may be entered if the input device 162 has not been activated for a predetermined period of time. This period of time may be adjustable by the patient or another individual. In this sleep mode, the processing circuit 109 and/or analyzer 152 typically continue to obtain measurements and process data, however, the display is not activated. The sleep mode may be deactivated by actions, such as activating the input device 162. The current analyte reading or other desired information may then be displayed.

In one embodiment, a receiver/display unit 46 initiates an audible or visual alarm when the unit 46 has not received a transmission from the on-skin sensor control unit within a predetermined amount of time. The alarm typically continues until the patient responds and/or a transmission is received. This can, for example, remind a patient if the receiver/display unit 46 is inadvertently left behind.

In another embodiment, the receiver/display unit 46, 48 is integrated with a calibration unit (not shown). For example, the receiver/display unit 46, 48 may, for example, include a conventional blood glucose monitor. Another useful calibration device utilizing electrochemical detection of analyte concentration is described in U.S. patent application Ser. No. 08/795,767, incorporated herein by reference. Other devices may be used including those that operate using, for example, electrochemical and colorimetric blood glucose assays, assays of interstitial or dermal fluid, and/or non-invasive optical assays. When a calibration of the implanted sensor is needed, the patient uses the integrated in vitro monitor to generate a reading. The reading may then, for example, automatically be sent by the transmitter 160 of the receiver/display unit 46, 48 to calibrate the sensor 42.

Integration with a Drug Administration System

Figure 25:
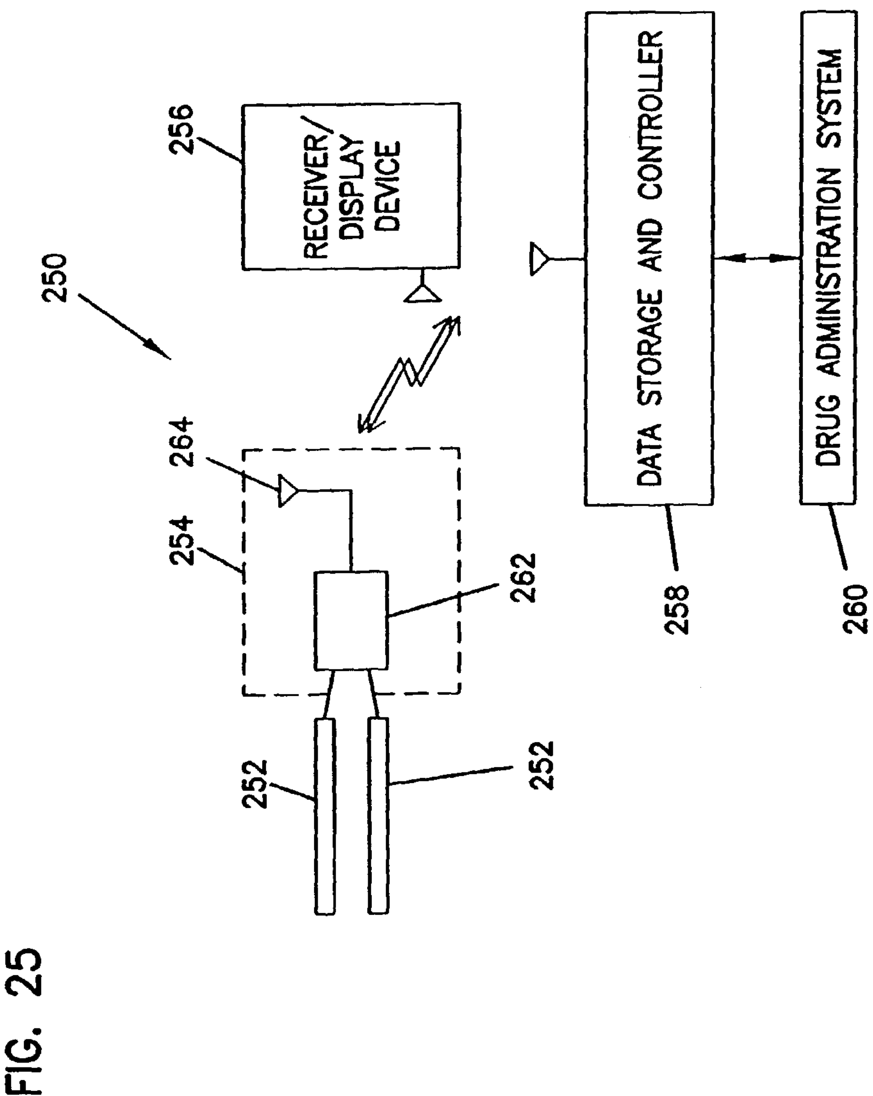
FIG. 25 is a block diagram of one embodiment of a drug delivery system, according to the invention.

FIG. 25 illustrates a block diagram of a sensor-based drug delivery system 250 according to the present invention. The system may provide a drug to counteract the high or low level of the analyte in response to the signals from one or more sensors 252. Alternatively, the system monitors the drug concentration to ensure that the drug remains within a desired therapeutic range. The drug delivery system includes one or more (and preferably two or more) subcutaneously implanted sensors 252, an on-skin sensor control unit 254, a receiver/display unit 256, a data storage and controller module 258, and a drug administration system 260. In some cases, the receiver/display unit 256, data storage and controller module 258, and drug administration system 260 may be integrated in a single unit. The sensor-based drug delivery system 250 uses data from the one or more sensors 252 to provide necessary input for a control algorithm/mechanism in the data storage and controller module 258 to adjust the administration of drugs. As an example; a glucose sensor could be used to control and adjust the administration of insulin.

In FIG. 25, sensor 252 produces signals correlated to the level of the drug or analyte in the patient. The level of the analyte will depend on the amount of drug delivered by the drug administration system. A processor 262 in the on-skin sensor control unit 254, as illustrated in FIG. 25, or in the receiver/display unit 256 determines the level of the analyte, and possibly other information, such as the rate or acceleration of the rate in the increase or decrease in analyte level. This information is then transmitted to the data storage and controller module 258 using a transmitter 264 in the on-skin sensor control unit 254, as illustrated in FIG. 25, or a non-integrated receiver/display unit 256.

If the drug delivery system 250 has two or more sensors 252, the data storage and controller module 258 may verify that the data from the two or more sensors 252 agrees within predetermined parameters before accepting the data as valid. This data may then be processed by the data storage and controller module 258, optionally with previously obtained data, to determine a drug administration protocol. The drug administration protocol is then executed using the drug administration system 260, which may be an internal or external infusion pump, syringe injector, transdermal delivery system (e.g., a patch containing the drug placed on the skin), or inhalation system. Alternatively, the drug storage and controller module 258 may provide a the drug administration protocol so that the patient or another person may provide the drug to the patient according to the profile.

In one embodiment of the invention, the data storage and controller module 258 is trainable. For example, the data storage and controller module 258 may store glucose readings over a predetermined period of time, e.g., several weeks. When an episode of hypoglycemia or hyperglycemia is encountered, the relevant history leading to such event may be analyzed to determine any patterns which might improve the system's ability to predict future episodes. Subsequent data might be compared to the known patterns to predict hypoglycemia or hyperglycemia and deliver the drug accordingly. In another embodiment, the analysis of trends is performed by an external system or by the processing circuit 109 in the on-skin sensor control unit 254 or the analyzer 152 in the receiver/display unit 256 and the trends are incorporated in the data storage and controller 258.

In one embodiment, the data storage and controller module 258, processing circuit 109, and/or analyzer 152 utilizes patient-specific data from multiple episodes to predict a patient's response to future episodes. The multiple episodes used in the prediction are typically responses to a same or similar external or internal stimulus. Examples of stimuli include periods of hypoglycemia or hyperglycemia (or corresponding conditions for analytes other than glucose), treatment of a condition, drug delivery (e.g., insulin for glucose), food intake, exercise, fasting, change in body temperature, elevated or lowered body temperature (e.g., fever), and diseases, viruses, infections, and the like. By analyzing multiple episodes, the data storage and controller module 258, processing circuit 109, and/or analyzer 152 can predict the course of a future episode and provide, for example, a drug administration protocol or administer a drug based on this analysis. An input device (not shown) may be used by the patient or another person to indicate when a particular episode is occurring so that, for example, the data storage and controller module 258, processing circuit 109, and/or analyzer 152 can tag the data as resulting from a particular episode, for use in further analyses.

In addition, the drug delivery system 250 may be capable of providing on-going drug sensitivity feedback. For example, the data from the sensor 252 obtained during the administration of the drug by the drug administration system 260 may provide data about the individual patient's response to the drug which can then be used to modify the current drug administration protocol accordingly, both immediately and in the future. An example of desirable data that can be extracted for each patient includes the patient's characteristic time constant for response to drug administration (e.g., how rapidly the glucose concentration falls when a known bolus of insulin is administered). Another example is the patient's response to administration of various amounts of a drug (e.g., a patient's drug sensitivity curve). The same information may be stored by the drug storage and controller module and then used to determine trends in the patient's drug response, which may be used in developing subsequent drug administration protocols, thereby personalizing the drug administration process for the needs of the patient.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. The claims are intended to cover such modifications and devices.

What is claimed is:

1. A glucose monitoring device, comprising:

a glucose sensor, at least a portion of which is adapted for implantation and contact with bodily fluid, the glucose sensor producing a signal representative of a level of glucose in the bodily fluid; and a transmitter coupled to the glucose sensor so that the transmitter converts the signal representative of the level of glucose in the bodily fluid into a digital signal representing the level of glucose in the bodily fluid, assembles a plurality of data words into a data message, at least one of the data words containing data derived from the digital signal representing the level of glucose in the bodily fluid, each of the data words comprising a set of bits, wherein for at least two of the data words, the set of bits are organized into a set of data bits and a set of error correction bits, and transmits the plurality of data words in an interleaving sequence, wherein the interleaving sequence includes transmitting a first bit in each of the set of bits of each of the data words of the data message followed by transmitting a second bit in each of the set of bits of each of the data words of the data message until the assembled plurality of data words are transmitted.

2. The device of claim 1, wherein the transmitter transmits each bit of each data word assembled into the data message starting with the least significant bit until the entire data message has been transmitted.

3. The device of claim 1, wherein the transmitter is further configured to transmit the data words of the data message at a predetermined transmission rate in the interleaving sequence to reduce error in the transmitted data message.

4. The device of claim 1, further including a processing unit operatively coupled to the transmitter.

5. The device of claim 1, further including a current to frequency conversion unit operatively coupled to the transmitter, the current to frequency conversion unit configured to receive the signal representative of the level of glucose in the bodily fluid.

6. The device of claim 1, wherein the transmitter is configured to transmit the data message to a remote location.

7. The device of claim 6, wherein the remote location includes one or more of a receiver device or a drug administration system.

8. The device of claim 7, wherein the transmitter is configured to transmit the data message using one or more of RF communication protocol, or infrared communication protocol.

9. The device of claim 1, wherein the transmitter is configured to transmit the data message using frequency modulation.

10. The device of claim 1, wherein the data message includes calibration data.

11. The device of claim 1, wherein the transmitter is configured to encrypt the data message.

12. The device of claim 1, wherein the glucose sensor comprises a plurality of electrodes including a working electrode, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

13. A method comprising:

collecting, using a glucose sensor, an analog signal representing a level of glucose in a bodily fluid;

converting, using a transmitter, the analog signal into a digital signal representing the level of glucose in the bodily fluid;

assembling, using the transmitter, a plurality of data words into a data message, at least one of the data words containing data derived from the digital signal representing the level of glucose in the bodily fluid, each of the data words comprising a set of bits, wherein for at least two of the data words, the set of bits are organized into a set of data bits and a set of error correction bits; and transmitting, using the transmitter, the data message, such that the plurality of data words assembled into the data message are transmitted in an interleaving sequence, wherein the interleaving sequence includes transmitting a first bit in each of the set of bits of each of the data words of the data message followed by transmitting a second bit in each of the set of bits of each of the data words of the data message until the assembled plurality of data words are transmitted.

14. The method of claim 13, wherein each bit of each data word assembled into the data message is transmitted starting with the least significant bit until the entire data message has been transmitted.

15. The method of claim 13, further including transmitting the data message to a remote location.

16. The method of claim 13, further including transmitting the data message using one or more of RF communication protocol, or infrared communication protocol.

17. The method of claim 13, further including transmitting the data message based on frequency modulation.

18. The method of claim 13, wherein the data message includes calibration data.

19. The method of claim 13, further including encrypting the data message.

20. The method of claim 13, wherein the glucose sensor comprises a plurality of electrodes including a working electrode, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

* * * * *